United States Patent
Oh et al.

(10) Patent No.: US 11,746,137 B2
(45) Date of Patent: Sep. 5, 2023

(54) IMMUNOSTIMULATING IL-2 ANALOGS

(71) Applicant: HANMI PHARM. CO., LTD., Hwaseong-si (KR)

(72) Inventors: Euh Lim Oh, Gyeonggi-do (KR); Sang Yun Kim, Gyeonggi-do (KR); Yong Ho Heo, Hwaseong-si (KR); Jin Young Kim, Hwaseong-si (KR); Cho Rong Park, Hwaseong-si (KR); Jun Sub Park, Hwaseong-si (KR); Hyun Soo Ryu, Hwaseong-si (KR)

(73) Assignee: HANMI PHARM. CO., LTD., Hwaseong-si (KR)

(*) Notice: Subject to any disclaimer, the term of this patent is extended or adjusted under 35 U.S.C. 154(b) by 0 days.

(21) Appl. No.: 17/915,808

(22) PCT Filed: Mar. 31, 2021

(86) PCT No.: PCT/KR2021/004028
§ 371 (c)(1),
(2) Date: Sep. 29, 2022

(87) PCT Pub. No.: WO2021/201615
PCT Pub. Date: Oct. 7, 2021

(65) Prior Publication Data
US 2023/0124171 A1    Apr. 20, 2023

(30) Foreign Application Priority Data
Mar. 31, 2020  (KR) .................. 10-2020-0039476

(51) Int. Cl.
C07K 14/55    (2006.01)
G01N 33/68    (2006.01)

(52) U.S. Cl.
CPC .......... *C07K 14/55* (2013.01); *G01N 33/6869* (2013.01)

(58) Field of Classification Search
CPC ..................................... C07K 14/55
See application file for complete search history.

(56) References Cited

U.S. PATENT DOCUMENTS

| | | |
|---|---|---|
| 9,428,567 B2 | 8/2016 | Garcia |
| 2005/0142106 A1 | 6/2005 | Wittrup et al. |
| 2006/0234205 A1 | 10/2006 | Cao et al. |
| 2014/0046026 A1 | 2/2014 | Garcia et al. |
| 2019/0321446 A1 | 10/2019 | Higginson-Scott et al. |
| 2021/0101953 A1 | 4/2021 | Sun et al. |

FOREIGN PATENT DOCUMENTS

| | | |
|---|---|---|
| AU | 2007201663 A1 | 10/2008 |
| CA | 2019714 A1 | 12/1990 |
| CN | 1309705 A | 8/2001 |
| CN | 101426916 A | 5/2009 |
| JP | 2016-533167 A | 10/2016 |
| KR | 10-2015-0087130 A | 7/2015 |
| KR | 10-2016-0134989 A | 11/2016 |
| KR | 10-2017-0070091 A | 6/2017 |
| KR | 10-1989201 B1 | 6/2019 |
| KR | 10-2413691 B1 | 6/2022 |
| WO | 89/04665 A2 | 6/1989 |
| WO | 2004/022593 A3 | 3/2004 |
| WO | 2005/007121 A2 | 1/2005 |
| WO | 2005/007121 A3 | 1/2005 |
| WO | 2005/086798 A2 | 9/2005 |
| WO | 2015/164815 A1 | 10/2015 |
| WO | 2018/234862 A1 | 12/2018 |
| WO | 2019/147837 A2 | 8/2019 |
| WO | 2019/196815 A1 | 10/2019 |
| WO | 2019/246404 A1 | 12/2019 |
| WO | 2020/020783 A1 | 1/2020 |
| WO | 2020/057646 A1 | 3/2020 |
| WO | 2020/130300 A1 | 6/2020 |
| WO | 2020/228791 A1 | 11/2020 |
| WO | 2021/120350 A1 | 6/2021 |
| WO | 2021/178833 A2 | 9/2021 |

OTHER PUBLICATIONS

International Search Report for PCT/KR2021/004028 dated, Jul. 26, 2021 (PCT/ISA/210).
Australian Office Action for AU Application No. 2021202825 dated Jun. 3, 2021.
Australian Office Action for AU Application No. 2021202825 dated May 31, 2022.
Australian Office Action (Acceptance) for AU Application No. 2021202825 dated Jun. 16, 2022.

*Primary Examiner* — Prema M Mertz
(74) *Attorney, Agent, or Firm* — Sughrue Mion, PLLC

(57) ABSTRACT

The present invention relates to changes in interleukin-2 alpha receptors and interleukin-2 analogs with increased binding affinity for interleukin-2 beta receptors.

1 Claim, 3 Drawing Sheets

Specification includes a Sequence Listing.

IMMUNOSTIMULATING IL-2 ANALOGS

CROSS REFERENCE TO RELATED APPLICATIONS

This application is a National Stage of International Application No. PCT/KR2021/004028 filed Mar. 31, 2021, claiming priority based on Korean Patent Application No. 10-2020-0039476 filed Mar. 31, 2020.

INCORPORATION BY REFERENCE OF SEQUENCE LISTING

The content of the electronically submitted sequence listing, file name: Sequence_Listing_As_Filed.txt; size: 243, 263 bytes; and date of creation: Sep. 29, 2022, filed herewith, is incorporated herein by reference in its entirety.

TECHNICAL FIELD

The present invention relates to a novel interleukin-2 analog.

BACKGROUND ART

Interleukin-2 is an important immunostimulator with a molecular weight of about 15 kDa, which consists of a total of 133 amino acid residues, and activates various cells of the immune system including T cells and B cells. The high efficacy of interleukin-2 as an immune stimulant can be used for the treatment of various immune-related conditions including cancer and AIDS (Korean Patent Application Publication No. 10-2017-0070091). Currently, interleukin-2 (trademark name: Proleukin) is an FDA-approved drug for the treatment of metastatic renal cell carcinoma and metastatic melanoma. However, due to the severe toxicity associated with high-dose interleukin-2 therapy, the applicable patients are limited. In fact, this therapy is applied to only a small number of eligible patients. The toxicity associated with interleukin-2 includes severe fever, nausea, vomiting, vascular leak, severe hypotension, pulmonary edema, and vascular leak syndrome, which causes liver damage.

The interleukin-2 receptor has three kinds of subunit receptors. The subunit consists of an alpha chain (IL-2Rα, CD25), a beta chain (IL-2Rβ or CD122), and a gamma chain (IL-2Rγ or CD132). Interleukin-2 can exhibit various functions by binding to receptor subunits of various combinations. A single interleukin-2 alpha receptor is called a low-affinity interleukin-2 receptor, and it is not involved in signaling. A complex of interleukin-2 beta and gamma receptors binds to interleukin-2 with intermediate affinity. A complex of interleukin-2 alpha, beta, and gamma receptors binds to interleukin-2 with high affinity. The complex of interleukin-2 beta and gamma receptors is required for effective signal conversion through kinase activation in multiple signaling pathways. In particular, interleukin-2 beta- and gamma-binding receptors are prominent in CD8+ cells and natural killer (NK) cells. In addition, complexes of high-affinity interleukin-2 alpha, beta, and gamma receptors are usually found in CD4+T regulatory cells (Treg), and recently they were also found in activated T cells. Since interleukin-2 beta receptors are distributed in CD8+ T cells or natural killer cells (NK cells) and are involved in the immune response in the body, studies have been conducted to develop therapeutic agents by increasing the activity of beta receptors for immune activation.

Meanwhile, despite the potential of interleukin-2 as a therapeutic agent for various immune-related conditions, there are still not many drugs which can reduce their doses while reducing toxicity and side effects, and thus there is an increasing demand for studies on new and improved drugs.

DISCLOSURE

Technical Problem

An object of the present invention is to provide an interleukin-2 analog.

Another object of the present invention is to provide an isolated nucleic acid encoding the interleukin-2 analog; a recombinant expression vector including the nucleic acid; and a transformant including the vector.

Still another object of the present invention is to provide a method for preparing the interleukin-2 analog.

Still another object of the present invention is to provide a method for increasing the binding affinity for interleukin-2 beta receptors, which includes modifying one or more amino acids in native interleukin-2.

Technical Solution

An aspect of the present invention provides a novel interleukin-2 analog (or IL-2 analog). The interleukin-2 analog is an interleukin-2 analog which has an increased binding affinity for interleukin-2 beta receptor compared to native interleukin-2 or aldesleukin (i.e., an interleukin-2 analog). In a specific embodiment, the interleukin-2 analog may include a sequence in which one or more amino acids in native interleukin-2 are modified.

In another specific embodiment, the interleukin-2 analog is characterized in that the interleukin-2 analog includes a sequence in which one or more amino acids corresponding to those at positions 1, 12, 18, 19, 20, 22, 32, 35, 38, 42, 43, 45, 48, 49, 61, 68, 69, 74, 76, 80, 81, 82, 84, 85, 86, 87, 88, 89, 91, 92, 94, 95, 96, 125, 126, and 133 in native interleukin-2 are modified.

The interleukin-2 analog according to any one of the previous specific embodiments is characterized in that it has an altered binding affinity for interleukin-2 alpha receptors and an increased binding affinity for interleukin-2 beta receptors compared to native interleukin-2 or aldesleukin.

The interleukin-2 analog according to any one of the previous specific embodiments is characterized in that one or more amino acids are added to the amino acid corresponding to position 133.

The interleukin-2 analog according to any one of the previous specific embodiments is characterized in that it is native interleukin-2, in which the amino acid at position 1 is removed and the amino acid at position 125 is substituted with a different amino acid.

The interleukin-2 analog according to any one of the previous specific embodiments is characterized in that it further includes 1 to 10 amino acid substitutions.

The interleukin-2 analog according to any one of the previous specific embodiments is characterized in that one or more amino acids at positions 18, 19, 20, 22, 38, 42, 43, 45, 61, 68, 69, 74, 80, 81, 84, 85, 86, 88, 89, 91, 92, 94, and 96 are further substituted with different amino acids.

The interleukin-2 analog according to any one of the previous specific embodiments is characterized in that one or more amino acids at positions 18, 19, 22, 38, 42, 43, 45, 61, 68, 74, 80, 81, 84, 85, 86, 88, 91, 92, 94, and 96 are further substituted with different amino acids.

The interleukin-2 analog according to any one of the previous specific embodiments is characterized in that it is any one of the following analogs:

(a) an interleukin-2 analog, wherein the interleukin-2 analog is native interleukin-2 in which the amino acid at position 1 is removed and the amino acids at positions 125 and 32 are substituted with different amino acids;

(b) an interleukin-2 analog, wherein the interleukin-2 analog is native interleukin-2 in which the amino acid at position 1 is removed and the amino acids at positions 125 and 35 are substituted with different amino acids;

(c) an interleukin-2 analog, wherein the interleukin-2 analog is native interleukin-2 in which the amino acid at position 1 is removed and the amino acids at positions 125 and 38 are substituted with different amino acids;

(d) an interleukin-2 analog, wherein the interleukin-2 analog is native interleukin-2 in which the amino acid at position 1 is removed and the amino acids at positions 125 and 42 are substituted with different amino acids;

(e) an interleukin-2 analog, wherein the interleukin-2 analog is native interleukin-2 in which the amino acid at position 1 is removed and the amino acids at positions 125 and 43 are substituted with different amino acids;

(f) an interleukin-2 analog, wherein the interleukin-2 analog is native interleukin-2 in which the amino acid at position 1 is removed and the amino acids at positions 125 and 48 are substituted with different amino acids;

(g) an interleukin-2 analog, wherein the interleukin-2 analog is native interleukin-2 in which the amino acid at position 1 is removed and the amino acids at positions 125 and 49 are substituted with different amino acids;

(h) an interleukin-2 analog, wherein the interleukin-2 analog is native interleukin-2 in which the amino acid at position 1 is removed and the amino acids at positions 125 and 76 are substituted with different amino acids;

(i) an interleukin-2 analog, wherein the interleukin-2 analog is native interleukin-2 in which the amino acid at position 1 is removed and the amino acids at positions 125, 38, 42, 81, 92, 94, and 96 are substituted with different amino acids;

(j) an interleukin-2 analog, wherein the interleukin-2 analog is native interleukin-2 in which the amino acid at position 1 is removed and the amino acids at positions 125 and 87 are substituted with different amino acids;

(k) an interleukin-2 analog, wherein the interleukin-2 analog is native interleukin-2 in which the amino acid at position 1 is removed and the amino acids at positions 125, 38, and 42 are substituted with different amino acids;

(l) an interleukin-2 analog, wherein the interleukin-2 analog is native interleukin-2 in which the amino acid at position 1 is removed and the amino acids at positions 125, 38, and 80 are substituted with different amino acids;

(m) an interleukin-2 analog, wherein the interleukin-2 analog is native interleukin-2 in which the amino acid at position 1 is removed and the amino acids at positions 125, 38, and 84 are substituted with different amino acids;

(n) an interleukin-2 analog, wherein the interleukin-2 analog is native interleukin-2 in which the amino acid at position 1 is removed and the amino acids at positions 125, 19, 38, and 42 are substituted with different amino acids;

(o) an interleukin-2 analog, wherein the interleukin-2 analog is native interleukin-2 in which the amino acid at position 1 is removed and the amino acids at positions 125, 12, 38, and 42 are substituted with different amino acids;

(p) an interleukin-2 analog, wherein the interleukin-2 analog is native interleukin-2 in which the amino acid at position 1 is removed and the amino acids at positions 125, 38, 42, and 61 are substituted with different amino acids;

(q) an interleukin-2 analog, wherein the interleukin-2 analog is native interleukin-2 in which the amino acid at position 1 is removed and the amino acids at positions 125, 38, 42, and 84 are substituted with different amino acids;

(r) an interleukin-2 analog, wherein the interleukin-2 analog is native interleukin-2 in which the amino acid at position 1 is removed and the amino acids at positions 125, 38, 42, and 88 are substituted with different amino acids;

(s) an interleukin-2 analog, wherein the interleukin-2 analog is native interleukin-2 in which the amino acid at position 1 is removed and the amino acids at positions 125, 38, 42, and 89 are substituted with different amino acids;

(t) an interleukin-2 analog, wherein the interleukin-2 analog is native interleukin-2 in which the amino acid at position 1 is removed and the amino acids at positions 125, 38, 42, and 91 are substituted with different amino acids;

(u) an interleukin-2 analog, wherein the interleukin-2 analog is native interleukin-2 in which the amino acid at position 1 is removed and the amino acids at positions 125, 38, 42, and 94 are substituted with different amino acids;

(v) an interleukin-2 analog, wherein the interleukin-2 analog is native interleukin-2 in which the amino acid at position 1 is removed and the amino acids at positions 125, 38, 42, and 126 are substituted with different amino acids;

(w) an interleukin-2 analog, wherein the interleukin-2 analog is native interleukin-2 in which the amino acid at position 1 is removed and the amino acids at positions 125, 38, 80, and 84 are substituted with different amino acids;

(x) an interleukin-2 analog, wherein the interleukin-2 analog is native interleukin-2 in which the amino acid at position 1 is removed and the amino acids at positions 125, 38, 94, and 96 are substituted with different amino acids;

(y) an interleukin-2 analog, wherein the interleukin-2 analog is native interleukin-2 in which the amino acid at position 1 is removed and the amino acids at positions 125, 38, 81, and 92 are substituted with different amino acids;

(z) an interleukin-2 analog, wherein the interleukin-2 analog is native interleukin-2 in which the amino acid at position 1 is removed and the amino acids at positions 125, 61, 81, and 92 are substituted with different amino acids;

(aa) an interleukin-2 analog, wherein the interleukin-2 analog is native interleukin-2 in which the amino acid at position 1 is removed and the amino acids at positions 125, 38, 42, 81, and 92 are substituted with different amino acids;

(ab) an interleukin-2 analog, wherein the interleukin-2 analog is native interleukin-2 in which the amino acid at position 1 is removed and the amino acids at positions 125, 38, 80, 81, and 92 are substituted with different amino acids;

(ac) an interleukin-2 analog, wherein the interleukin-2 analog is native interleukin-2 in which the amino acid at position 1 is removed and the amino acids at positions 125, 38, 81, 84, and 92 are substituted with different amino acids;

(ad) an interleukin-2 analog, wherein the interleukin-2 analog is native interleukin-2 in which the amino acid at position 1 is removed and the amino acids at positions 125, 20, 38, 42, 81, and 92 are substituted with different amino acids;

(ae) an interleukin-2 analog, wherein the interleukin-2 analog is native interleukin-2 in which the amino acid at position 1 is removed and the amino acids at positions 125, 38, 42, 80, 81, and 92 are substituted with different amino acids;

(af) an interleukin-2 analog, wherein the interleukin-2 analog is native interleukin-2 in which the amino acid at position 1 is removed and the amino acids at positions 125, 38, 42, 74, 81, and 92 are substituted with different amino acids;

(ag) an interleukin-2 analog, wherein the interleukin-2 analog is native interleukin-2 in which the amino acid at position 1 is removed and the amino acids at positions 125, 38, 42, 81, 84, and 92 are substituted with different amino acids;

(ah) an interleukin-2 analog, wherein the interleukin-2 analog is native interleukin-2 in which the amino acid at position 1 is removed and the amino acids at positions 125, 38, 42, 81, 88, and 92 are substituted with different amino acids;

(ai) an interleukin-2 analog, wherein the interleukin-2 analog is native interleukin-2 in which the amino acid at position 1 is removed and the amino acids at positions 125, 38, 42, 85, 86, and 92 are substituted with different amino acids;

(aj) an interleukin-2 analog, wherein the interleukin-2 analog is native interleukin-2 in which the amino acid at position 1 is removed and the amino acids at positions 125, 38, 80, 81, 85, and 92 are substituted with different amino acids;

(ak) an interleukin-2 analog, wherein the interleukin-2 analog is native interleukin-2 in which the amino acid at position 1 is removed and the amino acids at positions 125, 38, 80, 81, 86, and 92 are substituted with different amino acids;

(al) an interleukin-2 analog, wherein the interleukin-2 analog is native interleukin-2 in which the amino acid at position 1 is removed and the amino acids at positions 125, 80, 81, 85, 86, and 92 are substituted with different amino acids;

(am) an interleukin-2 analog, wherein the interleukin-2 analog is native interleukin-2 in which the amino acid at position 1 is removed and the amino acids at positions 125, 38, 42, 45, 74, 81, and 92 are substituted with different amino acids;

(an) an interleukin-2 analog, wherein the interleukin-2 analog is native interleukin-2 in which the amino acid at position 1 is removed and the amino acids at positions 125, 38, 42, 74, 80, 81, and 92 are substituted with different amino acids;

(ao) an interleukin-2 analog, wherein the interleukin-2 analog is native interleukin-2 in which the amino acid at position 1 is removed and the amino acids at positions 125, 38, 42, 80, 81, 84, and 92 are substituted with different amino acids;

(ap) an interleukin-2 analog, wherein the interleukin-2 analog is native interleukin-2 in which the amino acid at position 1 is removed and the amino acids at positions 125, 38, 45, 80, 85, 86, and 92 are substituted with different amino acids;

(aq) an interleukin-2 analog, wherein the interleukin-2 analog is native interleukin-2 in which the amino acid at position 1 is removed and the amino acids at positions 125, 38, 80, 81, 85, 86, and 92 are substituted with different amino acids;

(ar) an interleukin-2 analog, wherein the interleukin-2 analog is native interleukin-2 in which the amino acid at position 1 is removed and the amino acids at positions 125, 42, 80, 81, 85, 86, and 92 are substituted with different amino acids;

(as) an interleukin-2 analog, wherein the interleukin-2 analog is native interleukin-2 in which the amino acid at position 1 is removed and the amino acids at positions 125, 61, 80, 81, 85, 86, and 92 are substituted with different amino acids;

(at) an interleukin-2 analog, wherein the interleukin-2 analog is native interleukin-2 in which the amino acid at position 1 is removed and the amino acids at positions 125, 69, 80, 81, 85, 86, and 92 are substituted with different amino acids;

(au) an interleukin-2 analog, wherein the interleukin-2 analog is native interleukin-2 in which the amino acid at position 1 is removed and the amino acids at positions 125, 80, 81, 85, 86, 91, and 92 are substituted with different amino acids;

(av) an interleukin-2 analog, wherein the interleukin-2 analog is native interleukin-2 in which the amino acid at position 1 is removed and the amino acids at positions 125, 18, 22, 80, 81, 85, 86, and 92 are substituted with different amino acids;

(aw) an interleukin-2 analog, wherein the interleukin-2 analog is native interleukin-2 in which the amino acid at position 1 is removed and the amino acids at positions 125, 38, 42, 80, 81, 85, 86, and 92 are substituted with different amino acids;

(ax) an interleukin-2 analog, wherein the interleukin-2 analog is native interleukin-2 in which the amino acid at position 1 is removed and the amino acids at positions 125, 38, 42, 45, 74, 80, 81, and 92 are substituted with different amino acids;

(ay) an interleukin-2 analog, wherein the interleukin-2 analog is native interleukin-2 in which the amino acid at position 1 is removed and the amino acids at positions 125, 38, 68, 80, 81, 85, 86, and 92 are substituted with different amino acids;

(az) an interleukin-2 analog, wherein the interleukin-2 analog is native interleukin-2 in which the amino acid at position 1 is removed and the amino acids at positions 125, 69, 74, 80, 81, 85, 86, and 92 are substituted with different amino acids;
(ba) an interleukin-2 analog, wherein the interleukin-2 analog is native interleukin-2 in which the amino acid at position 1 is removed and the amino acids at positions 125, 80, 81, 84, 85, 86, 91, and 92 are substituted with different amino acids;
(bb) an interleukin-2 analog, wherein the interleukin-2 analog is native interleukin-2 in which the amino acid at position 1 is removed and the amino acids at positions 125, 80, 81, 85, 86, 92, 94, and 96 are substituted with different amino acids;
(bc) an interleukin-2 analog, wherein the interleukin-2 analog is native interleukin-2 in which the amino acid at position 1 is removed and the amino acids at positions 125, 18, 19, 22, 80, 81, 85, 86, and 92 are substituted with different amino acids;
(bd) an interleukin-2 analog, wherein the interleukin-2 analog is native interleukin-2 in which the amino acid at position 1 is removed and the amino acids at positions 125, 18, 22, 38, 80, 81, 85, 86, and 92 are substituted with different amino acids;
(be) an interleukin-2 analog, wherein the interleukin-2 analog is native interleukin-2 in which the amino acid at position 1 is removed and the amino acids at positions 125, 18, 22, 61, 80, 81, 85, 86, and 92 are substituted with different amino acids;
(bf) an interleukin-2 analog, wherein the interleukin-2 analog is native interleukin-2 in which the amino acid at position 1 is removed and the amino acids at positions 125, 18, 22, 68, 80, 81, 85, 86, and 92 are substituted with different amino acids;
(bg) an interleukin-2 analog, wherein the interleukin-2 analog is native interleukin-2 in which the amino acid at position 1 is removed and the amino acids at positions 125, 35, 38, 42, 80, 81, 85, 86, and 92 are substituted with different amino acids;
(bh) an interleukin-2 analog, wherein the interleukin-2 analog is native interleukin-2 in which the amino acid at position 1 is removed and the amino acids at positions 125, 38, 42, 45, 80, 81, 85, 86, and 92 are substituted with different amino acids;
(bi) an interleukin-2 analog, wherein the interleukin-2 analog is native interleukin-2 in which the amino acid at position 1 is removed and the amino acids at positions 125, 38, 42, 80, 81, 85, 86, 91, and 92 are substituted with different amino acids;
(bj) an interleukin-2 analog, wherein the interleukin-2 analog is native interleukin-2 in which the amino acid at position 1 is removed and the amino acids at positions 125, 38, 42, 80, 81, 85, 86, 92, and 95 are substituted with different amino acids;
(bk) an interleukin-2 analog, wherein the interleukin-2 analog is native interleukin-2 in which the amino acid at position 1 is removed and the amino acids at positions 125, 35, 38, 42, 74, 80, 81, 85, 86, and 92 are substituted with different amino acids;
(bl) an interleukin-2 analog, wherein the interleukin-2 analog is native interleukin-2 in which the amino acid at position 1 is removed and the amino acids at positions 125, 38, 42, 43, 61, 80, 81, 85, 86, and 92 are substituted with different amino acids;
(bm) an interleukin-2 analog, wherein the interleukin-2 analog is native interleukin-2 in which the amino acid at position 1 is removed and the amino acids at positions 125, 38, 42, 80, 81, 85, 86, 91, 92, and 95 are substituted with different amino acids;
(bn) an interleukin-2 analog, wherein the interleukin-2 analog is native interleukin-2 in which the amino acid at position 1 is removed and the amino acids at positions 125, 35, 38, 42, 74, 80, 81, 82, 85, 86, and 92 are substituted with different amino acids;
(bo) an interleukin-2 analog in which the amino acid at position 1 is removed and the amino acids at positions 125, 80, 81, 86, and 92 are substituted with different amino acids in native interleukin-2; and
(bp) an interleukin-2 analog in which the amino acid at position 1 is removed and the amino acids at positions 125, 80, 81, 85, and 86 are substituted with different amino acids in native interleukin-2.

The interleukin-2 analog according to any one of the previous specific embodiments is characterized in that it includes any one amino acid substitution selected from the group consisting of the following amino acid substitutions:
(a) a substitution in which the amino acid at position 12 is substituted with valine or phenylalanine;
(b) a substitution in which the amino acid at position 18 is substituted with arginine;
(c) a substitution in which the amino acid at position 19 is substituted with tyrosine, valine, phenylalanine, or arginine;
(d) a substitution in which the amino acid at position 20 is substituted with valine or phenylalanine;
(e) a substitution in which the amino acid at position 22 is substituted with glutamic acid;
(f) a substitution in which the amino acid at position 32 is substituted with cysteine;
(g) a substitution in which the amino acid at position 35 is substituted with cysteine or glutamic acid;
(h) a substitution in which the amino acid at position 38 is substituted with alanine or aspartic acid;
(i) a substitution in which the amino acid at position 42 is substituted with lysine, alanine, or tryptophan;
(j) a substitution in which the amino acid at position 43 is substituted with cysteine, glutamic acid, or glutamine;
(k) a substitution in which the amino acid at position 45 is substituted with alanine;
(l) a substitution in which the amino acid at position 48 is substituted with cysteine;
(m) a substitution in which the amino acid at position 49 is substituted with cysteine;
(n) a substitution in which the amino acid at position 61 is substituted with glutamine, arginine, or aspartic acid;
(o) a substitution in which the amino acid at position 68 is substituted with aspartic acid or glutamine;
(p) a substitution in which the amino acid at position 69 is substituted with glycine;
(q) a substitution in which the amino acid at position 74 is substituted with histidine or alanine;
(r) a substitution in which the amino acid at position 76 is substituted with cysteine;
(s) a substitution in which the amino acid at position 80 is substituted with phenylalanine, tyrosine, valine, aspartic acid, or tryptophan;
(t) a substitution in which the amino acid at position 81 is substituted with aspartic acid, glutamic acid, or asparagine;
(u) a substitution in which the amino acid at position 82 is substituted with glycine or valine;
(v) a substitution in which the amino acid at position 84 is substituted with glutamic acid, valine, or phenylalanine;

(w) a substitution in which the amino acid at position 85 is substituted with valine, alanine, glycine, tryptophan, tyrosine, threonine, isoleucine, glutamic acid, or phenylalanine;

(x) a substitution in which the amino acid at position 86 is substituted with valine, alanine, glycine, or leucine;

(y) a substitution in which the amino acid at position 87 is substituted with cysteine;

(z) a substitution in which the amino acid at position 88 is substituted with glutamine, valine, or phenylalanine;

(aa) a substitution in which the amino acid at position 89 is substituted with phenylalanine;

(ab) a substitution in which the amino acid at position 91 is substituted with threonine, phenylalanine, or glutamic acid;

(ac) a substitution in which the amino acid at position 92 is substituted with phenylalanine, leucine, tyrosine, or tryptophan;

(ad) a substitution in which the amino acid at position 95 is substituted with aspartic acid;

(ae) a substitution in which the amino acid at position 96 is substituted with phenylalanine, valine, or isoleucine; and (af) a substitution in which the amino acid at position 126 is substituted with threonine.

The interleukin-2 analog according to any one of the previous specific embodiments is characterized in that it is selected from the group consisting of SEQ ID NOS: 3 to 106.

Another aspect to implement the present invention provides an isolated nucleic acid encoding the interleukin-2 analog; a recombinant expression vector which includes the nucleic acid; and a transformant which includes the vector.

Still another aspect to implement the present invention provides a method for preparing the interleukin-2 analog.

Still another aspect to implement the present invention provides a method for increasing the binding affinity for interleukin-2 beta receptors, which includes modifying one or more amino acids in native interleukin-2, in which the modification may be modifications in one or more amino acids selected from the group consisting of amino acids corresponding to positions at 1, 12, 18, 19, 20, 22, 32, 35, 38, 42, 43, 45, 48, 49, 61, 68, 69, 74, 76, 80, 81, 82, 84, 85, 86, 87, 88, 89, 91, 92, 94, 95, 96, 125, 126, and 133.

Still another aspect to implement the present invention provides an interleukin-2 analog which includes any one sequence selected from the group consisting of amino acid sequences of SEQ ID NOS: 3 to 106.

Still another aspect to implement the present invention provides an interleukin-2 analog which includes an amino acid sequence represented by General Formula 1 below:

[General Formula 1]
(General Formula 1, SEQ ID NO: 212)
X1-P-T-S-S-S-T-K-K-T-Q-L-Q-L-E-H-L-X18-X

19-D-L-X22-M-I-L-N-G-I-N-N-Y-K-N-P-K-L-T

-X38-M-L-T-X42-X43-F-X45-M-P-K-K-A-T-E-L

-K-H-L-Q-C-L-E-X61-E-L-K-P-L-E-X68-V-L-N

-L-A-X74-S-K-N-F-H-X80-X81-P-R-X84-X85-X

86-S-N-I-N-X91-X92-V-X94-E-X96-K-G-S-E-T

-T-F-M-C-E-Y-A-D-E-T-A-T-I-V-E-F-L-N-R-W

-I-T-F-S-Q-S-I-I-S-T-L-T wherein in General Formula 1 above,

X1 is a deletion;
X18 is leucine (L) or arginine (R);
X19 is leucine (L) or tyrosine (Y);
X22 is glutamic acid (E) or glutamine (Q);
X38 is alanine (A), aspartic acid (D), or arginine (R);
X42 is alanine (A), phenylalanine (F), lysine (K), or tryptophan (W);
X43 is glutamic acid (E), lysine (K), or glutamine (Q);
X45 is alanine (A) or tyrosine (Y);
X61 is aspartic acid (D), glutamic acid (E), glutamine (Q), or arginine (R);
X68 is aspartic acid (D) or glutamic acid (E);
X74 is histidine (H) or glutamine (Q);
X80 is phenylalanine (F), leucine (L), valine (V), or tyrosine (Y);
X81 is aspartic acid (D), glutamic acid (E), or arginine (R);
X84 is aspartic acid (D) or glutamic acid (E);
X85 is alanine (A), glutamic acid (E), glycine (G), leucine (L), valine (V), tryptophan (W), or tyrosine (Y);
X86 is alanine (A), glycine (G), isoleucine (I), or valine (V);
X91 is threonine (T) or valine (V);
X92 is phenylalanine (F), isoleucine (I), or tyrosine (Y);
X94 is phenylalanine (F) or leucine (L); and
X96 is phenylalanine (F) or leucine (L).

In a specific embodiment, the interleukin-2 analog is characterized in that it includes any one sequence selected from the group consisting of amino acid sequences of SEQ ID NOS: 10, 13, 14, 15, 16, 17, 20, 21, 22, 32, 35, 36, 42, 53, 54, 56, 58, 59, 60, 62, 71, 72, 74, 75, 76, 77, 78, 85, 87, 89, 91, 92, 93, 94, 95, 98, 99, 100, 101, 103, 104, 105, and 106.

In another specific embodiment, the interleukin-2 analog is characterized in that in General Formula 1 above, X43 is lysine (K);
X45 is tyrosine (Y);
X61 is aspartic acid (D), glutamic acid (E), or glutamine (Q);
X68 is glutamic acid (E);
X74 is glutamine (Q);
X80 is phenylalanine (F) or leucine (L);
X85 is leucine (L), valine (V), or tyrosine (Y);
X86 is isoleucine (I) or valine (V); and
X92 is phenylalanine (F) or isoleucine (I).

The interleukin-2 analog according to any one of the previous specific embodiments is characterized in that it includes any one sequence selected from the group consisting of amino acid sequences of SEQ ID NOS: 10, 13, 14, 16, 17, 20, 21, 22, 32, 35, 36, 42, 53, 54, 87, 89, 91, 92, 93, 94, 98, 99, 100, 101, 103, 104, and 105.

The interleukin-2 analog according to any one of the previous specific embodiments is characterized in that it further includes one or more amino acids at the C-terminus thereof.

Still another aspect to implement the present invention provides an interleukin-2 analog which includes an amino acid sequence represented by General Formula 2 below:

[General Formula 2]
    (General Formula 2, SEQ ID NO: 213)
X1-P-T-S-S-T-K-K-T-Q-L-Q-L-E-H-L-X18-L

-D-L-X22-M-I-L-N-G-I-N-N-Y-K-N-P-K-L-T-X

38-M-L-T-X42-K-F-Y-M-P-K-K-A-T-E-L-K-H-L

-Q-C-L-E-X61-E-L-K-P-L-E-X68-V-L-N-L-A-Q

-S-K-N-F-H-F-X81-P-R-D-X85-X86-S-N-I-N-V

-F-V-L-E-L-K-G-S-E-T-T-F-M-C-E-Y-A-D-E-T

-A-T-I-V-E-F-L-N-R-W-I-T-F-S-Q-S-I-l-S-T

-L-T wherein in General Formula 2 above,
X1 is a deletion,
X18 is leucine (L) or arginine (R);
X22 is glutamic acid (E) or glutamine (Q);
X38 is alanine (A) or arginine (R);
X42 is phenylalanine (F) or lysine (K);
X61 is aspartic acid (D) or glutamic acid (E);
X68 is aspartic acid (D) or glutamic acid (E);
X81 is aspartic acid (D) or glutamic acid (E);
X85 is leucine (L) or valine (V); and
X86 is isoleucine (I) or valine (V).

In a specific embodiment, the interleukin-2 analog is characterized in that it includes any one sequence selected from the group consisting of amino acid sequences of SEQ ID NOS: 22, 42, 53, 87, 105, and 106.

In another specific embodiment, the interleukin-2 analog is characterized in that it further includes one or more amino acids at the C-terminus thereof.

Advantageous Effects

The interleukin-2 analog according to the present invention is an analog which has increased binding affinity for interleukin-2 beta receptors in vivo and can be for various purposes.

BRIEF DESCRIPTION OF DRAWINGS

FIG. 1(A)-FIG. 1(C) show the results confirming the binding affinity of an interleukin-2 analog for interleukin-2 alpha receptors, in which FIG. 1(A) represents interleukin-2 analog #86, FIG. 1(B) represents interleukin-2 analog #104, and FIG. 1(C) represents interleukin-2 analog #105.

FIG. 2(A)-FIG. 2(C) show the results confirming the binding affinity of an interleukin-2 analog for interleukin-2 beta receptors, in which FIG. 2(A) represents interleukin-2 analog #86, FIG. 2(B) represents interleukin-2 analog #104, and FIG. 2(C) represents interleukin-2 analog #105.

DETAILED DESCRIPTION FOR CARRYING OUT THE INVENTION

Figure 1A:
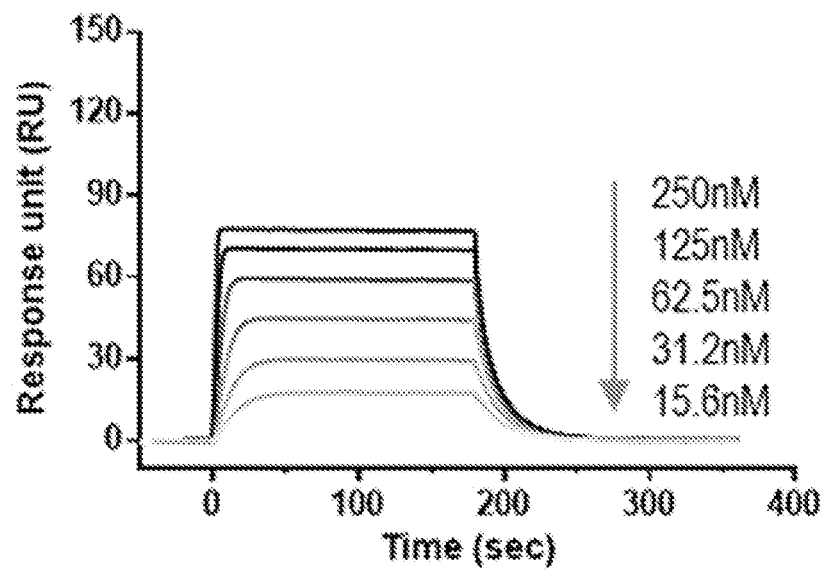

The details for carrying out the present invention will be described as follows. Meanwhile, respective descriptions and embodiments disclosed in the present invention may also be applied to other descriptions and embodiments. That is, all combinations of various elements disclosed in the present invention fall within the scope of the present invention. Further, the scope of the present invention cannot be considered to be limited by the specific description below.

Over the entire specification of the present invention, the conventional one-letter and three-letter codes for amino acids are used. Additionally, the amino acids mentioned herein are abbreviated according to the nomenclature rules of the IUPAC-IUB as follows:

| | | | |
|---|---|---|---|
| alanine | A | arginine | R |
| asparagine | N | aspartic acid | D |
| cysteine | C | glutamic acid | E |
| glutamine | Q | glycine | G |
| histidine | H | isoleucine | I |
| leucine | L | lysine | K |
| methionine | M | phenylalanine | F |
| proline | P | serine | S |
| threonine | T | tryptophan | W |
| tyrosine | Y | valine | V |

Still another aspect of the present invention provides an interleukin-analog. The interleukin-2 analog of the present invention is characterized in that its binding affinity for interleukin-2 receptors is altered, and in particular in that it has increased binding affinity for interleukin-2 beta receptors. Specifically, the interleukin-2 analog of the present invention may be one which has increased binding affinity for interleukin-2 beta receptors, and more specifically one which has altered (increased or decreased) binding affinity for interleukin-2 alpha receptors compared to native interleukin-2 or known aldesleukin.

As used herein, the term "interleukin-2 (IL-2)" refers to a type of cytokine which transmits signals in the immune system in vivo. The interleukin-2 is generally known as an important immunostimulator with a size of about 15 kDa.

As used herein, the term "interleukin-2 analog" refers to native interleukin-2 in which one or more amino acids in the sequence thereof are modified. Particularly in the present invention, the interleukin-2 analog may be one which has reduced or increased binding affinity for interleukin-2 receptors compared to native interleukin-2, in which amino acid(s) in native interleukin-2 is(are) modified. The interleukin-2 analog of the present invention may be one which is not naturally occurring.

The native interleukin-2 may be a human interleukin-2, and its sequence may be obtained from known databases, etc. Specifically, the native interleukin-2 may have an amino acid sequence of SEQ ID NO: 1, but is not limited thereto.

In the present invention, what is meant by "native interleukin-2 may have an amino acid sequence of SEQ ID NO: 1" is that not only the sequence which is the same as SEQ ID NO: 1, but also sequences which have a homology of 80% or higher, 85% or higher, 90% or higher, 91% or higher, 92% or higher, 93% or higher, 94% or higher, 95% or higher, 96% or higher, 97% or higher, 98% or higher, and 99% or higher to SEQ ID NO: 1 belong to the scope of native interleukin-2 of the present invention, and that the corresponding position(s) of amino acid modification is(are) altered on the amino acid sequence of SEQ ID NO: 1 when sequences having a homology of 80% or higher, 85% or higher, 90% or higher, 91% or higher, 92% or higher, 93% or higher, 94% or higher, 95% or higher, 96% or higher, 97% or higher, 98% or higher, and 99% or higher are aligned based on SEQ ID NO: 1.

In the present invention, what is meant by "one or more amino acids in the native sequence are altered" may be that a modification selected from the group consisting of substitution, addition, deletion, modification, and a combination thereof has occurred in at least one amino acid in the native sequence.

Specifically, the interleukin-2 analog of the present invention may include a sequence in which one or more amino acids corresponding to positions 1, 12, 18, 19, 20, 22, 32, 35, 38, 42, 43, 45, 48, 49, 61, 68, 69, 74, 76, 80, 81, 82, 84, 85, 86, 87, 88, 89, 91, 92, 94, 95, 96, 125, 126, and 133 in native interleukin-2 are modified. Specifically, the interleukin-2 analog of the present invention may be native interleukin-2 in which the amino acid at position 1 is removed and the amino acid at position 125 is substituted with a different amino acid; and which further includes 1, 2, 3, 4, 5, 6, 7, 8, 9, 10, or more amino acid substitutions. Although not limited thereto, the amino acid at position 125 (i.e., cysteine) may be substituted with serine, and the amino acid(s) at which a further substitution occurs may be amino acids corresponding to positions 12, 18, 19, 20, 22, 32, 35, 38, 42, 43, 45, 48, 49, 61, 68, 69, 74, 76, 80, 81, 82, 84, 85, 86, 87, 88, 89, 91, 92, 94, 95, 96, 126, and 133.

Additionally, interleukin-2 analogs which include substitution, addition, deletion, modification, etc. of amino acid residues in addition to the positions for modification above to the extent that can be performed for the stability and increase of half-life of a peptide known in the art are also included within the scope of the present invention.

As used herein, the term "aldesleukin" or "interleukin-2 analog (aldesleukin)", which is a commercially available interleukin-2 analog, may be aldesleukin (trademark name: Proleukin®), and specifically may be one which has the amino acid sequence of SEQ ID NO: 2. In the present invention, these terms are used interchangeably with "interleukin-2 analog 1". The interleukin analog according to the present invention may have altered binding affinity for interleukin-2 alpha receptors and/or increased binding affinity for interleukin-2 beta receptors compared to the interleukin-2 analog 1.

Although interleukin-2 alpha receptors are not known to be involved in the signaling system of interleukin-2, they increase the binding affinity of interleukin-2 for other interleukin-2 receptors (beta or gamma receptors) by 10 to 100 times and are expressed in $CD4^+$ regulatory T cells, etc.

Since interleukin-2 beta receptors are mainly distributed in $CD8^+$ T cells or natural killer cells (NK cells) and have an important role of activating immune responses and macrophages, it is expected that tumor cell death and activation of the body's immune responses can be promoted through the activation of interleukin-2 beta receptors.

Accordingly, the interleukin-2 analog of the present invention which has increased binding affinity for interleukin-2 beta receptors can have a therapeutic effect where the suppression and death of tumors is increased while side effects are reduced.

In the present invention, the interleukin-2 analog may include a sequence of native interleukin-2 in which the amino acid at position 1 is removed and the amino acid at position 125 is substituted with a different amino acid, and which further includes 1 to 10 amino acid modifications. For example, the interleukin-2 analog may include a sequence of native interleukin-2 in which the amino acid at position 125 is substituted with serine and one or more amino acids at positions 12, 18, 19, 20, 22, 32, 35, 38, 42, 43, 45, 48, 49, 61, 68, 69, 74, 76, 80, 81, 82, 84, 85, 86, 87, 88, 89, 91, 92, 94, 95, 96, and 126 are substituted with different amino acids and/or one or more amino acids are added on the amino acid at position 133, but the sequence is not limited thereto, and any interleukin-2 analog which has altered binding affinity for interleukin-2 alpha receptors and increased binding affinity for interleukin-2 beta receptors compared to native interleukin-2 and/or aldesleukin is included without limitation.

In an embodiment, the interleukin-2 analog may be one in which one or more amino acids are added to the amino acid corresponding to position 133, but the interleukin-2 analog is not limited thereto. For the purpose of the present invention, the amino acids to be added are not limited with regard to the type or length thereof as long as the interleukin-2 analog has altered binding affinity for interleukin-2 alpha receptors and increased binding affinity for interleukin-2 beta receptors compared to native interleukin-2 and/or aldesleukin, and amino acids which are not naturally occurring and amino acids with a chemical modification can also be added in addition to natural amino acids.

In another embodiment, the interleukin-2 analog may be native interleukin-2 in which the amino acid at position 1 is removed; the amino acid at position 125 is substituted with a different amino acid; and 1, 2, 3, 4, 5, 6, 7, 8, 9, or more amino acids among the amino acids at positions 18, 19, 20, 22, 38, 42, 43, 45, 61, 68, 69, 74, 80, 81, 84, 85, 86, 88, 89, 91, 92, 94, and 96 are substituted with different amino acids, but the interleukin-2 analog is not limited thereto.

In still another embodiment, the interleukin-2 analog may be native interleukin-2 in which the amino acid at position 1 is removed; the amino acid at position 125 is substituted with a different amino acid; and 1, 2, 3, 4, 5, 6, 7, 8, 9, or more amino acids among the amino acids at positions 18, 19, 22, 38, 42, 43, 45, 61, 68, 74, 80, 81, 84, 85, 86, 88, 91, 92, 94, and 96 are substituted with different amino acids, but the interleukin-2 analog is not limited thereto.

In still another embodiment, the interleukin-2 analog may be any one selected from the group consisting of the following analogs:

(a) an interleukin-2 analog, wherein the interleukin-2 analog is native interleukin-2 in which the amino acid at position 1 is removed and the amino acids at positions 125 and 32 are substituted with different amino acids;

(b) an interleukin-2 analog, wherein the interleukin-2 analog is native interleukin-2 in which the amino acid at position 1 is removed and the amino acids at positions 125 and 35 are substituted with different amino acids;

(c) an interleukin-2 analog, wherein the interleukin-2 analog is native interleukin-2 in which the amino acid at position 1 is removed and the amino acids at positions 125 and 38 are substituted with different amino acids;

(d) an interleukin-2 analog, wherein the interleukin-2 analog is native interleukin-2 in which the amino acid at position 1 is removed and the amino acids at positions 125 and 42 are substituted with different amino acids;

(e) an interleukin-2 analog, wherein the interleukin-2 analog is native interleukin-2 in which the amino acid at position 1 is removed and the amino acids at positions 125 and 43 are substituted with different amino acids;

(f) an interleukin-2 analog, wherein the interleukin-2 analog is native interleukin-2 in which the amino acid at position 1 is removed and the amino acids at positions 125 and 48 are substituted with different amino acids;

(g) an interleukin-2 analog, wherein the interleukin-2 analog is native interleukin-2 in which the amino acid at position 1 is removed and the amino acids at positions 125 and 49 are substituted with different amino acids;

(h) an interleukin-2 analog, wherein the interleukin-2 analog is native interleukin-2 in which the amino acid at position 1 is removed and the amino acids at positions 125 and 76 are substituted with different amino acids;
(i) an interleukin-2 analog, wherein the interleukin-2 analog is native interleukin-2 in which the amino acid at position 1 is removed and the amino acids at positions 125, 38, 42, 81, 92, 94, and 96 are substituted with different amino acids;
(j) an interleukin-2 analog, wherein the interleukin-2 analog is native interleukin-2 in which the amino acid at position 1 is removed and the amino acids at positions 125 and 87 are substituted with different amino acids;
(k) an interleukin-2 analog, wherein the interleukin-2 analog is native interleukin-2 in which the amino acid at position 1 is removed and the amino acids at positions 125, 38, and 42 are substituted with different amino acids;
(l) an interleukin-2 analog, wherein the interleukin-2 analog is native interleukin-2 in which the amino acid at position 1 is removed and the amino acids at positions 125, 38, and 80 are substituted with different amino acids;
(m) an interleukin-2 analog, wherein the interleukin-2 analog is native interleukin-2 in which the amino acid at position 1 is removed and the amino acids at positions 125, 38, and 84 are substituted with different amino acids;
(n) an interleukin-2 analog, wherein the interleukin-2 analog is native interleukin-2 in which the amino acid at position 1 is removed and the amino acids at positions 125, 19, 38, and 42 are substituted with different amino acids;
(o) an interleukin-2 analog, wherein the interleukin-2 analog is native interleukin-2 in which the amino acid at position 1 is removed and the amino acids at positions 125, 12, 38, and 42 are substituted with different amino acids;
(p) an interleukin-2 analog, wherein the interleukin-2 analog is native interleukin-2 in which the amino acid at position 1 is removed and the amino acids at positions 125, 38, 42, and 61 are substituted with different amino acids;
(q) an interleukin-2 analog, wherein the interleukin-2 analog is native interleukin-2 in which the amino acid at position 1 is removed and the amino acids at positions 125, 38, 42, and 84 are substituted with different amino acids;
(r) an interleukin-2 analog, wherein the interleukin-2 analog is native interleukin-2 in which the amino acid at position 1 is removed and the amino acids at positions 125, 38, 42, and 88 are substituted with different amino acids;
(s) an interleukin-2 analog, wherein the interleukin-2 analog is native interleukin-2 in which the amino acid at position 1 is removed and the amino acids at positions 125, 38, 42, and 89 are substituted with different amino acids;
(t) an interleukin-2 analog, wherein the interleukin-2 analog is native interleukin-2 in which the amino acid at position 1 is removed and the amino acids at positions 125, 38, 42, and 91 are substituted with different amino acids;
(u) an interleukin-2 analog, wherein the interleukin-2 analog is native interleukin-2 in which the amino acid at position 1 is removed and the amino acids at positions 125, 38, 42, and 94 are substituted with different amino acids;
(v) an interleukin-2 analog, wherein the interleukin-2 analog is native interleukin-2 in which the amino acid at position 1 is removed and the amino acids at positions 125, 38, 42, and 126 are substituted with different amino acids;
(w) an interleukin-2 analog, wherein the interleukin-2 analog is native interleukin-2 in which the amino acid at position 1 is removed and the amino acids at positions 125, 38, 80, and 84 are substituted with different amino acids;
(x) an interleukin-2 analog, wherein the interleukin-2 analog is native interleukin-2 in which the amino acid at position 1 is removed and the amino acids at positions 125, 38, 94, and 96 are substituted with different amino acids;
(y) an interleukin-2 analog, wherein the interleukin-2 analog is native interleukin-2 in which the amino acid at position 1 is removed and the amino acids at positions 125, 38, 81, and 92 are substituted with different amino acids;
(z) an interleukin-2 analog, wherein the interleukin-2 analog is native interleukin-2 in which the amino acid at position 1 is removed and the amino acids at positions 125, 61, 81, and 92 are substituted with different amino acids;
(aa) an interleukin-2 analog, wherein the interleukin-2 analog is native interleukin-2 in which the amino acid at position 1 is removed and the amino acids at positions 125, 38, 42, 81, and 92 are substituted with different amino acids;
(ab) an interleukin-2 analog, wherein the interleukin-2 analog is native interleukin-2 in which the amino acid at position 1 is removed and the amino acids at positions 125, 38, 80, 81, and 92 are substituted with different amino acids;
(ac) an interleukin-2 analog, wherein the interleukin-2 analog is native interleukin-2 in which the amino acid at position 1 is removed and the amino acids at positions 125, 38, 81, 84, and 92 are substituted with different amino acids;
(ad) an interleukin-2 analog, wherein the interleukin-2 analog is native interleukin-2 in which the amino acid at position 1 is removed and the amino acids at positions 125, 20, 38, 42, 81, and 92 are substituted with different amino acids;
(ae) an interleukin-2 analog, wherein the interleukin-2 analog is native interleukin-2 in which the amino acid at position 1 is removed and the amino acids at positions 125, 38, 42, 80, 81, and 92 are substituted with different amino acids;
(af) an interleukin-2 analog, wherein the interleukin-2 analog is native interleukin-2 in which the amino acid at position 1 is removed and the amino acids at positions 125, 38, 42, 74, 81, and 92 are substituted with different amino acids;
(ag) an interleukin-2 analog, wherein the interleukin-2 analog is native interleukin-2 in which the amino acid at position 1 is removed and the amino acids at positions 125, 38, 42, 81, 84, and 92 are substituted with different amino acids;
(ah) an interleukin-2 analog, wherein the interleukin-2 analog is native interleukin-2 in which the amino acid at position 1 is removed and the amino acids at positions 125, 38, 42, 81, 88, and 92 are substituted with different amino acids;
(ai) an interleukin-2 analog, wherein the interleukin-2 analog is native interleukin-2 in which the amino acid at position 1 is removed and the amino acids at positions 125, 38, 42, 85, 86, and 92 are substituted with different amino acids;
(aj) an interleukin-2 analog, wherein the interleukin-2 analog is native interleukin-2 in which the amino acid at position 1 is removed and the amino acids at positions 125, 38, 80, 81, 85, and 92 are substituted with different amino acids;
(ak) an interleukin-2 analog, wherein the interleukin-2 analog is native interleukin-2 in which the amino acid at position 1 is removed and the amino acids at positions 125, 38, 80, 81, 86, and 92 are substituted with different amino acids;
(al) an interleukin-2 analog, wherein the interleukin-2 analog is native interleukin-2 in which the amino acid at position 1 is removed and the amino acids at positions 125, 80, 81, 85, 86, and 92 are substituted with different amino acids;
(am) an interleukin-2 analog, wherein the interleukin-2 analog is native interleukin-2 in which the amino acid at position 1 is removed and the amino acids at positions 125, 38, 42, 45, 74, 81, and 92 are substituted with different amino acids;
(an) an interleukin-2 analog, wherein the interleukin-2 analog is native interleukin-2 in which the amino acid at position 1 is removed and the amino acids at positions 125, 38, 42, 74, 80, 81, and 92 are substituted with different amino acids;
(ao) an interleukin-2 analog, wherein the interleukin-2 analog is native interleukin-2 in which the amino acid at position 1 is removed and the amino acids at positions 125, 38, 42, 80, 81, 84, and 92 are substituted with different amino acids;
(ap) an interleukin-2 analog, wherein the interleukin-2 analog is native interleukin-2 in which the amino acid at position 1 is removed and the amino acids at positions 125, 38, 45, 80, 85, 86, and 92 are substituted with different amino acids;
(aq) an interleukin-2 analog, wherein the interleukin-2 analog is native interleukin-2 in which the amino acid at position 1 is removed and the amino acids at positions 125, 38, 80, 81, 85, 86, and 92 are substituted with different amino acids;
(ar) an interleukin-2 analog, wherein the interleukin-2 analog is native interleukin-2 in which the amino acid at position 1 is removed and the amino acids at positions 125, 42, 80, 81, 85, 86, and 92 are substituted with different amino acids;
(as) an interleukin-2 analog, wherein the interleukin-2 analog is native interleukin-2 in which the amino acid at position 1 is removed and the amino acids at positions 125, 61, 80, 81, 85, 86, and 92 are substituted with different amino acids;
(at) an interleukin-2 analog, wherein the interleukin-2 analog is native interleukin-2 in which the amino acid at position 1 is removed and the amino acids at positions 125, 69, 80, 81, 85, 86, and 92 are substituted with different amino acids;
(au) an interleukin-2 analog, wherein the interleukin-2 analog is native interleukin-2 in which the amino acid at position 1 is removed and the amino acids at positions 125, 80, 81, 85, 86, 91, and 92 are substituted with different amino acids;
(av) an interleukin-2 analog, wherein the interleukin-2 analog is native interleukin-2 in which the amino acid at position 1 is removed and the amino acids at positions 125, 18, 22, 80, 81, 85, 86, and 92 are substituted with different amino acids;
(aw) an interleukin-2 analog, wherein the interleukin-2 analog is native interleukin-2 in which the amino acid at position 1 is removed and the amino acids at positions 125, 38, 42, 80, 81, 85, 86, and 92 are substituted with different amino acids;
(ax) an interleukin-2 analog, wherein the interleukin-2 analog is native interleukin-2 in which the amino acid at position 1 is removed and the amino acids at positions 125, 38, 42, 45, 74, 80, 81, and 92 are substituted with different amino acids;
(ay) an interleukin-2 analog, wherein the interleukin-2 analog is native interleukin-2 in which the amino acid at position 1 is removed and the amino acids at positions 125, 38, 68, 80, 81, 85, 86, and 92 are substituted with different amino acids;
(az) an interleukin-2 analog, wherein the interleukin-2 analog is native interleukin-2 in which the amino acid at position 1 is removed and the amino acids at positions 125, 69, 74, 80, 81, 85, 86, and 92 are substituted with different amino acids;
(ba) an interleukin-2 analog, wherein the interleukin-2 analog is native interleukin-2 in which the amino acid at position 1 is removed and the amino acids at positions 125, 80, 81, 84, 85, 86, 91, and 92 are substituted with different amino acids;
(bb) an interleukin-2 analog, wherein the interleukin-2 analog is native interleukin-2 in which the amino acid at position 1 is removed and the amino acids at positions 125, 80, 81, 85, 86, 92, 94, and 96 are substituted with different amino acids;
(bc) an interleukin-2 analog, wherein the interleukin-2 analog is native interleukin-2 in which the amino acid at position 1 is removed and the amino acids at positions 125, 18, 19, 22, 80, 81, 85, 86, and 92 are substituted with different amino acids;
(bd) an interleukin-2 analog, wherein the interleukin-2 analog is native interleukin-2 in which the amino acid at position 1 is removed and the amino acids at positions 125, 18, 22, 38, 80, 81, 85, 86, and 92 are substituted with different amino acids;
(be) an interleukin-2 analog, wherein the interleukin-2 analog is native interleukin-2 in which the amino acid at position 1 is removed and the amino acids at positions 125, 18, 22, 61, 80, 81, 85, 86, and 92 are substituted with different amino acids;
(bf) an interleukin-2 analog, wherein the interleukin-2 analog is native interleukin-2 in which the amino acid at position 1 is removed and the amino acids at positions 125, 18, 22, 68, 80, 81, 85, 86, and 92 are substituted with different amino acids;
(bg) an interleukin-2 analog, wherein the interleukin-2 analog is native interleukin-2 in which the amino acid at position 1 is removed and the amino acids at positions 125, 35, 38, 42, 80, 81, 85, 86, and 92 are substituted with different amino acids;
(bh) an interleukin-2 analog, wherein the interleukin-2 analog is native interleukin-2 in which the amino acid at position 1 is removed and the amino acids at positions 125, 38, 42, 45, 80, 81, 85, 86, and 92 are substituted with different amino acids;
(bi) an interleukin-2 analog, wherein the interleukin-2 analog is native interleukin-2 in which the amino acid at position 1 is removed and the amino acids at positions 125, 38, 42, 80, 81, 85, 86, 91, and 92 are substituted with different amino acids;
(bj) an interleukin-2 analog, wherein the interleukin-2 analog is native interleukin-2 in which the amino acid at position 1 is removed and the amino acids at positions 125, 38, 42, 80, 81, 85, 86, 92, and 95 are substituted with different amino acids;
(bk) an interleukin-2 analog, wherein the interleukin-2 analog is native interleukin-2 in which the amino acid at position 1 is removed and the amino acids at positions 125, 35, 38, 42, 74, 80, 81, 85, 86, and 92 are substituted with different amino acids;
(bl) an interleukin-2 analog, wherein the interleukin-2 analog is native interleukin-2 in which the amino acid at position 1 is removed and the amino acids at positions 125, 38, 42, 43, 61, 80, 81, 85, 86, and 92 are substituted with different amino acids;
(bm) an interleukin-2 analog, wherein the interleukin-2 analog is native interleukin-2 in which the amino acid at position 1 is removed and the amino acids at positions 125, 38, 42, 80, 81, 85, 86, 91, 92, and 95 are substituted with different amino acids;
(bn) an interleukin-2 analog, wherein the interleukin-2 analog is native interleukin-2 in which the amino acid at position 1 is removed and the amino acids at positions 125, 35, 38, 42, 74, 80, 81, 82, 85, 86, and 92 are substituted with different amino acids;
(bo) an interleukin-2 analog, wherein the interleukin-2 analog is native interleukin-2 in which the amino acid at position 1 is removed and the amino acids at positions 125, 80, 81, 86, and 92 are substituted with different amino acids; and
(bp) an interleukin-2 analog, wherein the interleukin-2 analog is native interleukin-2 in which the amino acid at position 1 is removed and the amino acids at positions 125, 80, 81, 85, and 86 are substituted with different amino acids.

In particular, the amino acid substitutions included in the interleukin-2 analog may be any one or more selected from the group consisting of the following amino acid substitutions:

(a) a substitution in which the amino acid at position 12 is substituted with valine or phenylalanine;
(b) a substitution in which the amino acid at position 18 is substituted with arginine;
(c) a substitution in which the amino acid at position 19 is substituted with tyrosine, valine, phenylalanine, or arginine;
(d) a substitution in which the amino acid at position 20 is substituted with valine or phenylalanine;
(e) a substitution in which the amino acid at position 22 is substituted with glutamic acid;
(f) a substitution in which the amino acid at position 32 is substituted with cysteine;
(g) a substitution in which the amino acid at position 35 is substituted with cysteine or glutamic acid;
(h) a substitution in which the amino acid at position 38 is substituted with alanine or aspartic acid;
(i) a substitution in which the amino acid at position 42 is substituted with lysine, alanine, or tryptophan;
(j) a substitution in which the amino acid at position 43 is substituted with cysteine, glutamic acid, or glutamin;
(k) a substitution in which the amino acid at position 45 is substituted with alanine;
(l) a substitution in which the amino acid at position 48 is substituted with cysteine;
(m) a substitution in which the amino acid at position 49 is substituted with cysteine;
(n) a substitution in which the amino acid at position 61 is substituted with glutamine, arginine, or aspartic acid;
(o) a substitution in which the amino acid at position 68 is substituted with aspartic acid or glutamine;
(p) a substitution in which the amino acid at position 69 is substituted with glycine;
(q) a substitution in which the amino acid at position 74 is substituted with histidine or alanine;
(r) a substitution in which the amino acid at position 76 is substituted with cysteine;
(s) a substitution in which the amino acid at position 80 is substituted with phenylalanine, tyrosine, valine, aspartic acid, or tryptophan;
(t) a substitution in which the amino acid at position 81 is substituted with aspartic acid, glutamic acid, or asparagine;
(u) a substitution in which the amino acid at position 82 is substituted with glycine or valine;
(v) a substitution in which the amino acid at position 84 is substituted with glutamic acid, valine, or phenylalanine;
(w) a substitution in which the amino acid at position 85 is substituted with valine, alanine, glycine, tryptophan, tyrosine, threonine, isoleucine, glutamic acid, or phenylalanine;
(x) a substitution in which the amino acid at position 86 is substituted with valine, alanine, glycine, or leucine;
(y) a substitution in which the amino acid at position 87 is substituted with cysteine;
(z) a substitution in which the amino acid at position 88 is substituted with glutamine, valine, or phenylalanine;
(aa) a substitution in which the amino acid at position 89 is substituted with phenylalanine;
(ab) a substitution in which the amino acid at position 91 is substituted with threonine, phenylalanine, or glutamic acid;
(ac) a substitution in which the amino acid at position 92 is substituted with phenylalanine, leucine, tyrosine, or tryptophan;
(ad) a substitution in which the amino acid at position 95 is substituted with aspartic acid;
(ae) a substitution in which the amino acid at position 96 is substituted with phenylalanine, valine, or isoleucine; and
(af) a substitution in which the amino acid at position 126 is substituted with threonine.

As used herein, the term "corresponding to" refers to an amino acid residue at a position listed in a peptide, or an amino acid residue which is similar, identical, or homologous to a residue listed in a peptide. Confirmation of the amino acid at the corresponding position may be determining a specific amino acid in a sequence that refers to a specific sequence.

In an embodiment, each amino acid residue in the amino acid sequence can be numbered by aligning any amino acid sequence with SEQ ID NO: 1, and based on the same, referring to the numerical position of the amino acid residue corresponding to the amino acid residue of SEQ ID NO: 1.

As such an alignment, for example, the Needleman-Wunsch algorithm (Needleman and Wunsch, 1970, *J. Mol. Biol.* 48:443-453), the Needle program of the EMBOSS package (EMBOSS: The European Molecular Biology Open Software Suite, Rice et al., 2000), (*Trends Genet.* 16:276-277), etc. may be used, but the available programs are not limited thereto, and a sequence alignment program known in the art, a pairwise sequence comparison algorithm, etc. may be used appropriately.

In the present invention, even if expressed as a specific position of an amino acid in a peptide, such expression may refer to a corresponding position in a reference sequence.

In another embodiment, the interleukin-2 analog may include, consist of or essentially consist of an amino acid sequence which is selected from the group consisting of SEQ ID NOS: 3 to 106, but the interleukin-2 analog is not limited thereto.

Additionally, even if the interleukin-2 analog is expressed as "an interleukin-2 analog consisting of a particular SEQ ID NO" in the present invention, it does not exclude a mutation that may occur by the addition of a meaningless sequence upstream or downstream of the amino acid sequence of the corresponding SEQ ID NO, or a mutation that may occur naturally, or a silent mutation thereof, as long as the interleukin-2 analog has an activity identical or equivalent to the interleukin-2 analog consisting of the amino acid sequence of the corresponding SEQ ID NO, and even if the sequence addition or mutation is present, the interleukin-2 analog apparently belongs to the scope of the present invention.

The interleukin-2 analog of the present invention may include an amino acid sequence which has a homology of 40% or higher, 45% or higher, 50% or higher, 55% or higher, 60% or higher, 65% or higher, 70% or higher, 75% or higher, 80% or higher, 81% or higher, 82% or higher, 83% or higher, 84% or higher, 85% or higher, 86% or higher, 87% or higher, 88% or higher, 89% or higher, 90% or higher, 91% or higher, 92% or higher, 93% or higher, 94% or higher, 95% or higher, 96% or higher, 97% or higher, 98% or higher, or 99% or higher to the amino acid sequences of SEQ ID NOS: 3 to 106, but the interleukin-2 analog is not limited thereto.

In the present invention, the terms "homology" and "identity" refer to a degree of relatedness between two given amino acid sequences or nucleotide sequences and may be expressed as a percentage.

Sequence homology or identity of a conserved polynucleotide or polypeptide may be determined by a standard alignment algorithm, and default gap penalties established by a program to be used may be used in combination. Substantially, homologous or identical sequences may generally hybridize with all or part of the sequences under moderately or highly stringent conditions. It is apparent that hybridization also includes hybridization of a polynucleotide with a polynucleotide, which includes a general codon or a codon where codon degeneracy is considered.

The terms homology and identity can frequently be used interchangeably.

Whether any two nucleotide or peptide sequences have homology, similarity, or identity may be determined by, for example, a known computer algorithm (e.g., the "FASTA" program) using default parameters as in Pearson et al. (1988) *Proc. Natl. Acad. Sci. USA* 85:2444). Alternatively, they may be determined using the Needleman-Wunsch algorithm (Needleman and Wunsch, 1970, *J. Mol. Biol.* 48:443-453) as performed in the Needleman program of the EMBOSS package (EMBOSS: The European Molecular Biology Open Software Suite, Rice et al., 2000, *Trends Genet.* 16:276-277) (version 5.0.0 or later) (including GCG program package (Devereux, J. et al., *Nucleic Acids Research* 12:387 (1984)), BLASTP, BLASTN, FASTA (Atschul, S. F. et al., *J Molec Biol* 215:403 (1990); Guide to Huge Computers, Martin J.

Bishop, ed., Academic Press, San Diego, 1994, and CARILLO et al. (1988) *SIAM J Applied Math* 48:1073). For example, homology, similarity, or identity may be determined using BLAST or ClustalW of the National Center for Biotechnology Information.

Homology, similarity, or identity of nucleotide or peptide sequences may be determined by comparing sequence information using the GAP computer program (e.g., Needleman et al. (1970), *J Mol Biol* 48:443) as disclosed in Smith and Waterman, *Adv. Appl. Math* (1981) 2:482. Briefly, the GAP program defines homology, similarity, or identity as the number of similar aligned symbols (i.e., nucleotides or amino acids), divided by the total number of symbols in the shorter of the two sequences. The default parameters for the GAP program may include: (1) a unary comparison matrix (containing a value of 1 for identities and 0 for non-identities) and the weighted comparison matrix (or EDNAFULL (EMBOSS version of NCBI NUC4.4) substitution matrix) of Gribskov et al. (1986) *Nucl. Acids Res.* 14:6745, as disclosed by Schwartz and Dayhoff, eds., *Atlas Of Protein Sequence And Structure*, National Biomedical Research Foundation, pp. 353-358 (1979); (2) a penalty of 3.0 for each gap and an additional 0.10 penalty for each symbol in each gap (or gap open penalty 10, gap extension penalty 0.5); and (3) no penalty for end gaps. Therefore, the terms "homology" and "identity", as used herein, represent relevance between sequences.

The above may be applied to other embodiments or other aspects of the present invention, but is not limited thereto.

The interleukin-2 analog of the present invention may be used as a novel interleukin-2 substitute that alters its in vitro activity by weakening or increasing the binding affinity of the interleukin-2 analog for interleukin-2 alpha and/or beta receptors. In particular, the interleukin-2 analog of the present invention can be used as an effective therapeutic agent due to its activities for the two types of receptors because it not only has an increased binding affinity for beta receptors but also has altered (i.e., increased or decreased) binding affinity for alpha receptors.

In the present invention, such modification for preparing analogs of interleukin-2 includes all of the modifications using L-type or D-type amino acids and/or non-natural amino acids; and/or a modification of native sequence, for example, a modification of a side chain functional group, an intramolecular covalent bonding (e.g., a ring formation between side chains), methylation, acylation, ubiquitination, phosphorylation, aminohexanation, biotinylation, etc.

Additionally, the modification includes all of those where one or more amino acids are added to the amino and/or carboxy terminus of native interleukin-2.

As the amino acids to be substituted or added, not only the 20 amino acids commonly observed in human proteins, but also atypical amino acids or those which are not naturally occurring can be used. Commercial sources of atypical amino acids include Sigma-Aldrich, ChemPep Inc., and Genzyme Pharmaceuticals. The peptides including these amino acids and typical peptide sequences may be synthesized and purchased from commercial suppliers, e.g., American Peptide Company, Bachem (USA), or Anygen (Korea).

Amino acid derivatives may be obtained in the same manner, and as one such example, 4-imidazoacetic acid, etc. may be used.

Additionally, the interleukin-2 analog according to the present invention may be in a modified form where the N-terminus and/or C-terminus, etc. of the interleukin-2 is chemically modified or protected by organic groups, or amino acids may be added to the terminus of the peptide, etc. for its protection from proteases in vivo while increasing its stability.

In particular, in the case of a chemically synthesized peptide, its N- and C-termini are electrically charged, and thus the N-terminus of the peptide may be acetylated and/or C-terminus of the peptide may be amidated, but the peptide is not particularly limited thereto.

Additionally, since the interleukin-2 analog according to the present invention is in a peptide form, it may include all of those in the form of the peptide itself, a salt thereof (e.g., a pharmaceutically acceptable salt of the peptide), or a solvate thereof. Additionally, the peptide may be in any pharmaceutically acceptable form.

The kind of the salt is not particularly limited. However, it is desirable that the salt be in a safe and effective form for a subject (e.g., a mammal), but the salt type is not particularly limited thereto.

The term "pharmaceutically acceptable" refers to a material which can be effectively used for a desired purpose without causing excessive toxicity, irritation, allergic reactions, etc. within the scope of medical judgment.

As used herein, the term "pharmaceutically acceptable salt" includes salts which are derived from pharmaceutically acceptable inorganic acids, organic acids, or bases. Examples of suitable acids include hydrochloric acid, bromic acid, sulfuric acid, nitric acid, perchloric acid, fumaric acid, maleic acid, phosphoric acid, glycolic acid, lactic acid, salicylic acid, succinic acid, toluene-p-sulfonic acid, tartaric acid, acetic acid, citric acid, methanesulfonic acid, formic acid, benzoic acid, malonic acid, naphthalene-2-sulfonic acid, benzenesulfonic acid, etc. Salts derived from suitable bases may include alkali metals (e.g., sodium, potassium, etc.), alkaline earth metals (e.g., magnesium, etc.), ammonium, etc.

Additionally, as used herein, the term "solvate" refers to a complex formed between the peptide according to the present invention or a salt thereof and a solvent molecule.

In the present invention, the binding affinity of any interleukin-2 analog for native interleukin-2 receptors can be measured using various known techniques, which are methods for measuring the affinity for the receptors. For example, surface plasmon resonance (SPR) may be used, but the measurement method is not limited thereto.

More specifically, the interleukin-2 analog of the present invention may have reduced or increased binding affinity for interleukin-2 alpha receptors compared to native interleukin-2 or aldesleukin.

Specifically, the interleukin-2 analog of the present invention may have binding affinity for interleukin-2 alpha receptors of about 0.001-fold or greater, about 0.005-fold or greater, about 0.01-fold or greater, about 0.05-fold or greater, about 0.1-fold or greater, about 0.3-fold or greater, about 0.5-fold or greater, about 0.7-fold or greater, about 0.9-fold or greater, about 1.1-fold or greater, about 1.3-fold or greater, about 1.5-fold or greater, or about 1.7-fold or greater compared to the binding affinity of native interleukin-2 or aldesleukin for interleukin-2 alpha receptors, but the numerical value of the binding affinity is not limited, and the value will belong to the scope of the present invention as long as there is a change in the binding affinity compared to that of native interleukin-2 or aldesleukin.

Alternatively, based on the binding affinity of aldesleukin for interleukin-2 alpha receptors (set at 100%), the interleukin-2 analog of the present invention may have no binding affinity for interleukin-2 alpha receptors or have binding affinity for interleukin-2 alpha receptors of about 1% or greater, about 5% or greater, about 7% or greater, about 10% or greater, about 15% or greater, about 20% or greater, about 30% or greater, about 50% or greater, about 70% or greater, about 90% or greater, about 100% or greater, about 150% or greater, or about 200% or greater, but the numerical value of the binding affinity is not limited, and the value will belong to the scope of the present invention as long as there is a change in the binding affinity compared to that of native interleukin-2 or aldesleukin.

Additionally, the interleukin-2 analog of the present invention may specifically have binding affinity for interleukin-2 beta receptors of about 0.1-fold or greater, about 0.3-fold or greater, about 0.5-fold or greater, about 0.7-fold or greater, about 1.0-fold or greater, about 10-fold or greater, about 20-fold or greater, about 30-fold or greater, about 40-fold or greater, about 50-fold or greater, about 60-fold or greater, about 70-fold or greater, about 80-fold or greater, about 90-fold or greater, or about 100-fold or greater compared to the binding affinity of native interleukin-2 or aldesleukin for interleukin-2 beta receptors, but the numerical value of the binding affinity is not limited, and the value will belong to the scope of the present invention as long as there is a change or increase in the binding affinity compared to that of native interleukin-2 or aldesleukin.

Alternatively, based on the binding affinity of aldesleukin for interleukin-2 beta receptors (set at 100%), the interleukin-2 analog of the present invention may have binding affinity for interleukin-2 beta receptors of about 5% or greater, about 9% or greater, about 10% or greater, about 20% or greater, about 30% or greater, about 50% or greater, about 100% or greater, about 200% or greater, about 500% or greater, about 700% or greater, about 1,000% or greater, about 1,500% or greater, about 3,000% or greater, about 5,000% or greater, about 7,000% or greater, about 10,000% or greater, about 12,000% or greater, about 15,000% or greater, about 20,000% or greater, or about 25,000%, but the numerical value of the binding affinity is not limited, and the value will belong to the scope of the present invention as long as there is an increase in the binding affinity compared to that of native interleukin-2 or aldesleukin.

As used herein, the term "about" refers to a range which includes all of ±0.5, ±0.4, ±0.3, ±0.2, ±0.1, etc. and includes all of the values that are equivalent or similar to those following the values, but the range is not limited thereto.

The interleukin-2 analog of the present invention is characterized in that it has altered binding affinity for interleukin-2 alpha receptors and increased binding affinity for interleukin-2 beta receptors compared to native interleukin-2 or aldesleukin.

In a specific embodiment of the present invention, for the preparation of the interleukin-2 analog of the present invention, an interleukin-2 analog was prepared into which a modification was introduced based on native interleukin-2 (SEQ ID NO: 1). The interleukin-2 analog prepared in the present invention may be one which includes any one amino acid sequence among SEQ ID NOS: 3 to 106, or may be one which is encoded by any one nucleotide sequence among SEQ ID NOS: 108 to 211.

Still another aspect to implement the present invention provides a nucleic acid (polynucleotide) encoding the interleukin-2 analog, a recombinant expression vector including the nucleic acid, and a transformant which includes the nucleic acid or recombinant expression vector.

The nucleic acid encoding the interleukin-2 analog of the present invention may be one which is modified so that a modification (deletion, substitution, and/or addition of an amino acid) can be introduced into an amino acid at a particular position in a native interleukin-2 of SEQ ID NO: 1, and specifically, the interleukin-2 analog of the present invention may include a nucleotide sequence encoding any one amino acid sequence among SEQ ID NOS: 3 to 106. For example, the nucleic acid of the present invention may have or include a nucleotide sequence of any one among SEQ ID NOS: 108 to 211.

The nucleotide sequence of the present invention may be modified variously in the coding region within a range not altering the amino acid sequence of the interleukin-2 analog of the present invention, considering codon degeneracy or the codons preferred in the organism where the nucleic acid of the present invention is to be expressed. Specifically, the nucleic acid of the present invention may have or include a nucleotide sequence which has a homology or identity of 70% or higher, 75% or higher, 80% or higher, 85% or higher, 90% or higher, 95% or higher, 96% or higher, 97% or higher, 98% or higher, and less than 100% to any one of the sequences of SEQ ID NOS: 108 to 211; or may consist of or essentially consist of a nucleotide sequence which has a homology or identity of 70% or higher, 75% or higher, 80% or higher, 85% or higher, 90% or higher, 95% or higher, 96% or higher, 97% or higher, 98% or higher, and less than 100% to any one of the sequences of SEQ ID NOS: 108 to 211, but the nucleic acid is not limited thereto.

Additionally, the nucleic acid of the present invention can include, without limitation, a probe which can be prepared from a known gene sequence (e.g., a sequence that can hybridize with a sequence complementary to all or part of the nucleic acid sequence of the present invention under stringent conditions). The "stringent conditions" refer to conditions that enable specific hybridization between polynucleotides. Such conditions are described in detail in the literature (see J. Sambrook et al., *Molecular Cloning, A Laboratory Manual,* 2nd Edition, Cold Spring Harbor Laboratory press, Cold Spring Harbor, N.Y., 1989; F. M. Ausubel et al., *Current Protocols in Molecular Biology*, John Wiley & Sons, Inc., New York, 9.50-9.51, 11.7-11.8).

Hybridization requires that two nucleic acids have complementary sequences, although mismatches between bases may be possible depending on hybridization stringency. The term "complementary" is used to describe the relationship between nucleotide bases that can hybridize to each other. For example, with respect to DNA, adenine is complementary to thymine, and cytosine is complementary to guanine. Accordingly, the nucleic acid of the present invention can include isolated nucleic acid fragments complementary to the entire sequence as well as to substantially similar nucleic acid sequences.

The appropriate stringency for hybridizing polynucleotides depends on the length of the polynucleotides and the degree of complementarity, and variables are well known in the art (e.g., Sambrook et al., supra).

The homology and identity are as described above.

The recombination vector according to the present invention may be constructed as a vector for typical cloning or a vector for expression, and may be constructed as a vector for use of eukaryotic or prokaryotic cells as a host cell.

As used herein, the term "vector", which is a recombination vector capable of expressing a target protein in an appropriate host cell, refers to a nucleic acid construct that includes essential control elements operably linked to enable the expression of the nucleic acid insert. In the present invention, it is possible to prepare a recombination vector which includes a nucleic acid encoding an interleukin-2 analog, and the interleukin-2 analog of the present invention can be obtained by transforming or transfecting a host cell with the recombination vector.

As used herein, the term "transformation" refers to a phenomenon in which DNA is introduced into a host cell to allow DNA to be replicated as a factor of a chromosome or by completion of chromosome integration, and external DNA is introduced into cells to artificially cause genetic changes.

The host suitable for the present invention is not particularly limited as long as it enables the expression of the nucleic acid of the present invention. Specific examples of the host that can be used in the present invention include bacteria of the genus *Escherichia* (e.g., *E. coli*); bacteria of the genus *Bacillus* (e.g., *Bacillus subtilis*); bacteria of the genus *Pseudomonas* (e.g., *Pseudomonas putida*); yeasts (e.g., *Pichia pastoris, Saccharomyces cerevisiae*, and *Schizosaccharomyces pombe*); insect cells (e.g., *Spodoptera frugiperda* (SF9)); and animal cells (e.g., CHO, COS, BSC, etc.).

Still another aspect to implement the present invention provides a method for preparing an interleukin-2 analog which includes one or more modifications.

Specifically, the method may include introducing a modification into one or more amino acids selected from the group consisting of amino acids corresponding to those at positions 1, 12, 18, 19, 20, 22, 32, 35, 38, 42, 43, 45, 48, 49, 61, 68, 69, 74, 76, 80, 81, 82, 84, 85, 86, 87, 88, 89, 91, 92, 94, 95, 96, 125, 126, and 133 in native interleukin-2.

More specifically, the method may be:
(a) a method, wherein in native interleukin-2, the amino acid at position 1 is removed and the amino acids at positions 125 and 32 are substituted with different amino acids;
(b) a method, wherein in native interleukin-2, the amino acid at position 1 is removed and the amino acids at positions 125 and 35 are substituted with different amino acids;
(c) a method, wherein in native interleukin-2, the amino acid at position 1 is removed and the amino acids at positions 125 and 38 are substituted with different amino acids;
(d) a method, wherein in native interleukin-2, the amino acid at position 1 is removed and the amino acids at positions 125 and 42 are substituted with different amino acids;
(e) a method, wherein in native interleukin-2, the amino acid at position 1 is removed and the amino acids at positions 125 and 43 are substituted with different amino acids;
(f) a method, wherein in native interleukin-2, the amino acid at position 1 is removed and the amino acids at positions 125 and 48 are substituted with different amino acids;
(g) a method, wherein in native interleukin-2, the amino acid at position 1 is removed and the amino acids at positions 125 and 49 are substituted with different amino acids;
(h) a method, wherein in native interleukin-2, the amino acid at position 1 is removed and the amino acids at positions 125 and 76 are substituted with different amino acids;
(i) a method, wherein in native interleukin-2, the amino acid at position 1 is removed and the amino acids at positions 125, 38, 42, 81, 92, 94, and 96 are substituted with different amino acids;

(j) a method, wherein in native interleukin-2, the amino acid at position 1 is removed and the amino acids at positions 125 and 87 are substituted with different amino acids;

(k) a method, wherein in native interleukin-2, the amino acid at position 1 is removed and the amino acids at positions 125, 38, and 42 are substituted with different amino acids;

(l) a method, wherein in native interleukin-2, the amino acid at position 1 is removed and the amino acids at positions 125, 38, and 80 are substituted with different amino acids;

(m) a method, wherein in native interleukin-2, the amino acid at position 1 is removed and the amino acids at positions 125, 38, and 84 are substituted with different amino acids;

(n) a method, wherein in native interleukin-2, the amino acid at position 1 is removed and the amino acids at positions 125, 19, 38, and 42 are substituted with different amino acids;

(o) a method, wherein in native interleukin-2, the amino acid at position 1 is removed and the amino acids at positions 125, 12, 38, and 42 are substituted with different amino acids;

(p) a method, wherein in native interleukin-2, the amino acid at position 1 is removed and the amino acids at positions 125, 38, 42, and 61 are substituted with different amino acids;

(q) a method, wherein in native interleukin-2, the amino acid at position 1 is removed and the amino acids at positions 125, 38, 42, and 84 are substituted with different amino acids;

(r) a method, wherein in native interleukin-2, the amino acid at position 1 is removed and the amino acids at positions 125, 38, 42, and 88 are substituted with different amino acids;

(s) a method, wherein in native interleukin-2, the amino acid at position 1 is removed and the amino acids at positions 125, 38, 42, and 89 are substituted with different amino acids;

(t) a method, wherein in native interleukin-2, the amino acid at position 1 is removed and the amino acids at positions 125, 38, 42, and 91 are substituted with different amino acids;

(u) a method, wherein in native interleukin-2, the amino acid at position 1 is removed and the amino acids at positions 125, 38, 42, and 94 are substituted with different amino acids;

(v) a method, wherein in native interleukin-2, the amino acid at position 1 is removed and the amino acids at positions 125, 38, 42, and 126 are substituted with different amino acids;

(w) a method, wherein in native interleukin-2, the amino acid at position 1 is removed and the amino acids at positions 125, 38, 80, and 84 are substituted with different amino acids;

(x) a method, wherein in native interleukin-2, the amino acid at position 1 is removed and the amino acids at positions 125, 38, 94, and 96 are substituted with different amino acids;

(y) a method, wherein in native interleukin-2, the amino acid at position 1 is removed and the amino acids at positions 125, 38, 81, and 92 are substituted with different amino acids;

(z) a method, wherein in native interleukin-2, the amino acid at position 1 is removed and the amino acids at positions 125, 61, 81, and 92 are substituted with different amino acids;

(aa) a method, wherein in native interleukin-2, the amino acid at position 1 is removed and the amino acids at positions 125, 38, 42, 81, and 92 are substituted with different amino acids;

(ab) a method, wherein in native interleukin-2, the amino acid at position 1 is removed and the amino acids at positions 125, 38, 80, 81, and 92 are substituted with different amino acids;

(ac) a method, wherein in native interleukin-2, the amino acid at position 1 is removed and the amino acids at positions 125, 38, 81, 84, and 92 are substituted with different amino acids;

(ad) a method, wherein in native interleukin-2, the amino acid at position 1 is removed and the amino acids at positions 125, 20, 38, 42, 81, and 92 are substituted with different amino acids;

(ae) a method, wherein in native interleukin-2, the amino acid at position 1 is removed and the amino acids at positions 125, 38, 42, 80, 81, and 92 are substituted with different amino acids;

(af) a method, wherein in native interleukin-2, the amino acid at position 1 is removed and the amino acids at positions 125, 38, 42, 74, 81, and 92 are substituted with different amino acids;

(ag) a method, wherein in native interleukin-2, the amino acid at position 1 is removed and the amino acids at positions 125, 38, 42, 81, 84, and 92 are substituted with different amino acids;

(ah) a method, wherein in native interleukin-2, the amino acid at position 1 is removed and the amino acids at positions 125, 38, 42, 81, 88, and 92 are substituted with different amino acids;

(ai) a method, wherein in native interleukin-2, the amino acid at position 1 is removed and the amino acids at positions 125, 38, 42, 85, 86, and 92 are substituted with different amino acids;

(aj) a method, wherein in native interleukin-2, the amino acid at position 1 is removed and the amino acids at positions 125, 38, 80, 81, 85, and 92 are substituted with different amino acids;

(ak) a method, wherein in native interleukin-2, the amino acid at position 1 is removed and the amino acids at positions 125, 38, 80, 81, 86, and 92 are substituted with different amino acids;

(al) a method, wherein in native interleukin-2, the amino acid at position 1 is removed and the amino acids at positions 125, 80, 81, 85, 86, and 92 are substituted with different amino acids;

(am) a method, wherein in native interleukin-2, the amino acid at position 1 is removed and the amino acids at positions 125, 38, 42, 45, 74, 81, and 92 are substituted with different amino acids;

(an) a method, wherein in native interleukin-2, the amino acid at position 1 is removed and the amino acids at positions 125, 38, 42, 74, 80, 81, and 92 are substituted with different amino acids;

(ao) a method, wherein in native interleukin-2, the amino acid at position 1 is removed and the amino acids at positions 125, 38, 42, 80, 81, 84, and 92 are substituted with different amino acids;

(ap) a method, wherein in native interleukin-2, the amino acid at position 1 is removed and the amino acids at positions 125, 38, 45, 80, 85, 86, and 92 are substituted with different amino acids;

(aq) a method, wherein in native interleukin-2, the amino acid at position 1 is removed and the amino acids at positions 125, 38, 80, 81, 85, 86, and 92 are substituted with different amino acids;

(ar) a method, wherein in native interleukin-2, the amino acid at position 1 is removed and the amino acids at positions 125, 42, 80, 81, 85, 86, and 92 are substituted with different amino acids;

(as) a method, wherein in native interleukin-2, the amino acid at position 1 is removed and the amino acids at positions 125, 61, 80, 81, 85, 86, and 92 are substituted with different amino acids;

(at) a method, wherein in native interleukin-2, the amino acid at position 1 is removed and the amino acids at positions 125, 69, 80, 81, 85, 86, and 92 are substituted with different amino acids;

(au) a method, wherein in native interleukin-2, the amino acid at position 1 is removed and the amino acids at positions 125, 80, 81, 85, 86, 91, and 92 are substituted with different amino acids;

(av) a method, wherein in native interleukin-2, the amino acid at position 1 is removed and the amino acids at positions 125, 18, 22, 80, 81, 85, 86, and 92 are substituted with different amino acids;

(aw) a method, wherein in native interleukin-2, the amino acid at position 1 is removed and the amino acids at positions 125, 38, 42, 80, 81, 85, 86, and 92 are substituted with different amino acids;

(ax) a method, wherein in native interleukin-2, the amino acid at position 1 is removed and the amino acids at positions 125, 38, 42, 45, 74, 80, 81, and 92 are substituted with different amino acids;

(ay) a method, wherein in native interleukin-2, the amino acid at position 1 is removed and the amino acids at positions 125, 38, 68, 80, 81, 85, 86, and 92 are substituted with different amino acids;

(az) a method, wherein in native interleukin-2, the amino acid at position 1 is removed and the amino acids at positions 125, 69, 74, 80, 81, 85, 86, and 92 are substituted with different amino acids;

(ba) a method, wherein in native interleukin-2, the amino acid at position 1 is removed and the amino acids at positions 125, 80, 81, 84, 85, 86, 91, and 92 are substituted with different amino acids;

(bb) a method, wherein in native interleukin-2, the amino acid at position 1 is removed and the amino acids at positions 125, 80, 81, 85, 86, 92, 94, and 96 are substituted with different amino acids;

(bc) a method, wherein in native interleukin-2, the amino acid at position 1 is removed and the amino acids at positions 125, 18, 19, 22, 80, 81, 85, 86, and 92 are substituted with different amino acids;

(bd) a method, wherein in native interleukin-2, the amino acid at position 1 is removed and the amino acids at positions 125, 18, 22, 38, 80, 81, 85, 86, and 92 are substituted with different amino acids;

(be) a method, wherein in native interleukin-2, the amino acid at position 1 is removed and the amino acids at positions 125, 18, 22, 61, 80, 81, 85, 86, and 92 are substituted with different amino acids;

(bf) a method, wherein in native interleukin-2, the amino acid at position 1 is removed and the amino acids at positions 125, 18, 22, 68, 80, 81, 85, 86, and 92 are substituted with different amino acids;

(bg) a method, wherein in native interleukin-2, the amino acid at position 1 is removed and the amino acids at positions 125, 35, 38, 42, 80, 81, 85, 86, and 92 are substituted with different amino acids;

(bh) a method, wherein in native interleukin-2, the amino acid at position 1 is removed and the amino acids at positions 125, 38, 42, 45, 80, 81, 85, 86, and 92 are substituted with different amino acids;

(bi) a method, wherein in native interleukin-2, the amino acid at position 1 is removed and the amino acids at positions 125, 38, 42, 80, 81, 85, 86, 91, and 92 are substituted with different amino acids;

(bj) a method, wherein in native interleukin-2, the amino acid at position 1 is removed and the amino acids at positions 125, 38, 42, 80, 81, 85, 86, 92, and 95 are substituted with different amino acids;

(bk) a method, wherein in native interleukin-2, the amino acid at position 1 is removed and the amino acids at positions 125, 35, 38, 42, 74, 80, 81, 85, 86, and 92 are substituted with different amino acids;

(bl) a method, wherein in native interleukin-2, the amino acid at position 1 is removed and the amino acids at positions 125, 38, 42, 43, 61, 80, 81, 85, 86, and 92 are substituted with different amino acids;

(bm) a method, wherein in native interleukin-2, the amino acid at position 1 is removed and the amino acids at positions 125, 38, 42, 80, 81, 85, 86, 91, 92, and 95 are substituted with different amino acids;

(bn) a method, wherein in native interleukin-2, the amino acid at position 1 is removed and the amino acids at positions 125, 35, 38, 42, 74, 80, 81, 82, 85, 86, and 92 are substituted with different amino acids, (bo) a method, wherein in native interleukin-2, the amino acid at position 1 is removed and the amino acids at positions 125, 80, 81, 86, and 92 are substituted with different amino acids; or (bp) a method, wherein in native interleukin-2, the amino acid at position 1 is removed and the amino acids at positions 125, 80, 81, 85, and 86 are substituted with different amino acids;

but the method is not limited thereto.

The interleukin-2 analog and modification are the same as above.

In another embodiment of a method for preparing the interleukin-2 analog of the present invention, the method for preparing the interleukin-2 analog may include (a) culturing a transformant which includes a nucleic acid encoding the interleukin-2 analog and expressing the interleukin-2 analog; and (b) isolating and purifying the expressed interleukin-2 analog, but the method is not limited to any particular method, and any method known in the art may be used as long as the interleukin-2 analog can be prepared by the same.

In the present invention, the nucleic acid encoding the interleukin-2 analog may include or (essentially) consist of any one nucleotide sequence among SEQ ID NOS: 108 to 211.

The medium used for culturing a transformant in the present invention must meet the requirements for culturing host cells in an appropriate manner. The carbon sources that can be included in the medium for the growth of host cells can be appropriately selected as a decision by those skilled in the art according to the type of transformants being produced, and appropriate culture conditions can be adopted to control the time and amount of culture.

Sugar sources that can be used may include sugars and carbohydrates (e.g., glucose, saccharose, lactose, fructose, maltose, starch, and cellulose); oils and fats (e.g., soybean oil, sunflower oil, castor oil, coconut oil, etc.); fatty acids (e.g., palmitic acid, stearic acid, and linoleic acid); alcohols (e.g., glycerol and ethanol); and organic acids (e.g., acetic acid). These materials can be used individually or as a mixture.

Nitrogen sources that can be used may include peptone, yeast extract, gravy, malt extract, corn steep liquor, soybean meal, and urea, or inorganic compounds (e.g., ammonium sulfate, ammonium chloride, ammonium phosphate, ammonium carbonate, and ammonium nitrate). Nitrogen sources can also be used individually or as a mixture.

Phosphorous sources that can be used may include potassium dihydrogen phosphate or dipotassium hydrogen phosphate, or corresponding sodium-containing salts thereof. In addition, the culture medium may contain a metal salt (e.g., magnesium sulfate and iron sulfate) required for growth.

Finally, in addition to these materials, essential growth materials (e.g., amino acids and vitamins) may be used. In addition, suitable precursors for culture media may be used. The above-mentioned raw materials can be added in a batch or continuous mode in a manner appropriate to the culture during the cultivation. Basic compounds (e.g., sodium hydroxide, potassium hydroxide, and ammonia) or acidic compounds (e.g., phosphoric acid and sulfuric acid) can be used in an appropriate manner to adjust the pH of the culture. In addition, antifoaming agents (e.g., fatty acid polyglycol esters) may be used to inhibit bubble generation. In order to maintain aerobic conditions, oxygen or oxygen-containing gas (e.g., air) is injected into the culture.

Culturing of the transformant according to the present invention is usually performed at a temperature of 20° C. to 45° C., specifically 25° C. to 40° C. In addition, the culture is continued until the maximum amount of the desired interleukin-2 analog is obtained, and for this purpose, the culture can usually last for 10 to 160 hours.

As described above, if the appropriate culture conditions are established depending on the host cell, the transformant according to the present invention will produce an interleukin-2 analog, and depending on the composition of the vector and the characteristics of the host cell, the interleukin-2 analog produced can be secreted into the cytoplasm of the host cell, into the periplasmic space, or extracellularly.

Proteins expressed in the host cell or outside thereof can be purified in a conventional manner. Examples of purification methods include salting out (e.g.: ammonium sulfate precipitation, sodium phosphate precipitation, etc.), solvent precipitation (e.g., protein fractionation precipitation using acetone, ethanol, etc.), dialysis, gel filtration, ion exchange, chromatography (e.g., reverse-phase column chromatography), ultrafiltration, etc. and can be used alone or in combination.

In a specific embodiment of the present invention, a method for preparing an interleukin-2 analog may include:
(a) expressing the interleukin-2 analog; and
(b) isolating the expressed interleukin-2 analog.

In a specific embodiment of the present invention, the following steps may be further included to isolate and purify the interleukin-2 analog expressed in the form of an inclusion body from a transformant:
(b-1) collecting and disrupting a transformant from the culture medium of the step (a) above;
(b-2) recovering and refolding an interleukin-2 analog expressed in a disrupted cell lysate; and
(b-3) purifying the refolded interleukin-2 analog by size-exclusion chromatography.

Still another aspect to implement the present invention provides a method for preparing the interleukin-2 analog by way of a peptide synthesis method. Since the sequences of the interleukin-2 analogs of the present invention are already provided, the synthesis of peptides can be performed using a known peptide synthesis method.

The interleukin-2 analog and modification are as described above.

Still another aspect to implement the present invention provides a method for increasing the binding affinity for interleukin-2 beta receptors, which includes modifying one or more amino acids in native interleukin-2.

The method for increasing the binding affinity for interleukin-2 beta receptors according to the present invention may be one which not only increases the binding affinity for interleukin-2 beta receptors but also alters the binding affinity for interleukin-2 alpha receptors compared to native interleukin-2 or aldesleukin.

Specifically, the method may include a step of introducing a modification into one or more amino acids corresponding to those at positions 1, 12, 18, 19, 20, 22, 32, 35, 38, 42, 43, 45, 48, 49, 61, 68, 69, 74, 76, 80, 81, 82, 84, 85, 86, 87, 88, 89, 91, 92, 94, 95, 96, 125, 126, and 133 in native interleukin-2.

More specifically, the method may be:
(a) a method, wherein in native interleukin-2, the amino acid at position 1 is removed and the amino acids at positions 125 and 32 are substituted with different amino acids;
(b) a method, wherein in native interleukin-2, the amino acid at position 1 is removed and the amino acids at positions 125 and 35 are substituted with different amino acids;
(c) a method, wherein in native interleukin-2, the amino acid at position 1 is removed and the amino acids at positions 125 and 38 are substituted with different amino acids;
(d) a method, wherein in native interleukin-2, the amino acid at position 1 is removed and the amino acids at positions 125 and 42 are substituted with different amino acids;
(e) a method, wherein in native interleukin-2, the amino acid at position 1 is removed and the amino acids at positions 125 and 43 are substituted with different amino acids;
(f) a method, wherein in native interleukin-2, the amino acid at position 1 is removed and the amino acids at positions 125 and 48 are substituted with different amino acids;
(g) a method, wherein in native interleukin-2, the amino acid at position 1 is removed and the amino acids at positions 125 and 49 are substituted with different amino acids;
(h) a method, wherein in native interleukin-2, the amino acid at position 1 is removed and the amino acids at positions 125 and 76 are substituted with different amino acids;
(i) a method, wherein in native interleukin-2, the amino acid at position 1 is removed and the amino acids at positions 125, 38, 42, 81, 92, 94, and 96 are substituted with different amino acids;
(j) a method, wherein in native interleukin-2, the amino acid at position 1 is removed and the amino acids at positions 125 and 87 are substituted with different amino acids;

(k) a method, wherein in native interleukin-2, the amino acid at position 1 is removed and the amino acids at positions 125, 38, and 42 are substituted with different amino acids;

(l) a method, wherein in native interleukin-2, the amino acid at position 1 is removed and the amino acids at positions 125, 38, and 80 are substituted with different amino acids;

(m) a method, wherein in native interleukin-2, the amino acid at position 1 is removed and the amino acids at positions 125, 38, and 84 are substituted with different amino acids;

(n) a method, wherein in native interleukin-2, the amino acid at position 1 is removed and the amino acids at positions 125, 19, 38, and 42 are substituted with different amino acids;

(o) a method, wherein in native interleukin-2, the amino acid at position 1 is removed and the amino acids at positions 125, 12, 38, and 42 are substituted with different amino acids;

(p) a method, wherein in native interleukin-2, the amino acid at position 1 is removed and the amino acids at positions 125, 38, 42, and 61 are substituted with different amino acids;

(q) a method, wherein in native interleukin-2, the amino acid at position 1 is removed and the amino acids at positions 125, 38, 42, and 84 are substituted with different amino acids;

(r) a method, wherein in native interleukin-2, the amino acid at position 1 is removed and the amino acids at positions 125, 38, 42, and 88 are substituted with different amino acids;

(s) a method, wherein in native interleukin-2, the amino acid at position 1 is removed and the amino acids at positions 125, 38, 42, and 89 are substituted with different amino acids;

(t) a method, wherein in native interleukin-2, the amino acid at position 1 is removed and the amino acids at positions 125, 38, 42, and 91 are substituted with different amino acids;

(u) a method, wherein in native interleukin-2, the amino acid at position 1 is removed and the amino acids at positions 125, 38, 42, and 94 are substituted with different amino acids;

(v) a method, wherein in native interleukin-2, the amino acid at position 1 is removed and the amino acids at positions 125, 38, 42, and 126 are substituted with different amino acids;

(w) a method, wherein in native interleukin-2, the amino acid at position 1 is removed and the amino acids at positions 125, 38, 80, and 84 are substituted with different amino acids;

(x) a method, wherein in native interleukin-2, the amino acid at position 1 is removed and the amino acids at positions 125, 38, 94, and 96 are substituted with different amino acids;

(y) a method, wherein in native interleukin-2, the amino acid at position 1 is removed and the amino acids at positions 125, 38, 81, and 92 are substituted with different amino acids;

(z) a method, wherein in native interleukin-2, the amino acid at position 1 is removed and the amino acids at positions 125, 61, 81, and 92 are substituted with different amino acids;

(aa) a method, wherein in native interleukin-2, the amino acid at position 1 is removed and the amino acids at positions 125, 38, 42, 81, and 92 are substituted with different amino acids;

(ab) a method, wherein in native interleukin-2, the amino acid at position 1 is removed and the amino acids at positions 125, 38, 80, 81, and 92 are substituted with different amino acids;

(ac) a method, wherein in native interleukin-2, the amino acid at position 1 is removed and the amino acids at positions 125, 38, 81, 84, and 92 are substituted with different amino acids;

(ad) a method, wherein in native interleukin-2, the amino acid at position 1 is removed and the amino acids at positions 125, 20, 38, 42, 81, and 92 are substituted with different amino acids;

(ae) a method, wherein in native interleukin-2, the amino acid at position 1 is removed and the amino acids at positions 125, 38, 42, 80, 81, and 92 are substituted with different amino acids;

(af) a method, wherein in native interleukin-2, the amino acid at position 1 is removed and the amino acids at positions 125, 38, 42, 74, 81, and 92 are substituted with different amino acids;

(ag) a method, wherein in native interleukin-2, the amino acid at position 1 is removed and the amino acids at positions 125, 38, 42, 81, 84, and 92 are substituted with different amino acids;

(ah) a method, wherein in native interleukin-2, the amino acid at position 1 is removed and the amino acids at positions 125, 38, 42, 81, 88, and 92 are substituted with different amino acids;

(ai) a method, wherein in native interleukin-2, the amino acid at position 1 is removed and the amino acids at positions 125, 38, 42, 85, 86, and 92 are substituted with different amino acids;

(aj) a method, wherein in native interleukin-2, the amino acid at position 1 is removed and the amino acids at positions 125, 38, 80, 81, 85, and 92 are substituted with different amino acids;

(ak) a method, wherein in native interleukin-2, the amino acid at position 1 is removed and the amino acids at positions 125, 38, 80, 81, 86, and 92 are substituted with different amino acids;

(al) a method, wherein in native interleukin-2, the amino acid at position 1 is removed and the amino acids at positions 125, 80, 81, 85, 86, and 92 are substituted with different amino acids;

(am) a method, wherein in native interleukin-2, the amino acid at position 1 is removed and the amino acids at positions 125, 38, 42, 45, 74, 81, and 92 are substituted with different amino acids;

(an) a method, wherein in native interleukin-2, the amino acid at position 1 is removed and the amino acids at positions 125, 38, 42, 74, 80, 81, and 92 are substituted with different amino acids;

(ao) a method, wherein in native interleukin-2, the amino acid at position 1 is removed and the amino acids at positions 125, 38, 42, 80, 81, 84, and 92 are substituted with different amino acids;

(ap) a method, wherein in native interleukin-2, the amino acid at position 1 is removed and the amino acids at positions 125, 38, 45, 80, 85, 86, and 92 are substituted with different amino acids;

(aq) a method, wherein in native interleukin-2, the amino acid at position 1 is removed and the amino acids at positions 125, 38, 80, 81, 85, 86, and 92 are substituted with different amino acids;
(ar) a method, wherein in native interleukin-2, the amino acid at position 1 is removed and the amino acids at positions 125, 42, 80, 81, 85, 86, and 92 are substituted with different amino acids;
(as) a method, wherein in native interleukin-2, the amino acid at position 1 is removed and the amino acids at positions 125, 61, 80, 81, 85, 86, and 92 are substituted with different amino acids;
(at) a method, wherein in native interleukin-2, the amino acid at position 1 is removed and the amino acids at positions 125, 69, 80, 81, 85, 86, and 92 are substituted with different amino acids;
(au) a method, wherein in native interleukin-2, the amino acid at position 1 is removed and the amino acids at positions 125, 80, 81, 85, 86, 91, and 92 are substituted with different amino acids;
(av) a method, wherein in native interleukin-2, the amino acid at position 1 is removed and the amino acids at positions 125, 18, 22, 80, 81, 85, 86, and 92 are substituted with different amino acids;
(aw) a method, wherein in native interleukin-2, the amino acid at position 1 is removed and the amino acids at positions 125, 38, 42, 80, 81, 85, 86, and 92 are substituted with different amino acids;
(ax) a method, wherein in native interleukin-2, the amino acid at position 1 is removed and the amino acids at positions 125, 38, 42, 45, 74, 80, 81, and 92 are substituted with different amino acids;
(ay) a method, wherein in native interleukin-2, the amino acid at position 1 is removed and the amino acids at positions 125, 38, 68, 80, 81, 85, 86, and 92 are substituted with different amino acids;
(az) a method, wherein in native interleukin-2, the amino acid at position 1 is removed and the amino acids at positions 125, 69, 74, 80, 81, 85, 86, and 92 are substituted with different amino acids;
(ba) a method, wherein in native interleukin-2, the amino acid at position 1 is removed and the amino acids at positions 125, 80, 81, 84, 85, 86, 91, and 92 are substituted with different amino acids;
(bb) a method, wherein in native interleukin-2, the amino acid at position 1 is removed and the amino acids at positions 125, 80, 81, 85, 86, 92, 94, and 96 are substituted with different amino acids;
(bc) a method, wherein in native interleukin-2, the amino acid at position 1 is removed and the amino acids at positions 125, 18, 19, 22, 80, 81, 85, 86, and 92 are substituted with different amino acids;
(bd) a method, wherein in native interleukin-2, the amino acid at position 1 is removed and the amino acids at positions 125, 18, 22, 38, 80, 81, 85, 86, and 92 are substituted with different amino acids;
(be) a method, wherein in native interleukin-2, the amino acid at position 1 is removed and the amino acids at positions 125, 18, 22, 61, 80, 81, 85, 86, and 92 are substituted with different amino acids;
(bf) a method, wherein in native interleukin-2, the amino acid at position 1 is removed and the amino acids at positions 125, 18, 22, 68, 80, 81, 85, 86, and 92 are substituted with different amino acids;
(bg) a method, wherein in native interleukin-2, the amino acid at position 1 is removed and the amino acids at positions 125, 35, 38, 42, 80, 81, 85, 86, and 92 are substituted with different amino acids;
(bh) a method, wherein in native interleukin-2, the amino acid at position 1 is removed and the amino acids at positions 125, 38, 42, 45, 80, 81, 85, 86, and 92 are substituted with different amino acids;
(bi) a method, wherein in native interleukin-2, the amino acid at position 1 is removed and the amino acids at positions 125, 38, 42, 80, 81, 85, 86, 91, and 92 are substituted with different amino acids;
(bj) a method, wherein in native interleukin-2, the amino acid at position 1 is removed and the amino acids at positions 125, 38, 42, 80, 81, 85, 86, 92, and 95 are substituted with different amino acids;
(bk) a method, wherein in native interleukin-2, the amino acid at position 1 is removed and the amino acids at positions 125, 35, 38, 42, 74, 80, 81, 85, 86, and 92 are substituted with different amino acids;
(bl) a method, wherein in native interleukin-2, the amino acid at position 1 is removed and the amino acids at positions 125, 38, 42, 43, 61, 80, 81, 85, 86, and 92 are substituted with different amino acids;
(bm) a method, wherein in native interleukin-2, the amino acid at position 1 is removed and the amino acids at positions 125, 38, 42, 80, 81, 85, 86, 91, 92, and 95 are substituted with different amino acids; or
(bn) a method, wherein in native interleukin-2, the amino acid at position 1 is removed and the amino acids at positions 125, 35, 38, 42, 74, 80, 81, 82, 85, 86, and 92 are substituted with different amino acids;
(bo) a method, wherein in native interleukin-2, the amino acid at position 1 is removed and the amino acids at positions 125, 80, 81, 86, and 92 are substituted with different amino acids; or
(bp) a method, wherein in native interleukin-2, the amino acid at position 1 is removed and the amino acids at positions 125, 80, 81, 85, and 86 are substituted with different amino acids, but the method is not limited thereto.

The interleukin-2 analog and modification are the same as above.

Still another aspect to implement the present invention provides an interleukin-2 analog which includes any one sequence selected from the group consisting of amino acid sequences of SEQ ID NOS: 3 to 106.

The definitions of the interleukin-2 analog, modification, and analog represented by a SEQ ID NO are the same as above.

Specifically, the interleukin-2 analog may include, essentially consist of, or consist of any one nucleotide sequence selected from the group consisting of SEQ ID NOS: 3 to 106, but the interleukin-2 analog is not limited thereto.

Still another aspect to implement the present invention provides an interleukin-2 analog which includes an amino acid sequence represented by General Formula 1 below:

```
[General Formula 1]
          (General Formula 1, SEQ ID NO: 212)
X1-P-T-S-S-S-T-K-K-T-Q-L-Q-L-E-H-L-X18-X

19-D-L-X22-M-I-L-N-G-I-N-N-Y-K-N-P-K-L-T

-X38-M-L-T-X42-X43-F-X45-M-P-K-K-A-T-E-L

-K-H-L-Q-C-L-E-X61-E-L-K-P-L-E-X68-V-L-N

-L-A-X74-S-K-N-F-H-X80-X81-P-R-X84-X85-X
```

-continued

```
86-S-N-I-N-X91-X92-V-X94-E-X96-K-G-S-E-T

-T-F-M-C-E-Y-A-D-E-T-A-T-I-V-E-F-L-N-R-W

-I-T-F-S-Q-S-I-I-S-T-L-T
``` wherein in General Formula 1 above,
X1 is a deletion;
X18 is leucine (L) or arginine (R);
X19 is leucine (L) or tyrosine (Y);
X22 is glutamic acid (E) or glutamine (Q);
X38 is alanine (A), aspartic acid (D), or arginine (R);
X42 is alanine (A), phenylalanine (F), lysine (K), or tryptophan (W);
X43 is glutamic acid (E), lysine (K), or glutamine (Q);
X45 is alanine (A) or tyrosine (Y);
X61 is aspartic acid (D), glutamic acid (E), glutamine (Q), or arginine (R);
X68 is aspartic acid (D) or glutamic acid (E);
X74 is histidine (H) or glutamine (Q);
X80 is phenylalanine (F), leucine (L), valine (V), or tyrosine (Y);
X81 is aspartic acid (D), glutamic acid (E), or arginine (R);
X84 is aspartic acid (D) or glutamic acid (E);
X85 is alanine (A), glutamic acid (E), glycine (G), leucine (L), valine (V), tryptophan (W), or tyrosine (Y);
X86 is alanine (A), glycine (G), isoleucine (I), or valine (V);
X91 is threonine (T) or valine (V);
X92 is phenylalanine (F), isoleucine (I), or tyrosine (Y);
X94 is phenylalanine (F) or leucine (L); and
X96 is phenylalanine (F) or leucine (L).

Additionally, in General Formula 1 above, one or more amino acids may be added to threonine (T), which corresponds to X133, but the sequence is not limited thereto.

Specifically, the interleukin-2 analog may include, essentially consist of, or consist of any one sequence selected from the group consisting of amino acid sequences of SEQ ID NOS: 10, 13, 14, 15, 16, 17, 20, 21, 22, 32, 35, 36, 42, 53, 54, 56, 58, 59, 60, 62, 71, 72, 74, 75, 76, 77, 78, 85, 87, 89, 91, 92, 93, 94, 95, 98, 99, 100, 101, 103, 104, 105, and 106, but the interleukin-2 analog is not limited thereto.

Such an interleukin-2 analog may have increased binding affinity for beta receptors compared to aldesleukin or native interleukin-2, but the binding affinity of the interleukin-2 analog is not limited thereto.

In another embodiment, the interleukin-2 analog of the present invention may be:
in General Formula 1 above,
X43 is lysine (K);
X45 is tyrosine (Y);
X61 is aspartic acid (D), glutamic acid (E), or glutamine (Q);
X68 is glutamic acid (E);
X74 is glutamine (Q);
X80 is phenylalanine (F) or leucine (L);
X85 is leucine (L), valine (V), or tyrosine (Y);
X86 is isoleucine (I) or valine (V); and
X92 is phenylalanine (F) or isoleucine (I), but the interleukin-2 analog is not limited thereto.

Specifically, the interleukin-2 analog is characterized in that it includes any one sequence selected from the group consisting of amino acid sequences of SEQ ID NOS: 10, 13, 14, 16, 17, 20, 21, 22, 32, 35, 36, 42, 53, 54, 87, 89, 91, 92, 93, 94, 98, 99, 100, 101, 103, 104, and 105.

In the interleukin-2 analog of the present invention, one or more amino acids may be further added to a C-terminus thereof, but the interleukin-2 analog is not limited thereto.

Still another aspect to implement the present invention provides an interleukin-2 analog which includes an amino acid sequence expressed by General Formula 2 below:

[General Formula 2]
                (General Formula 2, SEQ ID NO: 213)
```
X1-P-T-S-S-S-T-K-K-T-Q-L-Q-L-E-H-L-X18-L

-D-L-X22-M-I-L-N-G-I-N-N-Y-K-N-P-K-L-T-X

38-M-L-T-X42-K-F-Y-M-P-K-K-A-T-E-L-K-H-L

-Q-C-L-E-X61-E-L-K-P-L-E-X68-V-L-N-L-A-Q

-S-K-N-F-H-F-X81-P-R-D-X85-X86-S-N-I-N-V

-F-V-L-E-L-K-G-S-E-T-T-F-M-C-E-Y-A-D-E-T

-A-T-I-V-E-F-L-N-R-W-I-T-F-S-Q-S-I-l-S-T

-L-T
``` wherein in General Formula 2 above,
X1 is a deletion,
X18 is leucine (L) or arginine (R);
X22 is glutamic acid (E) or glutamine (Q);
X38 is alanine (A) or arginine (R);
X42 is phenylalanine (F) or lysine (K);
X61 is aspartic acid (D) or glutamic acid (E);
X68 is aspartic acid (D) or glutamic acid (E);
X81 is aspartic acid (D) or glutamic acid (E);
X85 is leucine (L) or valine (V); and
X86 is isoleucine (I) or valine (V).

Specifically, the interleukin-2 analog may include any one sequence selected from the group consisting of amino acid sequences of SEQ ID NO: 22, 42, 53, 87, 105, and 106, but the sequence of the interleukin-2 analog is not limited thereto.

Additionally, in General Formula 2 above, one or more amino acids may be added to threonine (T), which corresponds to X133, or alternatively, in the interleukin-2 analog, one or more amino acids may be further added to a C-terminus thereof, but the present invention is not limited thereto.

Meanwhile, unless otherwise required by context in the present specification, expressions such as "include", "including", "containing", etc. mean that they include a specified integer or group of integers, but it should be understood that these expressions do not exclude other integers or a set of integers.

Hereinafter, the present invention will be described in more detail through examples. These Examples are only for describing the present invention in more detail, and the scope of the present invention is not limited by these Examples.

Example 1: Preparation of Expression Vectors for Native Interleukin-2 and Interleukin-2 Analogs For the preparation of expression vectors for native interleukin-2 encoding 133 amino acids, an interleukin-2 that was synthesized based on the reported interleukin-2 sequence (NM_000586.3; SEQ ID NO: 1) was cloned into the pET-22b vector (Novagen). Additionally, a novel interleukin-2 analog was prepared in which an amino acid(s) of interleukin-2 were modified using the interleukin-2 as a template. The PCR conditions for the amplification of the interleukin-2 analog were 16 cycles of a process consisting of 95° C. for 30 seconds, 55° C. for 60 seconds, and 65° C. for 6.5 minutes. In order to confirm whether the amino acid(s) at the desired position had been correctly substituted, sequence analysis was performed on the mutagenesis product obtained under the conditions above. As a result, it was confirmed that the modifications shown in Table 1 below were found based on the native type at the desired mutation positions for each interleukin-2 analog. The thus-obtained expression vectors were named pET22b-interleukin-2 analogs 1 to 105.

Table 1 below shows the altered sequences of amino acids and analog names for each. In order to prepare these interleukin-2 analogs, forward (F) and reverse (R) primers were synthesized, and then PCR was performed to amplify each analog gene.

In Table 1 below, analog 1 represents aldesleukin and primer nos 1 to 203 correspond to SEQ ID NOS: 214 to 417, respectively.

TABLE 1

Types of interleukin-2 analog, positions for modification, and altered sequences thereof

| Analog | Positions for Modification and Altered Sequences Thereof | Primer No. |
|---|---|---|
| 1 | desA1, C125S | 197, 198, 201, 202 |
| 2 | desA1, C125S, S87C | 197, 198, 201, 202, 149, 150 |
| 3 | desA1, C125S, K32C | 197, 198, 201, 202, 19, 20 |
| 4 | desA1, C125S, K35C | 197, 198, 201, 202, 21, 22 |
| 5 | desA1, C125S, K43C | 197, 198, 201, 202, 47, 48 |
| 6 | desA1, C125S, K48C | 197, 198, 201, 202, 53, 54 |
| 7 | desA1, C125S, K49C | 197, 198, 201, 202, 55, 56 |
| 8 | desA1, C125S, K76C | 197, 198, 201, 202, 73, 74 |
| 9 | desA1, C125S, R38A | 197, 198, 201, 202, 25, 26 |
| 10 | desA1, C125S, F42K | 197, 198, 201, 202, 35, 36 |
| 11 | desA1, C125S, F42A | 197, 198, 201, 202, 33, 34 |
| 12 | desA1, C125S, R38A, F42K | 197, 198, 201, 202, 25, 26, 35, 36 |
| 13 | desA1, C125S, R38A, F42A | 197, 198, 201, 202, 25, 26, 33, 34 |
| 14 | desA1, C125S, L19Y, R38A, F42K | 197, 198, 201, 202, 13, 14, 25, 26, 35, 36 |
| 15 | desA1, C125S, R38A, F42K, D84E | 197, 198, 201, 202, 25, 26, 35, 36, 109, 110 |
| 16 | desA1, C125S, R38A, F42K, N88Q | 197, 198, 201, 202, 25, 26, 35, 36, 153, 154 |
| 17 | desA1, C125S, R38A, F42K, V91T | 197, 198, 201, 202, 25, 26, 35, 36, 165, 166 |
| 18 | desA1, C125S, R38A, F42K, E61Q | 197, 198, 201, 202, 25, 26, 35, 36, 59, 60 |
| 19 | desA1, C125S, R38A, F42K, R81D, I92F | 197, 198, 201, 202, 25, 26, 35, 36, 97, 98, 167, 168 |
| 20 | desA1, C125S, R38A, F42K, L85V, I86V, I92F | 197, 198, 201, 202, 25, 26, 35, 36, 139, 140, 167, 168 |
| 21 | desA1, C125S, R38A, F42K, L80F, R81D, L85V, I86V, I92F | 197, 198, 201, 202, 25, 26, 35, 36, 79, 80, 167, 168 |
| 22 | desA1, C125S, L12V, R38A, F42K | 197, 198, 201, 202, 3, 4, 25, 26, 35, 36 |
| 23 | desA1, C125S, L12F, R38A, F42K | 197, 198, 201, 202, 1, 2, 25, 26, 35, 36 |
| 24 | desA1, C125S, L19V, R38A, F42K | 197, 198, 201, 202, 11, 12, 25, 26, 35, 36 |
| 25 | desA1, C125S, L19F, R38A, F42K | 197, 198, 201, 202, 9, 10, 25, 26, 35, 36 |
| 26 | desA1, C125S, R38A, F42K, I89F | 197, 198, 201, 202, 25, 26, 35, 36, 157, 158 |
| 27 | desA1, C125S, R38A, F42K, V91F | 197, 198, 201, 202, 25, 26, 35, 36, 163, 164 |
| 28 | desA1, C125S, R38A, F42K, L94V | 197, 198, 201, 202, 25, 26, 35, 36 |
| 29 | desA1, C125S, R38A, F42K, Q126T | 197, 198, 201, 202, 25, 26, 35, 36, 199, 200 |
| 30 | desA1, C125S, R38A, R81D, I92F | 197, 198, 201, 202, 27, 28, 97, 98, 169, 170 |
| 31 | desA1, C125S, R38A, D84E | 197, 198, 201, 202, 27, 28, 109, 110 |

TABLE 1-continued Types of interleukin-2 analog, positions for modification, and altered sequences thereof

| Analog | Positions for Modification and Altered Sequences Thereof | Primer No. |
|---|---|---|
| 32 | desA1, C125S, R38A, R81D, D84E, I92F | 197, 198, 201, 202, 27, 28, 95, 96, 169, 170 |
| 33 | desA1, C125S, R38A, L80F | 197, 198, 201, 202, 27, 28, 77, 78 |
| 34 | desA1, C125S, R38A, L80F, D84E | 197, 198, 201, 202, 27, 28, 77, 78, 109, 110 |
| 35 | desA1, C125S, R38A, L94F, L96F | 197, 198, 201, 202, 27, 28, 189, 190 |
| 36 | desA1, C125S, R38A, L94F, L96V | 197, 198, 201, 202, 27, 28, 193, 194 |
| 37 | desA1, C125S, R38A, L94F, L96I | 197, 198, 201, 202, 27, 28, 191, 192 |
| 38 | desA1, C125S, R38A, F42K, R81D, I92F, L94F, L96F | 197, 198, 201, 202, 25, 26, 35, 36, 97, 98, 175, 176 |
| 39 | desA1, C125S, R38A, F42K, R81D, I92F, L94F, L96V | 197, 198, 201, 202, 25, 26, 35, 36, 97, 98, 179, 180 |
| 40 | desA1, C125S, R38A, F42K, R81D, I92F, L94F, L96I | 197, 198, 201, 202, 25, 26, 35, 36, 97, 98, 177, 178 |
| 41 | desA1, C125S, L80F, R81D, L85V, I86V, I92F | 197, 198, 201, 202, 25, 26, 29, 30, 35, 36, 41, 42, 79, 80, 167, 168 |
| 42 | desA1, C125S, R38A, F42K, R81E, I92F | 197, 198, 201, 202, 25, 26, 35, 36, 103, 104, 169, 170 |
| 43 | desA1, C125S, R38A, F42K, R81D, I92L | 197, 198, 201, 202, 25, 26, 35, 36, 99, 100, 183, 184 |
| 44 | desA1, C125S, R38A, F42K, R81D, D84V, I92F | 197, 198, 201, 202, 25, 26, 35, 36, 99, 100, 113, 114, 169, 170 |
| 45 | desA1, C125S, R38A, F42K, R81D, D84F, I92F | 197, 198, 201, 202, 25, 26, 35, 36, 99, 100, 111, 112, 169, 170 |
| 46 | desA1, C125S, D20V, R38A, F42K, R81D, I92F | 197, 198, 201, 202, 17, 18, 25, 26, 35, 36, 99, 100, 169, 170 |
| 47 | desA1, C125S, D20F, R38A, F42K, R81D, I92F | 197, 198, 201, 202, 15, 16, 25, 26, 35, 36, 99, 100, 169, 170 |
| 48 | desA1, C125S, R38A, F42K, R81D, N88V, I92F | 197, 198, 201, 202, 25, 26, 35, 36, 99, 100, 155, 156, 169, 170 |
| 49 | desA1, C125S, R38A, F42K, R81D, N88F, I92F | 197, 198, 201, 202, 25, 26, 35, 36, 99, 100, 151, 152, 169, 170 |
| 50 | desA1, C125S, F42K, L80F, R81D, L85V, I86V, I92F | 197, 198, 201, 202, 25, 26, 29, 30, 35, 36, 79, 80, 139, 140, 169, 170 |
| 51 | desA1, C125S, E61Q, R81D, I92F | 197, 198, 201, 202, 59, 60, 99, 100, 169, 170 |
| 52 | desA1, C125S, R38A, F42K, L80F, R81D, I92F | 197, 198, 201, 202, 25, 26, 35, 36, 79, 80, 169, 170 |
| 53 | desA1, C125S, R38A, F42K, L80F, R81D, D84E, I92F | 197, 198, 201, 202, 25, 26, 35, 36, 79, 80, 95, 96, 169, 170 |
| 54 | desA1, C125S, R38A, F42K, Q74H, R81D, I92F | 197, 198, 201, 202, 25, 26, 35, 36, 71, 72, 99, 100, 169, 170 |
| 55 | desA1, C125S, R38A, F42K, Q74H, L80F, R81D, I92F | 197, 198, 201, 202, 25, 26, 35, 36, 71, 72, 79, 80, 169, 170 |
| 56 | desA1, C125S, R38A, F42K, Y45A, Q74H, R81D, I92F | 197, 198, 201, 202, 25, 26, 35, 36, 49, 50, 71, 72, 99, 100, 169, 170 |
| 57 | desA1, C125S, R38A, F42K, Y45A, Q74H, L80F, R81D, I92F | 197, 198, 201, 202, 25, 26, 35, 36, 49, 50, 71, 72, 79, 80, 169, 170 |
| 58 | desA1, C125S, R38A, F42K, L80F, R81D, L85A, I86A, I92F | 197, 198, 201, 202, 25, 26, 35, 36, 79, 80, 115, 116, 167, 168 |

TABLE 1-continued

Types of interleukin-2 analog, positions for modification, and altered sequences thereof

| Analog | Positions for Modification and Altered Sequences Thereof | Primer No. |
|---|---|---|
| 59 | desA1, C125S, R38A, F42K, L80F, R81D, L85A, I86A, I92Y | 197, 198, 201, 202, 25, 26, 35, 36, 79, 80, 115, 116, 187, 188 |
| 60 | desA1, C125S, R38A, Y45A, L80Y, L85A, I86A, I92Y | 197, 198, 201, 202, 27, 28, 35, 36, 41, 42, 51, 52, 93, 94, 115, 116, 187, 188 |
| 61 | desA1, C125S, R38A, F42K, L80Y, R81D, L85G, I86V, I92Y | 197, 198, 201, 202, 25, 26, 35, 36, 87, 88, 125, 126, 187, 188 |
| 62 | desA1, C125S, R38A, L80W, R81E, L85G, I86A, I92F | 197, 198, 201, 202, 27, 28, 35, 36, 41, 42, 85, 86, 123, 124, 171, 172 |
| 63 | desA1, C125S, R38A, F42K, L80D, R81E, L85T, I86G, I92F | 197, 198, 201, 202, 25, 26, 35, 36, 75, 76, 133, 134, 167, 168 |
| 64 | desA1, C125S, R38A, F42K, L80Y, R81N, L85V, I86V, I92F | 197, 198, 201, 202, 25, 26, 35, 36, 91, 92, 139, 140, 167, 168 |
| 65 | desA1, C125S, R38A, F42K, L80Y, R81E, L85V, I86V, I92F | 197, 198, 201, 202, 25, 26, 35, 36, 89, 90, 139, 140, 167, 168 |
| 66 | desA1, C125S, R38A, F42K, L80F, R81E, L85F, I86V, I92F | 197, 198, 201, 202, 25, 26, 35, 36, 81, 82, 121, 122, 167, 168 |
| 67 | desA1, C125S, R38A, F42K, L80Y, R81D, L85F, I86V, I92W, E95D | 197, 198, 201, 202, 25, 26, 35, 36, 87, 88, 121, 122, 185, 186, 195, 196 |
| 68 | desA1, C125S, R38A, F42K, L80F, R81E, L85I, I86V, V91E, I92F | 197, 198, 201, 202, 25, 26, 35, 36, 81, 82, 127, 128, 159, 160, 167, 168 |
| 69 | desA1, C125S, R38A, F42K, L80Y, R81E, L85F, I86L, V91E, I92W, E95D | 197, 198, 201, 202, 25, 26, 35, 36, 89, 90, 119, 120, 161, 162, 185, 186, 195, 196 |
| 70 | desA1, C125S, R38A, F42K, L80Y, R81D, L85V, I86V, I92F | 197, 198, 201, 202, 25, 26, 35, 36, 87, 88, 139, 140, 167, 168 |
| 71 | desA1, C125S, R38A, F42K, L80F, R81E, L85V, I86V, I92F | 197, 198, 201, 202, 25, 26, 35, 36, 81, 82, 139, 140, 167, 168 |
| 72 | desA1, C125S, R38A, F42K, L80F, R81D, L85V, I86G, I92F | 197, 198, 201, 202, 25, 26, 35, 36, 79, 80, 135, 136, 167, 168 |
| 73 | desA1, C125S, R38A, F42K, L80F, R81D, L85W, I86V, I92F | 197, 198, 201, 202, 25, 26, 35, 36, 79, 80, 141, 142, 167, 168 |
| 74 | desA1, C125S, R38D, F42K, L80Y, R81D, L85V, I86V, I92F | 197, 198, 201, 202, 31, 32, 35, 36, 87, 88, 139, 140, 167, 168 |
| 75 | desA1, C125S, R38A, F42K, Y45A, L80F, R81E, L85V, I86V, I92F | 197, 198, 201, 202, 25, 26, 35, 36, 51, 52, 81, 82, 139, 140, 167, 168 |
| 76 | desA1, C125S, R38A, F42K, K43Q, E61R, L80F, R81D, L85V, I86G, I92F | 197, 198, 201, 202, 25, 26, 39, 40, 61, 62, 79, 80, 135, 136, 167, 168 |
| 77 | desA1, C125S, R38A, F42K, K43E, E61R, L80F, R81D, L85W, I86V, I92F | 197, 198, 201, 202, 25, 26, 37, 38, 61, 62, 79, 80, 143, 144, 167, 168 |
| 78 | desA1, C125S, K35E, R38A, F42K, L80F, R81E, L85V, I86V, I92F | 197, 198, 201, 202, 23, 24, 25, 26, 35, 36, 81, 82, 139, 140, 167, 168 |
| 79 | desA1, C125S, K35E, R38A, F42K, Q74H, L80F, R81E, L85V, I86V, I92F | 197, 198, 201, 202, 23, 24, 25, 26, 35, 36, 71, 72, 81, 82, 139, 140, 167, 168 |
| 80 | desA1, C125S, K35E, R38A, F42K, Q74H, L80F, R81E, P82G, L85V, I86V, I92F | 197, 198, 201, 202, 23, 24, 25, 26, 35, 36, 71, 72, 81, 82, 105, 106, 139, 140, 167, 168 |
| 81 | desA1, C125S, K35E, R38A, F42K, Q74H, L80F, R81E, P82V, L85V, I86V, I92F | 197, 198, 201, 202, 23, 24, 25, 26, 35, 36, 71, 72, 81, 82, 107, 108, 139, 140, 167, 168 |

TABLE 1-continued

Types of interleukin-2 analog, positions for modification, and altered sequences thereof

| Analog | Positions for Modification and Altered Sequences Thereof | Primer No. |
|---|---|---|
| 82 | desA1, C125S, L18R, Q22E, L80F, R81D, L85E, I86V, I92F | 197, 198, 201, 202, 7, 8, 25, 26, 29, 30, 35, 36, 43, 44, 79, 80, 117, 118, 167, 168 |
| 83 | desA1, C125S, L18R, L19R, Q22E, L80F, R81D, L85E, I86V, I92F | 197, 198, 201, 202, 5, 6, 25, 26, 29, 30, 35, 36, 43, 44, 79, 80, 117, 118, 167, 168 |
| 84 | desA1, C125S, L18R, Q22E, L80V, R81D, L85E, I86V, I92F | 197, 198, 201, 202, 7, 8, 25, 26, 29, 30, 35, 36, 43, 44, 83, 84, 117, 118, 167, 168 |
| 85 | desA1, C125S, L80F, R81E, L85V, I86V, I92F | 197, 198, 201, 202, 25, 26, 29, 30, 35, 36, 43, 44, 81, 82, 139, 140, 167, 168 |
| 86 | desA1, C125S, L18R, Q22E, L80F, R81E, L85V, I86V, I92F | 197, 198, 201, 202, 7, 8, 25, 26, 29, 30, 35, 36, 43, 44, 81, 82, 139, 140, 167, 168 |
| 87 | desA1, C125S, L18R, L19R, Q22E, L80F, R81E, L85V, I86V, I92F | 197, 198, 201, 202, 5, 6, 25, 26, 29, 30, 35, 36, 43, 44, 81, 82, 139, 140, 167, 168 |
| 88 | desA1, C125S, E61D, L80F, R81E, L85V, I86V, I92F | 197, 198, 201, 202, 25, 26, 29, 30, 35, 36, 43, 44, 57, 58, 81, 82, 139, 140, 167, 168 |
| 89 | desA1, C125S, R38A, E68Q, L80F, R81E, L85V, I86V, I92F | 197, 198, 201, 202, 27, 28, 35, 36, 43, 44, 65, 66, 81, 82, 139, 140, 167, 168 |
| 90 | desA1, C125S, F42W, L80F, R81E, L85V, I86V, I92F | 197, 198, 201, 202, 25, 26, 29, 30, 45, 46, 81, 82, 139, 140, 167, 168 |
| 91 | desA1, C125S, E61Q, L80F, R81E, L85V, I86V, I92F | 197, 198, 201, 202, 25, 26, 29, 30, 35, 36, 43, 44, 59, 60, 81, 82, 139, 140, 167, 168 |
| 92 | desA1, C125S, L80F, R81E, L85V, I86V, V91T, I92F | 197, 198, 201, 202, 25, 26, 29, 30, 35, 36, 43, 44, 81, 82, 139, 140, 147, 148, 167, 168 |
| 93 | desA1, C125S, L80F, R81E, D84E, L85V, I86V, V91T, I92F | 197, 198, 201, 202, 25, 26, 29, 30, 35, 36, 43, 44, 81, 82, 101, 102, 139, 140, 167, 168 |
| 94 | desA1, C125S, L80F, R81E, L85V, I86V, I92F, L94F, L96F | 197, 198, 201, 202, 25, 26, 29, 30, 35, 36, 43, 44, 81, 82, 139, 140, 173, 174 |
| 95 | desA1, C125S, V69G, L80F, R81E, L85V, I86V, I92F | 197, 198, 201, 202, 25, 26, 29, 30, 35, 36, 43, 44, 67, 68, 81, 82, 139, 140, 167, 168 |
| 96 | desA1, C125S, V69G, Q74A, L80F, R81E, L85V, I86V, I92F | 197, 198, 201, 202, 25, 26, 29, 30, 35, 36, 43, 44, 69, 70, 81, 82, 139, 140, 167, 168 |
| 97 | desA1, C125S, R38A, L80F, R81D, I92F | 197, 198, 201, 202, 27, 28, 35, 36, 41, 42, 79, 80, 167, 168 |
| 98 | desA1, C125S, R38A, L80F, R81E, L85V, I92F | 197, 198, 201, 202, 27, 28, 35, 36, 41, 42, 81, 82, 137, 138, 167, 168 |
| 99 | desA1, C125S, R38A, L80F, R81E, I86V, I92F | 197, 198, 201, 202, 27, 28, 35, 36, 41, 42, 81, 82, 131, 132, 167, 168 |
| 100 | desA1, C125S, L80F, R81E, L85Y, I86V, I92F | 197, 198, 201, 202, 25, 26, 29, 30, 35, 36, 41, 42, 81, 82, 145, 146, 167, 168 |

TABLE 1-continued

Types of interleukin-2 analog, positions for modification, and altered sequences thereof

| Analog | Positions for Modification and Altered Sequences Thereof | Primer No. |
|---|---|---|
| 101 | desA1, C125S, L80F, R81E, I86A, I92F | 197, 198, 201, 202, 25, 26, 29, 30, 35, 36, 41, 42, 81, 82, 129, 130, 167, 168 |
| 102 | desA1, C125S, L80F, R81E, L85V, I86V | 197, 198, 201, 202, 25, 26, 29, 30, 35, 36, 41, 42, 81, 82, 139, 140, 181, 182 |
| 103 | desA1, C125S, L18R, Q22E, R38A, L80F, R81E, L85V, I86V, I92F | 197, 198, 201, 202, 7, 8, 27, 28, 35, 36, 41, 42, 81, 82, 139, 140, 167, 168 |
| 104 | desA1, C125S, L18R, Q22E, E61D, L80F, R81E, L85V, I86V, I92F | 197, 198, 201, 202, 7, 8, 25, 26, 29, 30, 35, 36, 41, 42, 57, 58, 81, 82, 139, 140, 167, 168 |
| 105 | desA1, C125S, L18R, Q22E, E68D, L80F, R81E, L85V, I86V, I92F | 197, 198, 201, 202, 7, 8, 25, 26, 29, 30, 35, 36, 41, 42, 63, 64, 81, 82, 139, 140, 167, 168 |

In Table 1 above, desA1 represents a deletion of alanine, which is the first amino acid in interleukin-2.

Table 2 below shows full-length protein sequences of interleukin-2 analogs. The letters shown in bold in Table 2 represent the positions for modification.

TABLE 2

Sequences of interleukin-2 analogs

| Analog | Protein Sequence | SEQ ID NO of Proteins | SEQ ID NO of Nucleotides |
|---|---|---|---|
| 1 | PTSSSTKKT QLQLEHLLLD LQMILNGINN YKNPKLTRML TFKFYMPKKA TELKHLQCLE EELKPLEEVL NLAQSKNFHL RPRDLISNIN VIVLELKGSE TTFMCEYADE TATIVEFLNR WITFSQSIIS TLT | 2 | 107 |
| 2 | PTSSSTKKT QLQLEHLLLD LQMILNGINN YKNPKLTRML TFKFYMPKKA TELKHLQCLE EELKPLEEVL NLAQSKNFHL RPRDLICNIN VIVLELKGSE TTFMCEYADE TATIVEFLNR WITFSQSIIS TLT | 3 | 108 |
| 3 | PTSSSTKKT QLQLEHLLLD LQMILNGINN YCNPKLTRML TFKFYMPKKA TELKHLQCLE EELKPLEEVL NLAQSKNFHL RPRDLISNIN VIVLELKGSE TTFMCEYADE TATIVEFLNR WITFSQSIIS TLT | 4 | 109 |
| 4 | PTSSSTKKT QLQLEHLLLD LQMILNGINN YKNPCLTRML TFKFYMPKKA TELKHLQCLE EELKPLEEVL NLAQSKNFHL RPRDLISNIN VIVLELKGSE TTFMCEYADE TATIVEFLNR WITFSQSIIS TLT | 5 | 110 |
| 5 | PTSSSTKKT QLQLEHLLLD LQMILNGINN YKNPKLTRML TFCFYMPKKA TELKHLQCLE EELKPLEEVL NLAQSKNFHL RPRDLISNIN VIVLELKGSE TTFMCEYADE TATIVEFLNR WITFSQSIIS TLT | 6 | 111 |
| 6 | PTSSSTKKT QLQLEHLLLD LQMILNGINN YKNPKLTRML TFKFYMPCKA TELKHLQCLE EELKPLEEVL NLAQSKNFHL RPRDLISNIN VIVLELKGSE TTFMCEYADE TATIVEFLNR WITFSQSIIS TLT | 7 | 112 |
| 7 | PTSSSTKKT QLQLEHLLLD LQMILNGINN YKNPKLTRML TFKFYMPKCA TELKHLQCLE EELKPLEEVL NLAQSKNFHL RPRDLISNIN VIVLELKGSE TTFMCEYADE TATIVEFLNR WITFSQSIIS TLT | 8 | 113 |

TABLE 2-continued

Sequences of interleukin-2 analogs

| Analog | Protein Sequence | SEQ ID NO of Proteins | SEQ ID NO of Nucleotides |
|---|---|---|---|
| 8 | PTSSSTKKT QLQLEHLLLD LQMILNGINN YKNPKLTRML TFKFYMPKKA TELKHLQCLE EELKPLEEVL NLAQSCNFHL RPRDLISNIN VIVLELKGSE TTFMCEYADE TATIVEFLNR WITFSQSIIS TLT | 9 | 114 |
| 9 | PTSSSTKKT QLQLEHLLLD LQMILNGINN YKNPKLTAML TFKFYMPKKA TELKHLQCLE EELKPLEEVL NLAQSKNFHL RPRDLISNIN VIVLELKGSE TTFMCEYADE TATIVEFLNR WITFSQSIIS TLT | 10 | 115 |
| 10 | PTSSSTKKT QLQLEHLLLD LQMILNGINN YKNPKLTRML TKKFYMPKKA TELKHLQCLE EELKPLEEVL NLAQSKNFHL RPRDLISNIN VIVLELKGSE TTFMCEYADE TATIVEFLNR WITFSQSIIS TLT | 11 | 116 |
| 11 | PTSSSTKKT QLQLEHLLLD LQMILNGINN YKNPKLTRML TAKFYMPKKA TELKHLQCLE EELKPLEEVL NLAQSKNFHL RPRDLISNIN VIVLELKGSE TTFMCEYADE TATIVEFLNR WITFSQSIIS TLT | 12 | 117 |
| 12 | PTSSSTKKT QLQLEHLLLD LQMILNGINN YKNPKLTAML TKKFYMPKKA TELKHLQCLE EELKPLEEVL NLAQSKNFHL RPRDLISNIN VIVLELKGSE TTFMCEYADE TATIVEFLNR WITFSQSIIS TLT | 13 | 118 |
| 13 | PTSSSTKKT QLQLEHLLLD LQMILNGINN YKNPKLTAML TAKFYMPKKA TELKHLQCLE EELKPLEEVL NLAQSKNFHL RPRDLISNIN VIVLELKGSE TTFMCEYADE TATIVEFLNR WITFSQSIIS TLT | 14 | 119 |
| 14 | PTSSSTKKT QLQLEHLLYD LQMILNGINN YKNPKLTAML TKKFYMPKKA TELKHLQCLE EELKPLEEVL NLAQSKNFHL RPRDLISNIN VIVLELKGSE TTFMCEYADE TATIVEFLNR WITFSQSIIS TLT | 15 | 120 |
| 15 | PTSSSTKKT QLQLEHLLLD LQMILNGINN YKNPKLTAML TKKFYMPKKA TELKHLQCLE EELKPLEEVL NLAQSKNFHL RPRELISNIN VIVLELKGSE TTFMCEYADE TATIVEFLNR WITFSQSIIS TLT | 16 | 121 |
| 16 | PTSSSTKKT QLQLEHLLLD LQMILNGINN YKNPKLTAML TKKFYMPKKA TELKHLQCLE EELKPLEEVL NLAQSKNFHL RPRDLISQIN VIVLELKGSE TTFMCEYADE TATIVEFLNR WITFSQSIIS TLT | 17 | 122 |
| 17 | PTSSSTKKT QLQLEHLLLD LQMILNGINN YKNPKLTAML TKKFYMPKKA TELKHLQCLE EELKPLEEVL NLAQSKNFHL RPRDLISNIN TIVLELKGSE TTFMCEYADE TATIVEFLNR WITFSQSIIS TLT | 18 | 123 |
| 18 | PTSSSTKKT QLQLEHLLLD LQMILNGINN YKNPKLTAML TKKFYMPKKA TELKHLQCLE QELKPLEEVL NLAQSKNFHL RPRDLISNIN VIVLELKGSE TTFMCEYADE TATIVEFLNR WITFSQSIIS TLT | 19 | 124 |
| 19 | PTSSSTKKT QLQLEHLLLD LQMILNGINN YKNPKLTAML TKKFYMPKKA TELKHLQCLE EELKPLEEVL NLAQSKNFHL DPRDLISNIN VFVLELKGSE TTFMCEYADE TATIVEFLNR WITFSQSIIS TLT | 20 | 125 |
| 20 | PTSSSTKKT QLQLEHLLLD LQMILNGINN YKNPKLTAML TKKFYMPKKA TELKHLQCLE EELKPLEEVL NLAQSKNFHL RPRDVVSNIN VFVLELKGSE TTFMCEYADE TATIVEFLNR WITFSQSIIS TLT | 21 | 126 |
| 21 | PTSSSTKKT QLQLEHLLLD LQMILNGINN YKNPKLTAML TKKFYMPKKA TELKHLQCLE EELKPLEEVL NLAQSKNFHF DPRDVVSNIN VFVLELKGSE TTFMCEYADE TATIVEFLNR WITFSQSIIS TLT | 22 | 127 |

TABLE 2-continued

Sequences of interleukin-2 analogs

| Analog | Protein Sequence | SEQ ID NO of Proteins | SEQ ID NO of Nucleotides |
|---|---|---|---|
| 22 | PTSSSTKKT QVQLEHLLLD LQMILNGINN YKNPKLTAML TKKFYMPKKA TELKHLQCLE EELKPLEEVL NLAQSKNFHL RPRDLISNIN VIVLELKGSE TTFMCEYADE TATIVEFLNR WITFSQSIIS TLT | 23 | 128 |
| 23 | PTSSSTKKT QFQLEHLLLD LQMILNGINN YKNPKLTAML TKKFYMPKKA TELKHLQCLE EELKPLEEVL NLAQSKNFHL RPRDLISNIN VIVLELKGSE TTFMCEYADE TATIVEFLNR WITFSQSIIS TLT | 24 | 129 |
| 24 | PTSSSTKKT QLQLEHLLVD LQMILNGINN YKNPKLTAML TKKFYMPKKA TELKHLQCLE EELKPLEEVL NLAQSKNFHL RPRDLISNIN VIVLELKGSE TTFMCEYADE TATIVEFLNR WITFSQSIIS TLT | 25 | 130 |
| 25 | PTSSSTKKT QLQLEHLLFD LQMILNGINN YKNPKLTAML TKKFYMPKKA TELKHLQCLE EELKPLEEVL NLAQSKNFHL RPRDLISNIN VIVLELKGSE TTFMCEYADE TATIVEFLNR WITFSQSIIS TLT | 26 | 131 |
| 26 | PTSSSTKKT QLQLEHLLLD LQMILNGINN YKNPKLTAML TKKFYMPKKA TELKHLQCLE EELKPLEEVL NLAQSKNFHL RPRDLISNFN VIVLELKGSE TTFMCEYADE TATIVEFLNR WITFSQSIIS TLT | 27 | 132 |
| 27 | PTSSSTKKT QLQLEHLLLD LQMILNGINN YKNPKLTAML TKKFYMPKKA TELKHLQCLE EELKPLEEVL NLAQSKNFHL RPRDLISNIN FIVLELKGSE TTFMCEYADE TATIVEFLNR WITFSQSIIS TLT | 28 | 133 |
| 28 | PTSSSTKKT QLQLEHLLLD LQMILNGINN YKNPKLTAML TKKFYMPKKA TELKHLQCLE EELKPLEEVL NLAQSKNFHL RPRDLISNIN VIVVELKGSE TTFMCEYADE TATIVEFLNR WITFSQSIIS TLT | 29 | 134 |
| 29 | PTSSSTKKT QLQLEHLLLD LQMILNGINN YKNPKLTAML TKKFYMPKKA TELKHLQCLE EELKPLEEVL NLAQSKNFHL RPRDLISNIN VIVLELKGSE TTFMCEYADE TATIVEFLNR WITFSTSIISTLT | 30 | 135 |
| 30 | PTSSSTKKT QLQLEHLLLD LQMILNGINN YKNPKLTAML TFKFYMPKKA TELKHLQCLE EELKPLEEVL NLAQSKNFHL DPRDLISNIN VFVLELKGSE TTFMCEYADE TATIVEFLNR WITFSQSIIS TLT | 31 | 136 |
| 31 | PTSSSTKKT QLQLEHLLLD LQMILNGINN YKNPKLTAML TFKFYMPKKA TELKHLQCLE EELKPLEEVL NLAQSKNFHL RPRELISNIN VIVLELKGSE TTFMCEYADE TATIVEFLNR WITFSQSIIS TLT | 32 | 137 |
| 32 | PTSSSTKKT QLQLEHLLLD LQMILNGINN YKNPKLTAML TFKFYMPKKA TELKHLQCLE EELKPLEEVL NLAQSKNFHL DPRELISNIN VFVLELKGSE TTFMCEYADE TATIVEFLNR WITFSQSIIS TLT | 33 | 138 |
| 33 | PTSSSTKKT QLQLEHLLLD LQMILNGINN YKNPKLTAML TFKFYMPKKA TELKHLQCLE EELKPLEEVL NLAQSKNFHF RPRDLISNIN VIVLELKGSE TTFMCEYADE TATIVEFLNR WITFSQSIIS TLT | 34 | 139 |
| 34 | PTSSSTKKT QLQLEHLLLD LQMILNGINN YKNPKLTAML TFKFYMPKKA TELKHLQCLE EELKPLEEVL NLAQSKNFHF RPRELISNIN VIVLELKGSE TTFMCEYADE TATIVEFLNR WITFSQSIIS TLT | 35 | 140 |
| 35 | PTSSSTKKT QLQLEHLLLD LQMILNGINN YKNPKLTAML TFKFYMPKKA TELKHLQCLE EELKPLEEVL NLAQSKNFHL RPRDLISNIN VIVFEFKGSE TTFMCEYADE TATIVEFLNR WITFSQSIIS TLT | 36 | 141 |
| 36 | PTSSSTKKT QLQLEHLLLD LQMILNGINN YKNPKLTAML TFKFYMPKKA TELKHLQCLE EELKPLEEVL NLAQSKNFHL | 37 | 142 |

TABLE 2-continued

Sequences of interleukin-2 analogs

| Analog | Protein Sequence | SEQ ID NO of Proteins | SEQ ID NO of Nucleotides |
|---|---|---|---|
| | RPRDLISNIN VIVFEVKGSE TTFMCEYADE TATIVEFLNR WITFSQSIIS TLT | | |
| 37 | PTSSSTKKT QLQLEHLLLD LQMILNGINN YKNPKLTAML TFKFYMPKKA TELKHLQCLE EELKPLEEVL NLAQSKNFHL RPRDLISNIN VIVFEIKGSE TTFMCEYADE TATIVEFLNR WITFSQSIIS TLT | 38 | 143 |
| 38 | PTSSSTKKT QLQLEHLLLD LQMILNGINN YKNPKLTAML TFKFYMPKKA TELKHLQCLE EELKPLEEVL NLAQSKNFHL DPRDLISNIN VFVFEFKGSE TTFMCEYADE TATIVEFLNR WITFSQSIIS TLT | 39 | 144 |
| 39 | PTSSSTKKT QLQLEHLLLD LQMILNGINN YKNPKLTAML TFKFYMPKKA TELKHLQCLE EELKPLEEVL NLAQSKNFHL DPRDLISNIN VFVFEVKGSE TTFMCEYADE TATIVEFLNR WITFSQSIIS TLT | 40 | 145 |
| 40 | PTSSSTKKT QLQLEHLLLD LQMILNGINN YKNPKLTAML TKKFYMPKKA TELKHLQCLE EELKPLEEVL NLAQSKNFHL DPRDLISNIN VFVFEIKGSE TTFMCEYADE TATIVEFLNR WITFSQSIIS TLT | 41 | 146 |
| 41 | PTSSSTKKT QLQLEHLLLD LQMILNGINN YKNPKLTRML TFKFYMPKKA TELKHLQCLE EELKPLEEVL NLAQSKNFHF DPRDVVSNIN VFVLELKGSE TTFMCEYADE TATIVEFLNR WITFSQSIIS TLT | 42 | 147 |
| 42 | PTSSSTKKT QLQLEHLLLD LQMILNGINN YKNPKLTAML TKKFYMPKKA TELKHLQCLE EELKPLEEVL NLAQSKNFHL EPRDLISNIN VFVLELKGSE TTFMCEYADE TATIVEFLNR WITFSQSIIS TLT | 43 | 148 |
| 43 | PTSSSTKKT QLQLEHLLLD LQMILNGINN YKNPKLTAML TKKFYMPKKA TELKHLQCLE EELKPLEEVL NLAQSKNFHL DPRDLISNIN VLVLELKGSE TTFMCEYADE TATIVEFLNR WITFSQSIIS TLT | 44 | 149 |
| 44 | PTSSSTKKT QLQLEHLLLD LQMILNGINN YKNPKLTAML TKKFYMPKKA TELKHLQCLE EELKPLEEVL NLAQSKNFHL DPRVLISNIN VFVLELKGSE TTFMCEYADE TATIVEFLNR WITFSQSIIS TLT | 45 | 150 |
| 45 | PTSSSTKKT QLQLEHLLLD LQMILNGINN YKNPKLTAML TKKFYMPKKA TELKHLQCLE EELKPLEEVL NLAQSKNFHL DPRFLISNIN VFVLELKGSE TTFMCEYADE TATIVEFLNR WITFSQSIIS TLT | 46 | 151 |
| 46 | PTSSSTKKT QLQLEHLLLV LQMILNGINN YKNPKLTAML TKKFYMPKKA TELKHLQCLE EELKPLEEVL NLAQSKNFHL DPRDLISNIN VFVLELKGSE TTFMCEYADE TATIVEFLNR WITFSQSIIS TLT | 47 | 152 |
| 47 | PTSSSTKKT QLQLEHLLLF LQMILNGINN YKNPKLTAML TKKFYMPKKA TELKHLQCLE EELKPLEEVL NLAQSKNFHL DPRDLISNIN VFVLELKGSE TTFMCEYADE TATIVEFLNR WITFSQSIIS TLT | 48 | 153 |
| 48 | PTSSSTKKT QLQLEHLLLD LQMILNGINN YKNPKLTAML TKKFYMPKKA TELKHLQCLE EELKPLEEVL NLAQSKNFHL DPRDLISVIN VFVLELKGSE TTFMCEYADE TATIVEFLNR WITFSQSIIS TLT | 49 | 154 |
| 49 | PTSSSTKKT QLQLEHLLLD LQMILNGINN YKNPKLTAML TKKFYMPKKA TELKHLQCLE EELKPLEEVL NLAQSKNFHL DPRDLISFIN VFVLELKGSE TTFMCEYADE TATIVEFLNR WITFSQSIIS TLT | 50 | 155 |
| 50 | PTSSSTKKT QLQLEHLLLD LQMILNGINN YKNPKLTRML TKKFYMPKKA TELKHLQCLE EELKPLEEVL NLAQSKNFHF DPRDVVSNIN VFVLELKGSE TTFMCEYADE TATIVEFLNR WITFSQSIIS TLT | 51 | 156 |

TABLE 2-continued

Sequences of interleukin-2 analogs

| Analog | Protein Sequence | SEQ ID NO of Proteins | SEQ ID NO of Nucleotides |
|---|---|---|---|
| 51 | PTSSSTKKT QLQLEHLLLD LQMILNGINN YKNPKLTRML TFKFYMPKKA TELKHLQCLE QELKPLEEVL NLAQSKNFHL DPRDLISNIN VFVLELKGSE TTFMCEYADE TATIVEFLNR WITFSQSIIS TLT | 52 | 157 |
| 52 | PTSSSTKKT QLQLEHLLLD LQMILNGINN YKNPKLTAML TKKFYMPKKA TELKHLQCLE EELKPLEEVL NLAQSKNFHF DPRDLISNIN VFVLELKGSE TTFMCEYADE TATIVEFLNR WITFSQSIIS TLT | 53 | 158 |
| 53 | PTSSSTKKT QLQLEHLLLD LQMILNGINN YKNPKLTAML TKKFYMPKKA TELKHLQCLE EELKPLEEVL NLAQSKNFHF DPRELISNIN VFVLELKGSE TTFMCEYADE TATIVEFLNR WITFSQSIIS TLT | 54 | 159 |
| 54 | PTSSSTKKT QLQLEHLLLD LQMILNGINN YKNPKLTAML TKKFYMPKKA TELKHLQCLE EELKPLEEVL NLAHSKNFHL DPRDLISNIN VFVLELKGSE TTFMCEYADE TATIVEFLNR WITFSQSIIS TLT | 55 | 160 |
| 55 | PTSSSTKKT QLQLEHLLLD LQMILNGINN YKNPKLTAML TKKFYMPKKA TELKHLQCLE EELKPLEEVL NLAHSKNFHF DPRDLISNIN VFVLELKGSE TTFMCEYADE TATIVEFLNR WITFSQSIIS TLT | 56 | 161 |
| 56 | PTSSSTKKT QLQLEHLLLD LQMILNGINN YKNPKLTAML TKKFAMPKKA TELKHLQCLE EELKPLEEVL NLAHSKNFHL DPRDLISNIN VFVLELKGSE TTFMCEYADE TATIVEFLNR WITFSQSIIS TLT | 57 | 162 |
| 57 | PTSSSTKKT QLQLEHLLLD LQMILNGINN YKNPKLTAML TKKFAMPKKA TELKHLQCLE EELKPLEEVL NLAHSKNFHF DPRDLISNIN VFVLELKGSE TTFMCEYADE TATIVEFLNR WITFSQSIIS TLT | 58 | 163 |
| 58 | PTSSSTKKT QLQLEHLLLD LQMILNGINN YKNPKLTAML TKKFYMPKKA TELKHLQCLE EELKPLEEVL NLAQSKNFHF DPRDAASNIN VFVLELKGSE TTFMCEYADE TATIVEFLNR WITFSQSIIS TLT | 59 | 164 |
| 59 | PTSSSTKKT QLQLEHLLLD LQMILNGINN YKNPKLTAML TKKFYMPKKA TELKHLQCLE EELKPLEEVL NLAQSKNFHF DPRDAASNIN VYVLELKGSE TTFMCEYADE TATIVEFLNR WITFSQSIIS TLT | 60 | 165 |
| 60 | PTSSSTKKT QLQLEHLLLD LQMILNGINN YKNPKLTAML TKKFAMPKKA TELKHLQCLE EELKPLEEVL NLAQSKNFHY RPRDAASNIN VYVLELKGSE TTFMCEYADE TATIVEFLNR WITFSQSIIS TLT | 61 | 166 |
| 61 | PTSSSTKKT QLQLEHLLLD LQMILNGINN YKNPKLTAML TKKFYMPKKA TELKHLQCLE EELKPLEEVL NLAQSKNFHY DPRDGVSNIN VYVLELKGSE TTFMCEYADE TATIVEFLNR WITFSQSIIS TLT | 62 | 167 |
| 62 | PTSSSTKKT QLQLEHLLLD LQMILNGINN YKNPKLTAML TKKFYMPKKA TELKHLQCLE EELKPLEEVL NLAQSKNFHW EPRDGASNIN VFVLELKGSE TTFMCEYADE TATIVEFLNR WITFSQSIIS TLT | 63 | 168 |
| 63 | PTSSSTKKT QLQLEHLLLD LQMILNGINN YKNPKLTAML TKKFYMPKKA TELKHLQCLE EELKPLEEVL NLAQSKNFHD EPRDTGSNIN VFVLELKGSE TTFMCEYADE TATIVEFLNR WITFSQSIIS TLT | 64 | 169 |
| 64 | PTSSSTKKT QLQLEHLLLD LQMILNGINN YKNPKLTAML TKKFYMPKKA TELKHLQCLE EELKPLEEVL NLAQSKNFHY NPRDVVSNIN VYVLELKGSE TTFMCEYADE TATIVEFLNR WITFSQSIIS TLT | 65 | 170 |

TABLE 2-continued

Sequences of interleukin-2 analogs

| Analog | Protein Sequence | SEQ ID NO of Proteins | SEQ ID NO of Nucleotides |
|---|---|---|---|
| 65 | PTSSSTKKT QLQLEHLLLD LQMILNGINN YKNPKLTAML TKKFYMPKKA TELKHLQCLE EELKPLEEVL NLAQSKNFHY EPRDVVSNIN VFVLELKGSE TTFMCEYADE TATIVEFLNR WITFSQSIIS TLT | 66 | 171 |
| 66 | PTSSSTKKT QLQLEHLLLD LQMILNGINN YKNPKLTAML TKKFYMPKKA TELKHLQCLE EELKPLEEVL NLAQSKNFHF EPRDFVSNIN VFVLELKGSE TTFMCEYADE TATIVEFLNR WITFSQSIIS TLT | 67 | 172 |
| 67 | PTSSSTKKT QLQLEHLLLD LQMILNGINN YKNPKLTAML TKKFYMPKKA TELKHLQCLE EELKPLEEVL NLAQSKNFHY DPRDFVSNIN VWVLDLKGSE TTFMCEYADE TATIVEFLNR WITFSQSIIS TLT | 68 | 173 |
| 68 | PTSSSTKKT QLQLEHLLLD LQMILNGINN YKNPKLTAML TKKFYMPKKA TELKHLQCLE EELKPLEEVL NLAQSKNFHF EPRDIVSNIN EFVLELKGSE TTFMCEYADE TATIVEFLNR WITFSQSIIS TLT | 69 | 174 |
| 69 | PTSSSTKKT QLQLEHLLLD LQMILNGINN YKNPKLTAML TKKFYMPKKA TELKHLQCLE EELKPLEEVL NLAQSKNFHY EPRDFLSNIN EWVLDLKGSE TTFMCEYADE TATIVEFLNR WITFSQSIIS TLT | 70 | 175 |
| 70 | PTSSSTKKT QLQLEHLLLD LQMILNGINN YKNPKLTAML TKKFYMPKKA TELKHLQCLE EELKPLEEVL NLAQSKNFHY DPRDVVSNIN VFVLELKGSE TTFMCEYADE TATIVEFLNR WITFSQSIIS TLT | 71 | 176 |
| 71 | PTSSSTKKT QLQLEHLLLD LQMILNGINN YKNPKLTAML TKKFYMPKKA TELKHLQCLE EELKPLEEVL NLAQSKNFHF EPRDVVSNIN VFVLELKGSE TTFMCEYADE TATIVEFLNR WITFSQSIIS TLT | 72 | 177 |
| 72 | PTSSSTKKT QLQLEHLLLD LQMILNGINN YKNPKLTAML TKKFYMPKKA TELKHLQCLE EELKPLEEVL NLAQSKNFHF DPRDVGSNIN VFVLELKGSE TTFMCEYADE TATIVEFLNR WITFSQSIIS TLT | 73 | 178 |
| 73 | PTSSSTKKT QLQLEHLLLD LQMILNGINN YKNPKLTAML TKKFYMPKKA TELKHLQCLE EELKPLEEVL NLAQSKNFHF DPRDWVSNIN VFVLELKGSE TTFMCEYADE TATIVEFLNR WITFSQSIIS TLT | 74 | 179 |
| 74 | PTSSSTKKT QLQLEHLLLD LQMILNGINN YKNPKLTDML TKKFYMPKKA TELKHLQCLE EELKPLEEVL NLAQSKNFHY DPRDVVSNIN VFVLELKGSE TTFMCEYADE TATIVEFLNR WITFSQSIIS TLT | 75 | 180 |
| 75 | PTSSSTKKT QLQLEHLLLD LQMILNGINN YKNPKLTAML TKKFAMPKKA TELKHLQCLE EELKPLEEVL NLAQSKNFHF EPRDVVSNIN VFVLELKGSE TTFMCEYADE TATIVEFLNR WITFSQSIIS TLT | 76 | 181 |
| 76 | PTSSSTKKT QLQLEHLLLD LQMILNGINN YKNPKLTAML TKQFYMPKKA TELKHLQCLE RELKPLEEVL NLAQSKNFHF DPRDVGSNIN VFVLELKGSE TTFMCEYADE TATIVEFLNR WITFSQSIIS TLT | 77 | 182 |
| 77 | PTSSSTKKT QLQLEHLLLD LQMILNGINN YKNPKLTAML TKEFYMPKKA TELKHLQCLE RELKPLEEVL NLAQSKNFHF DPRDWVSNIN VFVLELKGSE TTFMCEYADE TATIVEFLNR WITFSQSIIS TLT | 78 | 183 |
| 78 | PTSSSTKKT QLQLEHLLLD LQMILNGINN YKNPELTAML TKKFYMPKKA TELKHLQCLE EELKPLEEVL NLAQSKNFHF EPRDVVSNIN VFVLELKGSE TTFMCEYADE TATIVEFLNR WITFSQSIIS TLT | 79 | 184 |
| 79 | PTSSSTKKT QLQLEHLLLD LQMILNGINN YKNPELTAML TKKFYMPKKA TELKHLQCLE EELKPLEEVL NLAHSKNFHF | 80 | 185 |

TABLE 2-continued

Sequences of interleukin-2 analogs

| Analog | Protein Sequence | SEQ ID NO of Proteins | SEQ ID NO of Nucleotides |
|---|---|---|---|
|  | EPRDVVSNIN VFVLELKGSE TTFMCEYADE TATIVEFLNR WITFSQSIIS TLT |  |  |
| 80 | PTSSSTKKT QLQLEHLLLD LQMILNGINN YKNPELTAML TKKFYMPKKA TELKHLQCLE EELKPLEEVL NLAHSKNFHF EGRDVVSNIN VFVLELKGSE TTFMCEYADE TATIVEFLNR WITFSQSIIS TLT | 81 | 186 |
| 81 | PTSSSTKKT QLQLEHLLLD LQMILNGINN YKNPELTAML TKKFYMPKKA TELKHLQCLE EELKPLEEVL NLAHSKNFHF EVRDVVSNIN VFVLELKGSE TTFMCEYADE TATIVEFLNR WITFSQSIIS TLT | 82 | 187 |
| 82 | PTSSSTKKT QLQLEHLRLD LEMILNGINN YKNPKLTRML TFKFYMPKKA TELKHLQCLE EELKPLEEVL NLAQSKNFHF DPRDEVSNIN VFVLELKGSE TTFMCEYADE TATIVEFLNR WITFSQSIIS TLT | 83 | 188 |
| 83 | PTSSSTKKT QLQLEHLRRD LEMILNGINN YKNPKLTRML TFKFYMPKKA TELKHLQCLE EELKPLEEVL NLAQSKNFHF DPRDEVSNIN VFVLELKGSE TTFMCEYADE TATIVEFLNR WITFSQSIIS TLT | 84 | 189 |
| 84 | PTSSSTKKT QLQLEHLRLD LEMILNGINN YKNPKLTRML TFKFYMPKKA TELKHLQCLE EELKPLEEVL NLAQSKNFHV DPRDEVSNIN VFVLELKGSE TTFMCEYADE TATIVEFLNR WITFSQSIIS TLT | 85 | 190 |
| 85 | PTSSSTKKT QLQLEHLLLD LQMILNGINN YKNPKLTRML TFKFYMPKKA TELKHLQCLE EELKPLEEVL NLAQSKNFHF EPRDVVSNIN VFVLELKGSE TTFMCEYADE TATIVEFLNR WITFSQSIIS TLT | 86 | 191 |
| 86 | PTSSSTKKT QLQLEHLRLD LEMILNGINN YKNPKLTRML TFKFYMPKKA TELKHLQCLE EELKPLEEVL NLAQSKNFHF EPRDVVSNIN VFVLELKGSE TTFMCEYADE TATIVEFLNR WITFSQSIIS TLT | 87 | 192 |
| 87 | PTSSSTKKT QLQLEHLRRD LEMILNGINN YKNPKLTRML TFKFYMPKKA TELKHLQCLE EELKPLEEVL NLAQSKNFHF EPRDVVSNIN VFVLELKGSE TTFMCEYADE TATIVEFLNR WITFSQSIIS TLT | 88 | 193 |
| 88 | PTSSSTKKT QLQLEHLLLD LQMILNGINN YKNPKLTRML TFKFYMPKKA TELKHLQCLE DELKPLEEVL NLAQSKNFHF EPRDVVSNIN VFVLELKGSE TTFMCEYADE TATIVEFLNR WITFSQSIIS TLT | 89 | 194 |
| 89 | PTSSSTKKT QLQLEHLLLD LQMILNGINN YKNPKLTAML TFKFYMPKKA TELKHLQCLE EELKPLEQVL NLAQSKNFHF EPRDVVSNIN VFVLELKGSE TTFMCEYADE TATIVEFLNR WITFSQSIIS TLT | 90 | 195 |
| 90 | PTSSSTKKT QLQLEHLLLD LQMILNGINN YKNPKLTRML TWKFYMPKKA TELKHLQCLE EELKPLEEVL NLAQSKNFHF EPRDVVSNIN VFVLELKGSE TTFMCEYADE TATIVEFLNR WITFSQSIIS TLT | 91 | 196 |
| 91 | PTSSSTKKT QLQLEHLLLD LQMILNGINN YKNPKLTRML TFKFYMPKKA TELKHLQCLE QELKPLEEVL NLAQSKNFHF EPRDVVSNIN VFVLELKGSE TTFMCEYADE TATIVEFLNR WITFSQSIIS TLT | 92 | 197 |
| 92 | PTSSSTKKT QLQLEHLLLD LQMILNGINN YKNPKLTRML TFKFYMPKKA TELKHLQCLE EELKPLEEVL NLAQSKNFHF EPRDVVSNIN TFVLELKGSE TTFMCEYADE TATIVEFLNR WITFSQSIIS TLT | 93 | 198 |
| 93 | PTSSSTKKT QLQLEHLLLD LQMILNGINN YKNPKLTRML TFKFYMPKKA TELKHLQCLE EELKPLEEVL NLAQSKNFHF EPREWSNIN TFVLELKGSE TTFMCEYADE TATIVEFLNR WITFSQSIIS TLT | 94 | 199 |

TABLE 2-continued

Sequences of interleukin-2 analogs

| Analog | Protein Sequence | SEQ ID NO of Proteins | SEQ ID NO of Nucleotides |
|---|---|---|---|
| 94 | PTSSSTKKT QLQLEHLLLD LQMILNGINN YKNPKLTRML TFKFYMPKKA TELKHLQCLE EELKPLEEVL NLAQSKNFHF EPRDVVSNIN VFVFEFKGSE TTFMCEYADE TATIVEFLNR WITFSQSIIS TLT | 95 | 200 |
| 95 | PTSSSTKKT QLQLEHLLLD LQMILNGINN YKNPKLTRML TFKFYMPKKA TELKHLQCLE EELKPLEEGL NLAQSKNFHF EPRDVVSNIN VFVLELKGSE TTFMCEYADE TATIVEFLNR WITFSQSIIS TLT | 96 | 201 |
| 96 | PTSSSTKKT QLQLEHLLLD LQMILNGINN YKNPKLTRML TFKFYMPKKA TELKHLQCLE EELKPLEEGL NLAASKNFHF EPRDVVSNIN VFVLELKGSE TTFMCEYADE TATIVEFLNR WITFSQSIIS TLT | 97 | 202 |
| 97 | PTSSSTKKT QLQLEHLLLD LQMILNGINN YKNPKLTAML TFKFYMPKKA TELKHLQCLE EELKPLEEVL NLAQSKNFHF DPRDLISNIN VFVLELKGSE TTFMCEYADE TATIVEFLNR WITFSQSIIS TLT | 98 | 203 |
| 98 | PTSSSTKKT QLQLEHLLLD LQMILNGINN YKNPKLTAML TFKFYMPKKA TELKHLQCLE EELKPLEEVL NLAQSKNFHF EPRDVISNIN VFVLELKGSE TTFMCEYADE TATIVEFLNR WITFSQSIIS TLT | 99 | 204 |
| 99 | PTSSSTKKT QLQLEHLLLD LQMILNGINN YKNPKLTAML TFKFYMPKKA TELKHLQCLE EELKPLEEVL NLAQSKNFHF EPRDLVSNIN VFVLELKGSE TTFMCEYADE TATIVEFLNR WITFSQSIIS TLT | 100 | 205 |
| 100 | PTSSSTKKT QLQLEHLLLD LQMILNGINN YKNPKLTRML TFKFYMPKKA TELKHLQCLE EELKPLEEVL NLAQSKNFHF EPRDVVSNIN VFVLELKGSE TTFMCEYADE TATIVEFLNR WITFSQSIIS TLT | 101 | 206 |
| 101 | PTSSSTKKT QLQLEHLLLD LQMILNGINN YKNPKLTRML TFKFYMPKKA TELKHLQCLE EELKPLEEVL NLAQSKNFHF EPRDLASNIN VFVLELKGSE TTFMCEYADE TATIVEFLNR WITFSQSIIS TLT | 102 | 207 |
| 102 | PTSSSTKKT QLQLEHLLLD LQMILNGINN YKNPKLTRML TFKFYMPKKA TELKHLQCLE EELKPLEEVL NLAQSKNFHF EPRDVVSNIN VIVLELKGSE TTFMCEYADE TATIVEFLNR WITFSQSIIS TLT | 103 | 208 |
| 103 | PTSSSTKKT QLQLEHLRLD LEMILNGINN YKNPKLTAML TFKFYMPKKA TELKHLQCLE EELKPLEEVL NLAQSKNFHF EPRDVVSNIN VFVLELKGSE TTFMCEYADE TATIVEFLNR WITFSQSIIS TLT | 104 | 209 |
| 104 | PTSSSTKKT QLQLEHLRLD LEMILNGINN YKNPKLTRML TFKFYMPKKA TELKHLQCLE DELKPLEEVL NLAQSKNFHF EPRDVVSNIN VFVLELKGSE TTFMCEYADE TATIVEFLNR WITFSQSIIS TLT | 105 | 210 |
| 105 | PTSSSTKKT QLQLEHLRLD LEMILNGINN YKNPKLTRML TFKFYMPKKA TELKHLQCLE EELKPLEDVL NLAQSKNFHF EPRDVVSNIN VFVLELKGSE TTFMCEYADE TATIVEFLNR WITFSQSIIS TLT | 106 | 211 |

Example 2: Expression of Interleukin-2 Analogs

A recombinant interleukin-2 analog under the control of T7 promoter was expressed using the expression vectors prepared in Example 1.

An expression *E. coli* strain, *E. coli* BL21 DE3 (*E. coli* B F-dcm ompT hsdS(rB-mB-) gal λ(DE3); Novagen), was transformed with each recombinant interleukin-2 analog expression vector. As for the transformation method, a method recommended by Novagen was used. Each single colony, in which each recombinant expression vector was transformed, was collected, inoculated into a 2× Luria Broth medium containing ampicillin (50 μg/mL), and cultured at 37° C. for 15 hours. Each recombinant strain culture solution and the 2×LB medium containing 30% glycerol were mixed at a 1:1 (v/v) ratio, and each 1 mL of the mixture was dispensed into a cryo-tube, and stored at −150° C. This was used as a cell stock for the production of a recombinant protein.

For the expression of each recombinant interleukin-2 analog, one vial of each cell stock was dissolved, inoculated into 500 mL of 2×LB, and cultured with shaking at 37° C. for 14 to 16 hours. When the absorbance value at 600 nm reached 4.0 or higher, the culture was terminated, and this was used as a seed culture solution. The seed culture was inoculated into 1.6 L of a fermentation medium, and initial fermentation was started Using a 5 L fermentor (Bioflo-320, NBS, USA). Culture conditions were maintained at a pH of 6.70 using a temperature of 37° C., an air volume of 2.0 L/min (1 vvm), a stirring speed of 650 rpm, and 30% aqueous ammonia. As for the fermentation process, when nutrients in the culture medium were limited, fed-batch culture was performed by adding an additional medium (feeding solution). The growth of the strain was observed by absorbance, and a final concentration of 500 μM IPTG was introduced at an absorbance value of 70 or higher. The culture was performed further until for about 23 to 25 hours after the introduction of IPTG, and after termination of the culture, and the recombinant strain was recovered using a centrifuge and stored at −80° C. until use.

Example 3: Extraction and Refolding of Interleukin-2 Analogs

In order to convert the interleukin-2 analogs from the interleukin-2 analog expressing *E. coli* obtained in Example 2 in a soluble form, cells were disrupted and refolded. Cell pellets corresponding to 100 mL of the culture were suspended in 1-200 mL of a lysis buffer solution (20 mM Tris-HCl (pH 9.0), 1 mM EDTA (pH 9.0), 0.2 M NaCl, 0.5% Triton X-100), and the recombinant *E. coli* cells were disrupted at 15,000 psi using a microfluidizer. After centrifugation at 13,900 g for 30 minutes, the supernatant was discarded, and the pellet was washed with 400 mL of a first washing buffer solution (50 mM Tris-HCl (pH 8.0), 5 mM EDTA (pH 9.0)). After centrifugation under the same conditions as above, the supernatant was discarded, and the pellet was washed with 400 mL of a second washing buffer solution (50 mM Tris-HCl (pH 8.0), 5 mM EDTA (pH 9.0), 2% Triton X-100). After centrifugation under the same conditions as above, the supernatant was discarded, and the pellet was washed with 400 mL of a third washing buffer solution (50 mM Tris-HCl (pH 8.0), 5 mM EDTA (pH 9.0), 1% sodium deoxycholate). After centrifugation under the same conditions as above, the supernatant was discarded, and the pellet was washed with 400 mL of a fourth washing buffer solution (50 mM Tris-HCl (pH 8.0), 5 mM EDTA (pH 9.0), 1 M NaCl). The resultant was subjected to centrifugation under the same conditions as above and washing, and *E. coli* inclusion bodies were obtained therefrom. The pellet of the washed inclusion bodies was resuspended in 400 mL of soluble/reducing buffer (6 M guanidine, 100 mM Tris (pH 8.0), 2 mM EDTA (pH 9.0), 50 mM DTT) and stirred at 50° C. for 30 minutes. To the soluble/reduced interleukin-2 analogs, 100 mL of distilled water was added to dilute the 6 M guanidine to 4.8 M guanidine, and then the resultant was centrifuged at 13,900 g for 30 minutes and the pellet discarded to obtain only the solution therein. To the diluted solution was additionally added 185.7 mL of distilled water, and the 4.8 M guanidine was diluted to 3.5 M guanidine, and the pH was adjusted to 5.0 using 100% acetic acid. The pH-adjusted solution was stirred at room temperature for one hour. The solution with precipitated impurities was centrifuged at 13,900 g for 30 minutes, and the supernatant was discarded and the pellet washed with a final washing buffer solution (3.5 M guanidine, 20 mM sodium acetate (pH 5.0), 5 mM DTT). The resultant was centrifuged under the same conditions as above to obtain a pellet. The washed interleukin-2 analogs were dissolved in 400 mL of a refolding buffer solution (6 mM guanidine, 100 mM Tris (pH 8.0), 0.1 mM CuCl$_2$). The refolding process was performed by stirring the mixed solution at 4° C. for 15 to 24 hours.

Example 4: Size-Exclusion Column Chromatography

The interleukin-2 analog refolding solution obtained in Example 3 was concentrated to less than 1 mL to be applied to a size-exclusion column for purification. The column was equilibrated with a buffer solution (2 M guanidine, 100 mM Tris (pH 8.0)) before introducing with the refolding solution and was eluted by flowing a buffer solution thereto after the introduction of the refolding solution. Since the eluted sample contained guanidine, it was replaced with a stabilized solution (10 mM sodium acetate (pH 4.5), 5% trehalose), and the purity was measured through RP-HPLC and peptide mapping analysis. The sample was used in the experiment when its measured purity reached 80% or higher.

Example 5: Evaluation of Binding Affinity of Interleukin-2 Analogs for Receptors In order to measure the binding affinity of the interleukin-2 analogs obtained in Example 4 for each of interleukin-2 alpha receptors and beta receptors, surface plasmon resonance measurement (BIACORE T200, GE Healthcare) was used. The binding affinity of the prepared analogs for the alpha receptors and beta receptors was measured, and the binding affinity of each of the prepared analogs was compared with that of interleukin-2 analog 01 (aldesleukin).

First, an anti-human immunoglobulin antibody (Abcam, #ab97221) was immobilized to CM5 chips (GE Healthcare) by as much as about 5,000 RU (resonance unit) through amine coupling, and then, the immunoglobulin antibody was finally immobilized by allowing the interleukin-2 alpha receptors (SYMANSIS, #4102H) or interleukin-2 beta receptors (SYMANSIS, #4122H), to each of which a human immunoglobulin Fc region was bound, to bind to each immunoglobulin antibody using an antigen-antibody binding reaction. Thereafter, the recombinant interleukin-2 analog prepared above was diluted at various concentrations and was flowed onto the CM5 chips, to which the interleukin-2 receptors were finally immobilized, to measure the binding affinity of each interleukin-2 receptor. The measurement of binding affinity consisted of measurements of an association rate constant ($k_a$) and a dissociation rate constant ($k_d$), in which the binding rate was measured by flowing each interleukin-2 analog at a flow rate of 10 L/min for 3 minutes while the dissociation rate was measured from each interleukin-2 receptor by flowing only the experimental buffer for the same period of time and at the same flow rate. After the measurement was completed, the binding affinity for the receptors was evaluated according to the 1:1 binding fitting model in the Biaevaluation program.

relative binding affinity ($K_D$) (%)=binding affinity of analog 01 (aldesleukin) ($K_D$)/binding affinity of analog ($K_D$)×100

In Table 3 below, "cannot be defined" indicates that the corresponding physical quantity cannot be defined for the corresponding receptor because no binding to the receptor was observed in the surface plasmon resonance measurement.

TABLE 3

Relative binding affinity of interleukin-2 analogs for interleukin-2 alpha or beta receptors compared to analog 01 (aldesleukin)

| Interleukin-2 Receptor | Test Material | Relative Binding Affinity (%) |
|---|---|---|
| Alpha Receptor | analog 01 | 100.0 |
| | analog 09 | 74.5 |
| | analog 12 | cannot be defined |
| | analog 13 | 1.1 |
| | analog 15 | cannot be defined |
| | analog 16 | 0.2 |
| | analog 17 | 29.6 |
| | analog 19 | cannot be defined |
| | analog 20 | cannot be defined |
| | analog 21 | cannot be defined |
| | analog 31 | 5.0 |
| | analog 34 | 9.4 |
| | analog 35 | 31.7 |
| | analog 41 | 121.3 |
| | analog 52 | cannot be defined |
| | analog 53 | cannot be defined |
| | analog 86 | 71.1 |
| | analog 88 | 101.5 |
| | analog 90 | 98.4 |
| | analog 91 | 7.9 |
| | analog 92 | 97.3 |
| | analog 93 | 92.8 |
| | analog 95 | 10.7 |
| | analog 96 | 14.9 |
| | analog 97 | 18.8 |
| | analog 98 | 7.7 |
| | analog 99 | 19.9 |
| | analog 100 | 29.1 |
| | analog 101 | 24.7 |
| | analog 102 | 151.4 |
| | analog 103 | 6.1 |
| | analog 104 | 122.4 |
| | analog 105 | 246.8 |
| Beta Receptor | analog 01 | 100.0 |
| | analog 09 | 337.4 |
| | analog 12 | 166.2 |
| | analog 13 | 148.6 |
| | analog 14 | 129.7 |
| | analog 15 | 98.1 |
| | analog 16 | 1261.8 |
| | analog 17 | 9.4 |
| | analog 18 | 35.3 |
| | analog 19 | 455.0 |
| | analog 20 | 156.5 |
| | analog 21 | 14,084.2 |
| | analog 24 | 37.9 |
| | analog 25 | 21.7 |
| | analog 31 | 235.7 |
| | analog 34 | 321.8 |
| | analog 35 | 232.7 |
| | analog 41 | 22,776.2 |
| | analog 52 | 3,821.1 |
| | analog 53 | 690.7 |
| | analog 55 | 3,025.7 |
| | analog 57 | 2,569.7 |
| | analog 58 | 7,771.2 |
| | analog 59 | 1,533.5 |
| | analog 61 | 1,039.1 |
| | analog 70 | 10,199.2 |
| | analog 71 | 17,083.8 |
| | analog 73 | 1,591.8 |
| | analog 74 | 8,153.4 |
| | analog 75 | 9,571.2 |
| | analog 76 | 1,040.4 |
| | analog 77 | 644.4 |
| | analog 84 | 710.7 |
| | analog 86 | 18,745.8 |
| | analog 88 | 13,856.6 |
| | analog 90 | 12,776.2 |
| | analog 91 | 7,361.9 |
| | analog 92 | 1,510.3 |
| | analog 93 | 696.8 |
| | analog 94 | 35.5 |
| | analog 95 | 17.1 |
| | analog 96 | 229.3 |
| | analog 97 | 3,019.4 |
| | analog 98 | 11,084.5 |
| | analog 99 | 1,509.1 |
| | analog 100 | 2,534.1 |
| | analog 101 | 113.1 |
| | analog 102 | 4,452.0 |
| | analog 103 | 13,100.0 |
| | analog 104 | 25,439.8 |
| | analog 105 | 26,837.8 |

Figure 1B:
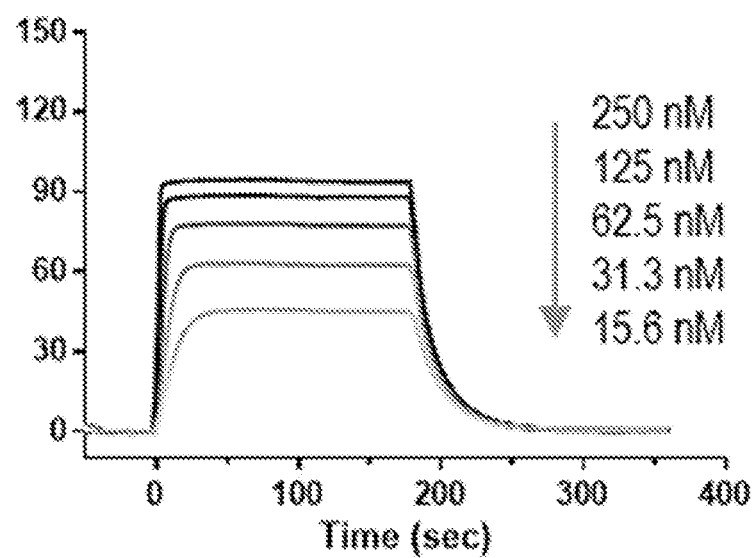
Figure 1C:
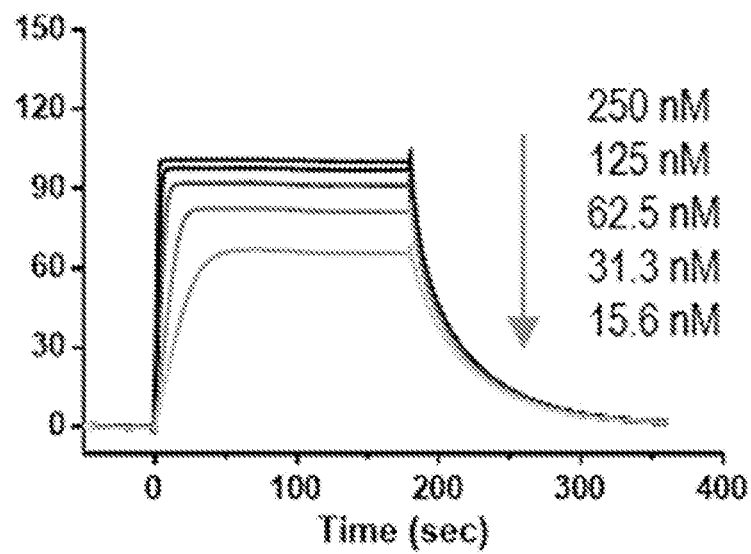
Figure 2A:
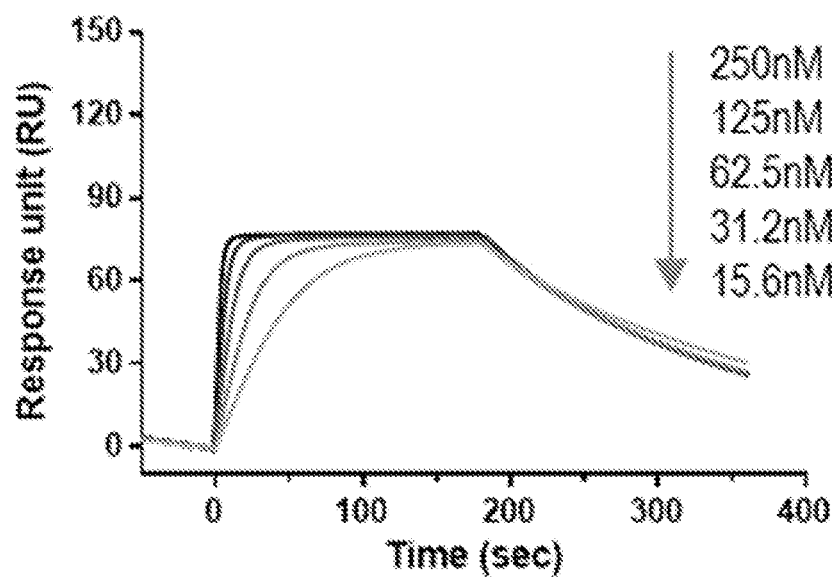
Figure 2B:
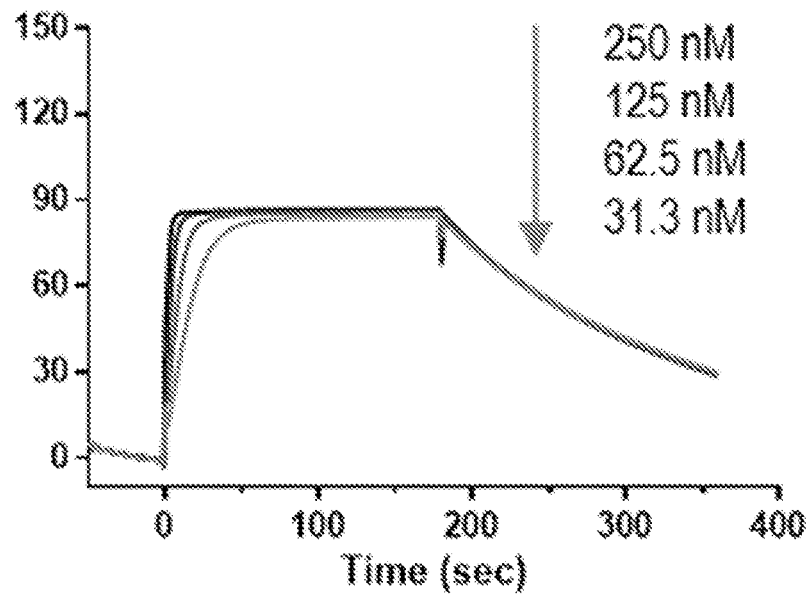
Figure 2C:
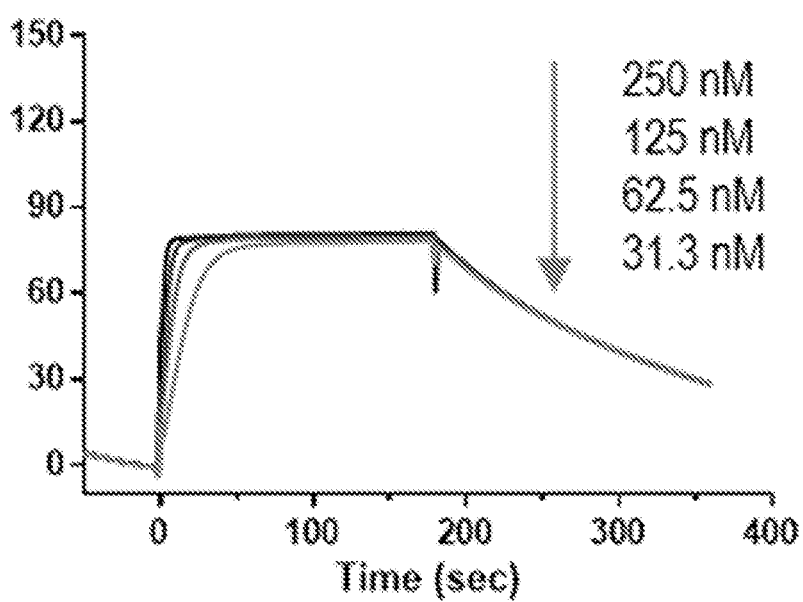

As explicitly shown in the test results (FIGS. 1 and 2 and Table 3), it was confirmed that the interleukin-2 analogs of the present invention had no binding affinity, increased/reduced binding affinity for interleukin-2 alpha receptors, etc., thus showing an altered binding affinity for interleukin-2 alpha receptors compared to native interleukin-2 or aldesleukin. In contrast, as for the interleukin-2 beta receptors, the interleukin-2 analogs of the present invention showed a stronger binding affinity of up to 100-fold compared to native interleukin-2 or aldesleukin. From the above results, it was confirmed that the amino acid sequence of the interleukin-2 analog has an effect on its binding to the interleukin-2 alpha or beta receptors. These results suggest that the binding affinity for interleukin-2 receptors can be altered by substituting an amino acid at a specific position.

These experimental results suggest that the interleukin-2 analogs according to the present invention have altered binding affinity for interleukin-2 alpha receptors and interleukin-2 beta receptors and thus can be used in the development of various drugs based on the same.

From the foregoing, one of ordinary skill in the art to which the present invention pertains will be able to understand that the present invention may be embodied in other specific forms without modifying the technical concepts or essential characteristics of the present invention. In this regard, the exemplary embodiments disclosed herein are only for illustrative purposes and should not be construed as limiting the scope of the present invention. On the contrary, the present invention is intended to cover not only the exemplary embodiments but also various alternatives, modifications, equivalents, and other embodiments that may be included within the spirit and scope of the present invention as defined by the appended claims.

The invention claimed is:

1. An interleukin-2 analog comprising any one sequence selected from the group consisting of the amino acid sequences of SEQ ID NOs: 22, 53, 87, 89, 91, 99, 104, 105, and 106.

* * * * *

SEQUENCE LISTING

```
<160> NUMBER OF SEQ ID NOS: 417

<210> SEQ ID NO 1
<211> LENGTH: 133
<212> TYPE: PRT
```

<213> ORGANISM: homo sapiens

<400> SEQUENCE: 1

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130

<210> SEQ ID NO 2
<211> LENGTH: 132
<212> TYPE: PRT
<213> ORGANISM: Artificial Sequence
<220> FEATURE:
<223> OTHER INFORMATION: IL-2 analog 1

<400> SEQUENCE: 2

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130

<210> SEQ ID NO 3
<211> LENGTH: 132
<212> TYPE: PRT
<213> ORGANISM: Artificial Sequence
<220> FEATURE:
<223> OTHER INFORMATION: IL-2 analog 2

<400> SEQUENCE: 3

Pro Thr Ser Ser Ser Thr Lys Lys Thr Gln Leu Gln Leu Glu His Leu

```
                  1               5                  10                 15
            Leu Leu Asp Leu Gln Met Ile Leu Asn Gly Ile Asn Asn Tyr Lys Asn
                            20                  25                 30

Pro Lys Leu Thr Arg Met Leu Thr Phe Lys Phe Tyr Met Pro Lys Lys
                        35                  40                 45

Ala Thr Glu Leu Lys His Leu Gln Cys Leu Glu Glu Leu Lys Pro
                50                  55                 60

Leu Glu Glu Val Leu Asn Leu Ala Gln Ser Lys Asn Phe His Leu Arg
             65                  70                 75                 80

Pro Arg Asp Leu Ile Cys Asn Ile Asn Val Ile Val Leu Glu Leu Lys
                                85                  90                 95

Gly Ser Glu Thr Thr Phe Met Cys Glu Tyr Ala Asp Glu Thr Ala Thr
                            100                 105                110

Ile Val Glu Phe Leu Asn Arg Trp Ile Thr Phe Ser Gln Ser Ile Ile
                        115                 120                125

Ser Thr Leu Thr
                    130

<210> SEQ ID NO 4
<211> LENGTH: 132
<212> TYPE: PRT
<213> ORGANISM: Artificial Sequence
<220> FEATURE:
<223> OTHER INFORMATION: IL-2 analog 3

<400> SEQUENCE: 4

Pro Thr Ser Ser Ser Thr Lys Lys Thr Gln Leu Gln Leu Glu His Leu
             1               5                  10                 15

Leu Leu Asp Leu Gln Met Ile Leu Asn Gly Ile Asn Asn Tyr Cys Asn
                            20                  25                 30

Pro Lys Leu Thr Arg Met Leu Thr Phe Lys Phe Tyr Met Pro Lys Lys
                        35                  40                 45

Ala Thr Glu Leu Lys His Leu Gln Cys Leu Glu Glu Leu Lys Pro
                50                  55                 60

Leu Glu Glu Val Leu Asn Leu Ala Gln Ser Lys Asn Phe His Leu Arg
             65                  70                 75                 80

Pro Arg Asp Leu Ile Ser Asn Ile Asn Val Ile Val Leu Glu Leu Lys
                                85                  90                 95

Gly Ser Glu Thr Thr Phe Met Cys Glu Tyr Ala Asp Glu Thr Ala Thr
                            100                 105                110

Ile Val Glu Phe Leu Asn Arg Trp Ile Thr Phe Ser Gln Ser Ile Ile
                        115                 120                125

Ser Thr Leu Thr
                    130

<210> SEQ ID NO 5
<211> LENGTH: 132
<212> TYPE: PRT
<213> ORGANISM: Artificial Sequence
<220> FEATURE:
<223> OTHER INFORMATION: IL-2 analog 4

<400> SEQUENCE: 5

Pro Thr Ser Ser Ser Thr Lys Lys Thr Gln Leu Gln Leu Glu His Leu
             1               5                  10                 15

Leu Leu Asp Leu Gln Met Ile Leu Asn Gly Ile Asn Asn Tyr Lys Asn
                            20                  25                 30
```

Pro Cys Leu Thr Arg Met Leu Thr Phe Lys Phe Tyr Met Pro Lys Lys
            35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
            115                 120                 125

Ser Thr Leu Thr
        130

<210> SEQ ID NO 6
<211> LENGTH: 132
<212> TYPE: PRT
<213> ORGANISM: Artificial Sequence
<220> FEATURE:
<223> OTHER INFORMATION: IL-2 analog 5

<400> SEQUENCE: 6

Pro Thr Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Cys Phe Tyr Met Pro Lys Lys
            35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
            115                 120                 125

Ser Thr Leu Thr
        130

<210> SEQ ID NO 7
<211> LENGTH: 132
<212> TYPE: PRT
<213> ORGANISM: Artificial Sequence
<220> FEATURE:
<223> OTHER INFORMATION: IL-2 analog 6

<400> SEQUENCE: 7

Pro Thr Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Cys Lys
            35                  40                  45

Ala Thr Glu Leu Lys His Leu Gln Cys Leu Glu Glu Glu Leu Lys Pro
    50                  55                  60

```
Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130

<210> SEQ ID NO 8
<211> LENGTH: 132
<212> TYPE: PRT
<213> ORGANISM: Artificial Sequence
<220> FEATURE:
<223> OTHER INFORMATION: IL-2 analog 7

<400> SEQUENCE: 8

Pro Thr Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
                20                  25                  30

Pro Lys Leu Thr Arg Met Leu Thr Phe Lys Phe Tyr Met Pro Lys Cys
            35                  40                  45

Ala Thr Glu Leu Lys His Leu Gln Cys Leu Glu Glu Glu Leu Lys Pro
        50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130

<210> SEQ ID NO 9
<211> LENGTH: 132
<212> TYPE: PRT
<213> ORGANISM: Artificial Sequence
<220> FEATURE:
<223> OTHER INFORMATION: IL-2 analog 9

<400> SEQUENCE: 9

Pro Thr Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
                20                  25                  30

Pro Lys Leu Thr Arg Met Leu Thr Phe Lys Phe Tyr Met Pro Lys Lys
            35                  40                  45

Ala Thr Glu Leu Lys His Leu Gln Cys Leu Glu Glu Glu Leu Lys Pro
        50                  55                  60

Leu Glu Glu Val Leu Asn Leu Ala Gln Ser Cys Asn Phe His Leu Arg
65                  70                  75                  80

Pro Arg Asp Leu Ile Ser Asn Ile Asn Val Ile Val Leu Glu Leu Lys
```

```
                     85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130

<210> SEQ ID NO 10
<211> LENGTH: 132
<212> TYPE: PRT
<213> ORGANISM: Artificial Sequence
<220> FEATURE:
<223> OTHER INFORMATION: IL-2 analog 10

<400> SEQUENCE: 10

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Ala Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130

<210> SEQ ID NO 11
<211> LENGTH: 132
<212> TYPE: PRT
<213> ORGANISM: Artificial Sequence
<220> FEATURE:
<223> OTHER INFORMATION: IL-2 analog 10

<400> SEQUENCE: 11

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Lys Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110
```

```
Ile Val Glu Phe Leu Asn Arg Trp Ile Thr Phe Ser Gln Ser Ile Ile
            115                 120                 125
Ser Thr Leu Thr
        130

<210> SEQ ID NO 12
<211> LENGTH: 132
<212> TYPE: PRT
<213> ORGANISM: Artificial Sequence
<220> FEATURE:
<223> OTHER INFORMATION: IL-2 analog 11

<400> SEQUENCE: 12

Pro Thr Ser Ser Ser Thr Lys Lys Thr Gln Leu Gln Leu Glu His Leu
1               5                   10                  15
Leu Leu Asp Leu Gln Met Ile Leu Asn Gly Ile Asn Asn Tyr Lys Asn
            20                  25                  30
Pro Lys Leu Thr Arg Met Leu Thr Ala Lys Phe Tyr Met Pro Lys Lys
        35                  40                  45
Ala Thr Glu Leu Lys His Leu Gln Cys Leu Glu Glu Glu Leu Lys Pro
    50                  55                  60
Leu Glu Glu Val Leu Asn Leu Ala Gln Ser Lys Asn Phe His Leu Arg
65                  70                  75                  80
Pro Arg Asp Leu Ile Ser Asn Ile Asn Val Ile Val Leu Glu Leu Lys
                85                  90                  95
Gly Ser Glu Thr Thr Phe Met Cys Glu Tyr Ala Asp Glu Thr Ala Thr
            100                 105                 110
Ile Val Glu Phe Leu Asn Arg Trp Ile Thr Phe Ser Gln Ser Ile Ile
            115                 120                 125
Ser Thr Leu Thr
        130

<210> SEQ ID NO 13
<211> LENGTH: 132
<212> TYPE: PRT
<213> ORGANISM: Artificial Sequence
<220> FEATURE:
<223> OTHER INFORMATION: IL-2 analog 12

<400> SEQUENCE: 13

Pro Thr Ser Ser Ser Thr Lys Lys Thr Gln Leu Gln Leu Glu His Leu
1               5                   10                  15
Leu Leu Asp Leu Gln Met Ile Leu Asn Gly Ile Asn Asn Tyr Lys Asn
            20                  25                  30
Pro Lys Leu Thr Ala Met Leu Thr Lys Lys Phe Tyr Met Pro Lys Lys
        35                  40                  45
Ala Thr Glu Leu Lys His Leu Gln Cys Leu Glu Glu Glu Leu Lys Pro
    50                  55                  60
Leu Glu Glu Val Leu Asn Leu Ala Gln Ser Lys Asn Phe His Leu Arg
65                  70                  75                  80
Pro Arg Asp Leu Ile Ser Asn Ile Asn Val Ile Val Leu Glu Leu Lys
                85                  90                  95
Gly Ser Glu Thr Thr Phe Met Cys Glu Tyr Ala Asp Glu Thr Ala Thr
            100                 105                 110
Ile Val Glu Phe Leu Asn Arg Trp Ile Thr Phe Ser Gln Ser Ile Ile
            115                 120                 125
Ser Thr Leu Thr
        130
```

<210> SEQ ID NO 14
<211> LENGTH: 132
<212> TYPE: PRT
<213> ORGANISM: Artificial Sequence
<220> FEATURE:
<223> OTHER INFORMATION: IL-2 analog 13

<400> SEQUENCE: 14

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Ala Met Leu Thr Ala Lys Phe Tyr Met Pro Lys Lys
        35                  40                  45

Ala Thr Glu Leu Lys His Leu Gln Cys Leu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130

<210> SEQ ID NO 15
<211> LENGTH: 132
<212> TYPE: PRT
<213> ORGANISM: Artificial Sequence
<220> FEATURE:
<223> OTHER INFORMATION: IL-2 analog 14

<400> SEQUENCE: 15

Pro Thr Ser Ser Ser Thr Lys Lys Thr Gln Leu Gln Leu Glu His Leu
1               5                   10                  15

Leu Tyr Asp Leu Gln Met Ile Leu Asn Gly Ile Asn Asn Tyr Lys Asn
            20                  25                  30

Pro Lys Leu Thr Ala Met Leu Thr Lys Lys Phe Tyr Met Pro Lys Lys
        35                  40                  45

Ala Thr Glu Leu Lys His Leu Gln Cys Leu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130

<210> SEQ ID NO 16
<211> LENGTH: 132
<212> TYPE: PRT

```
<213> ORGANISM: Artificial Sequence
<220> FEATURE:
<223> OTHER INFORMATION: IL-2 analog 15

<400> SEQUENCE: 16

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Ala Met Leu Thr Lys Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Glu Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130

<210> SEQ ID NO 17
<211> LENGTH: 132
<212> TYPE: PRT
<213> ORGANISM: Artificial Sequence
<220> FEATURE:
<223> OTHER INFORMATION: IL-2 analog 16

<400> SEQUENCE: 17

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Ala Met Leu Thr Lys Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Gln Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130

<210> SEQ ID NO 18
<211> LENGTH: 132
<212> TYPE: PRT
<213> ORGANISM: Artificial Sequence
<220> FEATURE:
<223> OTHER INFORMATION: IL-2 analog 17

<400> SEQUENCE: 18
```

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Ala Met Leu Thr Lys Lys Phe Tyr Met Pro Lys Lys
        35                  40                  45

Ala Thr Glu Leu Lys His Leu Gln Cys Leu Glu Gln Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Thr Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130

<210> SEQ ID NO 19
<211> LENGTH: 132
<212> TYPE: PRT
<213> ORGANISM: Artificial Sequence
<220> FEATURE:
<223> OTHER INFORMATION: IL-2 analog 18

<400> SEQUENCE: 19

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Ala Met Leu Thr Lys Lys Phe Tyr Met Pro Lys Lys
        35                  40                  45

Ala Thr Glu Leu Lys His Leu Gln Cys Leu Glu Gln Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130

<210> SEQ ID NO 20
<211> LENGTH: 132
<212> TYPE: PRT
<213> ORGANISM: Artificial Sequence
<220> FEATURE:
<223> OTHER INFORMATION: IL-2 analog 19

<400> SEQUENCE: 20

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn

```
                20                  25                  30

Pro Lys Leu Thr Ala Met Leu Thr Lys Lys Phe Tyr Met Pro Lys Lys
            35                  40                  45

Ala Thr Glu Leu Lys His Leu Gln Cys Leu Glu Glu Glu Leu Lys Pro
 50                  55                  60

Leu Glu Glu Val Leu Asn Leu Ala Gln Ser Lys Asn Phe His Leu Asp
 65                  70                  75                  80

Pro Arg Asp Leu Ile Ser Asn Ile Asn Val Phe Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
            115                 120                 125

Ser Thr Leu Thr
            130

<210> SEQ ID NO 21
<211> LENGTH: 132
<212> TYPE: PRT
<213> ORGANISM: Artificial Sequence
<220> FEATURE:
<223> OTHER INFORMATION: IL-2 analog 20

<400> SEQUENCE: 21

Pro Thr Ser Ser Ser Thr Lys Lys Thr Gln Leu Gln Leu Glu His Leu
 1               5                  10                  15

Leu Leu Asp Leu Gln Met Ile Leu Asn Gly Ile Asn Asn Tyr Lys Asn
            20                  25                  30

Pro Lys Leu Thr Ala Met Leu Thr Lys Lys Phe Tyr Met Pro Lys Lys
            35                  40                  45

Ala Thr Glu Leu Lys His Leu Gln Cys Leu Glu Glu Glu Leu Lys Pro
 50                  55                  60

Leu Glu Glu Val Leu Asn Leu Ala Gln Ser Lys Asn Phe His Leu Arg
 65                  70                  75                  80

Pro Arg Asp Val Val Ser Asn Ile Asn Val Phe Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
            115                 120                 125

Ser Thr Leu Thr
            130

<210> SEQ ID NO 22
<211> LENGTH: 132
<212> TYPE: PRT
<213> ORGANISM: Artificial Sequence
<220> FEATURE:
<223> OTHER INFORMATION: IL-2 analog 21

<400> SEQUENCE: 22

Pro Thr Ser Ser Ser Thr Lys Lys Thr Gln Leu Gln Leu Glu His Leu
 1               5                  10                  15

Leu Leu Asp Leu Gln Met Ile Leu Asn Gly Ile Asn Asn Tyr Lys Asn
            20                  25                  30

Pro Lys Leu Thr Ala Met Leu Thr Lys Lys Phe Tyr Met Pro Lys Lys
            35                  40                  45
```

Ala Thr Glu Leu Lys His Leu Gln Cys Leu Glu Glu Leu Lys Pro
 50                  55                  60

Leu Glu Glu Val Leu Asn Leu Ala Gln Ser Lys Asn Phe His Phe Asp
 65                  70                  75                  80

Pro Arg Asp Val Val Ser Asn Ile Asn Val Phe Val Leu Glu Leu Lys
                 85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130

<210> SEQ ID NO 23
<211> LENGTH: 132
<212> TYPE: PRT
<213> ORGANISM: Artificial Sequence
<220> FEATURE:
<223> OTHER INFORMATION: IL-2 analog 22

<400> SEQUENCE: 23

Pro Thr Ser Ser Ser Thr Lys Lys Thr Gln Val Gln Leu Glu His Leu
 1               5                  10                  15

Leu Leu Asp Leu Gln Met Ile Leu Asn Gly Ile Asn Asn Tyr Lys Asn
                 20                  25                  30

Pro Lys Leu Thr Ala Met Leu Thr Lys Lys Phe Tyr Met Pro Lys Lys
            35                  40                  45

Ala Thr Glu Leu Lys His Leu Gln Cys Leu Glu Glu Leu Lys Pro
 50                  55                  60

Leu Glu Glu Val Leu Asn Leu Ala Gln Ser Lys Asn Phe His Leu Arg
 65                  70                  75                  80

Pro Arg Asp Leu Ile Ser Asn Ile Asn Val Ile Val Leu Glu Leu Lys
                 85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130

<210> SEQ ID NO 24
<211> LENGTH: 132
<212> TYPE: PRT
<213> ORGANISM: Artificial Sequence
<220> FEATURE:
<223> OTHER INFORMATION: IL-2 analog 23

<400> SEQUENCE: 24

Pro Thr Ser Ser Ser Thr Lys Lys Thr Gln Phe Gln Leu Glu His Leu
 1               5                  10                  15

Leu Leu Asp Leu Gln Met Ile Leu Asn Gly Ile Asn Asn Tyr Lys Asn
                 20                  25                  30

Pro Lys Leu Thr Ala Met Leu Thr Lys Lys Phe Tyr Met Pro Lys Lys
            35                  40                  45

Ala Thr Glu Leu Lys His Leu Gln Cys Leu Glu Glu Leu Lys Pro
 50                  55                  60

Leu Glu Glu Val Leu Asn Leu Ala Gln Ser Lys Asn Phe His Leu Arg
 65                  70                  75                  80

Pro Arg Asp Leu Ile Ser Asn Ile Asn Val Ile Val Leu Glu Leu Lys
            85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
            115                 120                 125

Ser Thr Leu Thr
    130

<210> SEQ ID NO 25
<211> LENGTH: 132
<212> TYPE: PRT
<213> ORGANISM: Artificial Sequence
<220> FEATURE:
<223> OTHER INFORMATION: IL-2 analog 24

<400> SEQUENCE: 25

Pro Thr Ser Ser Ser Thr Lys Lys Thr Gln Leu Gln Leu Glu His Leu
1               5                   10                  15

Leu Val Asp Leu Gln Met Ile Leu Asn Gly Ile Asn Asn Tyr Lys Asn
            20                  25                  30

Pro Lys Leu Thr Ala Met Leu Thr Lys Lys Phe Tyr Met Pro Lys Lys
        35                  40                  45

Ala Thr Glu Leu Lys His Leu Gln Cys Leu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
            85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
            115                 120                 125

Ser Thr Leu Thr
    130

<210> SEQ ID NO 26
<211> LENGTH: 132
<212> TYPE: PRT
<213> ORGANISM: Artificial Sequence
<220> FEATURE:
<223> OTHER INFORMATION: IL-2 analog 25

<400> SEQUENCE: 26

Pro Thr Ser Ser Ser Thr Lys Lys Thr Gln Leu Gln Leu Glu His Leu
1               5                   10                  15

Leu Phe Asp Leu Gln Met Ile Leu Asn Gly Ile Asn Asn Tyr Lys Asn
            20                  25                  30

Pro Lys Leu Thr Ala Met Leu Thr Lys Lys Phe Tyr Met Pro Lys Lys
        35                  40                  45

Ala Thr Glu Leu Lys His Leu Gln Cys Leu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
            85                  90                  95

Gly Ser Glu Thr Thr Phe Met Cys Glu Tyr Ala Asp Glu Thr Ala Thr

```
                  100                 105                 110

Ile Val Glu Phe Leu Asn Arg Trp Ile Thr Phe Ser Gln Ser Ile Ile
            115                 120                 125

Ser Thr Leu Thr
        130

<210> SEQ ID NO 27
<211> LENGTH: 132
<212> TYPE: PRT
<213> ORGANISM: Artificial Sequence
<220> FEATURE:
<223> OTHER INFORMATION: IL-2 analog 26

<400> SEQUENCE: 27

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Ala Met Leu Thr Lys Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Phe Asn Val Ile Val Leu Glu Leu Lys
                85                  90                  95

Gly Ser Glu Thr Thr Phe Met Cys Glu Tyr Ala Asp Glu Thr Ala Thr
                100                 105                 110

Ile Val Glu Phe Leu Asn Arg Trp Ile Thr Phe Ser Gln Ser Ile Ile
            115                 120                 125

Ser Thr Leu Thr
        130

<210> SEQ ID NO 28
<211> LENGTH: 132
<212> TYPE: PRT
<213> ORGANISM: Artificial Sequence
<220> FEATURE:
<223> OTHER INFORMATION: IL-2 analog 27

<400> SEQUENCE: 28

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Ala Met Leu Thr Lys Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Phe Ile Val Leu Glu Leu Lys
                85                  90                  95

Gly Ser Glu Thr Thr Phe Met Cys Glu Tyr Ala Asp Glu Thr Ala Thr
                100                 105                 110

Ile Val Glu Phe Leu Asn Arg Trp Ile Thr Phe Ser Gln Ser Ile Ile
            115                 120                 125
```

Ser Thr Leu Thr
    130

<210> SEQ ID NO 29
<211> LENGTH: 132
<212> TYPE: PRT
<213> ORGANISM: Artificial Sequence
<220> FEATURE:
<223> OTHER INFORMATION: IL-2 analog 28

<400> SEQUENCE: 29

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Ala Met Leu Thr Lys Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Val Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130

<210> SEQ ID NO 30
<211> LENGTH: 132
<212> TYPE: PRT
<213> ORGANISM: Artificial Sequence
<220> FEATURE:
<223> OTHER INFORMATION: IL-2 analog 29

<400> SEQUENCE: 30

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Ala Met Leu Thr Lys Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Thr Ser Ile Ile
        115                 120                 125

Ser Thr Leu Thr
    130

<210> SEQ ID NO 31

```
<211> LENGTH: 132
<212> TYPE: PRT
<213> ORGANISM: Artificial Sequence
<220> FEATURE:
<223> OTHER INFORMATION: IL-2 analog 30

<400> SEQUENCE: 31

Pro Thr Ser Ser Ser Thr Lys Lys Thr Gln Leu Gln Leu Glu His Leu
 1               5                  10                  15

Leu Leu Asp Leu Gln Met Ile Leu Asn Gly Ile Asn Asn Tyr Lys Asn
            20                  25                  30

Pro Lys Leu Thr Ala Met Leu Thr Phe Lys Phe Tyr Met Pro Lys Lys
        35                  40                  45

Ala Thr Glu Leu Lys His Leu Gln Cys Leu Glu Glu Glu Leu Lys Pro
50                  55                  60

Leu Glu Glu Val Leu Asn Leu Ala Gln Ser Lys Asn Phe His Leu Asp
65                  70                  75                  80

Pro Arg Asp Leu Ile Ser Asn Ile Asn Val Phe Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130

<210> SEQ ID NO 32
<211> LENGTH: 132
<212> TYPE: PRT
<213> ORGANISM: Artificial Sequence
<220> FEATURE:
<223> OTHER INFORMATION: IL-2 analog 31

<400> SEQUENCE: 32

Pro Thr Ser Ser Ser Thr Lys Lys Thr Gln Leu Gln Leu Glu His Leu
 1               5                  10                  15

Leu Leu Asp Leu Gln Met Ile Leu Asn Gly Ile Asn Asn Tyr Lys Asn
            20                  25                  30

Pro Lys Leu Thr Ala Met Leu Thr Phe Lys Phe Tyr Met Pro Lys Lys
        35                  40                  45

Ala Thr Glu Leu Lys His Leu Gln Cys Leu Glu Glu Glu Leu Lys Pro
50                  55                  60

Leu Glu Glu Val Leu Asn Leu Ala Gln Ser Lys Asn Phe His Leu Arg
65                  70                  75                  80

Pro Arg Glu Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130

<210> SEQ ID NO 33
<211> LENGTH: 132
<212> TYPE: PRT
<213> ORGANISM: Artificial Sequence
<220> FEATURE:
<223> OTHER INFORMATION: IL-2 analog 32
```

```
<400> SEQUENCE: 33

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Ala Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Asp
65                  70                  75                  80

Pro Arg Glu Leu Ile Ser Asn Ile Asn Val Phe Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
            115                 120                 125

Ser Thr Leu Thr
    130

<210> SEQ ID NO 34
<211> LENGTH: 132
<212> TYPE: PRT
<213> ORGANISM: Artificial Sequence
<220> FEATURE:
<223> OTHER INFORMATION: IL-2 analog 33

<400> SEQUENCE: 34

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Ala Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Phe Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
            115                 120                 125

Ser Thr Leu Thr
    130

<210> SEQ ID NO 35
<211> LENGTH: 132
<212> TYPE: PRT
<213> ORGANISM: Artificial Sequence
<220> FEATURE:
<223> OTHER INFORMATION: IL-2 analog 34

<400> SEQUENCE: 35

Pro Thr Ser Ser Ser Thr Lys Lys Thr Gln Leu Gln Leu Glu His Leu
1               5                   10                  15
```

Leu Leu Asp Leu Gln Met Ile Leu Asn Gly Ile Asn Asn Tyr Lys Asn
            20                  25                  30

Pro Lys Leu Thr Ala Met Leu Thr Phe Lys Phe Tyr Met Pro Lys Lys
            35                  40                  45

Ala Thr Glu Leu Lys His Leu Gln Cys Leu Glu Glu Leu Lys Pro
 50                  55                  60

Leu Glu Glu Val Leu Asn Leu Ala Gln Ser Lys Asn Phe His Phe Arg
 65                  70                  75                  80

Pro Arg Glu Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
                100                 105                 110

Ile Val Glu Phe Leu Asn Arg Trp Ile Thr Phe Ser Gln Ser Ile Ile
            115                 120                 125

Ser Thr Leu Thr
    130

<210> SEQ ID NO 36
<211> LENGTH: 132
<212> TYPE: PRT
<213> ORGANISM: Artificial Sequence
<220> FEATURE:
<223> OTHER INFORMATION: IL-2 analog 35

<400> SEQUENCE: 36

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Ala Met Leu Thr Phe Lys Phe Tyr Met Pro Lys Lys
            35                  40                  45

Ala Thr Glu Leu Lys His Leu Gln Cys Leu Glu Glu Leu Lys Pro
 50                  55                  60

Leu Glu Glu Val Leu Asn Leu Ala Gln Ser Lys Asn Phe His Leu Arg
 65                  70                  75                  80

Pro Arg Asp Leu Ile Ser Asn Ile Asn Val Ile Val Phe Glu Phe Lys
                85                  90                  95

Gly Ser Glu Thr Thr Phe Met Cys Glu Tyr Ala Asp Glu Thr Ala Thr
                100                 105                 110

Ile Val Glu Phe Leu Asn Arg Trp Ile Thr Phe Ser Gln Ser Ile Ile
            115                 120                 125

Ser Thr Leu Thr
    130

<210> SEQ ID NO 37
<211> LENGTH: 132
<212> TYPE: PRT
<213> ORGANISM: Artificial Sequence
<220> FEATURE:
<223> OTHER INFORMATION: IL-2 analog 36

<400> SEQUENCE: 37

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Ala Met Leu Thr Phe Lys Phe Tyr Met Pro Lys Lys

```
                    35                  40                  45
Ala Thr Glu Leu Lys His Leu Gln Cys Leu Glu Glu Glu Leu Lys Pro
 50                      55                  60

Leu Glu Glu Val Leu Asn Leu Ala Gln Ser Lys Asn Phe His Leu Arg
 65                  70                  75                  80

Pro Arg Asp Leu Ile Ser Asn Ile Asn Val Ile Val Phe Glu Val Lys
                     85                  90                  95

Gly Ser Glu Thr Thr Phe Met Cys Glu Tyr Ala Asp Glu Thr Ala Thr
                100                 105                 110

Ile Val Glu Phe Leu Asn Arg Trp Ile Thr Phe Ser Gln Ser Ile Ile
                115                 120                 125

Ser Thr Leu Thr
    130

<210> SEQ ID NO 38
<211> LENGTH: 132
<212> TYPE: PRT
<213> ORGANISM: Artificial Sequence
<220> FEATURE:
<223> OTHER INFORMATION: IL-2 analog 37

<400> SEQUENCE: 38

Pro Thr Ser Ser Thr Lys Lys Thr Gln Leu Gln Leu Glu His Leu
  1               5                  10                  15

Leu Leu Asp Leu Gln Met Ile Leu Asn Gly Ile Asn Asn Tyr Lys Asn
                 20                  25                  30

Pro Lys Leu Thr Ala Met Leu Thr Phe Lys Phe Tyr Met Pro Lys Lys
             35                  40                  45

Ala Thr Glu Leu Lys His Leu Gln Cys Leu Glu Glu Glu Leu Lys Pro
 50                      55                  60

Leu Glu Glu Val Leu Asn Leu Ala Gln Ser Lys Asn Phe His Leu Arg
 65                  70                  75                  80

Pro Arg Asp Leu Ile Ser Asn Ile Asn Val Ile Val Phe Glu Ile Lys
                     85                  90                  95

Gly Ser Glu Thr Thr Phe Met Cys Glu Tyr Ala Asp Glu Thr Ala Thr
                100                 105                 110

Ile Val Glu Phe Leu Asn Arg Trp Ile Thr Phe Ser Gln Ser Ile Ile
                115                 120                 125

Ser Thr Leu Thr
    130

<210> SEQ ID NO 39
<211> LENGTH: 132
<212> TYPE: PRT
<213> ORGANISM: Artificial Sequence
<220> FEATURE:
<223> OTHER INFORMATION: IL-2 analog 38

<400> SEQUENCE: 39

Pro Thr Ser Ser Thr Lys Lys Thr Gln Leu Gln Leu Glu His Leu
  1               5                  10                  15

Leu Leu Asp Leu Gln Met Ile Leu Asn Gly Ile Asn Asn Tyr Lys Asn
                 20                  25                  30

Pro Lys Leu Thr Ala Met Leu Thr Lys Lys Phe Tyr Met Pro Lys Lys
             35                  40                  45

Ala Thr Glu Leu Lys His Leu Gln Cys Leu Glu Glu Glu Leu Lys Pro
 50                      55                  60
```

Leu Glu Glu Val Leu Asn Leu Ala Gln Ser Lys Asn Phe His Leu Asp
65                  70                  75                  80

Pro Arg Asp Leu Ile Ser Asn Ile Asn Val Phe Val Phe Glu Phe Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
        130

<210> SEQ ID NO 40
<211> LENGTH: 132
<212> TYPE: PRT
<213> ORGANISM: Artificial Sequence
<220> FEATURE:
<223> OTHER INFORMATION: IL-2 analog 39

<400> SEQUENCE: 40

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Ala Met Leu Thr Lys Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Asp
65                  70                  75                  80

Pro Arg Asp Leu Ile Ser Asn Ile Asn Val Phe Val Phe Glu Val Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
        130

<210> SEQ ID NO 41
<211> LENGTH: 132
<212> TYPE: PRT
<213> ORGANISM: Artificial Sequence
<220> FEATURE:
<223> OTHER INFORMATION: IL-2 analog 40

<400> SEQUENCE: 41

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Ala Met Leu Thr Lys Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Asp
65                  70                  75                  80

Pro Arg Asp Leu Ile Ser Asn Ile Asn Val Phe Val Phe Glu Ile Lys
                85                  90                  95

```
Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
            115                 120                 125

Ser Thr Leu Thr
        130

<210> SEQ ID NO 42
<211> LENGTH: 132
<212> TYPE: PRT
<213> ORGANISM: Artificial Sequence
<220> FEATURE:
<223> OTHER INFORMATION: IL-2 analog 41

<400> SEQUENCE: 42

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Leu Lys Pro
    50                  55                  60

Leu Glu Glu Val Leu Asn Leu Ala Gln Ser Lys Asn Phe His Phe Asp
65                  70                  75                  80

Pro Arg Asp Val Val Ser Asn Ile Asn Val Phe Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
            115                 120                 125

Ser Thr Leu Thr
        130

<210> SEQ ID NO 43
<211> LENGTH: 132
<212> TYPE: PRT
<213> ORGANISM: Artificial Sequence
<220> FEATURE:
<223> OTHER INFORMATION: IL-2 analog 42

<400> SEQUENCE: 43

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Ala Met Leu Thr Lys Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Glu
65                  70                  75                  80

Pro Arg Asp Leu Ile Ser Asn Ile Asn Val Phe Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
```

```
                115                 120                 125

Ser Thr Leu Thr
        130

<210> SEQ ID NO 44
<211> LENGTH: 132
<212> TYPE: PRT
<213> ORGANISM: Artificial Sequence
<220> FEATURE:
<223> OTHER INFORMATION: IL-2 analog 43

<400> SEQUENCE: 44

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Ala Met Leu Thr Lys Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Asp
65                  70                  75                  80

Pro Arg Asp Leu Ile Ser Asn Ile Asn Val Leu Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
        130

<210> SEQ ID NO 45
<211> LENGTH: 132
<212> TYPE: PRT
<213> ORGANISM: Artificial Sequence
<220> FEATURE:
<223> OTHER INFORMATION: IL-2 analog 44

<400> SEQUENCE: 45

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Ala Met Leu Thr Lys Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Asp
65                  70                  75                  80

Pro Arg Val Leu Ile Ser Asn Ile Asn Val Phe Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
        130
```

```
<210> SEQ ID NO 46
<211> LENGTH: 132
<212> TYPE: PRT
<213> ORGANISM: Artificial Sequence
<220> FEATURE:
<223> OTHER INFORMATION: IL-2 analog 45

<400> SEQUENCE: 46

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Ala Met Leu Thr Lys Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Asp
65                  70                  75                  80

Pro Arg Phe Leu Ile Ser Asn Ile Asn Val Phe Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130

<210> SEQ ID NO 47
<211> LENGTH: 132
<212> TYPE: PRT
<213> ORGANISM: Artificial Sequence
<220> FEATURE:
<223> OTHER INFORMATION: IL-2 analog 46

<400> SEQUENCE: 47

Pro Thr Ser Ser Ser Thr Lys Lys Thr Gln Leu Gln Leu Glu His Leu
1               5                   10                  15

Leu Leu Val Leu Gln Met Ile Leu Asn Gly Ile Asn Asn Tyr Lys Asn
            20                  25                  30

Pro Lys Leu Thr Ala Met Leu Thr Lys Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Asp
65                  70                  75                  80

Pro Arg Asp Leu Ile Ser Asn Ile Asn Val Phe Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130

<210> SEQ ID NO 48
<211> LENGTH: 132
<212> TYPE: PRT
<213> ORGANISM: Artificial Sequence
```

```
<220> FEATURE:
<223> OTHER INFORMATION: IL-2 analog 47

<400> SEQUENCE: 48

Pro Thr Ser Ser Ser Thr Lys Lys Thr Gln Leu Gln Leu Glu His Leu
1               5                   10                  15

Leu Leu Phe Leu Gln Met Ile Leu Asn Gly Ile Asn Asn Tyr Lys Asn
            20                  25                  30

Pro Lys Leu Thr Ala Met Leu Thr Lys Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Asp
65                  70                  75                  80

Pro Arg Asp Leu Ile Ser Asn Ile Asn Val Phe Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130

<210> SEQ ID NO 49
<211> LENGTH: 132
<212> TYPE: PRT
<213> ORGANISM: Artificial Sequence
<220> FEATURE:
<223> OTHER INFORMATION: IL-2 analog 48

<400> SEQUENCE: 49

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Ala Met Leu Thr Lys Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Asp
65                  70                  75                  80

Pro Arg Asp Leu Ile Ser Val Ile Asn Val Phe Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130

<210> SEQ ID NO 50
<211> LENGTH: 132
<212> TYPE: PRT
<213> ORGANISM: Artificial Sequence
<220> FEATURE:
<223> OTHER INFORMATION: IL-2 analog 49

<400> SEQUENCE: 50
```

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Ala Met Leu Thr Lys Lys Phe Tyr Met Pro Lys Lys
        35                  40                  45

Ala Thr Glu Leu Lys His Leu Gln Cys Leu Glu Glu Leu Lys Pro
50                  55                  60

Leu Glu Glu Val Leu Asn Leu Ala Gln Ser Lys Asn Phe His Leu Asp
65                  70                  75                  80

Pro Arg Asp Leu Ile Ser Phe Ile Asn Val Phe Val Leu Glu Leu Lys
            85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
            115                 120                 125

Ser Thr Leu Thr
        130

<210> SEQ ID NO 51
<211> LENGTH: 132
<212> TYPE: PRT
<213> ORGANISM: Artificial Sequence
<220> FEATURE:
<223> OTHER INFORMATION: IL-2 analog 50

<400> SEQUENCE: 51

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Lys Lys Phe Tyr Met Pro Lys Lys
        35                  40                  45

Ala Thr Glu Leu Lys His Leu Gln Cys Leu Glu Glu Leu Lys Pro
50                  55                  60

Leu Glu Glu Val Leu Asn Leu Ala Gln Ser Lys Asn Phe His Phe Asp
65                  70                  75                  80

Pro Arg Asp Val Val Ser Asn Ile Asn Val Phe Val Leu Glu Leu Lys
            85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
            115                 120                 125

Ser Thr Leu Thr
        130

<210> SEQ ID NO 52
<211> LENGTH: 132
<212> TYPE: PRT
<213> ORGANISM: Artificial Sequence
<220> FEATURE:
<223> OTHER INFORMATION: IL-2 analog 51

<400> SEQUENCE: 52

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

```
Pro Lys Leu Thr Arg Met Leu Thr Phe Lys Phe Tyr Met Pro Lys Lys
        35                  40                  45

Ala Thr Glu Leu Lys His Leu Gln Cys Leu Glu Gln Glu Leu Lys Pro
 50                  55                  60

Leu Glu Glu Val Leu Asn Leu Ala Gln Ser Lys Asn Phe His Leu Asp
65                  70                  75                  80

Pro Arg Asp Leu Ile Ser Asn Ile Asn Val Phe Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
            115                 120                 125

Ser Thr Leu Thr
        130

<210> SEQ ID NO 53
<211> LENGTH: 132
<212> TYPE: PRT
<213> ORGANISM: Artificial Sequence
<220> FEATURE:
<223> OTHER INFORMATION: IL-2 analog 52

<400> SEQUENCE: 53

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
                20                  25                  30

Pro Lys Leu Thr Ala Met Leu Thr Lys Lys Phe Tyr Met Pro Lys Lys
        35                  40                  45

Ala Thr Glu Leu Lys His Leu Gln Cys Leu Glu Glu Glu Leu Lys Pro
 50                  55                  60

Leu Glu Glu Val Leu Asn Leu Ala Gln Ser Lys Asn Phe His Phe Asp
65                  70                  75                  80

Pro Arg Asp Leu Ile Ser Asn Ile Asn Val Phe Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
            115                 120                 125

Ser Thr Leu Thr
        130

<210> SEQ ID NO 54
<211> LENGTH: 132
<212> TYPE: PRT
<213> ORGANISM: Artificial Sequence
<220> FEATURE:
<223> OTHER INFORMATION: IL-2 analog 53

<400> SEQUENCE: 54

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
                20                  25                  30

Pro Lys Leu Thr Ala Met Leu Thr Lys Lys Phe Tyr Met Pro Lys Lys
        35                  40                  45

Ala Thr Glu Leu Lys His Leu Gln Cys Leu Glu Glu Glu Leu Lys Pro
```

```
                50                  55                  60
Leu Glu Glu Val Leu Asn Leu Ala Gln Ser Lys Asn Phe His Phe Asp
 65                  70                  75                  80

Pro Arg Glu Leu Ile Ser Asn Ile Asn Val Phe Val Leu Glu Leu Lys
                 85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
        130

<210> SEQ ID NO 55
<211> LENGTH: 132
<212> TYPE: PRT
<213> ORGANISM: Artificial Sequence
<220> FEATURE:
<223> OTHER INFORMATION: IL-2 analog 54

<400> SEQUENCE: 55

Pro Thr Ser Ser Ser Thr Lys Lys Thr Gln Leu Gln Leu Glu His Leu
  1               5                  10                  15

Leu Leu Asp Leu Gln Met Ile Leu Asn Gly Ile Asn Asn Tyr Lys Asn
                 20                  25                  30

Pro Lys Leu Thr Ala Met Leu Thr Lys Lys Phe Tyr Met Pro Lys Lys
             35                  40                  45

Ala Thr Glu Leu Lys His Leu Gln Cys Leu Glu Glu Glu Leu Lys Pro
         50                  55                  60

Leu Glu Glu Val Leu Asn Leu Ala His Ser Lys Asn Phe His Leu Asp
 65                  70                  75                  80

Pro Arg Asp Leu Ile Ser Asn Ile Asn Val Phe Val Leu Glu Leu Lys
                 85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
        130

<210> SEQ ID NO 56
<211> LENGTH: 132
<212> TYPE: PRT
<213> ORGANISM: Artificial Sequence
<220> FEATURE:
<223> OTHER INFORMATION: IL-2 analog 55

<400> SEQUENCE: 56

Pro Thr Ser Ser Ser Thr Lys Lys Thr Gln Leu Gln Leu Glu His Leu
  1               5                  10                  15

Leu Leu Asp Leu Gln Met Ile Leu Asn Gly Ile Asn Asn Tyr Lys Asn
                 20                  25                  30

Pro Lys Leu Thr Ala Met Leu Thr Lys Lys Phe Tyr Met Pro Lys Lys
             35                  40                  45

Ala Thr Glu Leu Lys His Leu Gln Cys Leu Glu Glu Glu Leu Lys Pro
         50                  55                  60

Leu Glu Glu Val Leu Asn Leu Ala His Ser Lys Asn Phe His Phe Asp
 65                  70                  75                  80
```

-continued

Pro Arg Asp Leu Ile Ser Asn Ile Asn Val Phe Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130

<210> SEQ ID NO 57
<211> LENGTH: 132
<212> TYPE: PRT
<213> ORGANISM: Artificial Sequence
<220> FEATURE:
<223> OTHER INFORMATION: IL-2 analog 56

<400> SEQUENCE: 57

Pro Thr Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Ala Met Leu Thr Lys Lys Phe Ala Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala His Ser Lys Asn Phe His Leu Asp
65                  70                  75                  80

Pro Arg Asp Leu Ile Ser Asn Ile Asn Val Phe Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130

<210> SEQ ID NO 58
<211> LENGTH: 132
<212> TYPE: PRT
<213> ORGANISM: Artificial Sequence
<220> FEATURE:
<223> OTHER INFORMATION: IL-2 analog 57

<400> SEQUENCE: 58

Pro Thr Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Ala Met Leu Thr Lys Lys Phe Ala Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala His Ser Lys Asn Phe His Phe Asp
65                  70                  75                  80

Pro Arg Asp Leu Ile Ser Asn Ile Asn Val Phe Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
                115                 120                 125

Ser Thr Leu Thr
    130

<210> SEQ ID NO 59
<211> LENGTH: 132
<212> TYPE: PRT
<213> ORGANISM: Artificial Sequence
<220> FEATURE:
<223> OTHER INFORMATION: IL-2 analog 61

<400> SEQUENCE: 59

Pro Thr Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
                20                  25                  30

Pro Lys Leu Thr Ala Met Leu Thr Lys Lys Phe Tyr Met Pro Lys Lys
            35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Phe Asp
65                  70                  75                  80

Pro Arg Asp Ala Ala Ser Asn Ile Asn Val Phe Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
                115                 120                 125

Ser Thr Leu Thr
    130

<210> SEQ ID NO 60
<211> LENGTH: 132
<212> TYPE: PRT
<213> ORGANISM: Artificial Sequence
<220> FEATURE:
<223> OTHER INFORMATION: IL-2 analog 59

<400> SEQUENCE: 60

Pro Thr Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
                20                  25                  30

Pro Lys Leu Thr Ala Met Leu Thr Lys Lys Phe Tyr Met Pro Lys Lys
            35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Phe Asp
65                  70                  75                  80

Pro Arg Asp Ala Ala Ser Asn Ile Asn Val Tyr Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
                115                 120                 125

Ser Thr Leu Thr

130

<210> SEQ ID NO 61
<211> LENGTH: 132
<212> TYPE: PRT
<213> ORGANISM: Artificial Sequence
<220> FEATURE:
<223> OTHER INFORMATION: IL-2 analog 60

<400> SEQUENCE: 61

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Ala Met Leu Thr Lys Lys Phe Ala Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Tyr Arg
65                  70                  75                  80

Pro Arg Asp Ala Ala Ser Asn Ile Asn Val Tyr Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130

<210> SEQ ID NO 62
<211> LENGTH: 132
<212> TYPE: PRT
<213> ORGANISM: Artificial Sequence
<220> FEATURE:
<223> OTHER INFORMATION: IL-2 analog 61

<400> SEQUENCE: 62

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Ala Met Leu Thr Lys Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Tyr Asp
65                  70                  75                  80

Pro Arg Asp Gly Val Ser Asn Ile Asn Val Tyr Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130

<210> SEQ ID NO 63
<211> LENGTH: 132

<212> TYPE: PRT
<213> ORGANISM: Artificial Sequence
<220> FEATURE:
<223> OTHER INFORMATION: IL-2 analog 62

<400> SEQUENCE: 63

Pro Thr Ser Ser Ser Thr Lys Lys Thr Gln Leu Gln Leu Glu His Leu
1               5                   10                  15
Leu Leu Asp Leu Gln Met Ile Leu Asn Gly Ile Asn Asn Tyr Lys Asn
            20                  25                  30
Pro Lys Leu Thr Ala Met Leu Thr Lys Lys Phe Tyr Met Pro Lys Lys
        35                  40                  45
Ala Thr Glu Leu Lys His Leu Gln Cys Leu Glu Glu Leu Lys Pro
50                  55                  60
Leu Glu Glu Val Leu Asn Leu Ala Gln Ser Lys Asn Phe His Trp Glu
65                  70                  75                  80
Pro Arg Asp Gly Ala Ser Asn Ile Asn Val Phe Val Leu Glu Leu Lys
                85                  90                  95
Gly Ser Glu Thr Thr Phe Met Cys Glu Tyr Ala Asp Glu Thr Ala Thr
            100                 105                 110
Ile Val Glu Phe Leu Asn Arg Trp Ile Thr Phe Ser Gln Ser Ile Ile
        115                 120                 125
Ser Thr Leu Thr
    130

<210> SEQ ID NO 64
<211> LENGTH: 132
<212> TYPE: PRT
<213> ORGANISM: Artificial Sequence
<220> FEATURE:
<223> OTHER INFORMATION: IL-2 analog 63

<400> SEQUENCE: 64

Pro Thr Ser Ser Ser Thr Lys Lys Thr Gln Leu Gln Leu Glu His Leu
1               5                   10                  15
Leu Leu Asp Leu Gln Met Ile Leu Asn Gly Ile Asn Asn Tyr Lys Asn
            20                  25                  30
Pro Lys Leu Thr Ala Met Leu Thr Lys Lys Phe Tyr Met Pro Lys Lys
        35                  40                  45
Ala Thr Glu Leu Lys His Leu Gln Cys Leu Glu Glu Leu Lys Pro
50                  55                  60
Leu Glu Glu Val Leu Asn Leu Ala Gln Ser Lys Asn Phe His Asp Glu
65                  70                  75                  80
Pro Arg Asp Thr Gly Ser Asn Ile Asn Val Phe Val Leu Glu Leu Lys
                85                  90                  95
Gly Ser Glu Thr Thr Phe Met Cys Glu Tyr Ala Asp Glu Thr Ala Thr
            100                 105                 110
Ile Val Glu Phe Leu Asn Arg Trp Ile Thr Phe Ser Gln Ser Ile Ile
        115                 120                 125
Ser Thr Leu Thr
    130

<210> SEQ ID NO 65
<211> LENGTH: 132
<212> TYPE: PRT
<213> ORGANISM: Artificial Sequence
<220> FEATURE:
<223> OTHER INFORMATION: IL-2 analog 64

<400> SEQUENCE: 65

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Ala Met Leu Thr Lys Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Tyr Asn
65                  70                  75                  80

Pro Arg Asp Val Val Ser Asn Ile Asn Val Tyr Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130

<210> SEQ ID NO 66
<211> LENGTH: 132
<212> TYPE: PRT
<213> ORGANISM: Artificial Sequence
<220> FEATURE:
<223> OTHER INFORMATION: IL-2 analog 65

<400> SEQUENCE: 66

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Ala Met Leu Thr Lys Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Tyr Glu
65                  70                  75                  80

Pro Arg Asp Val Val Ser Asn Ile Asn Val Phe Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130

<210> SEQ ID NO 67
<211> LENGTH: 132
<212> TYPE: PRT
<213> ORGANISM: Artificial Sequence
<220> FEATURE:
<223> OTHER INFORMATION: IL-2 analog 66

<400> SEQUENCE: 67

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Ala Met Leu Thr Lys Lys Phe Tyr Met Pro Lys Lys
            35                  40                  45

Ala Thr Glu Leu Lys His Leu Gln Cys Leu Glu Glu Glu Leu Lys Pro
 50                  55                  60

Leu Glu Glu Val Leu Asn Leu Ala Gln Ser Lys Asn Phe His Phe Glu
 65                  70                  75                  80

Pro Arg Asp Phe Val Ser Asn Ile Asn Val Phe Val Leu Glu Leu Lys
            85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
            115                 120                 125

Ser Thr Leu Thr
            130

<210> SEQ ID NO 68
<211> LENGTH: 132
<212> TYPE: PRT
<213> ORGANISM: Artificial Sequence
<220> FEATURE:
<223> OTHER INFORMATION: IL-2 analog 67

<400> SEQUENCE: 68

Pro Thr Ser Ser Ser Thr Lys Lys Thr Gln Leu Gln Leu Glu His Leu
 1                   5                  10                  15

Leu Leu Asp Leu Gln Met Ile Leu Asn Gly Ile Asn Asn Tyr Lys Asn
            20                  25                  30

Pro Lys Leu Thr Ala Met Leu Thr Lys Lys Phe Tyr Met Pro Lys Lys
            35                  40                  45

Ala Thr Glu Leu Lys His Leu Gln Cys Leu Glu Glu Glu Leu Lys Pro
 50                  55                  60

Leu Glu Glu Val Leu Asn Leu Ala Gln Ser Lys Asn Phe His Tyr Asp
 65                  70                  75                  80

Pro Arg Asp Phe Val Ser Asn Ile Asn Val Trp Val Leu Asp Leu Lys
            85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
            115                 120                 125

Ser Thr Leu Thr
            130

<210> SEQ ID NO 69
<211> LENGTH: 132
<212> TYPE: PRT
<213> ORGANISM: Artificial Sequence
<220> FEATURE:
<223> OTHER INFORMATION: IL-2 analog 68

<400> SEQUENCE: 69

Pro Thr Ser Ser Ser Thr Lys Lys Thr Gln Leu Gln Leu Glu His Leu
 1                   5                  10                  15

Leu Leu Asp Leu Gln Met Ile Leu Asn Gly Ile Asn Asn Tyr Lys Asn
            20                  25                  30

Pro Lys Leu Thr Ala Met Leu Thr Lys Lys Phe Tyr Met Pro Lys Lys
            35                  40                  45

Ala Thr Glu Leu Lys His Leu Gln Cys Leu Glu Glu Glu Leu Lys Pro
        50                  55                  60

Leu Glu Glu Val Leu Asn Leu Ala Gln Ser Lys Asn Phe His Phe Glu
65                  70                  75                  80

Pro Arg Asp Ile Val Ser Asn Ile Asn Glu Phe Val Leu Glu Leu Lys
                85                  90                  95

Gly Ser Glu Thr Thr Phe Met Cys Glu Tyr Ala Asp Glu Thr Ala Thr
                100                 105                 110

Ile Val Glu Phe Leu Asn Arg Trp Ile Thr Phe Ser Gln Ser Ile Ile
            115                 120                 125

Ser Thr Leu Thr
        130

<210> SEQ ID NO 70
<211> LENGTH: 132
<212> TYPE: PRT
<213> ORGANISM: Artificial Sequence
<220> FEATURE:
<223> OTHER INFORMATION: IL-2 analog 69

<400> SEQUENCE: 70

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Ala Met Leu Thr Lys Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Tyr Glu
65                  70                  75                  80

Pro Arg Asp Phe Leu Ser Asn Ile Asn Glu Trp Val Leu Asp Leu Lys
                85                  90                  95

Gly Ser Glu Thr Thr Phe Met Cys Glu Tyr Ala Asp Glu Thr Ala Thr
                100                 105                 110

Ile Val Glu Phe Leu Asn Arg Trp Ile Thr Phe Ser Gln Ser Ile Ile
            115                 120                 125

Ser Thr Leu Thr
        130

<210> SEQ ID NO 71
<211> LENGTH: 132
<212> TYPE: PRT
<213> ORGANISM: Artificial Sequence
<220> FEATURE:
<223> OTHER INFORMATION: IL-2 analog 70

<400> SEQUENCE: 71

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Ala Met Leu Thr Lys Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Tyr Asp 65                  70                  75                  80

Pro Arg Asp Val Val Ser Asn Ile Asn Val Phe Val Leu Glu Leu Lys
                    85                  90                  95

Gly Ser Glu Thr Thr Phe Met Cys Glu Tyr Ala Asp Glu Thr Ala Thr
                    100                 105                 110

Ile Val Glu Phe Leu Asn Arg Trp Ile Thr Phe Ser Gln Ser Ile Ile
                    115                 120                 125

Ser Thr Leu Thr
            130

<210> SEQ ID NO 72
<211> LENGTH: 132
<212> TYPE: PRT
<213> ORGANISM: Artificial Sequence
<220> FEATURE:
<223> OTHER INFORMATION: IL-2 analog 71

<400> SEQUENCE: 72

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
                20                  25                  30

Pro Lys Leu Thr Ala Met Leu Thr Lys Lys Phe Tyr Met Pro Lys Lys
            35                  40                  45

Ala Thr Glu Leu Lys His Leu Gln Cys Leu Glu Glu Glu Leu Lys Pro
        50                  55                  60

Leu Glu Glu Val Leu Asn Leu Ala Gln Ser Lys Asn Phe His Phe Glu
65                  70                  75                  80

Pro Arg Asp Val Val Ser Asn Ile Asn Val Phe Val Leu Glu Leu Lys
                    85                  90                  95

Gly Ser Glu Thr Thr Phe Met Cys Glu Tyr Ala Asp Glu Thr Ala Thr
                    100                 105                 110

Ile Val Glu Phe Leu Asn Arg Trp Ile Thr Phe Ser Gln Ser Ile Ile
                    115                 120                 125

Ser Thr Leu Thr
            130

<210> SEQ ID NO 73
<211> LENGTH: 132
<212> TYPE: PRT
<213> ORGANISM: Artificial Sequence
<220> FEATURE:
<223> OTHER INFORMATION: IL-2 analog 72

<400> SEQUENCE: 73

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
                20                  25                  30

Pro Lys Leu Thr Ala Met Leu Thr Lys Lys Phe Tyr Met Pro Lys Lys
            35                  40                  45

Ala Thr Glu Leu Lys His Leu Gln Cys Leu Glu Glu Glu Leu Lys Pro
        50                  55                  60

Leu Glu Glu Val Leu Asn Leu Ala Gln Ser Lys Asn Phe His Phe Asp
65                  70                  75                  80

Pro Arg Asp Val Gly Ser Asn Ile Asn Val Phe Val Leu Glu Leu Lys
                    85                  90                  95

```
Gly Ser Glu Thr Thr Phe Met Cys Glu Tyr Ala Asp Glu Thr Ala Thr
                100                 105                 110

Ile Val Glu Phe Leu Asn Arg Trp Ile Thr Phe Ser Gln Ser Ile Ile
            115                 120                 125

Ser Thr Leu Thr
        130

<210> SEQ ID NO 74
<211> LENGTH: 132
<212> TYPE: PRT
<213> ORGANISM: Artificial Sequence
<220> FEATURE:
<223> OTHER INFORMATION: IL-2 analog 73

<400> SEQUENCE: 74

Pro Thr Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Ala Met Leu Thr Lys Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Phe Asp
65                  70                  75                  80

Pro Arg Asp Trp Val Ser Asn Ile Asn Val Phe Val Leu Glu Leu Lys
                85                  90                  95

Gly Ser Glu Thr Thr Phe Met Cys Glu Tyr Ala Asp Glu Thr Ala Thr
                100                 105                 110

Ile Val Glu Phe Leu Asn Arg Trp Ile Thr Phe Ser Gln Ser Ile Ile
            115                 120                 125

Ser Thr Leu Thr
        130

<210> SEQ ID NO 75
<211> LENGTH: 132
<212> TYPE: PRT
<213> ORGANISM: Artificial Sequence
<220> FEATURE:
<223> OTHER INFORMATION: IL-2 analog 74

<400> SEQUENCE: 75

Pro Thr Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Asp Met Leu Thr Lys Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Tyr Asp
65                  70                  75                  80

Pro Arg Asp Val Val Ser Asn Ile Asn Val Phe Val Leu Glu Leu Lys
                85                  90                  95

Gly Ser Glu Thr Thr Phe Met Cys Glu Tyr Ala Asp Glu Thr Ala Thr
                100                 105                 110

Ile Val Glu Phe Leu Asn Arg Trp Ile Thr Phe Ser Gln Ser Ile Ile
            115                 120                 125
```

Ser Thr Leu Thr
    130

<210> SEQ ID NO 76
<211> LENGTH: 132
<212> TYPE: PRT
<213> ORGANISM: Artificial Sequence
<220> FEATURE:
<223> OTHER INFORMATION: IL-2 analog 75

<400> SEQUENCE: 76

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Ala Met Leu Thr Lys Lys Phe Ala Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Phe Glu
65                  70                  75                  80

Pro Arg Asp Val Val Ser Asn Ile Asn Val Phe Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130

<210> SEQ ID NO 77
<211> LENGTH: 132
<212> TYPE: PRT
<213> ORGANISM: Artificial Sequence
<220> FEATURE:
<223> OTHER INFORMATION: IL-2 analog 76

<400> SEQUENCE: 77

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Ala Met Leu Thr Lys Gln Phe Tyr Met Pro Lys Lys
        35                  40                  45

Ala Thr Glu Leu Lys His Leu Gln Cys Leu Glu Arg Glu Leu Lys Pro
    50                  55                  60

Leu Glu Glu Val Leu Asn Leu Ala Gln Ser Lys Asn Phe His Phe Asp
65                  70                  75                  80

Pro Arg Asp Val Gly Ser Asn Ile Asn Val Phe Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130

```
<210> SEQ ID NO 78
<211> LENGTH: 132
<212> TYPE: PRT
<213> ORGANISM: Artificial Sequence
<220> FEATURE:
<223> OTHER INFORMATION: IL-2 analog 77

<400> SEQUENCE: 78

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Ala Met Leu Thr Lys Glu Phe Tyr Met Pro Lys Lys
        35                  40                  45

Ala Thr Glu Leu Lys His Leu Gln Cys Leu Glu Arg Glu Leu Lys Pro
    50                  55                  60

Leu Glu Glu Val Leu Asn Leu Ala Gln Ser Lys Asn Phe His Phe Asp
65                  70                  75                  80

Pro Arg Asp Trp Val Ser Asn Ile Asn Val Phe Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130

<210> SEQ ID NO 79
<211> LENGTH: 132
<212> TYPE: PRT
<213> ORGANISM: Artificial Sequence
<220> FEATURE:
<223> OTHER INFORMATION: IL-2 analog 78

<400> SEQUENCE: 79

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Glu Leu Thr Ala Met Leu Thr Lys Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Phe Glu
65                  70                  75                  80

Pro Arg Asp Val Val Ser Asn Ile Asn Val Phe Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130

<210> SEQ ID NO 80
<211> LENGTH: 132
<212> TYPE: PRT
<213> ORGANISM: Artificial Sequence
<220> FEATURE:
```

<223> OTHER INFORMATION: IL-2 analog 79

<400> SEQUENCE: 80

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Glu Leu Thr Ala Met Leu Thr Lys Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala His Ser Lys Asn Phe His Phe Glu
65                  70                  75                  80

Pro Arg Asp Val Val Ser Asn Ile Asn Val Phe Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130

<210> SEQ ID NO 81
<211> LENGTH: 132
<212> TYPE: PRT
<213> ORGANISM: Artificial Sequence
<220> FEATURE:
<223> OTHER INFORMATION: IL-2 analog 80

<400> SEQUENCE: 81

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Glu Leu Thr Ala Met Leu Thr Lys Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala His Ser Lys Asn Phe His Phe Glu
65                  70                  75                  80

Gly Arg Asp Val Val Ser Asn Ile Asn Val Phe Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130

<210> SEQ ID NO 82
<211> LENGTH: 132
<212> TYPE: PRT
<213> ORGANISM: Artificial Sequence
<220> FEATURE:
<223> OTHER INFORMATION: IL-2 analog 81

<400> SEQUENCE: 82

Pro Thr Ser Ser Ser Thr Lys Lys Thr Gln Leu Gln Leu Glu His Leu

```
                1               5                    10                  15
Leu Leu Asp Leu Gln Met Ile Leu Asn Gly Ile Asn Asn Tyr Lys Asn
                20                  25                  30

Pro Glu Leu Thr Ala Met Leu Thr Lys Lys Phe Tyr Met Pro Lys Lys
                35                  40                  45

Ala Thr Glu Leu Lys His Leu Gln Cys Leu Glu Glu Glu Leu Lys Pro
     50                  55                  60

Leu Glu Glu Val Leu Asn Leu Ala His Ser Lys Asn Phe His Phe Glu
 65                  70                  75                  80

Val Arg Asp Val Val Ser Asn Ile Asn Val Phe Val Leu Glu Leu Lys
                85                  90                  95

Gly Ser Glu Thr Thr Phe Met Cys Glu Tyr Ala Asp Glu Thr Ala Thr
                100                 105                 110

Ile Val Glu Phe Leu Asn Arg Trp Ile Thr Phe Ser Gln Ser Ile Ile
                115                 120                 125

Ser Thr Leu Thr
        130
```

<210> SEQ ID NO 83
<211> LENGTH: 132
<212> TYPE: PRT
<213> ORGANISM: Artificial Sequence
<220> FEATURE:
<223> OTHER INFORMATION: IL-2 analog 82

<400> SEQUENCE: 83

```
Pro Thr Ser Ser Thr Lys Lys Thr Gln Leu Gln Leu Glu His Leu
 1               5                    10                  15

Arg Leu Asp Leu Glu Met Ile Leu Asn Gly Ile Asn Asn Tyr Lys Asn
                20                  25                  30

Pro Lys Leu Thr Arg Met Leu Thr Phe Lys Phe Tyr Met Pro Lys Lys
                35                  40                  45

Ala Thr Glu Leu Lys His Leu Gln Cys Leu Glu Glu Glu Leu Lys Pro
     50                  55                  60

Leu Glu Glu Val Leu Asn Leu Ala Gln Ser Lys Asn Phe His Phe Asp
 65                  70                  75                  80

Pro Arg Asp Glu Val Ser Asn Ile Asn Val Phe Val Leu Glu Leu Lys
                85                  90                  95

Gly Ser Glu Thr Thr Phe Met Cys Glu Tyr Ala Asp Glu Thr Ala Thr
                100                 105                 110

Ile Val Glu Phe Leu Asn Arg Trp Ile Thr Phe Ser Gln Ser Ile Ile
                115                 120                 125

Ser Thr Leu Thr
        130
```

<210> SEQ ID NO 84
<211> LENGTH: 132
<212> TYPE: PRT
<213> ORGANISM: Artificial Sequence
<220> FEATURE:
<223> OTHER INFORMATION: IL-2 analog 83

<400> SEQUENCE: 84

```
Pro Thr Ser Ser Thr Lys Lys Thr Gln Leu Gln Leu Glu His Leu
 1               5                    10                  15

Arg Arg Asp Leu Glu Met Ile Leu Asn Gly Ile Asn Asn Tyr Lys Asn
                20                  25                  30
```

Pro Lys Leu Thr Arg Met Leu Thr Phe Lys Phe Tyr Met Pro Lys Lys
                35                  40                  45

Ala Thr Glu Leu Lys His Leu Gln Cys Leu Glu Glu Glu Leu Lys Pro
        50                  55                  60

Leu Glu Glu Val Leu Asn Leu Ala Gln Ser Lys Asn Phe His Phe Asp
65                  70                  75                  80

Pro Arg Asp Glu Val Ser Asn Ile Asn Val Phe Val Leu Glu Leu Lys
                85                  90                  95

Gly Ser Glu Thr Thr Phe Met Cys Glu Tyr Ala Asp Glu Thr Ala Thr
                100                 105                 110

Ile Val Glu Phe Leu Asn Arg Trp Ile Thr Phe Ser Gln Ser Ile Ile
            115                 120                 125

Ser Thr Leu Thr
            130

<210> SEQ ID NO 85
<211> LENGTH: 132
<212> TYPE: PRT
<213> ORGANISM: Artificial Sequence
<220> FEATURE:
<223> OTHER INFORMATION: IL-2 analog 84

<400> SEQUENCE: 85

Pro Thr Ser Ser Thr Lys Lys Thr Gln Leu Gln Leu Glu His Leu
1               5                   10                  15

Arg Leu Asp Leu Glu Met Ile Leu Asn Gly Ile Asn Asn Tyr Lys Asn
                20                  25                  30

Pro Lys Leu Thr Arg Met Leu Thr Phe Lys Phe Tyr Met Pro Lys Lys
                35                  40                  45

Ala Thr Glu Leu Lys His Leu Gln Cys Leu Glu Glu Glu Leu Lys Pro
        50                  55                  60

Leu Glu Glu Val Leu Asn Leu Ala Gln Ser Lys Asn Phe His Val Asp
65                  70                  75                  80

Pro Arg Asp Glu Val Ser Asn Ile Asn Val Phe Val Leu Glu Leu Lys
                85                  90                  95

Gly Ser Glu Thr Thr Phe Met Cys Glu Tyr Ala Asp Glu Thr Ala Thr
                100                 105                 110

Ile Val Glu Phe Leu Asn Arg Trp Ile Thr Phe Ser Gln Ser Ile Ile
            115                 120                 125

Ser Thr Leu Thr
            130

<210> SEQ ID NO 86
<211> LENGTH: 132
<212> TYPE: PRT
<213> ORGANISM: Artificial Sequence
<220> FEATURE:
<223> OTHER INFORMATION: IL-2 analog 85

<400> SEQUENCE: 86

Pro Thr Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
                20                  25                  30

Pro Lys Leu Thr Arg Met Leu Thr Phe Lys Phe Tyr Met Pro Lys Lys
                35                  40                  45

Ala Thr Glu Leu Lys His Leu Gln Cys Leu Glu Glu Glu Leu Lys Pro
        50                  55                  60

```
Leu Glu Glu Val Leu Asn Leu Ala Gln Ser Lys Asn Phe His Phe Glu
 65                  70                  75                  80

Pro Arg Asp Val Val Ser Asn Ile Asn Val Phe Val Leu Glu Leu Lys
                 85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130

<210> SEQ ID NO 87
<211> LENGTH: 132
<212> TYPE: PRT
<213> ORGANISM: Artificial Sequence
<220> FEATURE:
<223> OTHER INFORMATION: IL-2 analog 86

<400> SEQUENCE: 87

Pro Thr Ser Ser Ser Thr Lys Lys Thr Gln Leu Gln Leu Glu His Leu
1               5                   10                  15

Arg Leu Asp Leu Glu Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Phe Glu
 65                  70                  75                  80

Pro Arg Asp Val Val Ser Asn Ile Asn Val Phe Val Leu Glu Leu Lys
                 85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130

<210> SEQ ID NO 88
<211> LENGTH: 132
<212> TYPE: PRT
<213> ORGANISM: Artificial Sequence
<220> FEATURE:
<223> OTHER INFORMATION: IL-2 analog 87

<400> SEQUENCE: 88

Pro Thr Ser Ser Ser Thr Lys Lys Thr Gln Leu Gln Leu Glu His Leu
1               5                   10                  15

Arg Arg Asp Leu Glu Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Phe Glu
 65                  70                  75                  80

Pro Arg Asp Val Val Ser Asn Ile Asn Val Phe Val Leu Glu Leu Lys
```

```
                    85                  90                  95

Gly Ser Glu Thr Thr Phe Met Cys Glu Tyr Ala Asp Glu Thr Ala Thr
                100                 105                 110

Ile Val Glu Phe Leu Asn Arg Trp Ile Thr Phe Ser Gln Ser Ile Ile
            115                 120                 125

Ser Thr Leu Thr
        130

<210> SEQ ID NO 89
<211> LENGTH: 132
<212> TYPE: PRT
<213> ORGANISM: Artificial Sequence
<220> FEATURE:
<223> OTHER INFORMATION: IL-2 analog 88

<400> SEQUENCE: 89

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Asp Glu Leu Lys Pro
    50                  55                  60

Leu Glu Glu Val Leu Asn Leu Ala Gln Ser Lys Asn Phe His Phe Glu
65                  70                  75                  80

Pro Arg Asp Val Val Ser Asn Ile Asn Val Phe Val Leu Glu Leu Lys
                85                  90                  95

Gly Ser Glu Thr Thr Phe Met Cys Glu Tyr Ala Asp Glu Thr Ala Thr
                100                 105                 110

Ile Val Glu Phe Leu Asn Arg Trp Ile Thr Phe Ser Gln Ser Ile Ile
            115                 120                 125

Ser Thr Leu Thr
        130

<210> SEQ ID NO 90
<211> LENGTH: 132
<212> TYPE: PRT
<213> ORGANISM: Artificial Sequence
<220> FEATURE:
<223> OTHER INFORMATION: IL-2 analog 89

<400> SEQUENCE: 90

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Ala Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Gln Val Leu Asn Leu Ala Gln Ser Lys Asn Phe His Phe Glu
65                  70                  75                  80

Pro Arg Asp Val Val Ser Asn Ile Asn Val Phe Val Leu Glu Leu Lys
                85                  90                  95

Gly Ser Glu Thr Thr Phe Met Cys Glu Tyr Ala Asp Glu Thr Ala Thr
                100                 105                 110
```

```
Ile Val Glu Phe Leu Asn Arg Trp Ile Thr Phe Ser Gln Ser Ile Ile
            115                 120                 125
Ser Thr Leu Thr
        130

<210> SEQ ID NO 91
<211> LENGTH: 132
<212> TYPE: PRT
<213> ORGANISM: Artificial Sequence
<220> FEATURE:
<223> OTHER INFORMATION: IL-2 analog 90

<400> SEQUENCE: 91

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Trp Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Phe Glu
65                  70                  75                  80

Pro Arg Asp Val Val Ser Asn Ile Asn Val Phe Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
            115                 120                 125

Ser Thr Leu Thr
        130

<210> SEQ ID NO 92
<211> LENGTH: 132
<212> TYPE: PRT
<213> ORGANISM: Artificial Sequence
<220> FEATURE:
<223> OTHER INFORMATION: IL-2 analog 91

<400> SEQUENCE: 92

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Gln Glu Leu Lys Pro
    50                  55                  60

Leu Glu Glu Val Leu Asn Leu Ala Gln Ser Lys Asn Phe His Phe Glu
65                  70                  75                  80

Pro Arg Asp Val Val Ser Asn Ile Asn Val Phe Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
            115                 120                 125

Ser Thr Leu Thr
        130
```

<210> SEQ ID NO 93
<211> LENGTH: 132
<212> TYPE: PRT
<213> ORGANISM: Artificial Sequence
<220> FEATURE:
<223> OTHER INFORMATION: IL-2 analog 92

<400> SEQUENCE: 93

```
Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Leu Lys Pro
    50                  55                  60

Leu Glu Glu Val Leu Asn Leu Ala Gln Ser Lys Asn Phe His Phe Glu
65                  70                  75                  80

Pro Arg Asp Val Val Ser Asn Ile Asn Thr Phe Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130
```

<210> SEQ ID NO 94
<211> LENGTH: 132
<212> TYPE: PRT
<213> ORGANISM: Artificial Sequence
<220> FEATURE:
<223> OTHER INFORMATION: IL-2 analog 93

<400> SEQUENCE: 94

```
Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Leu Lys Pro
    50                  55                  60

Leu Glu Glu Val Leu Asn Leu Ala Gln Ser Lys Asn Phe His Phe Glu
65                  70                  75                  80

Pro Arg Glu Val Val Ser Asn Ile Asn Thr Phe Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130
```

<210> SEQ ID NO 95
<211> LENGTH: 132
<212> TYPE: PRT

```
<213> ORGANISM: Artificial Sequence
<220> FEATURE:
<223> OTHER INFORMATION: IL-2 analog 94

<400> SEQUENCE: 95

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Phe Glu
65                  70                  75                  80

Pro Arg Asp Val Val Ser Asn Ile Asn Val Phe Val Phe Glu Phe Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130

<210> SEQ ID NO 96
<211> LENGTH: 132
<212> TYPE: PRT
<213> ORGANISM: Artificial Sequence
<220> FEATURE:
<223> OTHER INFORMATION: IL-2 analog 95

<400> SEQUENCE: 96

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Gly Leu Asn Leu Ala Gln Ser Lys Asn Phe His Phe Glu
65                  70                  75                  80

Pro Arg Asp Val Val Ser Asn Ile Asn Val Phe Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130

<210> SEQ ID NO 97
<211> LENGTH: 132
<212> TYPE: PRT
<213> ORGANISM: Artificial Sequence
<220> FEATURE:
<223> OTHER INFORMATION: IL-2 analog 96

<400> SEQUENCE: 97
```

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
50                  55                  60

Leu Glu Glu Gly Leu Asn Leu Ala Ala Ser Lys Asn Phe His Phe Glu
65                  70                  75                  80

Pro Arg Asp Val Val Ser Asn Ile Asn Val Phe Val Leu Glu Leu Lys
                85                  90                  95

Gly Ser Glu Thr Thr Phe Met Cys Glu Tyr Ala Asp Glu Thr Ala Thr
                100                 105                 110

Ile Val Glu Phe Leu Asn Arg Trp Ile Thr Phe Ser Gln Ser Ile Ile
            115                 120                 125

Ser Thr Leu Thr
        130

<210> SEQ ID NO 98
<211> LENGTH: 132
<212> TYPE: PRT
<213> ORGANISM: Artificial Sequence
<220> FEATURE:
<223> OTHER INFORMATION: IL-2 analog 97

<400> SEQUENCE: 98

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Ala Met Leu Thr Phe Lys Phe Tyr Met Pro Lys Lys
        35                  40                  45

Ala Thr Glu Leu Lys His Leu Gln Cys Leu Glu Glu Glu Leu Lys Pro
50                  55                  60

Leu Glu Glu Val Leu Asn Leu Ala Gln Ser Lys Asn Phe His Phe Asp
65                  70                  75                  80

Pro Arg Asp Leu Ile Ser Asn Ile Asn Val Phe Val Leu Glu Leu Lys
                85                  90                  95

Gly Ser Glu Thr Thr Phe Met Cys Glu Tyr Ala Asp Glu Thr Ala Thr
                100                 105                 110

Ile Val Glu Phe Leu Asn Arg Trp Ile Thr Phe Ser Gln Ser Ile Ile
            115                 120                 125

Ser Thr Leu Thr
        130

<210> SEQ ID NO 99
<211> LENGTH: 132
<212> TYPE: PRT
<213> ORGANISM: Artificial Sequence
<220> FEATURE:
<223> OTHER INFORMATION: IL-2 analog 98

<400> SEQUENCE: 99

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn

```
                  20                  25                  30

Pro Lys Leu Thr Ala Met Leu Thr Phe Lys Phe Tyr Met Pro Lys Lys
            35                  40                  45

Ala Thr Glu Leu Lys His Leu Gln Cys Leu Glu Glu Glu Leu Lys Pro
        50                  55                  60

Leu Glu Glu Val Leu Asn Leu Ala Gln Ser Lys Asn Phe His Phe Glu
65                  70                  75                  80

Pro Arg Asp Val Ile Ser Asn Ile Asn Val Phe Val Leu Glu Leu Lys
                85                  90                  95

Gly Ser Glu Thr Thr Phe Met Cys Glu Tyr Ala Asp Glu Thr Ala Thr
                100                 105                 110

Ile Val Glu Phe Leu Asn Arg Trp Ile Thr Phe Ser Gln Ser Ile Ile
            115                 120                 125

Ser Thr Leu Thr
        130

<210> SEQ ID NO 100
<211> LENGTH: 132
<212> TYPE: PRT
<213> ORGANISM: Artificial Sequence
<220> FEATURE:
<223> OTHER INFORMATION: IL-2 analog 99

<400> SEQUENCE: 100

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Ala Met Leu Thr Phe Lys Phe Tyr Met Pro Lys Lys
            35                  40                  45

Ala Thr Glu Leu Lys His Leu Gln Cys Leu Glu Glu Glu Leu Lys Pro
        50                  55                  60

Leu Glu Glu Val Leu Asn Leu Ala Gln Ser Lys Asn Phe His Phe Glu
65                  70                  75                  80

Pro Arg Asp Leu Val Ser Asn Ile Asn Val Phe Val Leu Glu Leu Lys
                85                  90                  95

Gly Ser Glu Thr Thr Phe Met Cys Glu Tyr Ala Asp Glu Thr Ala Thr
                100                 105                 110

Ile Val Glu Phe Leu Asn Arg Trp Ile Thr Phe Ser Gln Ser Ile Ile
            115                 120                 125

Ser Thr Leu Thr
        130

<210> SEQ ID NO 101
<211> LENGTH: 132
<212> TYPE: PRT
<213> ORGANISM: Artificial Sequence
<220> FEATURE:
<223> OTHER INFORMATION: IL-2 analog 100

<400> SEQUENCE: 101

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
            35                  40                  45
```

```
Ala Thr Glu Leu Lys His Leu Gln Cys Leu Glu Glu Leu Lys Pro
    50                  55                  60

Leu Glu Glu Val Leu Asn Leu Ala Gln Ser Lys Asn Phe His Phe Glu
 65                  70                  75                  80

Pro Arg Asp Tyr Val Ser Asn Ile Asn Val Phe Val Leu Glu Leu Lys
                 85                  90                  95

Gly Ser Glu Thr Thr Phe Met Cys Glu Tyr Ala Asp Glu Thr Ala Thr
                100                 105                 110

Ile Val Glu Phe Leu Asn Arg Trp Ile Thr Phe Ser Gln Ser Ile Ile
                115                 120                 125

Ser Thr Leu Thr
    130

<210> SEQ ID NO 102
<211> LENGTH: 132
<212> TYPE: PRT
<213> ORGANISM: Artificial Sequence
<220> FEATURE:
<223> OTHER INFORMATION: IL-2 analog 101

<400> SEQUENCE: 102

Pro Thr Ser Ser Ser Thr Lys Lys Thr Gln Leu Gln Leu Glu His Leu
  1               5                  10                  15

Leu Leu Asp Leu Gln Met Ile Leu Asn Gly Ile Asn Asn Tyr Lys Asn
                 20                  25                  30

Pro Lys Leu Thr Arg Met Leu Thr Phe Lys Phe Tyr Met Pro Lys Lys
                 35                  40                  45

Ala Thr Glu Leu Lys His Leu Gln Cys Leu Glu Glu Leu Lys Pro
    50                  55                  60

Leu Glu Glu Val Leu Asn Leu Ala Gln Ser Lys Asn Phe His Phe Glu
 65                  70                  75                  80

Pro Arg Asp Leu Ala Ser Asn Ile Asn Val Phe Val Leu Glu Leu Lys
                 85                  90                  95

Gly Ser Glu Thr Thr Phe Met Cys Glu Tyr Ala Asp Glu Thr Ala Thr
                100                 105                 110

Ile Val Glu Phe Leu Asn Arg Trp Ile Thr Phe Ser Gln Ser Ile Ile
                115                 120                 125

Ser Thr Leu Thr
    130

<210> SEQ ID NO 103
<211> LENGTH: 132
<212> TYPE: PRT
<213> ORGANISM: Artificial Sequence
<220> FEATURE:
<223> OTHER INFORMATION: IL-2 analog 102

<400> SEQUENCE: 103

Pro Thr Ser Ser Ser Thr Lys Lys Thr Gln Leu Gln Leu Glu His Leu
  1               5                  10                  15

Leu Leu Asp Leu Gln Met Ile Leu Asn Gly Ile Asn Asn Tyr Lys Asn
                 20                  25                  30

Pro Lys Leu Thr Arg Met Leu Thr Phe Lys Phe Tyr Met Pro Lys Lys
                 35                  40                  45

Ala Thr Glu Leu Lys His Leu Gln Cys Leu Glu Glu Leu Lys Pro
    50                  55                  60

Leu Glu Glu Val Leu Asn Leu Ala Gln Ser Lys Asn Phe His Phe Glu
 65                  70                  75                  80
```

```
Pro Arg Asp Val Val Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130

<210> SEQ ID NO 104
<211> LENGTH: 132
<212> TYPE: PRT
<213> ORGANISM: Artificial Sequence
<220> FEATURE:
<223> OTHER INFORMATION: IL-2 analog 103

<400> SEQUENCE: 104

Pro Thr Ser Ser Thr Lys Lys Thr Gln Leu Gln Leu Glu His Leu
1               5                   10                  15

Arg Leu Asp Leu Glu Met Ile Leu Asn Gly Ile Asn Asn Tyr Lys Asn
            20                  25                  30

Pro Lys Leu Thr Ala Met Leu Thr Phe Lys Phe Tyr Met Pro Lys Lys
        35                  40                  45

Ala Thr Glu Leu Lys His Leu Gln Cys Leu Glu Glu Leu Lys Pro
    50                  55                  60

Leu Glu Glu Val Leu Asn Leu Ala Gln Ser Lys Asn Phe His Phe Glu
65                  70                  75                  80

Pro Arg Asp Val Val Ser Asn Ile Asn Val Phe Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130

<210> SEQ ID NO 105
<211> LENGTH: 132
<212> TYPE: PRT
<213> ORGANISM: Artificial Sequence
<220> FEATURE:
<223> OTHER INFORMATION: IL-2 analog 104

<400> SEQUENCE: 105

Pro Thr Ser Ser Thr Lys Lys Thr Gln Leu Gln Leu Glu His Leu
1               5                   10                  15

Arg Leu Asp Leu Glu Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Asp Glu Leu Lys Pro
    50                  55                  60

Leu Glu Glu Val Leu Asn Leu Ala Gln Ser Lys Asn Phe His Phe Glu
65                  70                  75                  80

Pro Arg Asp Val Val Ser Asn Ile Asn Val Phe Val Leu Glu Leu Lys
                85                  90                  95

Gly Ser Glu Thr Thr Phe Met Cys Glu Tyr Ala Asp Glu Thr Ala Thr
            100                 105                 110
```

```
                      100                 105                 110
Ile Val Glu Phe Leu Asn Arg Trp Ile Thr Phe Ser Gln Ser Ile Ile
                115                 120                 125

Ser Thr Leu Thr
        130

<210> SEQ ID NO 106
<211> LENGTH: 132
<212> TYPE: PRT
<213> ORGANISM: Artificial Sequence
<220> FEATURE:
<223> OTHER INFORMATION: IL-2 analog 105

<400> SEQUENCE: 106

Pro Thr Ser Ser Ser Thr Lys Lys Thr Gln Leu Gln Leu Glu His Leu
1               5                   10                  15

Arg Leu Asp Leu Glu Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Asp Val Leu Asn Leu Ala Gln Ser Lys Asn Phe His Phe Glu
65                  70                  75                  80

Pro Arg Asp Val Val Ser Asn Ile Asn Val Phe Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130

<210> SEQ ID NO 107
<211> LENGTH: 399
<212> TYPE: DNA
<213> ORGANISM: Artificial Sequence
<220> FEATURE:
<223> OTHER INFORMATION: IL-2 analog 1

<400> SEQUENCE: 107
cctacttcaa gttctacaaa gaaaacacag ctacaactgg agcatttact gctggattta      60
cagatgattt tgaatggaat taataattac aagaatccca aactcaccag gatgctcaca    120
tttaagtttt acatgcccaa gaaggccaca gaactgaaac atcttcagtg tctagaagaa    180
gaactcaaac ctctggagga agtgctaaat ttagctcaaa gcaaaaactt tcacttaaga    240
cccagggact taatcagcaa tatcaacgta atagttctgg aactaaaggg atctgaaaca    300
acattcatgt gtgaatatgc tgatgagaca gcaaccattg tagaatttct gaacagatgg    360 attacctta gtcaaagcat catctcaaca ctgacttga                            399

<210> SEQ ID NO 108
<211> LENGTH: 399
<212> TYPE: DNA
<213> ORGANISM: Artificial Sequence
<220> FEATURE:
<223> OTHER INFORMATION: IL-2 analog 2

<400> SEQUENCE: 108
```

```
cctacttcaa gttctacaaa gaaaacacag ctacaactgg agcatttact gctggattta      60
cagatgattt tgaatggaat taataattac aagaatccca aactcaccag gatgctcaca     120
tttaagtttt acatgcccaa gaaggccaca gaactgaaac atcttcagtg tctagaagaa     180
gaactcaaac ctctggagga agtgctaaat ttagctcaaa gcaaaaactt tcacttaaga    240
cccagggact taatctgcaa tatcaacgta atagttctgg aactaagggg atctgaaaca    300
acattcatgt gtgaatatgc tgatgagaca gcaaccattg tagaatttct gaacagatgg    360 attacccttta gtcaaagcat catctcaaca ctgacttga                           399
```

<210> SEQ ID NO 109
<211> LENGTH: 399
<212> TYPE: DNA
<213> ORGANISM: Artificial Sequence
<220> FEATURE:
<223> OTHER INFORMATION: IL-2 analog 3

<400> SEQUENCE: 109

```
cctacttcaa gttctacaaa gaaaacacag ctacaactgg agcatttact gctggattta     60
cagatgattt tgaatggaat taataattac tgtaatccca aactcaccag gatgctcaca    120
tttaagtttt acatgcccaa gaaggccaca gaactgaaac atcttcagtg tctagaagaa    180
gaactcaaac ctctggagga agtgctaaat ttagctcaaa gcaaaaactt tcacttaaga   240
cccagggact taatcagcaa tatcaacgta atagttctgg aactaagggg atctgaaaca   300
acattcatgt gtgaatatgc tgatgagaca gcaaccattg tagaatttct gaacagatgg   360 attacccttta gtcaaagcat catctcaaca ctgacttga                          399
```

<210> SEQ ID NO 110
<211> LENGTH: 399
<212> TYPE: DNA
<213> ORGANISM: Artificial Sequence
<220> FEATURE:
<223> OTHER INFORMATION: IL-2 analog 4

<400> SEQUENCE: 110

```
cctacttcaa gttctacaaa gaaaacacag ctacaactgg agcatttact gctggattta    60
cagatgattt tgaatggaat taataattac aagaatccct gtctcaccag gatgctcaca   120
tttaagtttt acatgcccaa gaaggccaca gaactgaaac atcttcagtg tctagaagaa   180
gaactcaaac ctctggagga agtgctaaat ttagctcaaa gcaaaaactt tcacttaaga  240
cccagggact taatcagcaa tatcaacgta atagttctgg aactaagggg atctgaaaca  300
acattcatgt gtgaatatgc tgatgagaca gcaaccattg tagaatttct gaacagatgg  360 attacccttta gtcaaagcat catctcaaca ctgacttga                         399
```

<210> SEQ ID NO 111
<211> LENGTH: 399
<212> TYPE: DNA
<213> ORGANISM: Artificial Sequence
<220> FEATURE:
<223> OTHER INFORMATION: IL-2 analog 5

<400> SEQUENCE: 111

```
cctacttcaa gttctacaaa gaaaacacag ctacaactgg agcatttact gctggattta    60
cagatgattt tgaatggaat taataattac aagaatccca aactcaccag gatgctcaca   120
ttttgttttt acatgcccaa gaaggccaca gaactgaaac atcttcagtg tctagaagaa   180
gaactcaaac ctctggagga agtgctaaat ttagctcaaa gcaaaaactt tcacttaaga  240
```

```
cccagggact taatcagcaa tatcaacgta atagttctgg aactaaaggg atctgaaaca    300
acattcatgt gtgaatatgc tgatgagaca gcaaccattg tagaatttct gaacagatgg    360
attaccttta gtcaaagcat catctcaaca ctgacttga                           399
```

```
<210> SEQ ID NO 112
<211> LENGTH: 399
<212> TYPE: DNA
<213> ORGANISM: Artificial Sequence
<220> FEATURE:
<223> OTHER INFORMATION: IL-2 analog 6

<400> SEQUENCE: 112
cctacttcaa gttctacaaa gaaaacacag ctacaactgg agcatttact gctggattta     60
cagatgattt tgaatggaat taataattac aagaatccca aactcaccag gatgctcaca    120
tttaagtttt acatgccctg taaggccaca gaactgaaac atcttcagtg tctagaagaa    180
gaactcaaac ctctggagga agtgctaaat ttagctcaaa gcaaaaactt tcacttaaga    240
cccagggact taatcagcaa tatcaacgta atagttctgg aactaaaggg atctgaaaca    300
acattcatgt gtgaatatgc tgatgagaca gcaaccattg tagaatttct gaacagatgg    360
attaccttta gtcaaagcat catctcaaca ctgacttga                           399
```

```
<210> SEQ ID NO 113
<211> LENGTH: 399
<212> TYPE: DNA
<213> ORGANISM: Artificial Sequence
<220> FEATURE:
<223> OTHER INFORMATION: IL-2 analog 7

<400> SEQUENCE: 113
cctacttcaa gttctacaaa gaaaacacag ctacaactgg agcatttact gctggattta     60
cagatgattt tgaatggaat taataattac aagaatccca aactcaccag gatgctcaca    120
tttaagtttt acatgcccaa gtgtgccaca gaactgaaac atcttcagtg tctagaagaa    180
gaactcaaac ctctggagga agtgctaaat ttagctcaaa gcaaaaactt tcacttaaga    240
cccagggact taatcagcaa tatcaacgta atagttctgg aactaaaggg atctgaaaca    300
acattcatgt gtgaatatgc tgatgagaca gcaaccattg tagaatttct gaacagatgg    360
attaccttta gtcaaagcat catctcaaca ctgacttga                           399
```

```
<210> SEQ ID NO 114
<211> LENGTH: 399
<212> TYPE: DNA
<213> ORGANISM: Artificial Sequence
<220> FEATURE:
<223> OTHER INFORMATION: IL-2 analog 8

<400> SEQUENCE: 114
cctacttcaa gttctacaaa gaaaacacag ctacaactgg agcatttact gctggattta     60
cagatgattt tgaatggaat taataattac aagaatccca aactcaccag gatgctcaca    120
tttaagtttt acatgcccaa gaaggccaca gaactgaaac atcttcagtg tctagaagaa    180
gaactcaaac ctctggagga agtgctaaat ttagctcaaa gctgtaactt tcacttaaga    240
cccagggact taatcagcaa tatcaacgta atagttctgg aactaaaggg atctgaaaca    300
acattcatgt gtgaatatgc tgatgagaca gcaaccattg tagaatttct gaacagatgg    360
attaccttta gtcaaagcat catctcaaca ctgacttga                           399
```

<210> SEQ ID NO 115
<211> LENGTH: 399
<212> TYPE: DNA
<213> ORGANISM: Artificial Sequence
<220> FEATURE:
<223> OTHER INFORMATION: IL-2 analog 9

<400> SEQUENCE: 115

```
cctacttcaa gttctacaaa gaaaacacag ctacaactgg agcatttact gctggattta      60
cagatgattt tgaatggaat taataattac aagaatccca aactcaccgc gatgctcaca     120
tttaagtttt acatgcccaa gaaggccaca gaactgaaac atcttcagtg tctagaagaa     180
gaactcaaac ctctggagga agtgctaaat ttagctcaaa gcaaaaactt tcacttaaga     240
cccagggact taatcagcaa tatcaacgta atagttctgg aactaaaggg atctgaaaca     300
acattcatgt gtgaatatgc tgatgagaca gcaaccattg tagaatttct gaacagatgg     360
attacccttta gtcaaagcat catctcaaca ctgacttga                           399
```

<210> SEQ ID NO 116
<211> LENGTH: 399
<212> TYPE: DNA
<213> ORGANISM: Artificial Sequence
<220> FEATURE:
<223> OTHER INFORMATION: IL-2 analog 10

<400> SEQUENCE: 116

```
cctacttcaa gttctacaaa gaaaacacag ctacaactgg agcatttact gctggattta      60
cagatgattt tgaatggaat taataattac aagaatccca aactcaccag gatgctcaca     120
aagaagtttt acatgcccaa gaaggccaca gaactgaaac atcttcagtg tctagaagaa     180
gaactcaaac ctctggagga agtgctaaat ttagctcaaa gcaaaaactt tcacttaaga     240
cccagggact taatcagcaa tatcaacgta atagttctgg aactaaaggg atctgaaaca     300
acattcatgt gtgaatatgc tgatgagaca gcaaccattg tagaatttct gaacagatgg     360
attacccttta gtcaaagcat catctcaaca ctgacttga                           399
```

<210> SEQ ID NO 117
<211> LENGTH: 399
<212> TYPE: DNA
<213> ORGANISM: Artificial Sequence
<220> FEATURE:
<223> OTHER INFORMATION: IL-2 analog 11

<400> SEQUENCE: 117

```
cctacttcaa gttctacaaa gaaaacacag ctacaactgg agcatttact gctggattta      60
cagatgattt tgaatggaat taataattac aagaatccca aactcaccag gatgctcaca     120
gctaagtttt acatgcccaa gaaggccaca gaactgaaac atcttcagtg tctagaagaa     180
gaactcaaac ctctggagga agtgctaaat ttagctcaaa gcaaaaactt tcacttaaga     240
cccagggact taatcagcaa tatcaacgta atagttctgg aactaaaggg atctgaaaca     300
acattcatgt gtgaatatgc tgatgagaca gcaaccattg tagaatttct gaacagatgg     360
attacccttta gtcaaagcat catctcaaca ctgacttga                           399
```

<210> SEQ ID NO 118
<211> LENGTH: 399
<212> TYPE: DNA
<213> ORGANISM: Artificial Sequence
<220> FEATURE:
<223> OTHER INFORMATION: IL-2 analog 12

<400> SEQUENCE: 118

```
cctacttcaa gttctacaaa gaaaacacag ctacaactgg agcatttact gctggattta      60
cagatgattt tgaatggaat taataattac aagaatccca aactcaccgc gatgctcaca     120
aagaagtttt acatgcccaa gaaggccaca gaactgaaac atcttcagtg tctagaagaa     180
gaactcaaac ctctggagga agtgctaaat ttagctcaaa gcaaaaactt tcacttaaga     240
cccagggact aatcagcaa tatcaacgta atagttctgg aactaaaggg atctgaaaca      300
acattcatgt gtgaatatgc tgatgagaca gcaaccattg tagaatttct gaacagatgg     360
attacctta gtcaaagcat catctcaaca ctgacttga                             399
```

<210> SEQ ID NO 119
<211> LENGTH: 399
<212> TYPE: DNA
<213> ORGANISM: Artificial Sequence
<220> FEATURE:
<223> OTHER INFORMATION: IL-2 analog 13

<400> SEQUENCE: 119

```
cctacttcaa gttctacaaa gaaaacacag ctacaactgg agcatttact gctggattta      60
cagatgattt tgaatggaat taataattac aagaatccca aactcaccgc gatgctcaca     120
gctaagtttt acatgcccaa gaaggccaca gaactgaaac atcttcagtg tctagaagaa     180
gaactcaaac ctctggagga agtgctaaat ttagctcaaa gcaaaaactt tcacttaaga     240
cccagggact aatcagcaa tatcaacgta atagttctgg aactaaaggg atctgaaaca      300
acattcatgt gtgaatatgc tgatgagaca gcaaccattg tagaatttct gaacagatgg     360
attacctta gtcaaagcat catctcaaca ctgacttga                             399
```

<210> SEQ ID NO 120
<211> LENGTH: 399
<212> TYPE: DNA
<213> ORGANISM: Artificial Sequence
<220> FEATURE:
<223> OTHER INFORMATION: IL-2 analog 14

<400> SEQUENCE: 120

```
cctacttcaa gttctacaaa gaaaacacag ctacaactgg agcatttact gtacgattta      60
cagatgattt tgaatggaat taataattac aagaatccca aactcaccgc gatgctcaca     120
aagaagtttt acatgcccaa gaaggccaca gaactgaaac atcttcagtg tctagaagaa     180
gaactcaaac ctctggagga agtgctaaat ttagctcaaa gcaaaaactt tcacttaaga     240
cccagggact aatcagcaa tatcaacgta atagttctgg aactaaaggg atctgaaaca      300
acattcatgt gtgaatatgc tgatgagaca gcaaccattg tagaatttct gaacagatgg     360
attacctta gtcaaagcat catctcaaca ctgacttga                             399
```

<210> SEQ ID NO 121
<211> LENGTH: 399
<212> TYPE: DNA
<213> ORGANISM: Artificial Sequence
<220> FEATURE:
<223> OTHER INFORMATION: IL-2 analog 15

<400> SEQUENCE: 121

```
cctacttcaa gttctacaaa gaaaacacag ctacaactgg agcatttact gctggattta      60
cagatgattt tgaatggaat taataattac aagaatccca aactcaccgc gatgctcaca     120
```

```
aagaagttttt acatgcccaa gaaggccaca gaactgaaac atcttcagtg tctagaagaa      180
gaactcaaac ctctggagga agtgctaaat ttagctcaaa gcaaaaactt tcacttaaga      240
cccagggagt taatcagcaa tatcaacgta atagttctgg aactaaaggg atctgaaaca      300
acattcatgt gtgaatatgc tgatgagaca gcaaccattg tagaatttct gaacagatgg      360
attaccttta gtcaaagcat catctcaaca ctgacttga                             399

<210> SEQ ID NO 122
<211> LENGTH: 399
<212> TYPE: DNA
<213> ORGANISM: Artificial Sequence
<220> FEATURE:
<223> OTHER INFORMATION: IL-2 analog 16

<400> SEQUENCE: 122
cctacttcaa gttctacaaa gaaaacacag ctacaactgg agcatttact gctggattta      60
cagatgattt tgaatggaat taataattac aagaatccca aactcaccgc gatgctcaca      120 aagaagttttt acatgcccaa gaaggccaca gaactgaaac atcttcagtg tctagaagaa      180
gaactcaaac ctctggagga agtgctaaat ttagctcaaa gcaaaaactt tcacttaaga      240
cccagggact taatcagcca atcaacgta atagttctgg aactaaaggg atctgaaaca      300
acattcatgt gtgaatatgc tgatgagaca gcaaccattg tagaatttct gaacagatgg      360
attaccttta gtcaaagcat catctcaaca ctgacttga                             399

<210> SEQ ID NO 123
<211> LENGTH: 399
<212> TYPE: DNA
<213> ORGANISM: Artificial Sequence
<220> FEATURE:
<223> OTHER INFORMATION: IL-2 analog 17

<400> SEQUENCE: 123
cctacttcaa gttctacaaa gaaaacacag ctacaactgg agcatttact gctggattta      60
cagatgattt tgaatggaat taataattac aagaatccca aactcaccgc gatgctcaca      120 aagaagttttt acatgcccaa gaaggccaca gaactgaaac atcttcagtg tctagaagaa      180
gaactcaaac ctctggagga agtgctaaat ttagctcaaa gcaaaaactt tcacttaaga      240
cccagggact taatcagcaa tatcaacaca atagttctgg aactaaaggg atctgaaaca      300
acattcatgt gtgaatatgc tgatgagaca gcaaccattg tagaatttct gaacagatgg      360
attaccttta gtcaaagcat catctcaaca ctgacttga                             399

<210> SEQ ID NO 124
<211> LENGTH: 399
<212> TYPE: DNA
<213> ORGANISM: Artificial Sequence
<220> FEATURE:
<223> OTHER INFORMATION: IL-2 analog 18

<400> SEQUENCE: 124
cctacttcaa gttctacaaa gaaaacacag ctacaactgg agcatttact gctggattta      60
cagatgattt tgaatggaat taataattac aagaatccca aactcaccgc gatgctcaca      120 aagaagttttt acatgcccaa gaaggccaca gaactgaaac atcttcagtg tctagaacag      180
gaactcaaac ctctggagga agtgctaaat ttagctcaaa gcaaaaactt tcacttaaga      240
cccagggact taatcagcaa tatcaacgta atagttctgg aactaaaggg atctgaaaca      300
acattcatgt gtgaatatgc tgatgagaca gcaaccattg tagaatttct gaacagatgg      360
```

```
attaccttta gtcaaagcat catctcaaca ctgacttga                           399

<210> SEQ ID NO 125
<211> LENGTH: 399
<212> TYPE: DNA
<213> ORGANISM: Artificial Sequence
<220> FEATURE:
<223> OTHER INFORMATION: IL-2 analog 19

<400> SEQUENCE: 125
cctacttcaa gttctacaaa gaaaacacag ctacaactgg agcatttact gctggattta    60
cagatgattt tgaatggaat taataattac aagaatccca aactcaccgc gatgctcaca   120
aagaagtttt acatgcccaa gaaggccaca gaactgaaac atcttcagtg tctagaagaa   180
gaactcaaac tctggagga agtgctaaat ttagctcaaa gcaaaaactt tcacttagac    240
cccagggact taatcagcaa tatcaacgta tttgttctgg aactaagggg atctgaaaca   300
acattcatgt gtgaatatgc tgatgagaca gcaaccattg tagaatttct gaacagatgg   360
attaccttta gtcaaagcat catctcaaca ctgacttga                           399

<210> SEQ ID NO 126
<211> LENGTH: 399
<212> TYPE: DNA
<213> ORGANISM: Artificial Sequence
<220> FEATURE:
<223> OTHER INFORMATION: IL-2 analog 20

<400> SEQUENCE: 126
cctacttcaa gttctacaaa gaaaacacag ctacaactgg agcatttact gctggattta    60
cagatgattt tgaatggaat taataattac aagaatccca aactcaccgc gatgctcaca   120
aagaagtttt acatgcccaa gaaggccaca gaactgaaac atcttcagtg tctagaagaa   180
gaactcaaac tctggagga agtgctaaat ttagctcaaa gcaaaaactt tcacttaaga    240
cccagggacg tagtcagcaa tatcaacgta tttgttctgg aactaagggg atctgaaaca   300
acattcatgt gtgaatatgc tgatgagaca gcaaccattg tagaatttct gaacagatgg   360
attaccttta gtcaaagcat catctcaaca ctgacttga                           399

<210> SEQ ID NO 127
<211> LENGTH: 399
<212> TYPE: DNA
<213> ORGANISM: Artificial Sequence
<220> FEATURE:
<223> OTHER INFORMATION: IL-2 analog 21

<400> SEQUENCE: 127
cctacttcaa gttctacaaa gaaaacacag ctacaactgg agcatttact gctggattta    60
cagatgattt tgaatggaat taataattac aagaatccca aactcaccgc gatgctcaca   120
aagaagtttt acatgcccaa gaaggccaca gaactgaaac atcttcagtg tctagaagaa   180
gaactcaaac tctggagga agtgctaaat ttagctcaaa gcaaaaactt tcactttgac    240
cccagggacg tagtcagcaa tatcaacgta tttgttctgg aactaagggg atctgaaaca   300
acattcatgt gtgaatatgc tgatgagaca gcaaccattg tagaatttct gaacagatgg   360
attaccttta gtcaaagcat catctcaaca ctgacttga                           399

<210> SEQ ID NO 128
<211> LENGTH: 399
<212> TYPE: DNA
```

<213> ORGANISM: Artificial Sequence
<220> FEATURE:
<223> OTHER INFORMATION: IL-2 analog 22

<400> SEQUENCE: 128

```
cctacttcaa gttctacaaa gaaaacacag gtacaactgg agcatttact gctggattta      60
cagatgattt tgaatggaat taataattac aagaatccca aactcaccgc gatgctcaca     120
aagaagtttt acatgcccaa gaaggccaca gaactgaaac atcttcagtg tctagaagaa     180
gaactcaaac ctctggagga agtgctaaat ttagctcaaa gcaaaaactt tcacttaaga     240
cccagggact taatcagcaa tatcaacgta atagttctgg aactaaaggg atctgaaaca     300
acattcatgt gtgaatatgc tgatgagaca gcaaccattg tagaatttct gaacagatgg     360
attacctttta gtcaaagcat catctcaaca ctgacttga                           399
```

<210> SEQ ID NO 129
<211> LENGTH: 399
<212> TYPE: DNA
<213> ORGANISM: Artificial Sequence
<220> FEATURE:
<223> OTHER INFORMATION: IL-2 analog 23

<400> SEQUENCE: 129

```
cctacttcaa gttctacaaa gaaaacacag tttcaactgg agcatttact gctggattta      60
cagatgattt tgaatggaat taataattac aagaatccca aactcaccgc gatgctcaca     120
aagaagtttt acatgcccaa gaaggccaca gaactgaaac atcttcagtg tctagaagaa     180
gaactcaaac ctctggagga agtgctaaat ttagctcaaa gcaaaaactt tcacttaaga     240
cccagggact taatcagcaa tatcaacgta atagttctgg aactaaaggg atctgaaaca     300
acattcatgt gtgaatatgc tgatgagaca gcaaccattg tagaatttct gaacagatgg     360
attacctttta gtcaaagcat catctcaaca ctgacttga                           399
```

<210> SEQ ID NO 130
<211> LENGTH: 399
<212> TYPE: DNA
<213> ORGANISM: Artificial Sequence
<220> FEATURE:
<223> OTHER INFORMATION: IL-2 analog 24

<400> SEQUENCE: 130

```
cctacttcaa gttctacaaa gaaaacacag ctacaactgg agcatttact ggtggattta      60
cagatgattt tgaatggaat taataattac aagaatccca aactcaccgc gatgctcaca     120
aagaagtttt acatgcccaa gaaggccaca gaactgaaac atcttcagtg tctagaagaa     180
gaactcaaac ctctggagga agtgctaaat ttagctcaaa gcaaaaactt tcacttaaga     240
cccagggact taatcagcaa tatcaacgta atagttctgg aactaaaggg atctgaaaca     300
acattcatgt gtgaatatgc tgatgagaca gcaaccattg tagaatttct gaacagatgg     360
attacctttta gtcaaagcat catctcaaca ctgacttga                           399
```

<210> SEQ ID NO 131
<211> LENGTH: 399
<212> TYPE: DNA
<213> ORGANISM: Artificial Sequence
<220> FEATURE:
<223> OTHER INFORMATION: IL-2 analog 25

<400> SEQUENCE: 131

```
cctacttcaa gttctacaaa gaaaacacag ctacaactgg agcatttact gttcgattta      60
```

```
cagatgattt tgaatggaat taataattac aagaatccca aactcaccgc gatgctcaca    120
aagaagtttt acatgcccaa gaaggccaca gaactgaaac atcttcagtg tctagaagaa    180
gaactcaaac ctctggagga agtgctaaat ttagctcaaa gcaaaaactt tcacttaaga    240
cccagggact taatcagcaa tatcaacgta atagttctgg aactaaaggg atctgaaaca    300
acattcatgt gtgaatatgc tgatgagaca gcaaccattg tagaatttct gaacagatgg    360
attaccttta gtcaaagcat catctcaaca ctgacttga                          399
```

<210> SEQ ID NO 132
<211> LENGTH: 399
<212> TYPE: DNA
<213> ORGANISM: Artificial Sequence
<220> FEATURE:
<223> OTHER INFORMATION: IL-2 analog 26

<400> SEQUENCE: 132

```
cctacttcaa gttctacaaa gaaaacacag ctacaactgg agcatttact gctggattta     60
cagatgattt tgaatggaat taataattac aagaatccca aactcaccgc gatgctcaca    120
aagaagtttt acatgcccaa gaaggccaca gaactgaaac atcttcagtg tctagaagaa    180
gaactcaaac ctctggagga agtgctaaat ttagctcaaa gcaaaaactt tcacttaaga    240
cccagggact taatcagcaa tttcaacgta atagttctgg aactaaaggg atctgaaaca    300
acattcatgt gtgaatatgc tgatgagaca gcaaccattg tagaatttct gaacagatgg    360
attaccttta gtcaaagcat catctcaaca ctgacttga                          399
```

<210> SEQ ID NO 133
<211> LENGTH: 399
<212> TYPE: DNA
<213> ORGANISM: Artificial Sequence
<220> FEATURE:
<223> OTHER INFORMATION: IL-2 analog 27

<400> SEQUENCE: 133

```
cctacttcaa gttctacaaa gaaaacacag ctacaactgg agcatttact gctggattta     60
cagatgattt tgaatggaat taataattac aagaatccca aactcaccgc gatgctcaca    120
aagaagtttt acatgcccaa gaaggccaca gaactgaaac atcttcagtg tctagaagaa    180
gaactcaaac ctctggagga agtgctaaat ttagctcaaa gcaaaaactt tcacttaaga    240
cccagggact taatcagcaa tatcaacttt atagttctgg aactaaaggg atctgaaaca    300
acattcatgt gtgaatatgc tgatgagaca gcaaccattg tagaatttct gaacagatgg    360
attaccttta gtcaaagcat catctcaaca ctgacttga                          399
```

<210> SEQ ID NO 134
<211> LENGTH: 399
<212> TYPE: DNA
<213> ORGANISM: Artificial Sequence
<220> FEATURE:
<223> OTHER INFORMATION: IL-2 analog 28

<400> SEQUENCE: 134

```
cctacttcaa gttctacaaa gaaaacacag ctacaactgg agcatttact gctggattta     60
cagatgattt tgaatggaat taataattac aagaatccca aactcaccgc gatgctcaca    120
aagaagtttt acatgcccaa gaaggccaca gaactgaaac atcttcagtg tctagaagaa    180
gaactcaaac ctctggagga agtgctaaat ttagctcaaa gcaaaaactt tcacttaaga    240
```

```
cccagggact taatcagcaa tatcaacgta atagttgtgg aactaaaggg atctgaaaca      300
acattcatgt gtgaatatgc tgatgagaca gcaaccattg tagaatttct gaacagatgg      360 attacccttta gtcaaagcat catctcaaca ctgacttga                            399

<210> SEQ ID NO 135
<211> LENGTH: 399
<212> TYPE: DNA
<213> ORGANISM: Artificial Sequence
<220> FEATURE:
<223> OTHER INFORMATION: IL-2 analog 29

<400> SEQUENCE: 135
cctacttcaa gttctacaaa gaaaacacag ctacaactgg agcatttact gctggattta       60
cagatgattt tgaatggaat taataattac aagaatccca aactcaccgc gatgctcaca      120
aagaagtttt acatgcccaa gaaggccaca gaactgaaac atcttcagtg tctagaagaa      180
gaactcaaac ctctggagga agtgctaaat ttagctcaaa gcaaaaactt tcacttaaga      240
cccagggact taatcagcaa tatcaacgta atagttctgg aactaaaggg atctgaaaca      300
acattcatgt gtgaatatgc tgatgagaca gcaaccattg tagaatttct gaacagatgg      360 attacccttta gtacaagcat catctcaaca ctgacttga                            399

<210> SEQ ID NO 136
<211> LENGTH: 399
<212> TYPE: DNA
<213> ORGANISM: Artificial Sequence
<220> FEATURE:
<223> OTHER INFORMATION: IL-2 analog 30

<400> SEQUENCE: 136
cctacttcaa gttctacaaa gaaaacacag ctacaactgg agcatttact gctggattta       60
cagatgattt tgaatggaat taataattac aagaatccca aactcaccgc gatgctcaca      120
tttaagtttt acatgcccaa gaaggccaca gaactgaaac atcttcagtg tctagaagaa      180
gaactcaaac ctctggagga agtgctaaat ttagctcaaa gcaaaaactt tcacttagac      240
cccagggact taatcagcaa tatcaacgta tttgttctgg aactaaaggg atctgaaaca      300
acattcatgt gtgaatatgc tgatgagaca gcaaccattg tagaatttct gaacagatgg      360 attacccttta gtcaaagcat catctcaaca ctgacttga                            399

<210> SEQ ID NO 137
<211> LENGTH: 399
<212> TYPE: DNA
<213> ORGANISM: Artificial Sequence
<220> FEATURE:
<223> OTHER INFORMATION: IL-2 analog 31

<400> SEQUENCE: 137
cctacttcaa gttctacaaa gaaaacacag ctacaactgg agcatttact gctggattta       60
cagatgattt tgaatggaat taataattac aagaatccca aactcaccgc gatgctcaca      120
tttaagtttt acatgcccaa gaaggccaca gaactgaaac atcttcagtg tctagaagaa      180
gaactcaaac ctctggagga agtgctaaat ttagctcaaa gcaaaaactt tcacttaaga      240
cccagggagt taatcagcaa tatcaacgta atagttctgg aactaaaggg atctgaaaca      300
acattcatgt gtgaatatgc tgatgagaca gcaaccattg tagaatttct gaacagatgg      360 attacccttta gtcaaagcat catctcaaca ctgacttga                            399
```

<210> SEQ ID NO 138
<211> LENGTH: 399
<212> TYPE: DNA
<213> ORGANISM: Artificial Sequence
<220> FEATURE:
<223> OTHER INFORMATION: IL-2 analog 32

<400> SEQUENCE: 138

```
cctacttcaa gttctacaaa gaaaacacag ctacaactgg agcatttact gctggattta      60
cagatgattt tgaatggaat taataattac aagaatccca aactcaccgc gatgctcaca     120
tttaagtttt acatgcccaa gaaggccaca gaactgaaac atcttcagtg tctagaagaa     180
gaactcaaac ctctggagga agtgctaaat ttagctcaaa gcaaaaactt tcacttagac     240
cccagggagt taatcagcaa tatcaacgta tttgttctgg aactaaaggg atctgaaaca     300
acattcatgt gtgaatatgc tgatgagaca gcaaccattg tagaatttct gaacagatgg     360
attaccttta gtcaaagcat catctcaaca ctgacttga                            399
```

<210> SEQ ID NO 139
<211> LENGTH: 399
<212> TYPE: DNA
<213> ORGANISM: Artificial Sequence
<220> FEATURE:
<223> OTHER INFORMATION: IL-2 analog 33

<400> SEQUENCE: 139

```
cctacttcaa gttctacaaa gaaaacacag ctacaactgg agcatttact gctggattta      60
cagatgattt tgaatggaat taataattac aagaatccca aactcaccgc gatgctcaca     120
tttaagtttt acatgcccaa gaaggccaca gaactgaaac atcttcagtg tctagaagaa     180
gaactcaaac ctctggagga agtgctaaat ttagctcaaa gcaaaaactt tcactttaga     240
cccagggact taatcagcaa tatcaacgta atagttctgg aactaaaggg atctgaaaca     300
acattcatgt gtgaatatgc tgatgagaca gcaaccattg tagaatttct gaacagatgg     360
attaccttta gtcaaagcat catctcaaca ctgacttga                            399
```

<210> SEQ ID NO 140
<211> LENGTH: 399
<212> TYPE: DNA
<213> ORGANISM: Artificial Sequence
<220> FEATURE:
<223> OTHER INFORMATION: IL-2 analog 34

<400> SEQUENCE: 140

```
cctacttcaa gttctacaaa gaaaacacag ctacaactgg agcatttact gctggattta      60
cagatgattt tgaatggaat taataattac aagaatccca aactcaccgc gatgctcaca     120
tttaagtttt acatgcccaa gaaggccaca gaactgaaac atcttcagtg tctagaagaa     180
gaactcaaac ctctggagga agtgctaaat ttagctcaaa gcaaaaactt tcactttaga     240
cccagggagt taatcagcaa tatcaacgta atagttctgg aactaaaggg atctgaaaca     300
acattcatgt gtgaatatgc tgatgagaca gcaaccattg tagaatttct gaacagatgg     360
attaccttta gtcaaagcat catctcaaca ctgacttga                            399
```

<210> SEQ ID NO 141
<211> LENGTH: 399
<212> TYPE: DNA
<213> ORGANISM: Artificial Sequence
<220> FEATURE:
<223> OTHER INFORMATION: IL-2 analog 35

<400> SEQUENCE: 141

```
cctacttcaa gttctacaaa gaaaacacag ctacaactgg agcatttact gctggattta    60
cagatgattt tgaatggaat taataattac aagaatccca aactcaccgc gatgctcaca   120
tttaagtttt acatgcccaa gaaggccaca gaactgaaac atcttcagtg tctagaagaa   180
gaactcaaac ctctggagga agtgctaaat ttagctcaaa gcaaaaactt tcacttaaga   240
cccagggact taatcagcaa tatcaacgta atagttttcg aatttaaggg atctgaaaca   300
acattcatgt gtgaatatgc tgatgagaca gcaaccattg tagaatttct gaacagatgg   360
attacctttta gtcaaagcat catctcaaca ctgacttga                         399
```

<210> SEQ ID NO 142
<211> LENGTH: 399
<212> TYPE: DNA
<213> ORGANISM: Artificial Sequence
<220> FEATURE:
<223> OTHER INFORMATION: IL-2 analog 36

<400> SEQUENCE: 142

```
cctacttcaa gttctacaaa gaaaacacag ctacaactgg agcatttact gctggattta    60
cagatgattt tgaatggaat taataattac aagaatccca aactcaccgc gatgctcaca   120
tttaagtttt acatgcccaa gaaggccaca gaactgaaac atcttcagtg tctagaagaa   180
gaactcaaac ctctggagga agtgctaaat ttagctcaaa gcaaaaactt tcacttaaga   240
cccagggact taatcagcaa tatcaacgta atagttttcg aagtaaaggg atctgaaaca   300
acattcatgt gtgaatatgc tgatgagaca gcaaccattg tagaatttct gaacagatgg   360
attacctttta gtcaaagcat catctcaaca ctgacttga                         399
```

<210> SEQ ID NO 143
<211> LENGTH: 399
<212> TYPE: DNA
<213> ORGANISM: Artificial Sequence
<220> FEATURE:
<223> OTHER INFORMATION: IL-2 analog 37

<400> SEQUENCE: 143

```
cctacttcaa gttctacaaa gaaaacacag ctacaactgg agcatttact gctggattta    60
cagatgattt tgaatggaat taataattac aagaatccca aactcaccgc gatgctcaca   120
aagaagtttt acatgcccaa gaaggccaca gaactgaaac atcttcagtg tctagaagaa   180
gaactcaaac ctctggagga agtgctaaat ttagctcaaa gcaaaaactt tcacttagac   240
cccagggact taatcagcaa tatcaacgta ttagttctgg aactaaaggg atctgaaaca   300
acattcatgt gtgaatatgc tgatgagaca gcaaccattg tagaatttct gaacagatgg   360
attacctttta gtcaaagcat catctcaaca ctgacttga                         399
```

<210> SEQ ID NO 144
<211> LENGTH: 399
<212> TYPE: DNA
<213> ORGANISM: Artificial Sequence
<220> FEATURE:
<223> OTHER INFORMATION: IL-2 analog 38

<400> SEQUENCE: 144

```
cctacttcaa gttctacaaa gaaaacacag ctacaactgg agcatttact gctggattta    60
cagatgattt tgaatggaat taataattac aagaatccca aactcaccgc gatgctcaca   120
aagaagtttt acatgcccaa gaaggccaca gaactgaaac atcttcagtg tctagaagaa   180
```

```
gaactcaaac ctctggagga agtgctaaat ttagctcaaa gcaaaaactt tcacttagac    240
cccagggact taatcagcaa tatcaacgta tttgttttcg aatttaaggg atctgaaaca    300
acattcatgt gtgaatatgc tgatgagaca gcaaccattg tagaatttct gaacagatgg    360
attacctttA gtcaaagcat catctcaaca ctgacttga                          399
```

<210> SEQ ID NO 145
<211> LENGTH: 399
<212> TYPE: DNA
<213> ORGANISM: Artificial Sequence
<220> FEATURE:
<223> OTHER INFORMATION: IL-2 analog 39

<400> SEQUENCE: 145

```
cctacttcaa gttctacaaa gaaaacacag ctacaactgg agcatttact gctggattta     60
cagatgattt tgaatggaat taataattac aagaatccca aactcaccgc gatgctcaca    120
aagaagtttt acatgcccaa gaaggccaca gaactgaaac atcttcagtg tctagaagaa    180
gaactcaaac ctctggagga agtgctaaat ttagctcaaa gcaaaaactt tcacttagac    240
cccagggact taatcagcaa tatcaacgta tttgttttcg aagtaaaggg atctgaaaca    300
acattcatgt gtgaatatgc tgatgagaca gcaaccattg tagaatttct gaacagatgg    360
attacctttA gtcaaagcat catctcaaca ctgacttga                          399
```

<210> SEQ ID NO 146
<211> LENGTH: 399
<212> TYPE: DNA
<213> ORGANISM: Artificial Sequence
<220> FEATURE:
<223> OTHER INFORMATION: IL-2 analog 40

<400> SEQUENCE: 146

```
cctacttcaa gttctacaaa gaaaacacag ctacaactgg agcatttact gctggattta     60
cagatgattt tgaatggaat taataattac aagaatccca aactcaccgc gatgctcaca    120
aagaagtttt acatgcccaa gaaggccaca gaactgaaac atcttcagtg tctagaagaa    180
gaactcaaac ctctggagga agtgctaaat ttagctcaaa gcaaaaactt tcacttagac    240
cccagggact taatcagcaa tatcaacgta tttgttttcg aaattaaggg atctgaaaca    300
acattcatgt gtgaatatgc tgatgagaca gcaaccattg tagaatttct gaacagatgg    360
attacctttA gtcaaagcat catctcaaca ctgacttga                          399
```

<210> SEQ ID NO 147
<211> LENGTH: 399
<212> TYPE: DNA
<213> ORGANISM: Artificial Sequence
<220> FEATURE:
<223> OTHER INFORMATION: IL-2 analog 41

<400> SEQUENCE: 147

```
cctacttcaa gttctacaaa gaaaacacag ctacaactgg agcatttact gctggattta     60
cagatgattt tgaatggaat taataattac aagaatccca aactcaccag gatgctcaca    120 tttagtttt acatgcccaa gaaggccaca gaactgaaac atcttcagtg tctagaagaa    180
gaactcaaac ctctggagga agtgctaaat ttagctcaaa gcaaaaactt tcactttgac    240
cccagggacg tagtcagcaa tatcaacgta tttgttctgg aactaaaggg atctgaaaca    300
acattcatgt gtgaatatgc tgatgagaca gcaaccattg tagaatttct gaacagatgg    360
``` attacctttta gtcaaagcat catctcaaca ctgacttga                              399

<210> SEQ ID NO 148
<211> LENGTH: 399
<212> TYPE: DNA
<213> ORGANISM: Artificial Sequence
<220> FEATURE:
<223> OTHER INFORMATION: IL-2 analog 42

<400> SEQUENCE: 148
cctacttcaa gttctacaaa gaaaacacag ctacaactgg agcatttact gctggattta     60
cagatgattt tgaatggaat taataattac aagaatccca aactcaccgc gatgctcaca    120
aagaagtttt acatgcccaa gaaggccaca gaactgaaac atcttcagtg tctagaagaa    180
gaactcaaac tctggagga agtgctaaat ttagctcaaa gcaaaaactt tcacttagaa    240
cccagggact taatcagcaa tatcaacgta tttgttctgg aactaaaggg atctgaaaca    300
acattcatgt gtgaatatgc tgatgagaca gcaaccattg tagaatttct gaacagatgg    360
attacctttta gtcaaagcat catctcaaca ctgacttga                          399

<210> SEQ ID NO 149
<211> LENGTH: 399
<212> TYPE: DNA
<213> ORGANISM: Artificial Sequence
<220> FEATURE:
<223> OTHER INFORMATION: IL-2 analog 43

<400> SEQUENCE: 149
cctacttcaa gttctacaaa gaaaacacag ctacaactgg agcatttact gctggattta     60
cagatgattt tgaatggaat taataattac aagaatccca aactcaccgc gatgctcaca    120
aagaagtttt acatgcccaa gaaggccaca gaactgaaac atcttcagtg tctagaagaa    180
gaactcaaac tctggagga agtgctaaat ttagctcaaa gcaaaaactt tcacttagac    240
cccagggact taatcagcaa tatcaacgta ttagttctgg aactaaaggg atctgaaaca    300
acattcatgt gtgaatatgc tgatgagaca gcaaccattg tagaatttct gaacagatgg    360
attacctttta gtcaaagcat catctcaaca ctgacttga                          399

<210> SEQ ID NO 150
<211> LENGTH: 399
<212> TYPE: DNA
<213> ORGANISM: Artificial Sequence
<220> FEATURE:
<223> OTHER INFORMATION: IL-2 analog 44

<400> SEQUENCE: 150
cctacttcaa gttctacaaa gaaaacacag ctacaactgg agcatttact gctggattta     60
cagatgattt tgaatggaat taataattac aagaatccca aactcaccgc gatgctcaca    120
aagaagtttt acatgcccaa gaaggccaca gaactgaaac atcttcagtg tctagaagaa    180
gaactcaaac tctggagga agtgctaaat ttagctcaaa gcaaaaactt tcacttagac    240
cccagggtct taatcagcaa tatcaacgta tttgttctgg aactaaaggg atctgaaaca    300
acattcatgt gtgaatatgc tgatgagaca gcaaccattg tagaatttct gaacagatgg    360
attacctttta gtcaaagcat catctcaaca ctgacttga                          399

<210> SEQ ID NO 151
<211> LENGTH: 399
<212> TYPE: DNA
<213> ORGANISM: Artificial Sequence
<220> FEATURE:
<223> OTHER INFORMATION: IL-2 analog 45

<400> SEQUENCE: 151

```
cctacttcaa gttctacaaa gaaaacacag ctacaactgg agcatttact gctggattta    60
cagatgattt tgaatggaat taataattac aagaatccca aactcaccgc gatgctcaca   120
aagaagtttt acatgcccaa gaaggccaca gaactgaaac atcttcagtg tctagaagaa   180
gaactcaaac ctctggagga agtgctaaat ttagctcaaa gcaaaaactt tcacttagac   240
cccaggttct taatcagcaa tatcaacgta tttgttctgg aactaaaggg atctgaaaca   300
acattcatgt gtgaatatgc tgatgagaca gcaaccattg tagaatttct gaacagatgg   360
attacccttta gtcaaagcat catctcaaca ctgacttga                         399
```

<210> SEQ ID NO 152
<211> LENGTH: 399
<212> TYPE: DNA
<213> ORGANISM: Artificial Sequence
<220> FEATURE:
<223> OTHER INFORMATION: IL-2 analog 46

<400> SEQUENCE: 152

```
cctacttcaa gttctacaaa gaaaacacag ctacaactgg agcatttact gctggtttta    60
cagatgattt tgaatggaat taataattac aagaatccca aactcaccgc gatgctcaca   120
aagaagtttt acatgcccaa gaaggccaca gaactgaaac atcttcagtg tctagaagaa   180
gaactcaaac ctctggagga agtgctaaat ttagctcaaa gcaaaaactt tcacttagac   240
cccagggact taatcagcaa tatcaacgta tttgttctgg aactaaaggg atctgaaaca   300
acattcatgt gtgaatatgc tgatgagaca gcaaccattg tagaatttct gaacagatgg   360
attacccttta gtcaaagcat catctcaaca ctgacttga                         399
```

<210> SEQ ID NO 153
<211> LENGTH: 399
<212> TYPE: DNA
<213> ORGANISM: Artificial Sequence
<220> FEATURE:
<223> OTHER INFORMATION: IL-2 analog 47

<400> SEQUENCE: 153

```
cctacttcaa gttctacaaa gaaaacacag ctacaactgg agcatttact gctgtttta    60
cagatgattt tgaatggaat taataattac aagaatccca aactcaccgc gatgctcaca   120
aagaagtttt acatgcccaa gaaggccaca gaactgaaac atcttcagtg tctagaagaa   180
gaactcaaac ctctggagga agtgctaaat ttagctcaaa gcaaaaactt tcacttagac   240
cccagggact taatcagcaa tatcaacgta tttgttctgg aactaaaggg atctgaaaca   300
acattcatgt gtgaatatgc tgatgagaca gcaaccattg tagaatttct gaacagatgg   360
attacccttta gtcaaagcat catctcaaca ctgacttga                         399
```

<210> SEQ ID NO 154
<211> LENGTH: 399
<212> TYPE: DNA
<213> ORGANISM: Artificial Sequence
<220> FEATURE:
<223> OTHER INFORMATION: IL-2 analog 48

<400> SEQUENCE: 154

```
cctacttcaa gttctacaaa gaaaacacag ctacaactgg agcatttact gctggattta    60
```

```
cagatgattt tgaatggaat taataattac aagaatccca aactcaccgc gatgctcaca    120
aagaagtttt acatgcccaa gaaggccaca gaactgaaac atcttcagtg tctagaagaa    180
gaactcaaac ctctggagga agtgctaaat ttagctcaaa gcaaaaactt tcacttagac    240
cccagggact taatcagcgt tatcaacgta tttgttctgg aactaaaggg atctgaaaca    300
acattcatgt gtgaatatgc tgatgagaca gcaaccattg tagaatttct gaacagatgg    360 attacccttta gtcaaagcat catctcaaca ctgacttga                         399
```

<210> SEQ ID NO 155
<211> LENGTH: 399
<212> TYPE: DNA
<213> ORGANISM: Artificial Sequence
<220> FEATURE:
<223> OTHER INFORMATION: IL-2 analog 49

<400> SEQUENCE: 155

```
cctacttcaa gttctacaaa gaaaacacag ctacaactgg agcatttact gctggattta     60
cagatgattt tgaatggaat taataattac aagaatccca aactcaccgc gatgctcaca    120
aagaagtttt acatgcccaa gaaggccaca gaactgaaac atcttcagtg tctagaagaa    180
gaactcaaac ctctggagga agtgctaaat ttagctcaaa gcaaaaactt tcacttagac    240
cccagggact taatcagctt tatcaacgta tttgttctgg aactaaaggg atctgaaaca    300
acattcatgt gtgaatatgc tgatgagaca gcaaccattg tagaatttct gaacagatgg    360
attaccttta gtcaaagcat catctcaaca ctgacttga                          399
```

<210> SEQ ID NO 156
<211> LENGTH: 399
<212> TYPE: DNA
<213> ORGANISM: Artificial Sequence
<220> FEATURE:
<223> OTHER INFORMATION: IL-2 analog 50

<400> SEQUENCE: 156

```
cctacttcaa gttctacaaa gaaaacacag ctacaactgg agcatttact gctggattta     60
cagatgattt tgaatggaat taataattac aagaatccca aactcaccag gatgctcaca    120
aagaagtttt acatgcccaa gaaggccaca gaactgaaac atcttcagtg tctagaagaa    180
gaactcaaac ctctggagga agtgctaaat ttagctcaaa gcaaaaactt tcactttgac    240
cccagggacg tagtcagcaa tatcaacgta tttgttctgg aactaaaggg atctgaaaca    300
acattcatgt gtgaatatgc tgatgagaca gcaaccattg tagaatttct gaacagatgg    360
attaccttta gtcaaagcat catctcaaca ctgacttga                          399
```

<210> SEQ ID NO 157
<211> LENGTH: 399
<212> TYPE: DNA
<213> ORGANISM: Artificial Sequence
<220> FEATURE:
<223> OTHER INFORMATION: IL-2 analog 51

<400> SEQUENCE: 157

```
cctacttcaa gttctacaaa gaaaacacag ctacaactgg agcatttact gctggattta     60
cagatgattt tgaatggaat taataattac aagaatccca aactcaccag gatgctcaca    120
tttaagtttt acatgcccaa gaaggccaca gaactgaaac atcttcagtg tctagaacag    180
gaactcaaac ctctggagga agtgctaaat ttagctcaaa gcaaaaactt tcacttagac    240
cccagggact taatcagcaa tatcaacgta tttgttctgg aactaaaggg atctgaaaca    300
```

| | |
|---|---|
| acattcatgt gtgaatatgc tgatgagaca gcaaccattg tagaatttct gaacagatgg | 360 |
| attaccttta gtcaaagcat catctcaaca ctgacttga | 399 |

<210> SEQ ID NO 158
<211> LENGTH: 399
<212> TYPE: DNA
<213> ORGANISM: Artificial Sequence
<220> FEATURE:
<223> OTHER INFORMATION: IL-2 analog 52

<400> SEQUENCE: 158

| | |
|---|---|
| cctacttcaa gttctacaaa gaaaacacag ctacaactgg agcatttact gctggattta | 60 |
| cagatgattt tgaatggaat taataattac aagaatccca aactcaccgc gatgctcaca | 120 |
| aagaagtttt acatgcccaa gaaggccaca gaactgaaac atcttcagtg tctagaagaa | 180 |
| gaactcaaac ctctggagga agtgctaaat ttagctcaaa gcaaaaactt tcactttgac | 240 |
| cccagggact taatcagcaa tatcaacgta tttgttctgg aactaaaggg atctgaaaca | 300 |
| acattcatgt gtgaatatgc tgatgagaca gcaaccattg tagaatttct gaacagatgg | 360 |
| attaccttta gtcaaagcat catctcaaca ctgacttga | 399 |

<210> SEQ ID NO 159
<211> LENGTH: 399
<212> TYPE: DNA
<213> ORGANISM: Artificial Sequence
<220> FEATURE:
<223> OTHER INFORMATION: IL-2 analog 53

<400> SEQUENCE: 159

| | |
|---|---|
| cctacttcaa gttctacaaa gaaaacacag ctacaactgg agcatttact gctggattta | 60 |
| cagatgattt tgaatggaat taataattac aagaatccca aactcaccgc gatgctcaca | 120 |
| aagaagtttt acatgcccaa gaaggccaca gaactgaaac atcttcagtg tctagaagaa | 180 |
| gaactcaaac ctctggagga agtgctaaat ttagctcaaa gcaaaaactt tcactttgac | 240 |
| cccagggagt taatcagcaa tatcaacgta tttgttctgg aactaaaggg atctgaaaca | 300 |
| acattcatgt gtgaatatgc tgatgagaca gcaaccattg tagaatttct gaacagatgg | 360 |
| attaccttta gtcaaagcat catctcaaca ctgacttga | 399 |

<210> SEQ ID NO 160
<211> LENGTH: 399
<212> TYPE: DNA
<213> ORGANISM: Artificial Sequence
<220> FEATURE:
<223> OTHER INFORMATION: IL-2 analog 54

<400> SEQUENCE: 160

| | |
|---|---|
| cctacttcaa gttctacaaa gaaaacacag ctacaactgg agcatttact gctggattta | 60 |
| cagatgattt tgaatggaat taataattac aagaatccca aactcaccgc gatgctcaca | 120 |
| aagaagtttt acatgcccaa gaaggccaca gaactgaaac atcttcagtg tctagaagaa | 180 |
| gaactcaaac ctctggagga agtgctaaat ttagctcaca gcaaaaactt tcacttagac | 240 |
| cccagggact taatcagcaa tatcaacgta tttgttctgg aactaaaggg atctgaaaca | 300 |
| acattcatgt gtgaatatgc tgatgagaca gcaaccattg tagaatttct gaacagatgg | 360 |
| attaccttta gtcaaagcat catctcaaca ctgacttga | 399 |

<210> SEQ ID NO 161

```
<211> LENGTH: 399
<212> TYPE: DNA
<213> ORGANISM: Artificial Sequence
<220> FEATURE:
<223> OTHER INFORMATION: IL-2 analog 55

<400> SEQUENCE: 161
cctacttcaa gttctacaaa gaaaacacag ctacaactgg agcatttact gctggattta      60
cagatgattt tgaatggaat taataattac aagaatccca aactcaccgc gatgctcaca     120
aagaagtttt acatgcccaa gaaggccaca gaactgaaac atcttcagtg tctagaagaa     180
gaactcaaac ctctggagga agtgctaaat ttagctcaca gcaaaaactt tcactttgac     240
cccagggact aatcagcaa tatcaacgta tttgttctgg aactaaaggg atctgaaaca      300
acattcatgt gtgaatatgc tgatgagaca gcaaccattg tagaatttct gaacagatgg     360 attacccttta gtcaaagcat catctcaaca ctgacttga                           399

<210> SEQ ID NO 162
<211> LENGTH: 399
<212> TYPE: DNA
<213> ORGANISM: Artificial Sequence
<220> FEATURE:
<223> OTHER INFORMATION: IL-2 analog 56

<400> SEQUENCE: 162
cctacttcaa gttctacaaa gaaaacacag ctacaactgg agcatttact gctggattta      60
cagatgattt tgaatggaat taataattac aagaatccca aactcaccgc gatgctcaca     120
aagaagtttg ccatgcccaa gaaggccaca gaactgaaac atcttcagtg tctagaagaa     180
gaactcaaac ctctggagga agtgctaaat ttagctcaca gcaaaaactt tcacttagac     240
cccagggact aatcagcaa tatcaacgta tttgttctgg aactaaaggg atctgaaaca      300
acattcatgt gtgaatatgc tgatgagaca gcaaccattg tagaatttct gaacagatgg     360 attacccttta gtcaaagcat catctcaaca ctgacttga                           399

<210> SEQ ID NO 163
<211> LENGTH: 399
<212> TYPE: DNA
<213> ORGANISM: Artificial Sequence
<220> FEATURE:
<223> OTHER INFORMATION: IL-2 analog 57

<400> SEQUENCE: 163
cctacttcaa gttctacaaa gaaaacacag ctacaactgg agcatttact gctggattta      60
cagatgattt tgaatggaat taataattac aagaatccca aactcaccgc gatgctcaca     120
aagaagtttg ccatgcccaa gaaggccaca gaactgaaac atcttcagtg tctagaagaa     180
gaactcaaac ctctggagga agtgctaaat ttagctcaca gcaaaaactt tcactttgac     240
cccagggact aatcagcaa tatcaacgta tttgttctgg aactaaaggg atctgaaaca      300
acattcatgt gtgaatatgc tgatgagaca gcaaccattg tagaatttct gaacagatgg     360 attacccttta gtcaaagcat catctcaaca ctgacttga                           399

<210> SEQ ID NO 164
<211> LENGTH: 399
<212> TYPE: DNA
<213> ORGANISM: Artificial Sequence
<220> FEATURE:
<223> OTHER INFORMATION: IL-2 analog 58

<400> SEQUENCE: 164
```

```
cctacttcaa gttctacaaa gaaaacacag ctacaactgg agcatttact gctggattta    60
cagatgattt tgaatggaat taataattac aagaatccca aactcaccgc gatgctcaca   120
aagaagtttt acatgcccaa gaaggccaca gaactgaaac atcttcagtg tctagaagaa   180
gaactcaaac ctctggagga agtgctaaat ttagctcaaa gcaaaaactt tcactttgac   240
cccagggacg ctgccagcaa tatcaacgta tttgttctgg aactaaaggg atctgaaaca   300
acattcatgt gtgaatatgc tgatgagaca gcaaccattg tagaatttct gaacagatgg   360 attacccttta gtcaaagcat catctcaaca ctgacttga                         399
```

<210> SEQ ID NO 165
<211> LENGTH: 399
<212> TYPE: DNA
<213> ORGANISM: Artificial Sequence
<220> FEATURE:
<223> OTHER INFORMATION: IL-2 analog 59

<400> SEQUENCE: 165

```
cctacttcaa gttctacaaa gaaaacacag ctacaactgg agcatttact gctggattta    60
cagatgattt tgaatggaat taataattac aagaatccca aactcaccgc gatgctcaca   120
aagaagtttt acatgcccaa gaaggccaca gaactgaaac atcttcagtg tctagaagaa   180
gaactcaaac ctctggagga agtgctaaat ttagctcaaa gcaaaaactt tcactttgac   240
cccagggacg ctgccagcaa tatcaacgta tatgttctgg aactaaaggg atctgaaaca   300
acattcatgt gtgaatatgc tgatgagaca gcaaccattg tagaatttct gaacagatgg   360
attaccttta gtcaaagcat catctcaaca ctgacttga                          399
```

<210> SEQ ID NO 166
<211> LENGTH: 399
<212> TYPE: DNA
<213> ORGANISM: Artificial Sequence
<220> FEATURE:
<223> OTHER INFORMATION: IL-2 analog 60

<400> SEQUENCE: 166

```
cctacttcaa gttctacaaa gaaaacacag ctacaactgg agcatttact gctggattta    60
cagatgattt tgaatggaat taataattac aagaatccca aactcaccgc gatgctcaca   120
aagaagtttg ccatgcccaa gaaggccaca gaactgaaac atcttcagtg tctagaagaa   180
gaactcaaac ctctggagga agtgctaaat ttagctcaaa gcaaaaactt tcactataga   240
cccagggacg ctgccagcaa tatcaacgta tatgttctgg aactaaaggg atctgaaaca   300
acattcatgt gtgaatatgc tgatgagaca gcaaccattg tagaatttct gaacagatgg   360
attaccttta gtcaaagcat catctcaaca ctgacttga                          399
```

<210> SEQ ID NO 167
<211> LENGTH: 399
<212> TYPE: DNA
<213> ORGANISM: Artificial Sequence
<220> FEATURE:
<223> OTHER INFORMATION: IL-2 analog 61

<400> SEQUENCE: 167

```
cctacttcaa gttctacaaa gaaaacacag ctacaactgg agcatttact gctggattta    60
cagatgattt tgaatggaat taataattac aagaatccca aactcaccgc gatgctcaca   120
aagaagtttt acatgcccaa gaaggccaca gaactgaaac atcttcagtg tctagaagaa   180
```

```
gaactcaaac ctctggagga agtgctaaat ttagctcaaa gcaaaaactt tcactatgac      240
cccagggacg gtgttagcaa tatcaacgta tatgttctgg aactaaaggg atctgaaaca      300
acattcatgt gtgaatatgc tgatgagaca gcaaccattg tagaatttct gaacagatgg      360 attacccttta gtcaaagcat catctcaaca ctgacttga                            399
```

<210> SEQ ID NO 168
<211> LENGTH: 399
<212> TYPE: DNA
<213> ORGANISM: Artificial Sequence
<220> FEATURE:
<223> OTHER INFORMATION: IL-2 analog 62

<400> SEQUENCE: 168

```
cctacttcaa gttctacaaa gaaaacacag ctacaactgg agcatttact gctggattta       60
cagatgattt tgaatggaat taataattac aagaatccca aactcaccgc gatgctcaca      120
aagaagtttt acatgcccaa gaaggccaca gaactgaaac atcttcagtg tctagaagaa      180
gaactcaaac ctctggagga agtgctaaat ttagctcaaa gcaaaaactt tcactgggaa      240
cccagggacg gagccagcaa tatcaacgta tttgttctgg aactaaaggg atctgaaaca      300
acattcatgt gtgaatatgc tgatgagaca gcaaccattg tagaatttct gaacagatgg      360 attacccttta gtcaaagcat catctcaaca ctgacttga                            399
```

<210> SEQ ID NO 169
<211> LENGTH: 399
<212> TYPE: DNA
<213> ORGANISM: Artificial Sequence
<220> FEATURE:
<223> OTHER INFORMATION: IL-2 analog 63

<400> SEQUENCE: 169

```
cctacttcaa gttctacaaa gaaaacacag ctacaactgg agcatttact gctggattta       60
cagatgattt tgaatggaat taataattac aagaatccca aactcaccgc gatgctcaca      120
aagaagtttt acatgcccaa gaaggccaca gaactgaaac atcttcagtg tctagaagaa      180
gaactcaaac ctctggagga agtgctaaat ttagctcaaa gcaaaaactt tcactgacgaa      240 cccagggaca caggcagcaa tatcaacgta tttgttctgg aactaaaggg atctgaaaca      300
acattcatgt gtgaatatgc tgatgagaca gcaaccattg tagaatttct gaacagatgg      360 attacccttta gtcaaagcat catctcaaca ctgacttga                            399
```

<210> SEQ ID NO 170
<211> LENGTH: 399
<212> TYPE: DNA
<213> ORGANISM: Artificial Sequence
<220> FEATURE:
<223> OTHER INFORMATION: IL-2 analog 64

<400> SEQUENCE: 170

```
cctacttcaa gttctacaaa gaaaacacag ctacaactgg agcatttact gctggattta       60
cagatgattt tgaatggaat taataattac aagaatccca aactcaccgc gatgctcaca      120
aagaagtttt acatgcccaa gaaggccaca gaactgaaac atcttcagtg tctagaagaa      180
gaactcaaac ctctggagga agtgctaaat ttagctcaaa gcaaaaactt tcactacaac      240
cccagggacg tagtcagcaa tatcaacgta tttgttctgg aactaaaggg atctgaaaca      300
acattcatgt gtgaatatgc tgatgagaca gcaaccattg tagaatttct gaacagatgg      360 attacccttta gtcaaagcat catctcaaca ctgacttga                            399
```

<210> SEQ ID NO 171
<211> LENGTH: 399
<212> TYPE: DNA
<213> ORGANISM: Artificial Sequence
<220> FEATURE:
<223> OTHER INFORMATION: IL-2 analog 65

<400> SEQUENCE: 171

```
cctacttcaa gttctacaaa gaaaacacag ctacaactgg agcatttact gctggattta      60
cagatgattt tgaatggaat taataattac aagaatccca aactcaccgc gatgctcaca     120
aagaagtttt acatgcccaa gaaggccaca gaactgaaac atcttcagtg tctagaagaa     180
gaactcaaac ctctggagga agtgctaaat ttagctcaaa gcaaaaactt tcactacgaa     240
cccagggacg tagtcagcaa tatcaacgta tttgttctgg aactaaaggg atctgaaaca     300
acattcatgt gtgaatatgc tgatgagaca gcaaccattg tagaatttct gaacagatgg     360
attaccttta gtcaaagcat catctcaaca ctgacttga                            399
```

<210> SEQ ID NO 172
<211> LENGTH: 399
<212> TYPE: DNA
<213> ORGANISM: Artificial Sequence
<220> FEATURE:
<223> OTHER INFORMATION: IL-2 analog 66

<400> SEQUENCE: 172

```
cctacttcaa gttctacaaa gaaaacacag ctacaactgg agcatttact gctggattta      60
cagatgattt tgaatggaat taataattac aagaatccca aactcaccgc gatgctcaca     120
aagaagtttt acatgcccaa gaaggccaca gaactgaaac atcttcagtg tctagaagaa     180
gaactcaaac ctctggagga agtgctaaat ttagctcaaa gcaaaaactt tcacttcgaa     240
cccagggact tcgtcagcaa tatcaacgta tttgttctgg aactaaaggg atctgaaaca     300
acattcatgt gtgaatatgc tgatgagaca gcaaccattg tagaatttct gaacagatgg     360
attaccttta gtcaaagcat catctcaaca ctgacttga                            399
```

<210> SEQ ID NO 173
<211> LENGTH: 399
<212> TYPE: DNA
<213> ORGANISM: Artificial Sequence
<220> FEATURE:
<223> OTHER INFORMATION: IL-2 analog 67

<400> SEQUENCE: 173

```
cctacttcaa gttctacaaa gaaaacacag ctacaactgg agcatttact gctggattta      60
cagatgattt tgaatggaat taataattac aagaatccca aactcaccgc gatgctcaca     120
aagaagtttt acatgcccaa gaaggccaca gaactgaaac atcttcagtg tctagaagaa     180
gaactcaaac ctctggagga agtgctaaat ttagctcaaa gcaaaaactt tcactatgac     240
cccagggact tcgtcagcaa tatcaacgta tgggttctgg acctaaaggg atctgaaaca     300
acattcatgt gtgaatatgc tgatgagaca gcaaccattg tagaatttct gaacagatgg     360
attaccttta gtcaaagcat catctcaaca ctgacttga                            399
```

<210> SEQ ID NO 174
<211> LENGTH: 399
<212> TYPE: DNA
<213> ORGANISM: Artificial Sequence
<220> FEATURE:

<223> OTHER INFORMATION: IL-2 analog 68

<400> SEQUENCE: 174

```
cctacttcaa gttctacaaa gaaaacacag ctacaactgg agcatttact gctggattta      60
cagatgattt tgaatggaat taataattac aagaatccca aactcaccgc gatgctcaca     120
aagaagtttt acatgcccaa gaaggccaca gaactgaaac atcttcagtg tctagaagaa     180
gaactcaaac ctctggagga agtgctaaat ttagctcaaa gcaaaaactt tcacttcgaa     240
cccagggaca tagtcagcaa tatcaacgaa ttcgttctgg aactaaaggg atctgaaaca     300
acattcatgt gtgaatatgc tgatgagaca gcaaccattg tagaatttct gaacagatgg     360
attacccttta gtcaaagcat catctcaaca ctgacttga                            399
```

<210> SEQ ID NO 175
<211> LENGTH: 399
<212> TYPE: DNA
<213> ORGANISM: Artificial Sequence
<220> FEATURE:
<223> OTHER INFORMATION: IL-2 analog 69

<400> SEQUENCE: 175

```
cctacttcaa gttctacaaa gaaaacacag ctacaactgg agcatttact gctggattta      60
cagatgattt tgaatggaat taataattac aagaatccca aactcaccgc gatgctcaca     120
aagaagtttt acatgcccaa gaaggccaca gaactgaaac atcttcagtg tctagaagaa     180
gaactcaaac ctctggagga agtgctaaat ttagctcaaa gcaaaaactt tcactacgaa     240
cccagggact cctcagcaa tatcaacgaa tgggttctgg acctaaaggg atctgaaaca      300
acattcatgt gtgaatatgc tgatgagaca gcaaccattg tagaatttct gaacagatgg     360
attaccttta gtcaaagcat catctcaaca ctgacttga                             399
```

<210> SEQ ID NO 176
<211> LENGTH: 399
<212> TYPE: DNA
<213> ORGANISM: Artificial Sequence
<220> FEATURE:
<223> OTHER INFORMATION: IL-2 analog 70

<400> SEQUENCE: 176

```
cctacttcaa gttctacaaa gaaaacacag ctacaactgg agcatttact gctggattta      60
cagatgattt tgaatggaat taataattac aagaatccca aactcaccgc gatgctcaca     120
aagaagtttt acatgcccaa gaaggccaca gaactgaaac atcttcagtg tctagaagaa     180
gaactcaaac ctctggagga agtgctaaat ttagctcaaa gcaaaaactt tcactatgac     240
cccagggacg tagtcagcaa tatcaacgta tttgttctgg aactaaaggg atctgaaaca     300
acattcatgt gtgaatatgc tgatgagaca gcaaccattg tagaatttct gaacagatgg     360
attaccttta gtcaaagcat catctcaaca ctgacttga                             399
```

<210> SEQ ID NO 177
<211> LENGTH: 399
<212> TYPE: DNA
<213> ORGANISM: Artificial Sequence
<220> FEATURE:
<223> OTHER INFORMATION: IL-2 analog 71

<400> SEQUENCE: 177

```
cctacttcaa gttctacaaa gaaaacacag ctacaactgg agcatttact gctggattta      60
cagatgattt tgaatggaat taataattac aagaatccca aactcaccgc gatgctcaca     120
```

```
aagaagttttt acatgcccaa gaaggccaca gaactgaaac atcttcagtg tctagaagaa      180
gaactcaaac ctctggagga agtgctaaat ttagctcaaa gcaaaaactt tcacttcgaa      240
cccagggacg tagtcagcaa tatcaacgta tttgttctgg aactaaaggg atctgaaaca      300
acattcatgt gtgaatatgc tgatgagaca gcaaccattg tagaatttct gaacagatgg      360 attacccttta gtcaaagcat catctcaaca ctgacttga                            399
```

```
<210> SEQ ID NO 178
<211> LENGTH: 399
<212> TYPE: DNA
<213> ORGANISM: Artificial Sequence
<220> FEATURE:
<223> OTHER INFORMATION: IL-2 analog 72

<400> SEQUENCE: 178
cctacttcaa gttctacaaa gaaaacacag ctacaactgg agcatttact gctggattta      60
cagatgattt tgaatggaat taataattac aagaatccca aactcaccgc gatgctcaca     120
aagaagtttt acatgcccaa gaaggccaca gaactgaaac atcttcagtg tctagaagaa     180
gaactcaaac ctctggagga agtgctaaat ttagctcaaa gcaaaaactt tcactttgac     240
cccagggacg taggcagcaa tatcaacgta tttgttctgg aactaaaggg atctgaaaca     300
acattcatgt gtgaatatgc tgatgagaca gcaaccattg tagaatttct gaacagatgg     360
attaccttta gtcaaagcat catctcaaca ctgacttga                            399
```

```
<210> SEQ ID NO 179
<211> LENGTH: 399
<212> TYPE: DNA
<213> ORGANISM: Artificial Sequence
<220> FEATURE:
<223> OTHER INFORMATION: IL-2 analog 73

<400> SEQUENCE: 179
cctacttcaa gttctacaaa gaaaacacag ctacaactgg agcatttact gctggattta      60
cagatgattt tgaatggaat taataattac aagaatccca aactcaccgc gatgctcaca     120
aagaagtttt acatgcccaa gaaggccaca gaactgaaac atcttcagtg tctagaagaa     180
gaactcaaac ctctggagga agtgctaaat ttagctcaaa gcaaaaactt tcactttgac     240
cccagggact gggtcagcaa tatcaacgta tttgttctgg aactaaaggg atctgaaaca     300
acattcatgt gtgaatatgc tgatgagaca gcaaccattg tagaatttct gaacagatgg     360
attaccttta gtcaaagcat catctcaaca ctgacttga                            399
```

```
<210> SEQ ID NO 180
<211> LENGTH: 399
<212> TYPE: DNA
<213> ORGANISM: Artificial Sequence
<220> FEATURE:
<223> OTHER INFORMATION: IL-2 analog 74

<400> SEQUENCE: 180
cctacttcaa gttctacaaa gaaaacacag ctacaactgg agcatttact gctggattta      60
cagatgattt tgaatggaat taataattac aagaatccca aactcaccga tatgctcaca     120
aagaagtttt acatgcccaa gaaggccaca gaactgaaac atcttcagtg tctagaagaa     180
gaactcaaac ctctggagga agtgctaaat ttagctcaaa gcaaaaactt tcactatgac     240
cccagggacg tagtcagcaa tatcaacgta tttgttctgg aactaaaggg atctgaaaca     300
```

```
acattcatgt gtgaatatgc tgatgagaca gcaaccattg tagaatttct gaacagatgg    360
attacctttc gtcaaagcat catctcaaca ctgacttga                           399
```

<210> SEQ ID NO 181
<211> LENGTH: 399
<212> TYPE: DNA
<213> ORGANISM: Artificial Sequence
<220> FEATURE:
<223> OTHER INFORMATION: IL-2 analog 75

<400> SEQUENCE: 181

```
cctacttcaa gttctacaaa gaaaacacag ctacaactgg agcatttact gctggattta    60
cagatgattt tgaatggaat taataattac aagaatccca aactcaccgc gatgctcaca    120
aagaagtttg ccatgcccaa gaaggccaca gaactgaaac atcttcagtg tctagaagaa    180
gaactcaaac ctctggagga agtgctaaat ttagctcaaa gcaaaaactt tcacttcgaa    240
cccagggacg tagtcagcaa tatcaacgta tttgttctgg aactaaaggg atctgaaaca    300
acattcatgt gtgaatatgc tgatgagaca gcaaccattg tagaatttct gaacagatgg    360
attacctttc gtcaaagcat catctcaaca ctgacttga                           399
```

<210> SEQ ID NO 182
<211> LENGTH: 399
<212> TYPE: DNA
<213> ORGANISM: Artificial Sequence
<220> FEATURE:
<223> OTHER INFORMATION: IL-2 analog 76

<400> SEQUENCE: 182

```
cctacttcaa gttctacaaa gaaaacacag ctacaactgg agcatttact gctggattta    60
cagatgattt tgaatggaat taataattac aagaatccca aactcaccgc gatgctcaca    120
aagcagtttt acatgcccaa gaaggccaca gaactgaaac atcttcagtg tctagaacgg    180
gaactcaaac ctctggagga agtgctaaat ttagctcaaa gcaaaaactt tcactttgac    240
cccagggacg taggcagcaa tatcaacgta tttgttctgg aactaaaggg atctgaaaca    300
acattcatgt gtgaatatgc tgatgagaca gcaaccattg tagaatttct gaacagatgg    360
attacctttc gtcaaagcat catctcaaca ctgacttga                           399
```

<210> SEQ ID NO 183
<211> LENGTH: 399
<212> TYPE: DNA
<213> ORGANISM: Artificial Sequence
<220> FEATURE:
<223> OTHER INFORMATION: IL-2 analog 77

<400> SEQUENCE: 183

```
cctacttcaa gttctacaaa gaaaacacag ctacaactgg agcatttact gctggattta    60
cagatgattt tgaatggaat taataattac aagaatccca aactcaccgc gatgctcaca    120
aaggagtttt acatgcccaa gaaggccaca gaactgaaac atcttcagtg tctagaacgg    180
gaactcaaac ctctggagga agtgctaaat ttagctcaaa gcaaaaactt tcactttgac    240
cccagggact gggtcagcaa tatcaacgta tttgttctgg aactaaaggg atctgaaaca    300
acattcatgt gtgaatatgc tgatgagaca gcaaccattg tagaatttct gaacagatgg    360
attacctttc gtcaaagcat catctcaaca ctgacttga                           399
```

<210> SEQ ID NO 184
<211> LENGTH: 399

<212> TYPE: DNA
<213> ORGANISM: Artificial Sequence
<220> FEATURE:
<223> OTHER INFORMATION: IL-2 analog 78

<400> SEQUENCE: 184

```
cctacttcaa gttctacaaa gaaaacacag ctacaactgg agcatttact gctggattta      60
cagatgattt tgaatggaat taataattac aagaatcccg aactcaccgc gatgctcaca     120
aagaagtttt acatgcccaa gaaggccaca gaactgaaac atcttcagtg tctagaagaa     180
gaactcaaac ctctggagga agtgctaaat ttagctcaaa gcaaaaactt tcacttcgaa     240
cccagggacg tagtcagcaa tatcaacgta tttgttctgg aactaaaggg atctgaaaca     300
acattcatgt gtgaatatgc tgatgagaca gcaaccattg tagaatttct gaacagatgg     360
attacctta gtcaaagcat catctcaaca ctgacttga                             399
```

<210> SEQ ID NO 185
<211> LENGTH: 399
<212> TYPE: DNA
<213> ORGANISM: Artificial Sequence
<220> FEATURE:
<223> OTHER INFORMATION: IL-2 analog 79

<400> SEQUENCE: 185

```
cctacttcaa gttctacaaa gaaaacacag ctacaactgg agcatttact gctggattta      60
cagatgattt tgaatggaat taataattac aagaatcccg aactcaccgc gatgctcaca     120
aagaagtttt acatgcccaa gaaggccaca gaactgaaac atcttcagtg tctagaagaa     180
gaactcaaac ctctggagga agtgctaaat ttagctcaca gcaaaaactt tcacttcgaa     240
cccagggacg tagtcagcaa tatcaacgta tttgttctgg aactaaaggg atctgaaaca     300
acattcatgt gtgaatatgc tgatgagaca gcaaccattg tagaatttct gaacagatgg     360
attacctta gtcaaagcat catctcaaca ctgacttga                             399
```

<210> SEQ ID NO 186
<211> LENGTH: 399
<212> TYPE: DNA
<213> ORGANISM: Artificial Sequence
<220> FEATURE:
<223> OTHER INFORMATION: IL-2 analog 80

<400> SEQUENCE: 186

```
cctacttcaa gttctacaaa gaaaacacag ctacaactgg agcatttact gctggattta      60
cagatgattt tgaatggaat taataattac aagaatcccg aactcaccgc gatgctcaca     120
aagaagtttt acatgcccaa gaaggccaca gaactgaaac atcttcagtg tctagaagaa     180
gaactcaaac ctctggagga agtgctaaat ttagctcaca gcaaaaactt tcacttcgaa     240
ggcagggacg tagtcagcaa tatcaacgta tttgttctgg aactaaaggg atctgaaaca     300
acattcatgt gtgaatatgc tgatgagaca gcaaccattg tagaatttct gaacagatgg     360
attacctta gtcaaagcat catctcaaca ctgacttga                             399
```

<210> SEQ ID NO 187
<211> LENGTH: 399
<212> TYPE: DNA
<213> ORGANISM: Artificial Sequence
<220> FEATURE:
<223> OTHER INFORMATION: IL-2 analog 81

<400> SEQUENCE: 187

```
cctacttcaa gttctacaaa gaaaacacag ctacaactgg agcatttact gctggattta    60
cagatgattt tgaatggaat taataattac aagaatcccg aactcaccgc gatgctcaca   120
aagaagtttt acatgcccaa gaaggccaca gaactgaaac atcttcagtg tctagaagaa   180
gaactcaaac ctctggagga agtgctaaat ttagctcaca gcaaaaactt tcacttcgaa   240
gtcagggacg tagtcagcaa tatcaacgta tttgttctgg aactaaaggg atctgaaaca   300
acattcatgt gtgaatatgc tgatgagaca gcaaccattg tagaatttct gaacagatgg   360 attacccttta gtcaaagcat catctcaaca ctgacttga                         399
```

<210> SEQ ID NO 188
<211> LENGTH: 399
<212> TYPE: DNA
<213> ORGANISM: Artificial Sequence
<220> FEATURE:
<223> OTHER INFORMATION: IL-2 analog 82

<400> SEQUENCE: 188

```
cctacttcaa gttctacaaa gaaaacacag ctacaactgg agcatttacg tctggattta    60
gaaatgattt tgaatggaat taataattac aagaatccca aactcaccag gatgctcaca   120
tttaagtttt acatgcccaa gaaggccaca gaactgaaac atcttcagtg tctagaagaa   180
gaactcaaac ctctggagga agtgctaaat ttagctcaaa gcaaaaactt tcactttgac   240
cccagggacg aagtgagcaa tatcaacgta tttgttctgg aactaaaggg atctgaaaca   300
acattcatgt gtgaatatgc tgatgagaca gcaaccattg tagaatttct gaacagatgg   360 attacctttta gtcaaagcat catctcaaca ctgacttga                         399
```

<210> SEQ ID NO 189
<211> LENGTH: 399
<212> TYPE: DNA
<213> ORGANISM: Artificial Sequence
<220> FEATURE:
<223> OTHER INFORMATION: IL-2 analog 83

<400> SEQUENCE: 189

```
cctacttcaa gttctacaaa gaaaacacag ctacaactgg agcatttacg tcgtgattta    60
gaaatgattt tgaatggaat taataattac aagaatccca aactcaccag gatgctcaca   120
tttaagtttt acatgcccaa gaaggccaca gaactgaaac atcttcagtg tctagaagaa   180
gaactcaaac ctctggagga agtgctaaat ttagctcaaa gcaaaaactt tcactttgac   240
cccagggacg aagtgagcaa tatcaacgta tttgttctgg aactaaaggg atctgaaaca   300
acattcatgt gtgaatatgc tgatgagaca gcaaccattg tagaatttct gaacagatgg   360
attaccttta gtcaaagcat catctcaaca ctgacttga                          399
```

<210> SEQ ID NO 190
<211> LENGTH: 399
<212> TYPE: DNA
<213> ORGANISM: Artificial Sequence
<220> FEATURE:
<223> OTHER INFORMATION: IL-2 analog 84

<400> SEQUENCE: 190

```
cctacttcaa gttctacaaa gaaaacacag ctacaactgg agcatttacg tctggattta    60
gaaatgattt tgaatggaat taataattac aagaatccca aactcaccag gatgctcaca   120
tttaagtttt acatgcccaa gaaggccaca gaactgaaac atcttcagtg tctagaagaa   180
gaactcaaac ctctggagga agtgctaaat ttagctcaaa gcaaaaactt tcacgtggat   240
```

```
cccagggacg aagtgagcaa tatcaacgta tttgttctgg aactaaaggg atctgaaaca    300
acattcatgt gtgaatatgc tgatgagaca gcaaccattg tagaatttct gaacagatgg    360 attacccttta gtcaaagcat catctcaaca ctgacttga                          399
```

<210> SEQ ID NO 191
<211> LENGTH: 399
<212> TYPE: DNA
<213> ORGANISM: Artificial Sequence
<220> FEATURE:
<223> OTHER INFORMATION: IL-2 analog 85

<400> SEQUENCE: 191

```
cctacttcaa gttctacaaa gaaaacacag ctacaactgg agcatttact gctggattta     60
cagatgattt tgaatggaat taataattac aagaatccca aactcaccag gatgctcaca    120
tttaagtttt acatgcccaa gaaggccaca gaactgaaac atcttcagtg tctagaagaa    180
gaactcaaac tctggagga agtgctaaat ttagctcaaa gcaaaaactt tcacttcgaa     240
cccagggacg tagtcagcaa tatcaacgta tttgttctgg aactaaaggg atctgaaaca    300
acattcatgt gtgaatatgc tgatgagaca gcaaccattg tagaatttct gaacagatgg    360 attacccttta gtcaaagcat catctcaaca ctgacttga                          399
```

<210> SEQ ID NO 192
<211> LENGTH: 399
<212> TYPE: DNA
<213> ORGANISM: Artificial Sequence
<220> FEATURE:
<223> OTHER INFORMATION: IL-2 analog 86

<400> SEQUENCE: 192

```
cctacttcaa gttctacaaa gaaaacacag ctacaactgg agcatttacg tctggattta     60
gaaatgattt tgaatggaat taataattac aagaatccca aactcaccag gatgctcaca    120
tttaagtttt acatgcccaa gaaggccaca gaactgaaac atcttcagtg tctagaagaa    180
gaactcaaac tctggagga agtgctaaat ttagctcaaa gcaaaaactt tcacttcgaa     240
cccagggacg tagtcagcaa tatcaacgta tttgttctgg aactaaaggg atctgaaaca    300
acattcatgt gtgaatatgc tgatgagaca gcaaccattg tagaatttct gaacagatgg    360 attacccttta gtcaaagcat catctcaaca ctgacttga                          399
```

<210> SEQ ID NO 193
<211> LENGTH: 399
<212> TYPE: DNA
<213> ORGANISM: Artificial Sequence
<220> FEATURE:
<223> OTHER INFORMATION: IL-2 analog 87

<400> SEQUENCE: 193

```
cctacttcaa gttctacaaa gaaaacacag ctacaactgg agcatttacg tcgtgattta     60
gaaatgattt tgaatggaat taataattac aagaatccca aactcaccag gatgctcaca    120
tttaagtttt acatgcccaa gaaggccaca gaactgaaac atcttcagtg tctagaagaa    180
gaactcaaac tctggagga agtgctaaat ttagctcaaa gcaaaaactt tcacttcgaa     240
cccagggacg tagtcagcaa tatcaacgta tttgttctgg aactaaaggg atctgaaaca    300
acattcatgt gtgaatatgc tgatgagaca gcaaccattg tagaatttct gaacagatgg    360 attacccttta gtcaaagcat catctcaaca ctgacttga                          399
```

<210> SEQ ID NO 194
<211> LENGTH: 399
<212> TYPE: DNA
<213> ORGANISM: Artificial Sequence
<220> FEATURE:
<223> OTHER INFORMATION: IL-2 analog 88

<400> SEQUENCE: 194

```
cctacttcaa gttctacaaa gaaaacacag ctacaactgg agcatttact gctggattta      60
cagatgattt tgaatggaat taataattac aagaatccca aactcaccag gatgctcaca     120
tttaagtttt acatgcccaa gaaggccaca gaactgaaac atcttcagtg tctagaagac     180
gaactcaaac ctctggagga agtgctaaat ttagctcaaa gcaaaaactt tcacttcgaa     240
cccagggacg tagtcagcaa tatcaacgta tttgttctgg aactaaaggg atctgaaaca     300
acattcatgt gtgaatatgc tgatgagaca gcaaccattg tagaatttct gaacagatgg     360 attacctta gtcaaagcat catctcaaca ctgacttga                             399
```

<210> SEQ ID NO 195
<211> LENGTH: 399
<212> TYPE: DNA
<213> ORGANISM: Artificial Sequence
<220> FEATURE:
<223> OTHER INFORMATION: IL-2 analog 89

<400> SEQUENCE: 195

```
cctacttcaa gttctacaaa gaaaacacag ctacaactgg agcatttact gctggattta      60
cagatgattt tgaatggaat taataattac aagaatccca aactcaccgc gatgctcaca     120
tttaagtttt acatgcccaa gaaggccaca gaactgaaac atcttcagtg tctagaagaa     180
gaactcaaac ctctggagca ggtgctaaat ttagctcaaa gcaaaaactt tcacttcgaa     240
cccagggacg tagtcagcaa tatcaacgta tttgttctgg aactaaaggg atctgaaaca     300
acattcatgt gtgaatatgc tgatgagaca gcaaccattg tagaatttct gaacagatgg     360 attacctta gtcaaagcat catctcaaca ctgacttga                             399
```

<210> SEQ ID NO 196
<211> LENGTH: 399
<212> TYPE: DNA
<213> ORGANISM: Artificial Sequence
<220> FEATURE:
<223> OTHER INFORMATION: IL-2 analog 90

<400> SEQUENCE: 196

```
cctacttcaa gttctacaaa gaaaacacag ctacaactgg agcatttact gctggattta      60
cagatgattt tgaatggaat taataattac aagaatccca aactcaccag gatgctcaca     120
tggaagtttt acatgcccaa gaaggccaca gaactgaaac atcttcagtg tctagaagaa     180
gaactcaaac ctctggagga agtgctaaat ttagctcaaa gcaaaaactt tcacttcgaa     240
cccagggacg tagtcagcaa tatcaacgta tttgttctgg aactaaaggg atctgaaaca     300
acattcatgt gtgaatatgc tgatgagaca gcaaccattg tagaatttct gaacagatgg     360 attacctta gtcaaagcat catctcaaca ctgacttga                             399
```

<210> SEQ ID NO 197
<211> LENGTH: 399
<212> TYPE: DNA
<213> ORGANISM: Artificial Sequence
<220> FEATURE:
<223> OTHER INFORMATION: IL-2 analog 91

<400> SEQUENCE: 197

```
cctacttcaa gttctacaaa gaaaacacag ctacaactgg agcatttact gctggattta    60
cagatgattt tgaatggaat taataattac aagaatccca aactcaccag gatgctcaca   120
tttaagtttt acatgcccaa gaaggccaca gaactgaaac atcttcagtg tctagaacaa   180
gaactcaaac ctctggagga agtgctaaat ttagctcaaa gcaaaaactt tcacttcgaa   240
cccagggacg tagtcagcaa tatcaacgta tttgttctgg aactaaaggg atctgaaaca   300
acattcatgt gtgaatatgc tgatgagaca gcaaccattg tagaatttct gaacagatgg   360
attaccttta gtcaaagcat catctcaaca ctgacttga                          399
```

<210> SEQ ID NO 198
<211> LENGTH: 399
<212> TYPE: DNA
<213> ORGANISM: Artificial Sequence
<220> FEATURE:
<223> OTHER INFORMATION: IL-2 analog 92

<400> SEQUENCE: 198

```
cctacttcaa gttctacaaa gaaaacacag ctacaactgg agcatttact gctggattta    60
cagatgattt tgaatggaat taataattac aagaatccca aactcaccag gatgctcaca   120
tttaagtttt acatgcccaa gaaggccaca gaactgaaac atcttcagtg tctagaagaa   180
gaactcaaac ctctggagga agtgctaaat ttagctcaaa gcaaaaactt tcacttcgaa   240
cccagggacg tagtcagcaa tatcaacaca tttgttctgg aactaaaggg atctgaaaca   300
acattcatgt gtgaatatgc tgatgagaca gcaaccattg tagaatttct gaacagatgg   360
attaccttta gtcaaagcat catctcaaca ctgacttga                          399
```

<210> SEQ ID NO 199
<211> LENGTH: 399
<212> TYPE: DNA
<213> ORGANISM: Artificial Sequence
<220> FEATURE:
<223> OTHER INFORMATION: IL-2 analog 93

<400> SEQUENCE: 199

```
cctacttcaa gttctacaaa gaaaacacag ctacaactgg agcatttact gctggattta    60
cagatgattt tgaatggaat taataattac aagaatccca aactcaccag gatgctcaca   120
tttaagtttt acatgcccaa gaaggccaca gaactgaaac atcttcagtg tctagaagaa   180
gaactcaaac ctctggagga agtgctaaat ttagctcaaa gcaaaaactt tcacttcgaa   240
cccagggagg tagtcagcaa tatcaacaca tttgttctgg aactaaaggg atctgaaaca   300
acattcatgt gtgaatatgc tgatgagaca gcaaccattg tagaatttct gaacagatgg   360
attaccttta gtcaaagcat catctcaaca ctgacttga                          399
```

<210> SEQ ID NO 200
<211> LENGTH: 399
<212> TYPE: DNA
<213> ORGANISM: Artificial Sequence
<220> FEATURE:
<223> OTHER INFORMATION: IL-2 analog 94

<400> SEQUENCE: 200

```
cctacttcaa gttctacaaa gaaaacacag ctacaactgg agcatttact gctggattta    60
cagatgattt tgaatggaat taataattac aagaatccca aactcaccag gatgctcaca   120
```

```
tttaagtttt acatgcccaa gaaggccaca gaactgaaac atcttcagtg tctagaagaa    180
gaactcaaac ctctggagga agtgctaaat ttagctcaaa gcaaaaactt tcacttcgaa    240
cccagggacg tagtcagcaa tatcaacgta tttgttttcg aattcaaggg atctgaaaca    300
acattcatgt gtgaatatgc tgatgagaca gcaaccattg tagaatttct gaacagatgg    360 attacctttta gtcaaagcat catctcaaca ctgacttga                          399
```

```
<210> SEQ ID NO 201
<211> LENGTH: 399
<212> TYPE: DNA
<213> ORGANISM: Artificial Sequence
<220> FEATURE:
<223> OTHER INFORMATION: IL-2 analog 95

<400> SEQUENCE: 201
cctacttcaa gttctacaaa gaaaacacag ctacaactgg agcatttact gctggattta     60
cagatgattt tgaatggaat taataattac aagaatccca aactcaccag gatgctcaca    120
tttaagtttt acatgcccaa gaaggccaca gaactgaaac atcttcagtg tctagaagaa    180
gaactcaaac ctctggagga agggctaaat ttagctcaaa gcaaaaactt tcacttcgaa    240
cccagggacg tagtcagcaa tatcaacgta tttgttctgg aactaaaggg atctgaaaca    300
acattcatgt gtgaatatgc tgatgagaca gcaaccattg tagaatttct gaacagatgg    360
attaccttta gtcaaagcat catctcaaca ctgacttga                           399
```

```
<210> SEQ ID NO 202
<211> LENGTH: 399
<212> TYPE: DNA
<213> ORGANISM: Artificial Sequence
<220> FEATURE:
<223> OTHER INFORMATION: IL-2 analog 96

<400> SEQUENCE: 202
cctacttcaa gttctacaaa gaaaacacag ctacaactgg agcatttact gctggattta     60
cagatgattt tgaatggaat taataattac aagaatccca aactcaccag gatgctcaca    120
tttaagtttt acatgcccaa gaaggccaca gaactgaaac atcttcagtg tctagaagaa    180
gaactcaaac ctctggagga agggctaaat ttagctgcaa gcaaaaactt tcacttcgaa    240
cccagggacg tagtcagcaa tatcaacgta tttgttctgg aactaaaggg atctgaaaca    300
acattcatgt gtgaatatgc tgatgagaca gcaaccattg tagaatttct gaacagatgg    360
attaccttta gtcaaagcat catctcaaca ctgacttga                           399
```

```
<210> SEQ ID NO 203
<211> LENGTH: 399
<212> TYPE: DNA
<213> ORGANISM: Artificial Sequence
<220> FEATURE:
<223> OTHER INFORMATION: IL-2 analog 97

<400> SEQUENCE: 203
cctacttcaa gttctacaaa gaaaacacag ctacaactgg agcatttact gctggattta     60
cagatgattt tgaatggaat taataattac aagaatccca aactcaccgc gatgctcaca    120
tttaagtttt acatgcccaa gaaggccaca gaactgaaac atcttcagtg tctagaagaa    180
gaactcaaac ctctggagga agtgctaaat ttagctcaaa gcaaaaactt tcactttgac    240
cccagggact taatcagcaa tatcaacgta tttgttctgg aactaaaggg atctgaaaca    300
acattcatgt gtgaatatgc tgatgagaca gcaaccattg tagaatttct gaacagatgg    360
```

```
attacccttta gtcaaagcat catctcaaca ctgacttga                          399
```

<210> SEQ ID NO 204
<211> LENGTH: 399
<212> TYPE: DNA
<213> ORGANISM: Artificial Sequence
<220> FEATURE:
<223> OTHER INFORMATION: IL-2 analog 98

<400> SEQUENCE: 204

```
cctacttcaa gttctacaaa gaaaacacag ctacaactgg agcatttact gctggattta    60
cagatgattt tgaatggaat taataattac aagaatccca aactcaccgc gatgctcaca   120
tttaagtttt acatgcccaa gaaggccaca gaactgaaac atcttcagtg tctagaagaa   180
gaactcaaac ctctggagga agtgctaaat ttagctcaaa gcaaaaactt tcactttgag   240
cccagggacg taatcagcaa tatcaacgta tttgttctgg aactaaaggg atctgaaaca   300
acattcatgt gtgaatatgc tgatgagaca gcaaccattg tagaatttct gaacagatgg   360
attaccttta gtcaaagcat catctcaaca ctgacttga                          399
```

<210> SEQ ID NO 205
<211> LENGTH: 399
<212> TYPE: DNA
<213> ORGANISM: Artificial Sequence
<220> FEATURE:
<223> OTHER INFORMATION: IL-2 analog 99

<400> SEQUENCE: 205

```
cctacttcaa gttctacaaa gaaaacacag ctacaactgg agcatttact gctggattta    60
cagatgattt tgaatggaat taataattac aagaatccca aactcaccgc gatgctcaca   120
tttaagtttt acatgcccaa gaaggccaca gaactgaaac atcttcagtg tctagaagaa   180
gaactcaaac ctctggagga agtgctaaat ttagctcaaa gcaaaaactt tcactttgag   240
cccagggact tagtcagcaa tatcaacgta tttgttctgg aactaaaggg atctgaaaca   300
acattcatgt gtgaatatgc tgatgagaca gcaaccattg tagaatttct gaacagatgg   360
attaccttta gtcaaagcat catctcaaca ctgacttga                          399
```

<210> SEQ ID NO 206
<211> LENGTH: 399
<212> TYPE: DNA
<213> ORGANISM: Artificial Sequence
<220> FEATURE:
<223> OTHER INFORMATION: IL-2 analog 100

<400> SEQUENCE: 206

```
cctacttcaa gttctacaaa gaaaacacag ctacaactgg agcatttact gctggattta    60
cagatgattt tgaatggaat taataattac aagaatccca aactcaccag gatgctcaca   120
tttaagtttt acatgcccaa gaaggccaca gaactgaaac atcttcagtg tctagaagaa   180
gaactcaaac ctctggagga agtgctaaat ttagctcaaa gcaaaaactt tcacttcgaa   240
cccagggact acgtcagcaa tatcaacgta tttgttctgg aactaaaggg atctgaaaca   300
acattcatgt gtgaatatgc tgatgagaca gcaaccattg tagaatttct gaacagatgg   360
attaccttta gtcaaagcat catctcaaca ctgacttga                          399
```

<210> SEQ ID NO 207
<211> LENGTH: 399
<212> TYPE: DNA

```
<213> ORGANISM: Artificial Sequence
<220> FEATURE:
<223> OTHER INFORMATION: IL-2 analog 101

<400> SEQUENCE: 207
cctacttcaa gttctacaaa gaaaacacag ctacaactgg agcatttact gctggattta      60
cagatgattt tgaatggaat taataattac aagaatccca aactcaccag gatgctcaca     120
tttaagtttt acatgcccaa gaaggccaca gaactgaaac atcttcagtg tctagaagaa     180
gaactcaaac ctctggagga agtgctaaat ttagctcaaa gcaaaaactt tcacttcgaa     240
cccagggacc tggccagcaa tatcaacgta tttgttctgg aactaaaggg atctgaaaca     300
acattcatgt gtgaatatgc tgatgagaca gcaaccattg tagaatttct gaacagatgg     360 attacctttta gtcaaagcat catctcaaca ctgacttga                           399

<210> SEQ ID NO 208
<211> LENGTH: 399
<212> TYPE: DNA
<213> ORGANISM: Artificial Sequence
<220> FEATURE:
<223> OTHER INFORMATION: IL-2 analog 102

<400> SEQUENCE: 208
cctacttcaa gttctacaaa gaaaacacag ctacaactgg agcatttact gctggattta      60
cagatgattt tgaatggaat taataattac aagaatccca aactcaccag gatgctcaca     120
tttaagtttt acatgcccaa gaaggccaca gaactgaaac atcttcagtg tctagaagaa     180
gaactcaaac ctctggagga agtgctaaat ttagctcaaa gcaaaaactt tcacttcgaa     240
cccagggacg tagtcagcaa tatcaacgta attgttctgg aactaaaggg atctgaaaca     300
acattcatgt gtgaatatgc tgatgagaca gcaaccattg tagaatttct gaacagatgg     360 attacctttta gtcaaagcat catctcaaca ctgacttga                           399

<210> SEQ ID NO 209
<211> LENGTH: 399
<212> TYPE: DNA
<213> ORGANISM: Artificial Sequence
<220> FEATURE:
<223> OTHER INFORMATION: IL-2 analog 103

<400> SEQUENCE: 209
cctacttcaa gttctacaaa gaaaacacag ctacaactgg agcatttacg tctggattta      60
gaaatgattt tgaatggaat taataattac aagaatccca aactcaccgc gatgctcaca     120
tttaagtttt acatgcccaa gaaggccaca gaactgaaac atcttcagtg tctagaagaa     180
gaactcaaac ctctggagga agtgctaaat ttagctcaaa gcaaaaactt tcacttcgaa     240
cccagggacg tagtcagcaa tatcaacgta tttgttctgg aactaaaggg atctgaaaca     300
acattcatgt gtgaatatgc tgatgagaca gcaaccattg tagaatttct gaacagatgg     360 attacctttta gtcaaagcat catctcaaca ctgacttga                           399

<210> SEQ ID NO 210
<211> LENGTH: 399
<212> TYPE: DNA
<213> ORGANISM: Artificial Sequence
<220> FEATURE:
<223> OTHER INFORMATION: IL-2 analog 104

<400> SEQUENCE: 210
cctacttcaa gttctacaaa gaaaacacag ctacaactgg agcatttacg tctggattta      60
```

```
gaaatgattt tgaatggaat taataattac aagaatccca aactcaccag gatgctcaca    120
tttaagtttt acatgcccaa gaaggccaca gaactgaaac atcttcagtg tctagaagac    180
gaactcaaac ctctggagga agtgctaaat ttagctcaaa gcaaaaactt tcacttcgaa    240
cccagggacg tagtcagcaa tatcaacgta tttgttctgg aactaaaggg atctgaaaca    300
acattcatgt gtgaatatgc tgatgagaca gcaaccattg tagaatttct gaacagatgg    360 attacctttta gtcaaagcat catctcaaca ctgacttga                          399
```

<210> SEQ ID NO 211
<211> LENGTH: 399
<212> TYPE: DNA
<213> ORGANISM: Artificial Sequence
<220> FEATURE:
<223> OTHER INFORMATION: IL-2 analog 105

<400> SEQUENCE: 211

```
cctacttcaa gttctacaaa gaaaacacag ctacaactgg agcatttacg tctggattta     60
gaaatgattt tgaatggaat taataattac aagaatccca aactcaccag gatgctcaca    120
tttaagtttt acatgcccaa gaaggccaca gaactgaaac atcttcagtg tctagaagaa    180
gaactcaaac ctctggagga cgtgctaaat ttagctcaaa gcaaaaactt tcacttcgaa    240
cccagggacg tagtcagcaa tatcaacgta tttgttctgg aactaaaggg atctgaaaca    300
acattcatgt gtgaatatgc tgatgagaca gcaaccattg tagaatttct gaacagatgg    360 attacctttta gtcaaagcat catctcaaca ctgacttga                          399
```

<210> SEQ ID NO 212
<211> LENGTH: 133
<212> TYPE: PRT
<213> ORGANISM: Artificial Sequence
<220> FEATURE:
<223> OTHER INFORMATION: General Formula 1
<220> FEATURE:
<221> NAME/KEY: MISC_FEATURE
<222> LOCATION: (1)
<223> OTHER INFORMATION: Xaa is a deletion
<220> FEATURE:
<221> NAME/KEY: MISC_FEATURE
<222> LOCATION: (18)
<223> OTHER INFORMATION: Xaa is leucine (L) or arginine (R)
<220> FEATURE:
<221> NAME/KEY: MISC_FEATURE
<222> LOCATION: (19)
<223> OTHER INFORMATION: Xaa is leucine (L) or tyrosine (Y)
<220> FEATURE:
<221> NAME/KEY: MISC_FEATURE
<222> LOCATION: (22)
<223> OTHER INFORMATION: Xaa is glutamic acid (E) or glutamine (Q)
<220> FEATURE:
<221> NAME/KEY: MISC_FEATURE
<222> LOCATION: (38)
<223> OTHER INFORMATION: Xaa is alanine (A), aspartic acid (D), or
      arginine (R)
<220> FEATURE:
<221> NAME/KEY: MISC_FEATURE
<222> LOCATION: (42)
<223> OTHER INFORMATION: Xaa is alanine (A), phenylalanine (F), lysine
      (K), or tryptophan (W)
<220> FEATURE:
<221> NAME/KEY: MISC_FEATURE
<222> LOCATION: (43)
<223> OTHER INFORMATION: Xaa is glutamic acid (E), lysine (K), or
      glutamine (Q)
<220> FEATURE:
<221> NAME/KEY: MISC_FEATURE
<222> LOCATION: (45)
<223> OTHER INFORMATION: Xaa is alanine (A) or tyrosine (Y)

```
<220> FEATURE:
<221> NAME/KEY: MISC_FEATURE
<222> LOCATION: (61)
<223> OTHER INFORMATION: Xaa is aspartic acid (D), glutamic acid (E),
      glutamine (Q), or arginine (R)
<220> FEATURE:
<221> NAME/KEY: MISC_FEATURE
<222> LOCATION: (68)
<223> OTHER INFORMATION: Xaa is aspartic acid (D) or glutamic acid (E)
<220> FEATURE:
<221> NAME/KEY: MISC_FEATURE
<222> LOCATION: (74)
<223> OTHER INFORMATION: Xaa is histidine (H) or glutamine (Q)
<220> FEATURE:
<221> NAME/KEY: MISC_FEATURE
<222> LOCATION: (80)
<223> OTHER INFORMATION: Xaa is phenylalanine (F), leucine (L), valine
      (V), or tyrosine (Y)
<220> FEATURE:
<221> NAME/KEY: MISC_FEATURE
<222> LOCATION: (81)
<223> OTHER INFORMATION: Xaa is aspartic acid (D), glutamic acid (E), or
      arginine (R)
<220> FEATURE:
<221> NAME/KEY: MISC_FEATURE
<222> LOCATION: (84)
<223> OTHER INFORMATION: Xaa is aspartic acid (D) or glutamic acid (E)
<220> FEATURE:
<221> NAME/KEY: MISC_FEATURE
<222> LOCATION: (85)
<223> OTHER INFORMATION: Xaa is alanine (A), glutamic acid (E), glycine
      (G), leucine (L), valine (V), tryptophan (W), or tyrosine (Y)
<220> FEATURE:
<221> NAME/KEY: MISC_FEATURE
<222> LOCATION: (86)
<223> OTHER INFORMATION: Xaa is alanine (A), glycine (G), isoleucine
      (I), or valine (V)
<220> FEATURE:
<221> NAME/KEY: MISC_FEATURE
<222> LOCATION: (91)
<223> OTHER INFORMATION: Xaa is threonine (T) or valine (V)
<220> FEATURE:
<221> NAME/KEY: MISC_FEATURE
<222> LOCATION: (92)
<223> OTHER INFORMATION: Xaa is phenylalanine (F), isoleucine (I), or
      tyrosine (Y)
<220> FEATURE:
<221> NAME/KEY: MISC_FEATURE
<222> LOCATION: (94)
<223> OTHER INFORMATION: Xaa is phenylalanine (F) or leucine (L)
<220> FEATURE:
<221> NAME/KEY: MISC_FEATURE
<222> LOCATION: (96)
<223> OTHER INFORMATION: Xaa is phenylalanine (F) or leucine (L)

<400> SEQUENCE: 212

Xaa Pro Thr Ser Ser Thr Lys Lys Thr Gln Leu Gln Leu Glu His
1               5                   10                  15

Leu Xaa Xaa Asp Leu Xaa Met Ile Leu Asn Gly Ile Asn Asn Tyr Lys
            20                  25                  30

Asn Pro Lys Leu Thr Xaa Met Leu Thr Xaa Xaa Phe Xaa Met Pro Lys
        35                  40                  45

Lys Ala Thr Glu Leu Lys His Leu Gln Cys Leu Glu Xaa Glu Leu Lys
    50                  55                  60

Pro Leu Glu Xaa Val Leu Asn Leu Ala Xaa Ser Lys Asn Phe His Xaa
65                  70                  75                  80

Xaa Pro Arg Xaa Xaa Xaa Ser Asn Ile Asn Xaa Xaa Val Xaa Glu Xaa
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
```

```
                115                 120                 125

Ile Ser Thr Leu Thr
        130

<210> SEQ ID NO 213
<211> LENGTH: 133
<212> TYPE: PRT
<213> ORGANISM: Artificial Sequence
<220> FEATURE:
<223> OTHER INFORMATION: General Formula 2
<220> FEATURE:
<221> NAME/KEY: MISC_FEATURE
<222> LOCATION: (1)
<223> OTHER INFORMATION: Xaa is a deletion
<220> FEATURE:
<221> NAME/KEY: MISC_FEATURE
<222> LOCATION: (18)
<223> OTHER INFORMATION: Xaa is leucine (L) or arginine (R)
<220> FEATURE:
<221> NAME/KEY: MISC_FEATURE
<222> LOCATION: (22)
<223> OTHER INFORMATION: Xaa is glutamic acid (E) or glutamine (Q)
<220> FEATURE:
<221> NAME/KEY: MISC_FEATURE
<222> LOCATION: (38)
<223> OTHER INFORMATION: Xaa is alanine (A) or arginine (R)
<220> FEATURE:
<221> NAME/KEY: MISC_FEATURE
<222> LOCATION: (42)
<223> OTHER INFORMATION: Xaa is phenylalanine (F) or lysine (K)
<220> FEATURE:
<221> NAME/KEY: MISC_FEATURE
<222> LOCATION: (61)
<223> OTHER INFORMATION: Xaa is aspartic acid (D) or glutamic acid (E)
<220> FEATURE:
<221> NAME/KEY: MISC_FEATURE
<222> LOCATION: (68)
<223> OTHER INFORMATION: Xaa is aspartic acid (D) or glutamic acid (E)
<220> FEATURE:
<221> NAME/KEY: MISC_FEATURE
<222> LOCATION: (81)
<223> OTHER INFORMATION: Xaais aspartic acid (D) or glutamic acid (E)
<220> FEATURE:
<221> NAME/KEY: MISC_FEATURE
<222> LOCATION: (85)
<223> OTHER INFORMATION: Xaa is leucine (L) or valine (V)
<220> FEATURE:
<221> NAME/KEY: MISC_FEATURE
<222> LOCATION: (86)
<223> OTHER INFORMATION: Xaa is isoleucine (I) or valine (V)

<400> SEQUENCE: 213

Xaa Pro Thr Ser Ser Thr Lys Lys Thr Gln Leu Gln Leu Glu His
1               5                   10                  15

Leu Xaa Leu Asp Leu Xaa Met Ile Leu Asn Gly Ile Asn Asn Tyr Lys
            20                  25                  30

Asn Pro Lys Leu Thr Xaa Met Leu Thr Xaa Lys Phe Tyr Met Pro Lys
                35                  40                  45

Lys Ala Thr Glu Leu Lys His Leu Gln Cys Leu Glu Xaa Glu Leu Lys
    50                  55                  60

Pro Leu Glu Xaa Val Leu Asn Leu Ala Gln Ser Lys Asn Phe His Phe
65                  70                  75                  80

Xaa Pro Arg Asp Xaa Xaa Ser Asn Ile Asn Val Phe Val Leu Glu Leu
                85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Ser Gln Ser Ile
            115                 120                 125
```

Ile Ser Thr Leu Thr
    130

<210> SEQ ID NO 214
<211> LENGTH: 33
<212> TYPE: DNA
<213> ORGANISM: Artificial Sequence
<220> FEATURE:
<223> OTHER INFORMATION: primer #1 (IL2_L12F_F)

<400> SEQUENCE: 214
caaagaaaac acagtttcaa ctggagcatt tac                33

<210> SEQ ID NO 215
<211> LENGTH: 33
<212> TYPE: DNA
<213> ORGANISM: Artificial Sequence
<220> FEATURE:
<223> OTHER INFORMATION: primer #2 (IL2_L12F_R)

<400> SEQUENCE: 215
gtaaatgctc cagttgaaac tgtgttttct ttg                33

<210> SEQ ID NO 216
<211> LENGTH: 33
<212> TYPE: DNA
<213> ORGANISM: Artificial Sequence
<220> FEATURE:
<223> OTHER INFORMATION: primer #3 (IL2_L12V_F)

<400> SEQUENCE: 216
caaagaaaac acaggtacaa ctggagcatt tac                33

<210> SEQ ID NO 217
<211> LENGTH: 33
<212> TYPE: DNA
<213> ORGANISM: Artificial Sequence
<220> FEATURE:
<223> OTHER INFORMATION: primer #4 (IL2_L12V_R)

<400> SEQUENCE: 217
gtaaatgctc cagttgtacc tgtgttttct ttg                33

<210> SEQ ID NO 218
<211> LENGTH: 39
<212> TYPE: DNA
<213> ORGANISM: Artificial Sequence
<220> FEATURE:
<223> OTHER INFORMATION: primer #5 (IL2_L18R_L19R_Q22E_F)

<400> SEQUENCE: 218
ctggagcatt tacgtcgtga tttagaaatg attttgaat            39

<210> SEQ ID NO 219
<211> LENGTH: 39
<212> TYPE: DNA
<213> ORGANISM: Artificial Sequence
<220> FEATURE:
<223> OTHER INFORMATION: primer #6 (IL2_L18R_L19R_Q22E_R)

<400> SEQUENCE: 219
attcaaaatc atttctaaat cacgacgtaa atgctccag            39

<210> SEQ ID NO 220
<211> LENGTH: 39
<212> TYPE: DNA

```
<213> ORGANISM: Artificial Sequence
<220> FEATURE:
<223> OTHER INFORMATION: primer #7 (IL2_L18R_Q22E_F)

<400> SEQUENCE: 220
ctggagcatt tacgtctgga tttagaaatg attttgaat                              39

<210> SEQ ID NO 221
<211> LENGTH: 39
<212> TYPE: DNA
<213> ORGANISM: Artificial Sequence
<220> FEATURE:
<223> OTHER INFORMATION: primer #8 (IL2_L18R_Q22E_R)

<400> SEQUENCE: 221
attcaaaatc atttctaaat ccagacgtaa atgctccag                              39

<210> SEQ ID NO 222
<211> LENGTH: 33
<212> TYPE: DNA
<213> ORGANISM: Artificial Sequence
<220> FEATURE:
<223> OTHER INFORMATION: primer #9 (IL2_L19F_F)

<400> SEQUENCE: 222
gagcatttac tgttcgattt acagatgatt ttg                                    33

<210> SEQ ID NO 223
<211> LENGTH: 33
<212> TYPE: DNA
<213> ORGANISM: Artificial Sequence
<220> FEATURE:
<223> OTHER INFORMATION: primer #10 (IL2_L19F_R)

<400> SEQUENCE: 223
caaaatcatc tgtaaatcga acagtaaatg ctc                                    33

<210> SEQ ID NO 224
<211> LENGTH: 33
<212> TYPE: DNA
<213> ORGANISM: Artificial Sequence
<220> FEATURE:
<223> OTHER INFORMATION: primer #11 (IL2_L19V_F)

<400> SEQUENCE: 224
gagcatttac tggtggattt acagatgatt ttg                                    33

<210> SEQ ID NO 225
<211> LENGTH: 33
<212> TYPE: DNA
<213> ORGANISM: Artificial Sequence
<220> FEATURE:
<223> OTHER INFORMATION: primer #12 (IL2_L19V_R)

<400> SEQUENCE: 225
caaaatcatc tgtaaatcca ccagtaaatg ctc                                    33

<210> SEQ ID NO 226
<211> LENGTH: 33
<212> TYPE: DNA
<213> ORGANISM: Artificial Sequence
<220> FEATURE:
<223> OTHER INFORMATION: primer #13 (IL2_L19Y_F)

<400> SEQUENCE: 226
caactggagc atttactgta cgatttacag atg                                    33
```

<210> SEQ ID NO 227
<211> LENGTH: 33
<212> TYPE: DNA
<213> ORGANISM: Artificial Sequence
<220> FEATURE:
<223> OTHER INFORMATION: primer #14 (IL2_L19Y_R)

<400> SEQUENCE: 227
catctgtaaa tcgtacagta aatgctccag ttg                                  33

<210> SEQ ID NO 228
<211> LENGTH: 34
<212> TYPE: DNA
<213> ORGANISM: Artificial Sequence
<220> FEATURE:
<223> OTHER INFORMATION: primer #15 (IL2_D20F_F)

<400> SEQUENCE: 228
ggagcattta ctgctgtttt tacagatgat tttg                                 34

<210> SEQ ID NO 229
<211> LENGTH: 34
<212> TYPE: DNA
<213> ORGANISM: Artificial Sequence
<220> FEATURE:
<223> OTHER INFORMATION: primer #16 (IL2_D20F_R)

<400> SEQUENCE: 229
caaaatcatc tgtaaaaaca gcagtaaatg ctcc                                 34

<210> SEQ ID NO 230
<211> LENGTH: 33
<212> TYPE: DNA
<213> ORGANISM: Artificial Sequence
<220> FEATURE:
<223> OTHER INFORMATION: primer #17 (IL2_D20V_F)

<400> SEQUENCE: 230
gagcatttac tgctggtttt acagatgatt ttg                                  33

<210> SEQ ID NO 231
<211> LENGTH: 33
<212> TYPE: DNA
<213> ORGANISM: Artificial Sequence
<220> FEATURE:
<223> OTHER INFORMATION: primer #18 (IL2_D20V_R)

<400> SEQUENCE: 231
caaaatcatc tgtaaaacca gcagtaaatg ctc                                  33

<210> SEQ ID NO 232
<211> LENGTH: 33
<212> TYPE: DNA
<213> ORGANISM: Artificial Sequence
<220> FEATURE:
<223> OTHER INFORMATION: primer #19 (IL2_K32C_F)

<400> SEQUENCE: 232
ggaattaata attactgtaa tcccaaactc acc                                  33

<210> SEQ ID NO 233
<211> LENGTH: 33
<212> TYPE: DNA
<213> ORGANISM: Artificial Sequence
<220> FEATURE:

```
<223> OTHER INFORMATION: primer #20 (IL2_K32C_R)

<400> SEQUENCE: 233
ggtgagtttg ggattacagt aattattaat tcc                                33

<210> SEQ ID NO 234
<211> LENGTH: 33
<212> TYPE: DNA
<213> ORGANISM: Artificial Sequence
<220> FEATURE:
<223> OTHER INFORMATION: primer #21 (IL2_K35C_F)

<400> SEQUENCE: 234
aattacaaga atccctgtct caccaggatg ctc                                33

<210> SEQ ID NO 235
<211> LENGTH: 33
<212> TYPE: DNA
<213> ORGANISM: Artificial Sequence
<220> FEATURE:
<223> OTHER INFORMATION: primer #22 (IL2_K35C_R)

<400> SEQUENCE: 235
gagcatcctg gtgagacagg gattcttgta att                                33

<210> SEQ ID NO 236
<211> LENGTH: 33
<212> TYPE: DNA
<213> ORGANISM: Artificial Sequence
<220> FEATURE:
<223> OTHER INFORMATION: primer #23 (IL2_K35E_F)

<400> SEQUENCE: 236
taattacaag aatcccgaac tcaccgcgat gct                                33

<210> SEQ ID NO 237
<211> LENGTH: 33
<212> TYPE: DNA
<213> ORGANISM: Artificial Sequence
<220> FEATURE:
<223> OTHER INFORMATION: primer #24 (IL2_K35E_R)

<400> SEQUENCE: 237
agcatcgcgg tgagttcggg attcttgtaa tta                                33

<210> SEQ ID NO 238
<211> LENGTH: 25
<212> TYPE: DNA
<213> ORGANISM: Artificial Sequence
<220> FEATURE:
<223> OTHER INFORMATION: primer #25 (IL2_R38A_F)

<400> SEQUENCE: 238
ccaaactcac cgcgatgctc acatt                                         25

<210> SEQ ID NO 239
<211> LENGTH: 25
<212> TYPE: DNA
<213> ORGANISM: Artificial Sequence
<220> FEATURE:
<223> OTHER INFORMATION: primer #26 (IL2_R38A_R)

<400> SEQUENCE: 239
aatgtgagca tcgcggtgag tttgg                                         25
```

```
<210> SEQ ID NO 240
<211> LENGTH: 33
<212> TYPE: DNA
<213> ORGANISM: Artificial Sequence
<220> FEATURE:
<223> OTHER INFORMATION: primer #27 (IL2_R38A_F42F_F)

<400> SEQUENCE: 240
caccgcgatg ctcacattta agttttacat gcc                          33

<210> SEQ ID NO 241
<211> LENGTH: 33
<212> TYPE: DNA
<213> ORGANISM: Artificial Sequence
<220> FEATURE:
<223> OTHER INFORMATION: primer #28 (IL2_R38A_F42F_R)

<400> SEQUENCE: 241
ggcatgtaaa acttaaatgt gagcatcgcg gtg                          33

<210> SEQ ID NO 242
<211> LENGTH: 25
<212> TYPE: DNA
<213> ORGANISM: Artificial Sequence
<220> FEATURE:
<223> OTHER INFORMATION: primer #29 (IL2_A38R_F)

<400> SEQUENCE: 242
ccaaactcac caggatgctc acatt                                   25

<210> SEQ ID NO 243
<211> LENGTH: 25
<212> TYPE: DNA
<213> ORGANISM: Artificial Sequence
<220> FEATURE:
<223> OTHER INFORMATION: primer #30 (IL2_A38R_R)

<400> SEQUENCE: 243
aatgtgagca tcctggtgag tttgg                                   25

<210> SEQ ID NO 244
<211> LENGTH: 30
<212> TYPE: DNA
<213> ORGANISM: Artificial Sequence
<220> FEATURE:
<223> OTHER INFORMATION: primer #31 (IL2_R38D_F)

<400> SEQUENCE: 244
aagaatccca aactcaccga tatgctcaca                              30

<210> SEQ ID NO 245
<211> LENGTH: 30
<212> TYPE: DNA
<213> ORGANISM: Artificial Sequence
<220> FEATURE:
<223> OTHER INFORMATION: primer #32 (IL2_R38D_R)

<400> SEQUENCE: 245
tgtgagcata tcggtgagtt tgggattctt                              30

<210> SEQ ID NO 246
<211> LENGTH: 30
<212> TYPE: DNA
<213> ORGANISM: Artificial Sequence
<220> FEATURE:
<223> OTHER INFORMATION: primer #33 (IL2_F42A_F)
```

```
<400> SEQUENCE: 246
ccaggatgct cacagctaag ttttacatgc                                          30

<210> SEQ ID NO 247
<211> LENGTH: 30
<212> TYPE: DNA
<213> ORGANISM: Artificial Sequence
<220> FEATURE:
<223> OTHER INFORMATION: primer #34 (IL2_F42A_R)

<400> SEQUENCE: 247
gcatgtaaaa cttagctgtg agcatcctgg                                          30

<210> SEQ ID NO 248
<211> LENGTH: 30
<212> TYPE: DNA
<213> ORGANISM: Artificial Sequence
<220> FEATURE:
<223> OTHER INFORMATION: primer #35 (IL2_F42K_F)

<400> SEQUENCE: 248
ccaggatgct cacaaagaag ttttacatgc                                          30

<210> SEQ ID NO 249
<211> LENGTH: 30
<212> TYPE: DNA
<213> ORGANISM: Artificial Sequence
<220> FEATURE:
<223> OTHER INFORMATION: primer #36 (IL2_F42K_R)

<400> SEQUENCE: 249
gcatgtaaaa cttctttgtg agcatcctgg                                          30

<210> SEQ ID NO 250
<211> LENGTH: 30
<212> TYPE: DNA
<213> ORGANISM: Artificial Sequence
<220> FEATURE:
<223> OTHER INFORMATION: primer #37 (IL2_F42K_K43E_F)

<400> SEQUENCE: 250
atgctcacaa aggagtttta catgcccaag                                          30

<210> SEQ ID NO 251
<211> LENGTH: 30
<212> TYPE: DNA
<213> ORGANISM: Artificial Sequence
<220> FEATURE:
<223> OTHER INFORMATION: primer #38 (IL2_F42K_K43E_R)

<400> SEQUENCE: 251
cttgggcatg taaaactcct ttgtgagcat                                          30

<210> SEQ ID NO 252
<211> LENGTH: 30
<212> TYPE: DNA
<213> ORGANISM: Artificial Sequence
<220> FEATURE:
<223> OTHER INFORMATION: primer #39 (IL2_F42K_K43Q_F)

<400> SEQUENCE: 252
atgctcacaa agcagtttta catgcccaag                                          30

<210> SEQ ID NO 253
<211> LENGTH: 30
```

-continued

<210> SEQ ID NO 253
<211> LENGTH: 30
<212> TYPE: DNA
<213> ORGANISM: Artificial Sequence
<220> FEATURE:
<223> OTHER INFORMATION: primer #40 (IL2_F42K_K43Q_R)

<400> SEQUENCE: 253
cttgggcatg taaaactgct ttgtgagcat        30

<210> SEQ ID NO 254
<211> LENGTH: 30
<212> TYPE: DNA
<213> ORGANISM: Artificial Sequence
<220> FEATURE:
<223> OTHER INFORMATION: primer #41 (IL2_K42F_F)

<400> SEQUENCE: 254
ccaggatgct cacatttaag ttttacatgc        30

<210> SEQ ID NO 255
<211> LENGTH: 30
<212> TYPE: DNA
<213> ORGANISM: Artificial Sequence
<220> FEATURE:
<223> OTHER INFORMATION: primer #42 (IL2_K42F_R)

<400> SEQUENCE: 255
gcatgtaaaa cttaaatgtg agcatcctgg        30

<210> SEQ ID NO 256
<211> LENGTH: 39
<212> TYPE: DNA
<213> ORGANISM: Artificial Sequence
<220> FEATURE:
<223> OTHER INFORMATION: primer #43 (IL2_K42F_F_long)

<400> SEQUENCE: 256
ctcaccagga tgctcacatt taagttttac atgcccaag        39

<210> SEQ ID NO 257
<211> LENGTH: 39
<212> TYPE: DNA
<213> ORGANISM: Artificial Sequence
<220> FEATURE:
<223> OTHER INFORMATION: primer #44 (IL2_K42F_R_long)

<400> SEQUENCE: 257
cttgggcatg taaaacttaa atgtgagcat cctggtgag        39

<210> SEQ ID NO 258
<211> LENGTH: 33
<212> TYPE: DNA
<213> ORGANISM: Artificial Sequence
<220> FEATURE:
<223> OTHER INFORMATION: primer #45 (IL2_F42W_F)

<400> SEQUENCE: 258
accaggatgc tcacatggaa gttttacatg ccc        33

<210> SEQ ID NO 259
<211> LENGTH: 33
<212> TYPE: DNA
<213> ORGANISM: Artificial Sequence
<220> FEATURE:
<223> OTHER INFORMATION: primer #46 (IL2_F42W_R)

<400> SEQUENCE: 259
gggcatgtaa aacttccatg tgagcatcct ggt                                    33

<210> SEQ ID NO 260
<211> LENGTH: 33
<212> TYPE: DNA
<213> ORGANISM: Artificial Sequence
<220> FEATURE:
<223> OTHER INFORMATION: primer #47 (IL2_K43C_F)

<400> SEQUENCE: 260
aggatgctca cattttgttt ttacatgccc aag                                    33

<210> SEQ ID NO 261
<211> LENGTH: 33
<212> TYPE: DNA
<213> ORGANISM: Artificial Sequence
<220> FEATURE:
<223> OTHER INFORMATION: primer #48 (IL2_K43C_R)

<400> SEQUENCE: 261
cttgggcatg taaaaacaaa atgtgagcat cct                                    33

<210> SEQ ID NO 262
<211> LENGTH: 19
<212> TYPE: DNA
<213> ORGANISM: Artificial Sequence
<220> FEATURE:
<223> OTHER INFORMATION: primer #49 (IL2_Y45A_F)

<400> SEQUENCE: 262
gaagtttgcc atgcccaag                                                    19

<210> SEQ ID NO 263
<211> LENGTH: 19
<212> TYPE: DNA
<213> ORGANISM: Artificial Sequence
<220> FEATURE:
<223> OTHER INFORMATION: primer #50 (IL2_Y45A_R)

<400> SEQUENCE: 263
cttgggcatg gcaaacttc                                                    19

<210> SEQ ID NO 264
<211> LENGTH: 34
<212> TYPE: DNA
<213> ORGANISM: Artificial Sequence
<220> FEATURE:
<223> OTHER INFORMATION: primer #51 (IL2_Y45A_F_long)

<400> SEQUENCE: 264
gctcacaaag aagtttgcca tgcccaagaa ggcc                                   34

<210> SEQ ID NO 265
<211> LENGTH: 34
<212> TYPE: DNA
<213> ORGANISM: Artificial Sequence
<220> FEATURE:
<223> OTHER INFORMATION: primer #52 (IL2_Y45A_R_long)

<400> SEQUENCE: 265
ggccttcttg ggcatggcaa acttctttgt gagc                                   34

<210> SEQ ID NO 266
<211> LENGTH: 33
<212> TYPE: DNA
<213> ORGANISM: Artificial Sequence

```
<220> FEATURE:
<223> OTHER INFORMATION: primer #53 (IL2_K48C_F)

<400> SEQUENCE: 266 aagtttttaca tgccctgtaa ggccacagaa ctg                              33

<210> SEQ ID NO 267
<211> LENGTH: 33
<212> TYPE: DNA
<213> ORGANISM: Artificial Sequence
<220> FEATURE:
<223> OTHER INFORMATION: primer #54 (IL2_K48C_R)

<400> SEQUENCE: 267
cagttctgtg gccttacagg gcatgtaaaa ctt                               33

<210> SEQ ID NO 268
<211> LENGTH: 33
<212> TYPE: DNA
<213> ORGANISM: Artificial Sequence
<220> FEATURE:
<223> OTHER INFORMATION: primer #55 (IL2_K49C_F)

<400> SEQUENCE: 268
ttttacatgc ccaagtgtgc cacagaactg aaa                               33

<210> SEQ ID NO 269
<211> LENGTH: 33
<212> TYPE: DNA
<213> ORGANISM: Artificial Sequence
<220> FEATURE:
<223> OTHER INFORMATION: primer #56 (IL2_K49C_R)

<400> SEQUENCE: 269
tttcagttct gtggcacact tgggcatgta aaa                               33

<210> SEQ ID NO 270
<211> LENGTH: 33
<212> TYPE: DNA
<213> ORGANISM: Artificial Sequence
<220> FEATURE:
<223> OTHER INFORMATION: primer #57 (IL2_E61D_F)

<400> SEQUENCE: 270
cttcagtgtc tagaagacga actcaaacct ctg                               33

<210> SEQ ID NO 271
<211> LENGTH: 33
<212> TYPE: DNA
<213> ORGANISM: Artificial Sequence
<220> FEATURE:
<223> OTHER INFORMATION: primer #58 (IL2_E61D_R)

<400> SEQUENCE: 271
cagaggtttg agttcgtctt ctagacactg aag                               33

<210> SEQ ID NO 272
<211> LENGTH: 33
<212> TYPE: DNA
<213> ORGANISM: Artificial Sequence
<220> FEATURE:
<223> OTHER INFORMATION: primer #59 (IL2_E61Q_F)

<400> SEQUENCE: 272
cttcagtgtc tagaacaaga actcaaacct ctg                               33
```

<210> SEQ ID NO 273
<211> LENGTH: 33
<212> TYPE: DNA
<213> ORGANISM: Artificial Sequence
<220> FEATURE:
<223> OTHER INFORMATION: primer #60 (IL2_E61Q_R)

<400> SEQUENCE: 273
cagaggtttg agttcttgtt ctagacactg aag                           33

<210> SEQ ID NO 274
<211> LENGTH: 30
<212> TYPE: DNA
<213> ORGANISM: Artificial Sequence
<220> FEATURE:
<223> OTHER INFORMATION: primer #61 (IL2_E61R_F)

<400> SEQUENCE: 274
cttcagtgtc tagaacggga actcaaacct                               30

<210> SEQ ID NO 275
<211> LENGTH: 30
<212> TYPE: DNA
<213> ORGANISM: Artificial Sequence
<220> FEATURE:
<223> OTHER INFORMATION: primer #62 (IL2_E61R_R)

<400> SEQUENCE: 275
aggtttgagt tcccgttcta gacactgaag                               30

<210> SEQ ID NO 276
<211> LENGTH: 33
<212> TYPE: DNA
<213> ORGANISM: Artificial Sequence
<220> FEATURE:
<223> OTHER INFORMATION: primer #63 (IL2_E68D_F)

<400> SEQUENCE: 276
ctcaaacctc tggaggacgt gctaaattta gct                           33

<210> SEQ ID NO 277
<211> LENGTH: 33
<212> TYPE: DNA
<213> ORGANISM: Artificial Sequence
<220> FEATURE:
<223> OTHER INFORMATION: primer #64 (IL2_E68D_R)

<400> SEQUENCE: 277
agctaaattt agcacgtcct ccagaggttt gag                           33

<210> SEQ ID NO 278
<211> LENGTH: 33
<212> TYPE: DNA
<213> ORGANISM: Artificial Sequence
<220> FEATURE:
<223> OTHER INFORMATION: primer #65 (IL2_E68Q_F)

<400> SEQUENCE: 278
ctcaaacctc tggagcaggt gctaaattta gct                           33

<210> SEQ ID NO 279
<211> LENGTH: 33
<212> TYPE: DNA
<213> ORGANISM: Artificial Sequence
<220> FEATURE:
<223> OTHER INFORMATION: primer #66 (IL2_E68Q_R)

```
<400> SEQUENCE: 279
agctaaattt agcacctgct ccagaggttt gag                              33

<210> SEQ ID NO 280
<211> LENGTH: 32
<212> TYPE: DNA
<213> ORGANISM: Artificial Sequence
<220> FEATURE:
<223> OTHER INFORMATION: primer #67 (IL2_V69G_F)

<400> SEQUENCE: 280
caaacctctg gaggaagggc taaatttagc tc                               32

<210> SEQ ID NO 281
<211> LENGTH: 32
<212> TYPE: DNA
<213> ORGANISM: Artificial Sequence
<220> FEATURE:
<223> OTHER INFORMATION: primer #68 (IL2_V69G_R)

<400> SEQUENCE: 281
gagctaaatt tagcccttcc tccagaggtt tg                               32

<210> SEQ ID NO 282
<211> LENGTH: 40
<212> TYPE: DNA
<213> ORGANISM: Artificial Sequence
<220> FEATURE:
<223> OTHER INFORMATION: primer #69 (IL2_V69G_Q74A_F)

<400> SEQUENCE: 282
ctggaggaag ggctaaattt agctgcaagc aaaaactttc                       40

<210> SEQ ID NO 283
<211> LENGTH: 40
<212> TYPE: DNA
<213> ORGANISM: Artificial Sequence
<220> FEATURE:
<223> OTHER INFORMATION: primer #70 (IL2_V69G_Q74A_R)

<400> SEQUENCE: 283
gaaagttttt gcttgcagct aaatttagcc cttcctccag                       40

<210> SEQ ID NO 284
<211> LENGTH: 24
<212> TYPE: DNA
<213> ORGANISM: Artificial Sequence
<220> FEATURE:
<223> OTHER INFORMATION: primer #71 (IL2_Q74H_F)

<400> SEQUENCE: 284
ctaaatttag ctcacagcaa aaac                                        24

<210> SEQ ID NO 285
<211> LENGTH: 24
<212> TYPE: DNA
<213> ORGANISM: Artificial Sequence
<220> FEATURE:
<223> OTHER INFORMATION: primer #72 (IL2_Q74H_R)

<400> SEQUENCE: 285 gttttgctg tgagctaaat ttag                                         24

<210> SEQ ID NO 286
```

```
<211> LENGTH: 33
<212> TYPE: DNA
<213> ORGANISM: Artificial Sequence
<220> FEATURE:
<223> OTHER INFORMATION: primer #73 (IL2_K76C_F)

<400> SEQUENCE: 286
aatttagctc aaagctgtaa ctttcactta aga                                    33

<210> SEQ ID NO 287
<211> LENGTH: 33
<212> TYPE: DNA
<213> ORGANISM: Artificial Sequence
<220> FEATURE:
<223> OTHER INFORMATION: primer #74 (IL2_K76C_R)

<400> SEQUENCE: 287
tcttaagtga agttacagc tttgagctaa att                                     33

<210> SEQ ID NO 288
<211> LENGTH: 32
<212> TYPE: DNA
<213> ORGANISM: Artificial Sequence
<220> FEATURE:
<223> OTHER INFORMATION: primer #75 (IL2_L80D_R81E_F)

<400> SEQUENCE: 288
aaagcaaaaa ctttcacgac gaacccaggg ac                                     32

<210> SEQ ID NO 289
<211> LENGTH: 32
<212> TYPE: DNA
<213> ORGANISM: Artificial Sequence
<220> FEATURE:
<223> OTHER INFORMATION: primer #76 (IL2_L80D_R81E_R)

<400> SEQUENCE: 289
gtccctgggt tcgtcgtgaa agttttgct tt                                      32

<210> SEQ ID NO 290
<211> LENGTH: 29
<212> TYPE: DNA
<213> ORGANISM: Artificial Sequence
<220> FEATURE:
<223> OTHER INFORMATION: primer #77 (IL2_L80F_F)

<400> SEQUENCE: 290
gcaaaaactt tcactttaga cccagggac                                         29

<210> SEQ ID NO 291
<211> LENGTH: 29
<212> TYPE: DNA
<213> ORGANISM: Artificial Sequence
<220> FEATURE:
<223> OTHER INFORMATION: primer #78 (IL2_L80F_R)

<400> SEQUENCE: 291
gtccctgggt ctaaagtgaa agttttgc                                          29

<210> SEQ ID NO 292
<211> LENGTH: 29
<212> TYPE: DNA
<213> ORGANISM: Artificial Sequence
<220> FEATURE:
<223> OTHER INFORMATION: primer #79 (IL2_L80F_R81D_F)

<400> SEQUENCE: 292
```

```
gcaaaaactt tcactttgac cccagggac                                      29

<210> SEQ ID NO 293
<211> LENGTH: 29
<212> TYPE: DNA
<213> ORGANISM: Artificial Sequence
<220> FEATURE:
<223> OTHER INFORMATION: primer #80 (IL2_L80F_R81D_R)

<400> SEQUENCE: 293
gtccctgggg tcaaagtgaa agttttgc                                       29

<210> SEQ ID NO 294
<211> LENGTH: 32
<212> TYPE: DNA
<213> ORGANISM: Artificial Sequence
<220> FEATURE:
<223> OTHER INFORMATION: primer #81 (IL2_L80F_R81E_F)

<400> SEQUENCE: 294
aaagcaaaaa ctttcacttc gaacccaggg ac                                  32

<210> SEQ ID NO 295
<211> LENGTH: 32
<212> TYPE: DNA
<213> ORGANISM: Artificial Sequence
<220> FEATURE:
<223> OTHER INFORMATION: primer #82 (IL2_L80F_R81E_R)

<400> SEQUENCE: 295
gtccctgggt tcgaagtgaa agttttgct tt                                   32

<210> SEQ ID NO 296
<211> LENGTH: 32
<212> TYPE: DNA
<213> ORGANISM: Artificial Sequence
<220> FEATURE:
<223> OTHER INFORMATION: primer #83 (IL2_L80V_R81D_F)

<400> SEQUENCE: 296
aaagcaaaaa ctttcacgtg gatcccaggg ac                                  32

<210> SEQ ID NO 297
<211> LENGTH: 32
<212> TYPE: DNA
<213> ORGANISM: Artificial Sequence
<220> FEATURE:
<223> OTHER INFORMATION: primer #84 (IL2_L80V_R81D_R)

<400> SEQUENCE: 297
gtccctggga tccacgtgaa agttttgct tt                                   32

<210> SEQ ID NO 298
<211> LENGTH: 32
<212> TYPE: DNA
<213> ORGANISM: Artificial Sequence
<220> FEATURE:
<223> OTHER INFORMATION: primer #85 (IL2_L80W_R81E_F)

<400> SEQUENCE: 298
aaagcaaaaa ctttcactgg gaacccaggg ac                                  32

<210> SEQ ID NO 299
<211> LENGTH: 32
<212> TYPE: DNA
```

```
<213> ORGANISM: Artificial Sequence
<220> FEATURE:
<223> OTHER INFORMATION: primer #86 (IL2_L80W_R81E_R)

<400> SEQUENCE: 299
gtccctgggt tcccagtgaa agttttttgct tt                              32

<210> SEQ ID NO 300
<211> LENGTH: 29
<212> TYPE: DNA
<213> ORGANISM: Artificial Sequence
<220> FEATURE:
<223> OTHER INFORMATION: primer #87 (IL2_L80Y_R81D_F)

<400> SEQUENCE: 300
gcaaaaactt tcactatgac cccagggac                                   29

<210> SEQ ID NO 301
<211> LENGTH: 29
<212> TYPE: DNA
<213> ORGANISM: Artificial Sequence
<220> FEATURE:
<223> OTHER INFORMATION: primer #88 (IL2_L80Y_R81D_R)

<400> SEQUENCE: 301
gtccctgggg tcatagtgaa agttttttgc                                  29

<210> SEQ ID NO 302
<211> LENGTH: 32
<212> TYPE: DNA
<213> ORGANISM: Artificial Sequence
<220> FEATURE:
<223> OTHER INFORMATION: primer #89 (IL2_L80Y_R81E_F)

<400> SEQUENCE: 302
aaagcaaaaa ctttcactac gaacccaggg ac                               32

<210> SEQ ID NO 303
<211> LENGTH: 32
<212> TYPE: DNA
<213> ORGANISM: Artificial Sequence
<220> FEATURE:
<223> OTHER INFORMATION: primer #90 (IL2_L80Y_R81E_R)

<400> SEQUENCE: 303
gtccctgggt tcgtagtgaa agttttttgct tt                              32

<210> SEQ ID NO 304
<211> LENGTH: 32
<212> TYPE: DNA
<213> ORGANISM: Artificial Sequence
<220> FEATURE:
<223> OTHER INFORMATION: primer #91 (IL2_L80Y_R81N_F)

<400> SEQUENCE: 304
aaagcaaaaa ctttcactac aaccccaggg ac                               32

<210> SEQ ID NO 305
<211> LENGTH: 32
<212> TYPE: DNA
<213> ORGANISM: Artificial Sequence
<220> FEATURE:
<223> OTHER INFORMATION: primer #92 (IL2_L80Y_R81N_R)

<400> SEQUENCE: 305
gtccctgggg ttgtagtgaa agttttttgct tt                              32
```

<210> SEQ ID NO 306
<211> LENGTH: 29
<212> TYPE: DNA
<213> ORGANISM: Artificial Sequence
<220> FEATURE:
<223> OTHER INFORMATION: primer #93 (IL2_L80Y_R81R_F)

<400> SEQUENCE: 306
gcaaaaactt tcactataga cccagggac                                29

<210> SEQ ID NO 307
<211> LENGTH: 29
<212> TYPE: DNA
<213> ORGANISM: Artificial Sequence
<220> FEATURE:
<223> OTHER INFORMATION: primer #94 (IL2_L80Y_R81R_R)

<400> SEQUENCE: 307
gtccctgggt ctatagtgaa agttttttgc                                29

<210> SEQ ID NO 308
<211> LENGTH: 31
<212> TYPE: DNA
<213> ORGANISM: Artificial Sequence
<220> FEATURE:
<223> OTHER INFORMATION: primer #95 (IL2_R81D_D84E_F)

<400> SEQUENCE: 308
ctttcactta gacccagggg agttaatcag c                              31

<210> SEQ ID NO 309
<211> LENGTH: 31
<212> TYPE: DNA
<213> ORGANISM: Artificial Sequence
<220> FEATURE:
<223> OTHER INFORMATION: primer #96 (IL2_R81D_D84E_R)

<400> SEQUENCE: 309
gctgattaac tccctggggt ctaagtgaaa g                              31

<210> SEQ ID NO 310
<211> LENGTH: 34
<212> TYPE: DNA
<213> ORGANISM: Artificial Sequence
<220> FEATURE:
<223> OTHER INFORMATION: primer #97 (IL2_R81D_F)

<400> SEQUENCE: 310
caaaaacttt cacttagacc ccagggactt aatc                           34

<210> SEQ ID NO 311
<211> LENGTH: 34
<212> TYPE: DNA
<213> ORGANISM: Artificial Sequence
<220> FEATURE:
<223> OTHER INFORMATION: primer #98 (IL2_R81D_R)

<400> SEQUENCE: 311
gattaagtcc ctggggtcta agtgaaagtt tttg                           34

<210> SEQ ID NO 312
<211> LENGTH: 51
<212> TYPE: DNA
<213> ORGANISM: Artificial Sequence
<220> FEATURE:

<223> OTHER INFORMATION: primer #99 (IL2_R81D_F_long)

<400> SEQUENCE: 312
ctcaaagcaa aaactttcac ttagacccca gggacttaat cagcaaatat c        51

<210> SEQ ID NO 313
<211> LENGTH: 51
<212> TYPE: DNA
<213> ORGANISM: Artificial Sequence
<220> FEATURE:
<223> OTHER INFORMATION: primer #100 (IL2_R81D_R_long)

<400> SEQUENCE: 313
gatatttgct gattaagtcc ctggggtcta agtgaaagtt tttgctttga g        51

<210> SEQ ID NO 314
<211> LENGTH: 43
<212> TYPE: DNA
<213> ORGANISM: Artificial Sequence
<220> FEATURE:
<223> OTHER INFORMATION: primer #101
       (IL2_R81E_D84E_L85V_I86V_V91T_I92F_F)

<400> SEQUENCE: 314
gaacccaggg aggtagtcag caatatcaac acatttgttc tgg                  43

<210> SEQ ID NO 315
<211> LENGTH: 43
<212> TYPE: DNA
<213> ORGANISM: Artificial Sequence
<220> FEATURE:
<223> OTHER INFORMATION: primer #102
       (IL2_R81E_D84E_L85V_I86V_V91T_I92F_R)

<400> SEQUENCE: 315
ccagaacaaa tgtgttgata ttgctgacta cctccctggg ttc                  43

<210> SEQ ID NO 316
<211> LENGTH: 31
<212> TYPE: DNA
<213> ORGANISM: Artificial Sequence
<220> FEATURE:
<223> OTHER INFORMATION: primer #103 (IL2_R81E_F)

<400> SEQUENCE: 316
aaactttcac ttagaaccca gggacttaat c                               31

<210> SEQ ID NO 317
<211> LENGTH: 31
<212> TYPE: DNA
<213> ORGANISM: Artificial Sequence
<220> FEATURE:
<223> OTHER INFORMATION: primer #104 (IL2_R81E_R)

<400> SEQUENCE: 317
gattaagtcc ctgggttcta agtgaaagtt t                               31

<210> SEQ ID NO 318
<211> LENGTH: 33
<212> TYPE: DNA
<213> ORGANISM: Artificial Sequence
<220> FEATURE:
<223> OTHER INFORMATION: primer #105 (IL2_P82G_F)

<400> SEQUENCE: 318
aactttcact tcgaaggcag ggacgtagtc agc                             33

<210> SEQ ID NO 319
<211> LENGTH: 33
<212> TYPE: DNA
<213> ORGANISM: Artificial Sequence
<220> FEATURE:
<223> OTHER INFORMATION: primer #106 (IL2_P82G_R)

<400> SEQUENCE: 319
gctgactacg tccctgcctt cgaagtgaaa gtt                33

<210> SEQ ID NO 320
<211> LENGTH: 33
<212> TYPE: DNA
<213> ORGANISM: Artificial Sequence
<220> FEATURE:
<223> OTHER INFORMATION: primer #107 (IL2_P82V_F)

<400> SEQUENCE: 320
aactttcact tcgaagtcag ggacgtagtc agc                33

<210> SEQ ID NO 321
<211> LENGTH: 33
<212> TYPE: DNA
<213> ORGANISM: Artificial Sequence
<220> FEATURE:
<223> OTHER INFORMATION: primer #108 (IL2_P82V_R)

<400> SEQUENCE: 321
gctgactacg tccctgactt cgaagtgaaa gtt                33

<210> SEQ ID NO 322
<211> LENGTH: 34
<212> TYPE: DNA
<213> ORGANISM: Artificial Sequence
<220> FEATURE:
<223> OTHER INFORMATION: primer #109 (IL2_D84E_F)

<400> SEQUENCE: 322
cttaagaccc agggagttaa tcagcaatat caac               34

<210> SEQ ID NO 323
<211> LENGTH: 34
<212> TYPE: DNA
<213> ORGANISM: Artificial Sequence
<220> FEATURE:
<223> OTHER INFORMATION: primer #110 (IL2_D84E_R)

<400> SEQUENCE: 323
gttgatattg ctgattaact ccctgggtct taag               34

<210> SEQ ID NO 324
<211> LENGTH: 32
<212> TYPE: DNA
<213> ORGANISM: Artificial Sequence
<220> FEATURE:
<223> OTHER INFORMATION: primer #111 (IL2_D84F_F)

<400> SEQUENCE: 324
cacttagacc ccaggttctt aatcagcaat at                 32

<210> SEQ ID NO 325
<211> LENGTH: 32
<212> TYPE: DNA
<213> ORGANISM: Artificial Sequence
<220> FEATURE:

<223> OTHER INFORMATION: primer #112 (IL2_D84F_R)

<400> SEQUENCE: 325
atattgctga ttaagaacct ggggtctaag tg                    32

<210> SEQ ID NO 326
<211> LENGTH: 31
<212> TYPE: DNA
<213> ORGANISM: Artificial Sequence
<220> FEATURE:
<223> OTHER INFORMATION: primer #113 (IL2_D84V_F)

<400> SEQUENCE: 326
acttagaccc cagggtctta atcagcaata t                     31

<210> SEQ ID NO 327
<211> LENGTH: 31
<212> TYPE: DNA
<213> ORGANISM: Artificial Sequence
<220> FEATURE:
<223> OTHER INFORMATION: primer #114 (IL2_D84V_R)

<400> SEQUENCE: 327
atattgctga ttaagaccct ggggtctaag t                     31

<210> SEQ ID NO 328
<211> LENGTH: 35
<212> TYPE: DNA
<213> ORGANISM: Artificial Sequence
<220> FEATURE:
<223> OTHER INFORMATION: primer #115 (IL2_L85A_I86A_F)

<400> SEQUENCE: 328
ctttgacccc agggacgctg ccagcaatat caacg                 35

<210> SEQ ID NO 329
<211> LENGTH: 35
<212> TYPE: DNA
<213> ORGANISM: Artificial Sequence
<220> FEATURE:
<223> OTHER INFORMATION: primer #116 (IL2_L85A_I86A_R)

<400> SEQUENCE: 329
cgttgatatt gctggcagcg tccctggggt caaag                 35

<210> SEQ ID NO 330
<211> LENGTH: 30
<212> TYPE: DNA
<213> ORGANISM: Artificial Sequence
<220> FEATURE:
<223> OTHER INFORMATION: primer #117 (IL2_L85E_I86V_F)

<400> SEQUENCE: 330
cccagggacg aagtgagcaa tatcaacgta                       30

<210> SEQ ID NO 331
<211> LENGTH: 30
<212> TYPE: DNA
<213> ORGANISM: Artificial Sequence
<220> FEATURE:
<223> OTHER INFORMATION: primer #118 (IL2_L85E_I86V_R)

<400> SEQUENCE: 331
tacgttgata ttgctcactt cgtccctggg                       30

```
<210> SEQ ID NO 332
<211> LENGTH: 27
<212> TYPE: DNA
<213> ORGANISM: Artificial Sequence
<220> FEATURE:
<223> OTHER INFORMATION: primer #119 (IL2_L85F_I86L_F)

<400> SEQUENCE: 332
cccagggact tcctcagcaa tatcaac                                              27

<210> SEQ ID NO 333
<211> LENGTH: 27
<212> TYPE: DNA
<213> ORGANISM: Artificial Sequence
<220> FEATURE:
<223> OTHER INFORMATION: primer #120 (IL2_L85F_I86L_R)

<400> SEQUENCE: 333
gttgatattg ctgaggaagt ccctggg                                              27

<210> SEQ ID NO 334
<211> LENGTH: 27
<212> TYPE: DNA
<213> ORGANISM: Artificial Sequence
<220> FEATURE:
<223> OTHER INFORMATION: primer #121 (IL2_L85F_I86V_F)

<400> SEQUENCE: 334
cccagggact tcgtcagcaa tatcaac                                              27

<210> SEQ ID NO 335
<211> LENGTH: 27
<212> TYPE: DNA
<213> ORGANISM: Artificial Sequence
<220> FEATURE:
<223> OTHER INFORMATION: primer #122 (IL2_L85F_I86V_R)

<400> SEQUENCE: 335
gttgatattg ctgacgaagt ccctggg                                              27

<210> SEQ ID NO 336
<211> LENGTH: 27
<212> TYPE: DNA
<213> ORGANISM: Artificial Sequence
<220> FEATURE:
<223> OTHER INFORMATION: primer #123 (IL2_L85G_I86A_F)

<400> SEQUENCE: 336
cccagggacg gagccagcaa tatcaac                                              27

<210> SEQ ID NO 337
<211> LENGTH: 27
<212> TYPE: DNA
<213> ORGANISM: Artificial Sequence
<220> FEATURE:
<223> OTHER INFORMATION: primer #124 (IL2_L85G_I86A_R)

<400> SEQUENCE: 337
gttgatattg ctggctccgt ccctggg                                              27

<210> SEQ ID NO 338
<211> LENGTH: 35
<212> TYPE: DNA
<213> ORGANISM: Artificial Sequence
<220> FEATURE:
<223> OTHER INFORMATION: primer #125 (IL2_L85G_I86V_F)
```

<400> SEQUENCE: 338
ctttgacccc agggacggtg ttagcaatat caacg                                35

<210> SEQ ID NO 339
<211> LENGTH: 35
<212> TYPE: DNA
<213> ORGANISM: Artificial Sequence
<220> FEATURE:
<223> OTHER INFORMATION: primer #126 (IL2_L85G_I86V_R)

<400> SEQUENCE: 339
cgttgatatt gctaacccag tccctggggt caaag                                35

<210> SEQ ID NO 340
<211> LENGTH: 27
<212> TYPE: DNA
<213> ORGANISM: Artificial Sequence
<220> FEATURE:
<223> OTHER INFORMATION: primer #127 (IL2_L85I_I86V_F)

<400> SEQUENCE: 340
cccagggaca tagtcagcaa tatcaac                                         27

<210> SEQ ID NO 341
<211> LENGTH: 27
<212> TYPE: DNA
<213> ORGANISM: Artificial Sequence
<220> FEATURE:
<223> OTHER INFORMATION: primer #128 (IL2_L85I_I86V_R)

<400> SEQUENCE: 341
gttgatattg ctgactatgt ccctggg                                         27

<210> SEQ ID NO 342
<211> LENGTH: 34
<212> TYPE: DNA
<213> ORGANISM: Artificial Sequence
<220> FEATURE:
<223> OTHER INFORMATION: primer #129 (IL2_L85L_I86A_F)

<400> SEQUENCE: 342
cttcgaaccc agggacctgg ccagcaatat caac                                 34

<210> SEQ ID NO 343
<211> LENGTH: 34
<212> TYPE: DNA
<213> ORGANISM: Artificial Sequence
<220> FEATURE:
<223> OTHER INFORMATION: primer #130 (IL2_L85L_I86A_R)

<400> SEQUENCE: 343
gttgatattg ctggccaggt ccctgggttc gaag                                 34

<210> SEQ ID NO 344
<211> LENGTH: 34
<212> TYPE: DNA
<213> ORGANISM: Artificial Sequence
<220> FEATURE:
<223> OTHER INFORMATION: primer #131 (IL2_L85L_I86V_F)

<400> SEQUENCE: 344
ctttgagccc agggacttag tcagcaatat caac                                 34

<210> SEQ ID NO 345
<211> LENGTH: 34

```
<212> TYPE: DNA
<213> ORGANISM: Artificial Sequence
<220> FEATURE:
<223> OTHER INFORMATION: primer #132 (IL2_L85L_I86V_R)

<400> SEQUENCE: 345
gttgatattg ctgactaagt ccctgggctc aaag                          34

<210> SEQ ID NO 346
<211> LENGTH: 27
<212> TYPE: DNA
<213> ORGANISM: Artificial Sequence
<220> FEATURE:
<223> OTHER INFORMATION: primer #133 (IL2_L85T_I86G_F)

<400> SEQUENCE: 346
cccagggaca caggcagcaa tatcaac                                  27

<210> SEQ ID NO 347
<211> LENGTH: 27
<212> TYPE: DNA
<213> ORGANISM: Artificial Sequence
<220> FEATURE:
<223> OTHER INFORMATION: primer #134 (IL2_L85T_I86G_R)

<400> SEQUENCE: 347
gttgatattg ctgcctgtgt ccctggg                                  27

<210> SEQ ID NO 348
<211> LENGTH: 29
<212> TYPE: DNA
<213> ORGANISM: Artificial Sequence
<220> FEATURE:
<223> OTHER INFORMATION: primer #135 (IL2_L85V_I86G_F)

<400> SEQUENCE: 348
cccagggacg taggcagcaa tatcaacgt                                29

<210> SEQ ID NO 349
<211> LENGTH: 29
<212> TYPE: DNA
<213> ORGANISM: Artificial Sequence
<220> FEATURE:
<223> OTHER INFORMATION: primer #136 (IL2_L85V_I86G_R)

<400> SEQUENCE: 349
acgttgatat tgctgcctac gtccctggg                                29

<210> SEQ ID NO 350
<211> LENGTH: 31
<212> TYPE: DNA
<213> ORGANISM: Artificial Sequence
<220> FEATURE:
<223> OTHER INFORMATION: primer #137 (IL2_L85V_I86I_codon_F)

<400> SEQUENCE: 350
gaacccaggg acgtaatcag caatatcaac g                             31

<210> SEQ ID NO 351
<211> LENGTH: 31
<212> TYPE: DNA
<213> ORGANISM: Artificial Sequence
<220> FEATURE:
<223> OTHER INFORMATION: primer #138 (IL2_L85V_I86I_codon_R)

<400> SEQUENCE: 351
```
cgttgatatt gctgattacg tccctgggtt c                                    31

<210> SEQ ID NO 352
<211> LENGTH: 30
<212> TYPE: DNA
<213> ORGANISM: Artificial Sequence
<220> FEATURE:
<223> OTHER INFORMATION: primer #139 (IL2_L85V_I86V_F)

<400> SEQUENCE: 352
gacccaggga cgtagtcagc aatatcaacg                                       30

<210> SEQ ID NO 353
<211> LENGTH: 30
<212> TYPE: DNA
<213> ORGANISM: Artificial Sequence
<220> FEATURE:
<223> OTHER INFORMATION: primer #140 (IL2_L85V_I86V_R)

<400> SEQUENCE: 353
cgttgatatt gctgactacg tccctgggtc                                       30

<210> SEQ ID NO 354
<211> LENGTH: 29
<212> TYPE: DNA
<213> ORGANISM: Artificial Sequence
<220> FEATURE:
<223> OTHER INFORMATION: primer #141 (IL2_L85W_I86V_F)

<400> SEQUENCE: 354
cccagggact gggtcagcaa tatcaacgt                                        29

<210> SEQ ID NO 355
<211> LENGTH: 29
<212> TYPE: DNA
<213> ORGANISM: Artificial Sequence
<220> FEATURE:
<223> OTHER INFORMATION: primer #142 (IL2_L85W_I86V_R)

<400> SEQUENCE: 355
acgttgatat tgctgaccca gtccctggg                                        29

<210> SEQ ID NO 356
<211> LENGTH: 30
<212> TYPE: DNA
<213> ORGANISM: Artificial Sequence
<220> FEATURE:
<223> OTHER INFORMATION: primer #143 (IL2_L85W_I86V_Long_F)

<400> SEQUENCE: 356
tttgacccca gggactgggt cagcaatatc                                       30

<210> SEQ ID NO 357
<211> LENGTH: 30
<212> TYPE: DNA
<213> ORGANISM: Artificial Sequence
<220> FEATURE:
<223> OTHER INFORMATION: primer #144 (IL2_L85W_I86V_Long_R)

<400> SEQUENCE: 357
gatattgctg acccagtccc tggggtcaaa                                       30

<210> SEQ ID NO 358
<211> LENGTH: 34
<212> TYPE: DNA
<213> ORGANISM: Artificial Sequence

```
<220> FEATURE:
<223> OTHER INFORMATION: primer #145 (IL2_L85Y_I86V_F)

<400> SEQUENCE: 358
cttcgaaccc agggactacg tcagcaatat caac                              34

<210> SEQ ID NO 359
<211> LENGTH: 34
<212> TYPE: DNA
<213> ORGANISM: Artificial Sequence
<220> FEATURE:
<223> OTHER INFORMATION: primer #146 (IL2_L85Y_I86V_R)

<400> SEQUENCE: 359
gttgatattg ctgacgtagt ccctgggttc gaag                              34

<210> SEQ ID NO 360
<211> LENGTH: 31
<212> TYPE: DNA
<213> ORGANISM: Artificial Sequence
<220> FEATURE:
<223> OTHER INFORMATION: primer #147 (IL2_I86V_V91T_I92F_F)

<400> SEQUENCE: 360
gtcagcaata tcaacacatt tgttctggaa c                                 31

<210> SEQ ID NO 361
<211> LENGTH: 31
<212> TYPE: DNA
<213> ORGANISM: Artificial Sequence
<220> FEATURE:
<223> OTHER INFORMATION: primer #148 (IL2_I86V_V91T_I92F_R)

<400> SEQUENCE: 361
gttccagaac aaatgtgttg atattgctga c                                 31

<210> SEQ ID NO 362
<211> LENGTH: 33
<212> TYPE: DNA
<213> ORGANISM: Artificial Sequence
<220> FEATURE:
<223> OTHER INFORMATION: primer #149 (IL2_S87C_F)

<400> SEQUENCE: 362
cccagggact taatctgcaa tatcaacgta ata                               33

<210> SEQ ID NO 363
<211> LENGTH: 33
<212> TYPE: DNA
<213> ORGANISM: Artificial Sequence
<220> FEATURE:
<223> OTHER INFORMATION: primer #150 (IL2_S87C_R)

<400> SEQUENCE: 363
tattacgttg atattgcaga ttaagtccct ggg                               33

<210> SEQ ID NO 364
<211> LENGTH: 34
<212> TYPE: DNA
<213> ORGANISM: Artificial Sequence
<220> FEATURE:
<223> OTHER INFORMATION: primer #151 (IL2_N88F_F)

<400> SEQUENCE: 364
cagggactta atcagcttta tcaacgtatt tgtt                              34
```

<210> SEQ ID NO 365
<211> LENGTH: 34
<212> TYPE: DNA
<213> ORGANISM: Artificial Sequence
<220> FEATURE:
<223> OTHER INFORMATION: primer #152 (IL2_N88F_R)

<400> SEQUENCE: 365
aacaaatacg ttgataaagc tgattaagtc cctg                    34

<210> SEQ ID NO 366
<211> LENGTH: 33
<212> TYPE: DNA
<213> ORGANISM: Artificial Sequence
<220> FEATURE:
<223> OTHER INFORMATION: primer #153 (IL2_N88Q_F)

<400> SEQUENCE: 366
gggacttaat cagccaaatc aacgtaatag ttc                     33

<210> SEQ ID NO 367
<211> LENGTH: 33
<212> TYPE: DNA
<213> ORGANISM: Artificial Sequence
<220> FEATURE:
<223> OTHER INFORMATION: primer #154 (IL2_N88Q_R)

<400> SEQUENCE: 367
gaactattac gttgatttgg ctgattaagt ccc                     33

<210> SEQ ID NO 368
<211> LENGTH: 34
<212> TYPE: DNA
<213> ORGANISM: Artificial Sequence
<220> FEATURE:
<223> OTHER INFORMATION: primer #155 (IL2_N88V_F)

<400> SEQUENCE: 368
cagggactta atcagcgtta tcaacgtatt tgtt                    34

<210> SEQ ID NO 369
<211> LENGTH: 34
<212> TYPE: DNA
<213> ORGANISM: Artificial Sequence
<220> FEATURE:
<223> OTHER INFORMATION: primer #156 (IL2_N88V_R)

<400> SEQUENCE: 369
aacaaatacg ttgataacgc tgattaagtc cctg                    34

<210> SEQ ID NO 370
<211> LENGTH: 33
<212> TYPE: DNA
<213> ORGANISM: Artificial Sequence
<220> FEATURE:
<223> OTHER INFORMATION: primer #157 (IL2_I89F_F)

<400> SEQUENCE: 370
gacttaatca gcaatttcaa cgtaatagtt ctg                     33

<210> SEQ ID NO 371
<211> LENGTH: 33
<212> TYPE: DNA
<213> ORGANISM: Artificial Sequence
<220> FEATURE:
<223> OTHER INFORMATION: primer #158 (IL2_I89F_R)

<400> SEQUENCE: 371
cagaactatt acgttgaaat tgctgattaa gtc    33

<210> SEQ ID NO 372
<211> LENGTH: 33
<212> TYPE: DNA
<213> ORGANISM: Artificial Sequence
<220> FEATURE:
<223> OTHER INFORMATION: primer #159 (IL2_V91E_I92F_F)

<400> SEQUENCE: 372
agcaatatca acgaattcgt tctggaacta aag    33

<210> SEQ ID NO 373
<211> LENGTH: 33
<212> TYPE: DNA
<213> ORGANISM: Artificial Sequence
<220> FEATURE:
<223> OTHER INFORMATION: primer #160 (IL2_V91E_I92F_R)

<400> SEQUENCE: 373
ctttagttcc agaacgaatt cgttgatatt gct    33

<210> SEQ ID NO 374
<211> LENGTH: 33
<212> TYPE: DNA
<213> ORGANISM: Artificial Sequence
<220> FEATURE:
<223> OTHER INFORMATION: primer #161 (IL2_V91E_I92W_F)

<400> SEQUENCE: 374
agcaatatca acgaatgggt tctggaacta aag    33

<210> SEQ ID NO 375
<211> LENGTH: 33
<212> TYPE: DNA
<213> ORGANISM: Artificial Sequence
<220> FEATURE:
<223> OTHER INFORMATION: primer #162 (IL2_V91E_I92W_R)

<400> SEQUENCE: 375
ctttagttcc agaacccatt cgttgatatt gct    33

<210> SEQ ID NO 376
<211> LENGTH: 34
<212> TYPE: DNA
<213> ORGANISM: Artificial Sequence
<220> FEATURE:
<223> OTHER INFORMATION: primer #163 (IL2_V91F_F)

<400> SEQUENCE: 376
cagcaatatc aactttatag ttctggaact aaag    34

<210> SEQ ID NO 377
<211> LENGTH: 34
<212> TYPE: DNA
<213> ORGANISM: Artificial Sequence
<220> FEATURE:
<223> OTHER INFORMATION: primer #164 (IL2_V91F_R)

<400> SEQUENCE: 377
ctttagttcc agaactataa agttgatatt gctg    34

<210> SEQ ID NO 378

<211> LENGTH: 34
<212> TYPE: DNA
<213> ORGANISM: Artificial Sequence
<220> FEATURE:
<223> OTHER INFORMATION: primer #165 (IL2_V91T_F)

<400> SEQUENCE: 378
cagcaatatc aacacaatag ttctggaact aaag        34

<210> SEQ ID NO 379
<211> LENGTH: 34
<212> TYPE: DNA
<213> ORGANISM: Artificial Sequence
<220> FEATURE:
<223> OTHER INFORMATION: primer #166 (IL2_V91T_R)

<400> SEQUENCE: 379
ctttagttcc agaactattg tgttgatatt gctg        34

<210> SEQ ID NO 380
<211> LENGTH: 32
<212> TYPE: DNA
<213> ORGANISM: Artificial Sequence
<220> FEATURE:
<223> OTHER INFORMATION: primer #167 (IL2_I92F_F)

<400> SEQUENCE: 380
gcaatatcaa cgtatttgtt ctggaactaa ag          32

<210> SEQ ID NO 381
<211> LENGTH: 32
<212> TYPE: DNA
<213> ORGANISM: Artificial Sequence
<220> FEATURE:
<223> OTHER INFORMATION: primer #168 (IL2_I92F_R)

<400> SEQUENCE: 381
ctttagttcc agaacaaata cgttgatatt gc          32

<210> SEQ ID NO 382
<211> LENGTH: 49
<212> TYPE: DNA
<213> ORGANISM: Artificial Sequence
<220> FEATURE:
<223> OTHER INFORMATION: primer #169 (IL2_I92F_F_long)

<400> SEQUENCE: 382
gacttaatca gcaatatcaa cgtatttgtt ctggaactaa agggatctg        49

<210> SEQ ID NO 383
<211> LENGTH: 49
<212> TYPE: DNA
<213> ORGANISM: Artificial Sequence
<220> FEATURE:
<223> OTHER INFORMATION: primer #170 (IL2_I92F_R_long)

<400> SEQUENCE: 383
cagatccctt tagttccaga acaaatacgt tgatattgct gattaagtc        49

<210> SEQ ID NO 384
<211> LENGTH: 45
<212> TYPE: DNA
<213> ORGANISM: Artificial Sequence
<220> FEATURE:
<223> OTHER INFORMATION: primer #171 (IL2_I92F_F_long2)

<400> SEQUENCE: 384
cttaatcagc aatatcaacg tatttgttct ggaactaaag ggatc    45

<210> SEQ ID NO 385
<211> LENGTH: 45
<212> TYPE: DNA
<213> ORGANISM: Artificial Sequence
<220> FEATURE:
<223> OTHER INFORMATION: primer #172 (IL2_I92F_R_long2)

<400> SEQUENCE: 385
gatcccttta gttccagaac aaatacgttg atattgctga ttaag    45

<210> SEQ ID NO 386
<211> LENGTH: 32
<212> TYPE: DNA
<213> ORGANISM: Artificial Sequence
<220> FEATURE:
<223> OTHER INFORMATION: primer #173 (IL2_I92F_L94F_L96F_F)

<400> SEQUENCE: 386
caacgtattt gttttcgaat tcaagggatc tg    32

<210> SEQ ID NO 387
<211> LENGTH: 32
<212> TYPE: DNA
<213> ORGANISM: Artificial Sequence
<220> FEATURE:
<223> OTHER INFORMATION: primer #174 (IL2_I92F_L94F_L96F_R)

<400> SEQUENCE: 387
cagatccctt gaattcgaaa acaaatacgt tg    32

<210> SEQ ID NO 388
<211> LENGTH: 39
<212> TYPE: DNA
<213> ORGANISM: Artificial Sequence
<220> FEATURE:
<223> OTHER INFORMATION: primer #175 (IL2_I92F_L94F_L96F_F)

<400> SEQUENCE: 388
gcaatatcaa cgtatttgtt ttcgaattta agggatctg    39

<210> SEQ ID NO 389
<211> LENGTH: 39
<212> TYPE: DNA
<213> ORGANISM: Artificial Sequence
<220> FEATURE:
<223> OTHER INFORMATION: primer #176 (IL2_I92F_L94F_L96F_R)

<400> SEQUENCE: 389
cagatccctt aaattcgaaa acaaatacgt tgatattgc    39

<210> SEQ ID NO 390
<211> LENGTH: 39
<212> TYPE: DNA
<213> ORGANISM: Artificial Sequence
<220> FEATURE:
<223> OTHER INFORMATION: primer #177 (IL2_I92F_L94F_L96I_F)

<400> SEQUENCE: 390
gcaatatcaa cgtatttgtt ttcgaaatta agggatctg    39

<210> SEQ ID NO 391
<211> LENGTH: 39
<212> TYPE: DNA

```
<213> ORGANISM: Artificial Sequence
<220> FEATURE:
<223> OTHER INFORMATION: primer #178 (IL2_I92F_L94F_L96I_R)

<400> SEQUENCE: 391
cagatccctt aatttcgaaa acaaatacgt tgatattgc                              39

<210> SEQ ID NO 392
<211> LENGTH: 39
<212> TYPE: DNA
<213> ORGANISM: Artificial Sequence
<220> FEATURE:
<223> OTHER INFORMATION: primer #179 (IL2_I92F_L94F_L96V_F)

<400> SEQUENCE: 392
gcaatatcaa cgtatttgtt ttcgaagtaa agggatctg                              39

<210> SEQ ID NO 393
<211> LENGTH: 39
<212> TYPE: DNA
<213> ORGANISM: Artificial Sequence
<220> FEATURE:
<223> OTHER INFORMATION: primer #180 (IL2_I92F_L94F_L96V_R)

<400> SEQUENCE: 393
cagatccctt tacttcgaaa acaaatacgt tgatattgc                              39

<210> SEQ ID NO 394
<211> LENGTH: 33
<212> TYPE: DNA
<213> ORGANISM: Artificial Sequence
<220> FEATURE:
<223> OTHER INFORMATION: primer #181 (IL2_I92I_F)

<400> SEQUENCE: 394
gcaatatcaa cgtaattgtt ctggaactaa agg                                    33

<210> SEQ ID NO 395
<211> LENGTH: 33
<212> TYPE: DNA
<213> ORGANISM: Artificial Sequence
<220> FEATURE:
<223> OTHER INFORMATION: primer #182 (IL2_I92I_R)

<400> SEQUENCE: 395
cctttagttc cagaacaatt acgttgatat tgc                                    33

<210> SEQ ID NO 396
<211> LENGTH: 33
<212> TYPE: DNA
<213> ORGANISM: Artificial Sequence
<220> FEATURE:
<223> OTHER INFORMATION: primer #183 (IL2_I92L_F)

<400> SEQUENCE: 396
gcaatatcaa cgtattagtt ctggaactaa agg                                    33

<210> SEQ ID NO 397
<211> LENGTH: 33
<212> TYPE: DNA
<213> ORGANISM: Artificial Sequence
<220> FEATURE:
<223> OTHER INFORMATION: primer #184 (IL2_I92L_R)

<400> SEQUENCE: 397
cctttagttc cagaactaat acgttgatat tgc                                    33
```

<210> SEQ ID NO 398
<211> LENGTH: 33
<212> TYPE: DNA
<213> ORGANISM: Artificial Sequence
<220> FEATURE:
<223> OTHER INFORMATION: primer #185 (IL2_I92W_F)

<400> SEQUENCE: 398
agcaatatca acgtatgggt tctggaacta aag                                    33

<210> SEQ ID NO 399
<211> LENGTH: 33
<212> TYPE: DNA
<213> ORGANISM: Artificial Sequence
<220> FEATURE:
<223> OTHER INFORMATION: primer #186 (IL2_I92W_R)

<400> SEQUENCE: 399
ctttagttcc agaacccata cgttgatatt gct                                    33

<210> SEQ ID NO 400
<211> LENGTH: 32
<212> TYPE: DNA
<213> ORGANISM: Artificial Sequence
<220> FEATURE:
<223> OTHER INFORMATION: primer #187 (IL2_I92Y_F)

<400> SEQUENCE: 400
gcaatatcaa cgtatatgtt ctggaactaa ag                                     32

<210> SEQ ID NO 401
<211> LENGTH: 32
<212> TYPE: DNA
<213> ORGANISM: Artificial Sequence
<220> FEATURE:
<223> OTHER INFORMATION: primer #188 (IL2_I92Y_R)

<400> SEQUENCE: 401
ctttagttcc agaacatata cgttgatatt gc                                     32

<210> SEQ ID NO 402
<211> LENGTH: 33
<212> TYPE: DNA
<213> ORGANISM: Artificial Sequence
<220> FEATURE:
<223> OTHER INFORMATION: primer #189 (IL2_L94F_L96F_F)

<400> SEQUENCE: 402
cgtaatagtt ttcgaattta agggatctga aac                                    33

<210> SEQ ID NO 403
<211> LENGTH: 33
<212> TYPE: DNA
<213> ORGANISM: Artificial Sequence
<220> FEATURE:
<223> OTHER INFORMATION: primer #190 (IL2_L94F_L96F_R)

<400> SEQUENCE: 403
gtttcagatc ccttaaattc gaaaactatt acg                                    33

<210> SEQ ID NO 404
<211> LENGTH: 33
<212> TYPE: DNA
<213> ORGANISM: Artificial Sequence
<220> FEATURE:

```
<223> OTHER INFORMATION: primer #191 (IL2_L94F_L96I_F)

<400> SEQUENCE: 404
cgtaatagtt ttcgaaatta agggatctga aac                                   33

<210> SEQ ID NO 405
<211> LENGTH: 33
<212> TYPE: DNA
<213> ORGANISM: Artificial Sequence
<220> FEATURE:
<223> OTHER INFORMATION: primer #192 (IL2_L94F_L96I_R)

<400> SEQUENCE: 405
gtttcagatc ccttaatttc gaaaactatt acg                                   33

<210> SEQ ID NO 406
<211> LENGTH: 33
<212> TYPE: DNA
<213> ORGANISM: Artificial Sequence
<220> FEATURE:
<223> OTHER INFORMATION: primer #193 (IL2_L94F_L96V_F)

<400> SEQUENCE: 406
cgtaatagtt ttcgaagtaa agggatctga aac                                   33

<210> SEQ ID NO 407
<211> LENGTH: 33
<212> TYPE: DNA
<213> ORGANISM: Artificial Sequence
<220> FEATURE:
<223> OTHER INFORMATION: primer #194 (IL2_L94F_L96V_R)

<400> SEQUENCE: 407
gtttcagatc cctttacttc gaaaactatt acg                                   33

<210> SEQ ID NO 408
<211> LENGTH: 30
<212> TYPE: DNA
<213> ORGANISM: Artificial Sequence
<220> FEATURE:
<223> OTHER INFORMATION: primer #195 (IL2_E95D_F)

<400> SEQUENCE: 408
gttctggacc taaagggatc tgaaacaaca                                       30

<210> SEQ ID NO 409
<211> LENGTH: 30
<212> TYPE: DNA
<213> ORGANISM: Artificial Sequence
<220> FEATURE:
<223> OTHER INFORMATION: primer #196 (IL2_E95D_R)

<400> SEQUENCE: 409
tgttgtttca gatcccttta ggtccagaac                                       30

<210> SEQ ID NO 410
<211> LENGTH: 33
<212> TYPE: DNA
<213> ORGANISM: Artificial Sequence
<220> FEATURE:
<223> OTHER INFORMATION: primer #197 (IL2_C125S_F)

<400> SEQUENCE: 410
agatggatta cctttagtca aagcatcatc tca                                   33
```

```
<210> SEQ ID NO 411
<211> LENGTH: 33
<212> TYPE: DNA
<213> ORGANISM: Artificial Sequence
<220> FEATURE:
<223> OTHER INFORMATION: primer #198 (IL2_C125S_R)

<400> SEQUENCE: 411
tgagatgatg ctttgactaa aggtaatcca tct                                33

<210> SEQ ID NO 412
<211> LENGTH: 34
<212> TYPE: DNA
<213> ORGANISM: Artificial Sequence
<220> FEATURE:
<223> OTHER INFORMATION: primer #199 (IL2_Q126T_F)

<400> SEQUENCE: 412
gatggattac ctttagtaca agcatcatct caac                               34

<210> SEQ ID NO 413
<211> LENGTH: 34
<212> TYPE: DNA
<213> ORGANISM: Artificial Sequence
<220> FEATURE:
<223> OTHER INFORMATION: primer #200 (IL2_Q126T_R)

<400> SEQUENCE: 413
gttgagatga tgcttgtact aaaggtaatc catc                               34

<210> SEQ ID NO 414
<211> LENGTH: 33
<212> TYPE: DNA
<213> ORGANISM: Artificial Sequence
<220> FEATURE:
<223> OTHER INFORMATION: primer #201 (IL2_desA1_F)

<400> SEQUENCE: 414
taagaatata catatgccta cttcaagttc tac                                33

<210> SEQ ID NO 415
<211> LENGTH: 33
<212> TYPE: DNA
<213> ORGANISM: Artificial Sequence
<220> FEATURE:
<223> OTHER INFORMATION: primer #202 (IL2_desA1_R)

<400> SEQUENCE: 415
gtagaacttg aagtaggcat atgtatattc tta                                33

<210> SEQ ID NO 416
<211> LENGTH: 34
<212> TYPE: DNA
<213> ORGANISM: Artificial Sequence
<220> FEATURE:
<223> OTHER INFORMATION: primer #203 (IL2_NdeI_desA1_N-term)

<400> SEQUENCE: 416
cgccatatgc ctacttcaag ttctacaaag aaaa                               34
```

<210> SEQ ID NO 417
<211> LENGTH: 34
<212> TYPE: DNA
<213> ORGANISM: Artificial Sequence
<220> FEATURE:
<223> OTHER INFORMATION: primer #204 (IL2_BHI_C-term)

<400> SEQUENCE: 417
cgggatcctc aagtcagtgt tgagatgatg cttt    34